United States Patent
Toda et al.

(10) Patent No.: US 6,884,774 B2
(45) Date of Patent: Apr. 26, 2005

(54) CYCLIC HEXAPEPTIDE DERIVATIVES

(75) Inventors: Ayako Toda, Osaka (JP); Takahiro Matsuya, Osaka (JP); Hiroaki Mizuno, Osaka (JP); Hiroshi Matsuda, Osaka (JP); Kenji Murano, Osaka (JP); David Barrett, Osaka (JP); Takashi Ogino, Osaka (JP); Keiji Matsuda, Osaka (JP)

(73) Assignee: Fujisawa Pharmaceutical Co. Ltd., Osaka (JP)

( * ) Notice: Subject to any disclaimer, the term of this patent is extended or adjusted under 35 U.S.C. 154(b) by 400 days.

(21) Appl. No.: 10/030,161

(22) PCT Filed: Feb. 20, 2001

(86) PCT No.: PCT/JP01/01204

§ 371 (c)(1),
(2), (4) Date: Jan. 30, 2002

(87) PCT Pub. No.: WO01/60846

PCT Pub. Date: Aug. 23, 2001

(65) Prior Publication Data

US 2003/0083238 A1 May 1, 2003

(30) Foreign Application Priority Data

Feb. 21, 2000 (AU) .............................................. PQ5752
Aug. 21, 2000 (AU) .............................................. PQ9552
Dec. 28, 2000 (AU) .............................................. PR2344

(51) Int. Cl.$^7$ ......................... A61K 38/00; A61K 38/12; C07K 5/00
(52) U.S. Cl. .............................. 514/9; 514/11; 530/317; 530/321; 530/344; 530/345; 435/7.2; 424/9.1
(58) Field of Search ....................... 514/9, 11; 530/317, 530/321, 344, 345; 435/7.2; 424/9.1

(56) References Cited

FOREIGN PATENT DOCUMENTS

| EP | 0 535 959 | 4/1993 |
|---|---|---|
| WO | 94 25048 | 11/1994 |
| WO | 96 11210 | 4/1996 |
| WO | 99 40108 | 8/1999 |

*Primary Examiner*—Jon Weber
*Assistant Examiner*—Chih-Min Kam
(74) *Attorney, Agent, or Firm*—Oblon, Spivak, McClelland, Maier & Neustadt, P.C.

(57) ABSTRACT

This invention relates to new polypeptide compound represented by the general formula (I) wherein $R^1$, $R^2$, $R^3$, $R^4$, $R^5$ and $R^6$ are as defined in the description or a salt thereof which has antimicrobial activities (especially, antifungal activities), inhibitory activity on β-1,3-glucan synthase, to process for preparation thereof, to a pharmaceutical composition comprising the same, and to a method for prophylactic and/or therapeutic treatment of infectious diseases including *Pneumocystic carinii* infection (e.g. *Pneumocystis carinii* pneumonia) in a human being or an animal.

13 Claims, No Drawings

CYCLIC HEXAPEPTIDE DERIVATIVES

The present application is a 371 of PCT International Application No. PCT/JP01/01204, filed Feb. 20, 2001, which claims the foreign priority benefits of Australia Application No. PQ5752, filed Feb. 21, 2000, Australia Application No. PQ9552, filed Aug. 21, 2000, and Australia Application No. PR2344, filed Dec. 28, 2000.

TECHNICAL FIELD

The present invention relates to new polypeptide compounds and salts thereof which are useful as a medicament.

BACKGROUND ART

In U.S. Pat. Nos. 5,376,634, 5,569,646, WO 96/11210 and WO 99/40108, there are disclosed the polypeptide compound and a pharmaceutically acceptable salt thereof, which have antimicrobial activities (especially antifungal activity).

DISCLOSURE OF INVENTION

The present invention relates to new polypeptide compound and a salt thereof.

More particularly, it relates to new polypeptide compound and a salt thereof, which have antimicrobial activities [especially, antifungal activities, in which the fungi may include *Aspergillus, Cryptococcus, Candida, Mucor, Actinomyces, Histoplasma, Dermatophyte, Malassezia, Fusarium* and the like.], inhibitory activity on β-1,3-glucan synthase, and further which are expected to be useful for the prophylactic and/or therapeutic treatment of *Pneumocystis carinii* infection (e.g. *Pneumocystis carinii* pneumonia) in a human being or an animal, to a process for preparation thereof, to a pharmaceutical composition comprising the same, and to a method for the prophylactic and/or therapeutic treatment of infectious disease including *Pneumocystis carinii* infection (e.g. *Pneumocystis carinii* pneumonia) in a human being or an animal.

The object polypeptide compounds of the present invention are new and can be represented by the following general formula (I):

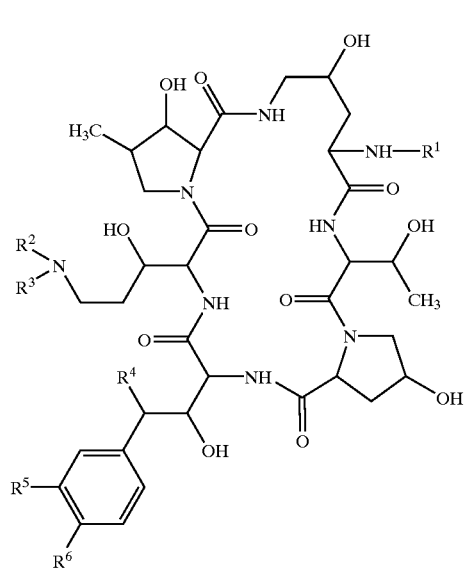

(I)

wherein
$R^1$ is hydrogen or acyl group,
$R^2$ is hydrogen or acyl group,
$R^3$ is lower alkyl which has one or more hydroxy or protected hydroxy,
$R^4$ is hydrogen or hydroxy,
$R^5$ is hydrogen, hydroxy, lower alkoxy or hydroxysulfonyloxy, and
$R^6$ is hydroxy or acyloxy,
or a salt thereof.

The new polypeptide compound (I) or a salt thereof can be prepared by the process as illustrated in the following reaction schemes.

Process 1

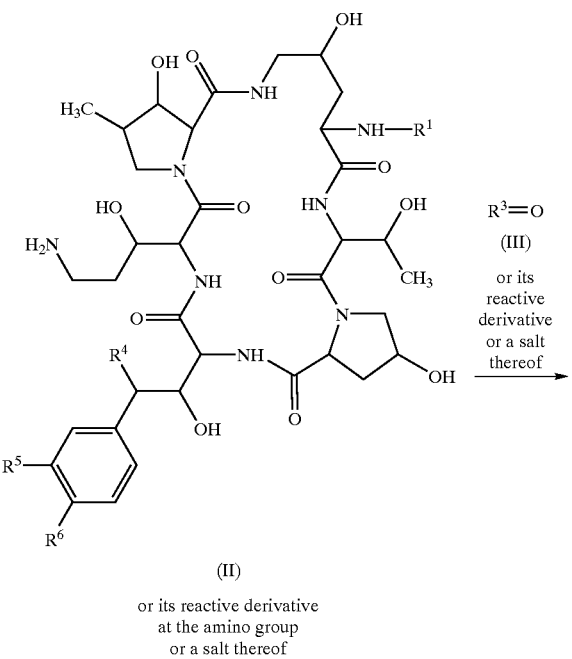

(II)

or its reactive derivative
at the amino group
or a salt thereof $R^3$=O (III)

or its
reactive
derivative
or a salt
thereof

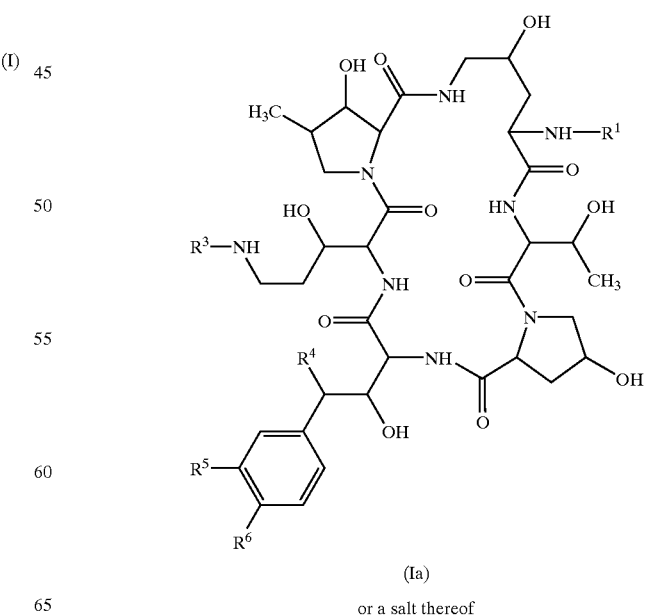

(Ia)

or a salt thereof

Process 2
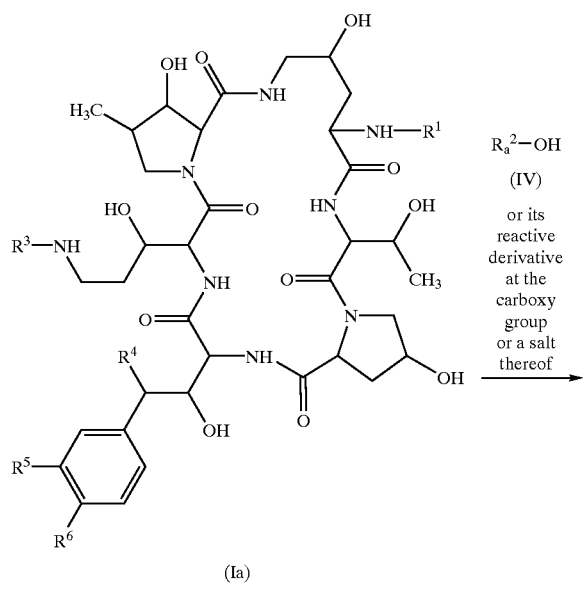
(Ia)
or its reactive derivative
at the amino group
or a salt thereof
$R_a^2$—OH
(IV)
or its
reactive
derivative
at the
carboxy
group
or a salt
thereof
Process 3
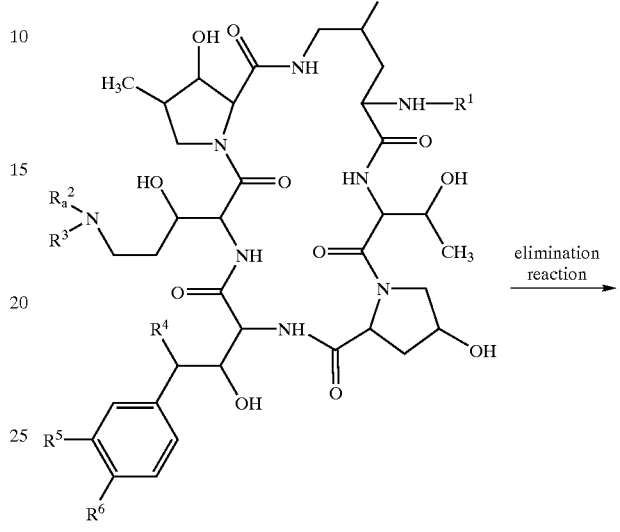
(Ib)
or a salt thereof
elimination
reaction
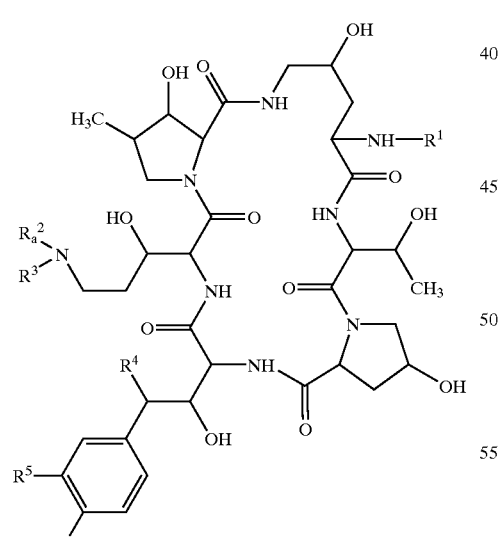
(Ib)
or a salt thereof
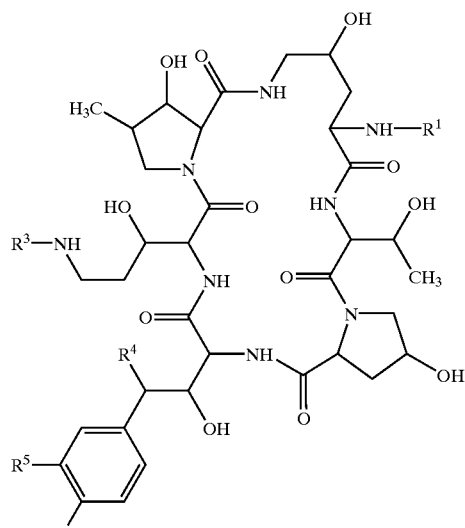
(Ia)
or a salt thereof Process 4

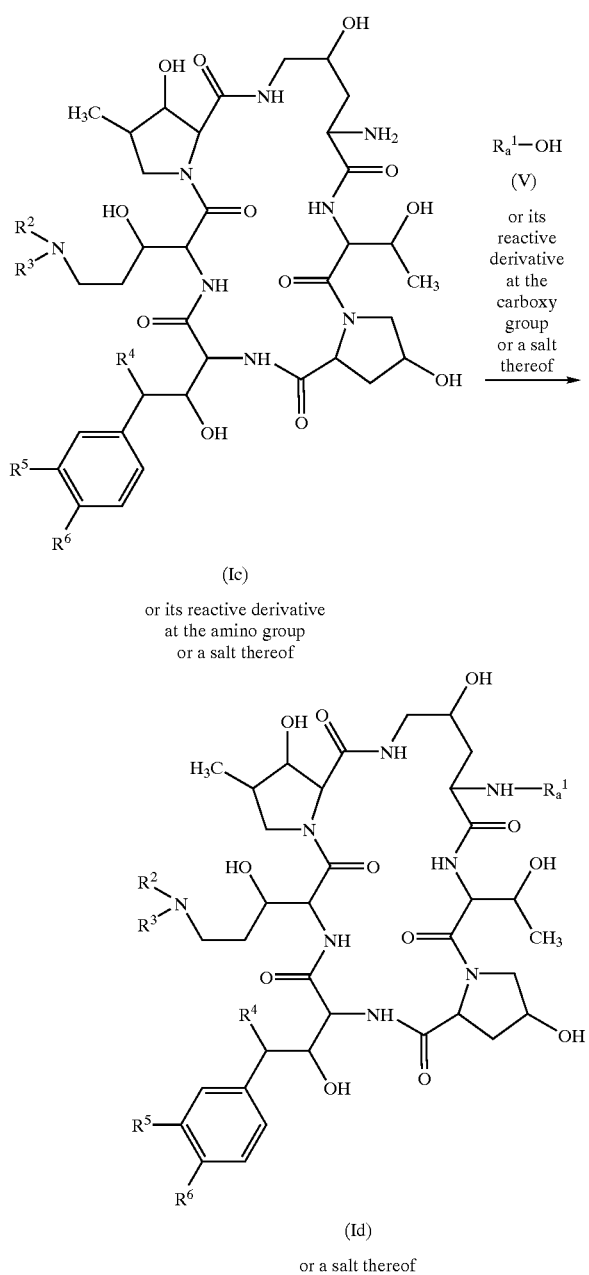

wherein $R^1$, $R^2$, $R^3$, $R^4$, $R^5$ and $R^6$ are defined above, $R_a^1$ is acyl group, and $R_a^2$ is acyl group.

Suitable salt of the new polypeptide compound (I) is a pharmaceutically acceptable and conventional non-toxic salt, and may include a salt with a base or an acid addition salt such as a salt with an inorganic base, for example, an alkali metal salt (e.g., sodium salt, potassium salt, etc.), an alkaline earth metal salt (e.g., calcium salt, magnesium salt, etc.), an ammonium salt;

a salt with an organic base, for example, an organic amine salt (e.g., triethylamine salt, diisopropylethylamine salt, pyridine salt, picoline salt, ethanolamine salt, triethanolamine salt, dicyclohexylamine salt, N,N'-dibenzylethylenediamine salt, 4-dimethylaminopyridine salt, etc.);

an inorganic acid addition salt (e.g., hydrochloride hydrobromide, sulfate, phosphate, etc.);

an organic carboxylic sulfonic acid addition salt (e.g., formate, acetate, trifluoroacetate, maleate, tartrate, fumarate, methanesulfonate, benzenesulfonate, toluenesulfonate, etc.);

a salt with a basic or acidic amino acid (e.g., arginine, aspartic acid, glutamic acid, etc.).

Suitable examples and illustration of the various definitions in the above and subsequent descriptions of the present specification, which the present invention intends to include within the scope thereof, are explained in detail as follows:

The term "lower" is used to intend a group having 1 to 6 carbon atom(s), unless otherwise provided.

Suitable example of "one or more" may be the number of 1 to 6, in which the preferred one may be the number of 1 to 3, and the most preferred one may be the number of 1 or 2.

Suitable example of "halogen" may be fluorine, chlorine, bromine, iodine and the like.

Suitable example of "lower alkoxy" may include straight or branched one such as methoxy, ethoxy, propoxy, isopropoxy, butoxy, isobutoxy, tert-butoxy, pentyloxy, tert-pentyloxy, neo-pentyloxy, hexyloxy, isohexyloxy and the like.

Suitable example of "higher alkoxy" may include straight or branched one such as heptyloxy, octyloxy, 3,5-dimethyloctyloxy, 3,7-dimethyloctyloxy, nonyloxy, decyloxy, undecyloxy, dodecyloxy, tridecyloxy, tetradecyloxy, hexadecyloxy, heptadecyloxy, octadecyloxy, nonadecyloxy, icosyloxy, and the like.

Suitable example of "lower alkyl" may include straight or branched one having 1 to 6 carbon atom(s), such as methyl, ethyl, propyl, isopropyl, butyl, isobutyl, sec-butyl, tert-butyl, pentyl, tert-pentyl, neo-pentyl, hexyl, isohexyl and the like.

Suitable example of "higher alkyl" may include straight or branched one such as heptyl, octyl, 3,5-dimethyloctyl, 3,7-dimethyloctyl, nonyl, decyl, undecyl, dodecyl, tridecyl, tetradecyl, hexadecyl, heptadecyl, octadecyl, nonadecyl, icosyl, and the like.

Suitable example of "aryl" and "ar" moiety may include phenyl which may have lower alkyl (e.g., phenyl, mesityl, xylyl, tolyl, etc.), naphthyl, anthryl, indanyl, fluorenyl, and the like, and this "aryl" and "ar" moiety may have one or more halogen.

Suitable example of "aroyl" may include benzoyl, toluoyl, naphthoyl, anthrylcarbonyl, and the like.

Suitable example of "heterocyclic group" may include unsaturated 3 to 8-membered (more preferably 5 or 6-membered) heteromonocyclic group containing 1 to 4 nitrogen atom(s), for example, pyrrolyl, pyrrolinyl, imidazolyl, pyrazolyl, pyridyl, dihydropyridyl, pyrimidyl, pyrazinyl, pyridazinyl, triazolyl (e.g., 4H-1,2,4-triazolyl, 1H-1,2,3-triazolyl, 2H-1,2,3-triazolyl, etc.), tetrazolyl (e.g. 1H-tetrazolyl, 2H-tetrazolyl, etc.), etc.;

saturated 3 to 8-membered (more preferably 5 or 6-membered) heteromonocyclic group containing 1 to 4 nitrogen atom(s), for example, pyrrolidinyl, imidazolidinyl, piperidyl, piperazinyl, azetidinyl, etc.;

unsaturated condensed heterocyclic group containing 1 to 4 nitrogen atom(s), for example, indolyl, isoindolyl, indolinyl, indolizinyl, benzimidazolyl, quinolyl, isoquinolyl, indazolyl, benzotriazolyl, etc.;

unsaturated 3 to 8-membered (more preferably 5 or 6-membered) heteromonocyclic group containing 1 or 2 oxygen atom(s) and 1 to 3 nitrogen atom(s), for example, oxazolyl, isoxazolyl, oxadiazolyl (e.g., 1,2,4-oxadiazolyl, 1,3,4-oxadiazolyl, 1,2,5-oxadiazolyl, etc.), etc.;

saturated 3 to 8-membered (more preferably 5 or 6-membered) heteromonocyclic group containing 1 or 2 oxygen atom(s) and 1 to 3 nitrogen atom(s), for example, morpholinyl, sydnonyl, morpholino, etc.;

unsaturated condensed heterocyclic group containing 1 or 2 oxygen atom(s) and 1 to 3 nitrogen atom(s), for example, benzoxazolyl, benzoxadiazolyl, etc.;

unsaturated 3 to 8-membered (more preferably 5 or 6-membered) heteromonocyclic group containing 1 or 2 sulfur atom(s) and 1 to 3 nitrogen atom(s), for example, thiazolyl, isothiazolyl, thiadiazolyl (e.g., 1,2,3-thiadiazolyl, 1,2,4-thiadiazolyl, 1,3,4-thiadiazolyl, 1,2,5-thiadiazolyl, etc.), dihydrothiazinyl, etc.;

saturated 3 to 8-membered (more preferably 5 or 6-membered) heteromonocyclic group containing 1 or 2 sulfur atom(s) and 1 to 3 nitrogen atom(s), for example thiazolidinyl, thiomorpholinyl, thiomorpholino, etc.;

unsaturated 3 to 8-membered (more preferably 5 or 6-membered) heteromonocyclic group containing 1 or 2 sulfur atom(s), for example, thienyl, dihydrodithiinyl, dihydrodithionyl, etc.;

unsaturated condensed heterocyclic group containing 1 or 2 sulfur atom(s) and 1 to 3 nitrogen atom(s), for example, benzothiazolyl, benzothiadiazolyl, imidazothiadiazolyl, etc.;

unsaturated 3 to 8-membered (more preferably 5 or 6-membered) heteromonocyclic group containing an oxygen atom, for example, furyl etc.;

saturated 3 to 8-membered (more preferably 5 or 6-membered) heteromonocyclic group containing 1 or 2 oxygen atom(s), for example, tetrahydrofuran, tetrahydropyran, dioxacyclopentane, dioxacyclohexane, etc.;

unsaturated 3 to 8-membered (more preferably 5 or 6-membered) heteromonocyclic group containing an oxygen atom and 1 or 2 sulfur atom(s), for example, dihydrooxathiinyl, etc.;

unsaturated condensed heterocyclic group containing 1 or 2 sulfur atom(s), for example benzothienyl, benzodithiinyl, etc.;

unsaturated condensed heterocyclic group containing an oxygen atom and 1 or 2 sulfur atom(s), for example, benzoxathiinyl, etc.; and the like, and this "heterocyclic group" may have one or more suitable substituent(s) selected from the group consisting of lower alkyl, oxo, cyclo(lower)alkyl, hydroxy(lower)alkyl, carboxy(lower) alkanoyl which may have amino and heterocycliccarbonyl.

Suitable example of "cyclo(lower)alkyl" may include cyclopropyl, cyclobutyl, cyclopentyl, cyclohexyl, and the like, and this "cyclo(lower)alkyl" may have one or more lower alkyl.

Suitable example of "cyclo(lower)alkyloxy" may include cyclopropyloxy, cyclobutyloxy, cyclopentyloxy, cyclohexyloxy, and the like.

Suitable example of "acyl group" may include aliphatic acyl, aromatic acyl, arylaliphatic acyl and heterocyclic-aliphatic acyl derived from carboxylic acid, carbonic acid, carbamic acid, sulfonic acid, and the like.

Suitable example of said "acyl group" may be illustrated as follows. Carboxy; carbamoyl; mono or di(lower) alkylcarbamoyl (e.g., methylcarbamoyl, dimethylcarbamoyl, ethylcarbamoyl, diethylcarbamoyl, etc.)

Aliphatic acyl such as lower or higher alkanoyl (e.g., formyl, acetyl, propanoyl, butanoyl, 2-methylpropanoyl, pentanoyl, 2,2-dimethylpropanoyl, hexanoyl, heptanoyl, octanoyl, nonanoyl, decanoyl, undecanoyl, dodecanoyl, tridecanoyl, tetradecanoyl, pentadecanoyl, hexadecanoyl, heptadecanoyl, octadecanoyl, nonadecanoyl, icosanoyl, etc.);

lower or higher alkoxycarbonyl (e.g., methoxycarbonyl, ethoxycarbonyl, t-butoxycarbonyl, t-pentyloxycarbonyl, heptyloxycarbonyl, etc.); lower alkenyloxycarbonyl (e.g., vinyloxycarbonyl, propenyloxycarbonyl, allyloxycarbonyl, butenyloxycarbonyl, butedienyloxycarbonyl, pentenyloxycarbonyl, hexenyloxycarbonyl, etc.);

lower or higher alkylsulfonyl (e.g., methylsulfonyl, ethylsulfonyl, etc.);

lower or higher alkoxysulfonyl (e.g., methoxysulfonyl, ethoxysulfonyl, etc.); or the like;

Aromatic acyl such as aroyl (e.g., benzoyl, toluoyl, naphthoyl, etc.);

ar(lower)alkanoyl [e.g., phenyl($C_1$–$C_6$)alkanoyl (e.g., phenylacetyl, phenylpropanoyl, phenylbutanoyl, phenylisobutanoyl, phenylpentanoyl, phenylhexanoyl, etc.), naphthyl($C_1$–$C_6$)alkanoyl (e.g., naphthylacetyl, naphthylpropanoyl, naphthylbutanoyl, etc.), etc.];

ar(lower)alkenoyl [e.g., phenyl($C_3$–$C_6$)alkenoyl (e.g., phenylpropenoyl, phenylbutenoyl, phenylmethacryloyl, phenylpentanoyl, phenylhexenoyl, etc.), naphthyl($C_3$–$C_6$) alkenoyl (e.g., naphthylpropenoyl, naphthylbutenoyl, etc.), etc.];

ar(lower)alkoxycarbonyl [e.g., phenyl($C_1$–$C_6$) alkoxycarbonyl (e.g., benzyloxycarbonyl, etc.), fluorenyl ($C_1$–$C_6$)alkoxycarbonyl (e.g., fluorenylmethyloxycarbonyl, etc.), etc.];

aryloxycarbonyl (e.g., phenoxycarbonyl, naphthyloxycarbonyl, etc.);

aryloxy(lower)alkanoyl (e.g., phenoxyacetyl, phenoxypropionyl, etc.);

arylcarbamoyl (e.g., phenylcarbamoyl, etc.);

arylthiocarbamoyl (e.g., phenylthiocarbamoyl, etc.);

arylglyoxyloyl (e.g., phenylglyoxyloyl, naphthylglyoxyloyl, etc.);

arylsulfonyl which may have 1 to 4 lower alkyl (e.g., phenylsulfonyl, p-tolylsulfonyl, etc.);

aroyl (e.g., benzoyl) substituted with one or more suitable substituent(s); or the like;

Heterocyclic acyl such as heterocycliccarbonyl;

heterocyclic(lower)alkanoyl (e.g., heterocyclicacetyl, heterocyclicpropanoyl, heterocyclicbutanoyl, heterocyclicpentanoyl, heterocyclichexanoyl, etc.);

heterocyclic(lower)alkenoyl (e.g., heterocyclicpropenoyl, heterocyclicbutenoyl, heterocyclicpentenoyl, heterocyclichexenoyl, etc.);

heterocyclicglyoxyloyl; or the like;

in which suitable "heterocyclic" moiety in the terms "heterocycliccarbonyl", "heterocyclic(lower)alkanoyl", "heterocyclic(lower)alkenoyl" and "heterocyclicglyoxyloyl" can be referred to aforementioned "heterocyclic" moiety.

Suitable example of "acyl group" of $R^1$ can be referred to aforementioned "acyl group", in which the preferred one may be lower alkoxycarbonyl, higher alkanoyl and benzoyl substituted with one or more suitable substituent(s).

Suitable example of "suitable substituent(s)" in the term of "benzoyl substituted with one or more suitable substituent (s)" may be thiadiazolyl substituted with phenyl having phenyl substituted with morphlino having lower alkyl, thiadiazolyl substituted with phenyl having a suitable substituent selected from the group consisting of lower alkoxy(lower)alkoxy and lower alkoxy(higher)alkoxy, piperazinyl substituted with phenyl having piperidyl substituted with a suitable substituent selected from the group consisting of phenyl having lower alkoxy(lower)alkoxy, cyclo(lower)alkyloxy and lower alkoxy(lower)alkylthio, piperazinyl substituted with phenyl having phenyl substituted with morpholino having lower alkyl, imidazothiadiazolyl substituted with phenyl having piperidyl substituted with a suitable substituent selected from the group consisting of lower alkoxy(lower)alkoxy and lower alkoxy(lower)alkylthio, imidazothiadiazolyl substituted with phenyl having lower alkoxy(lower)alkoxy, phenyl subsutituted with piperazinyl having phenyl substituted with morpholino having lower alkyl, isoxazolyl substituted with phenyl having lower alkoxy (lower)alkoxy, isoxazolyl substituted with phenyl having higher alkoxy substituted with morpholino having lower alkyl, thiadiazolyl substituted with phenyl having piperazinyl substituted with cyclo(lower)alkyl which has one or more suitable substituent(s) selected from the group consisting of lower alkyl, lower alkenyl, lower alkoxy(higher)alkoxy and phenyl, thiadiazolyl substituted with phenyl having piperazinyl substituted with lower alkyl having cyclo(lower)alkyl, thiadiazolyl substituted with phenyl having piperidyl substituted with one or more suitable substituent(s) selected from the group consisting of cyclo(lower)alkyloxy, lower alkoxy(lower)alkoxy and lower alkoxy(lower)alkoxy (lower)alkyl, thiadiazolyl substituted with phenyl having piperidyl substituted with cyclo(lower)alkyl and lower alkoxy, thiadiazolyl substituted with pyridyl having piperazinyl substituted with cyclo(lower)alkyl having lower alkyl, imidazothiadiazolyl substituted with phenyl having piperidyl substituted with cyclo(lower)alkyl, imidazothiadiazolyl substituted with phenyl having piperazinyl substituted with cyclo(lower)alkyl having lower alkyl, phenyl substituted with piperazinyl having cyclo(lower) alkyl substituted with one or more suitable substituent(s) selected from the group consisting of cyclo(lower)alkyl which may have lower alkoxy, lower alkyl, lower alkoxy and phenyl which may have lower alkoxy, in which the preferred one may be thiadiazolyl substituted with phenyl having phenyl substituted with morpholino having dimethyl, thiadiazolyl substituted with phenyl having a substituent selected from the group consisting of methoxyhexyloxy and methoxyheptyloxy, piperazinyl substituted with phenyl having piperidyl substituted with a substituent selected from the group consisting of phenyl having methoxybutoxy, cyclohexyloxy and methoxyhexylthio, piperazinyl substituted with phenyl having phenyl substituted with morpholino having dimethyl, imidazothiadiazolyl substituted with phenyl having piperidyl substituted with a substituent selected from the group consisting of methoxypropoxy, methoxybutoxy, methoxypentyloxy and methoxyhexylthio, imidazothiadiazolyl substituted with phenyl having methoxybutoxy, phenyl subsutituted with piperazinyl having phenyl substituted with morpholino having dimethyl, isoxazolyl substituted with phenyl having methoxyhexyloxy, isoxazolyl substituted with phenyl having heptyloxy substituted with morphlino having dimethyl, thiadiazolyl substituted with phenyl having piperazinyl substituted with cyclohexyl which has one or two substituent(s) selected from the group consisting of methyl, methylene, methoxyheptyloxy, methoxyoctyloxy and phenyl, thiadiazolyl substituted with phenyl having piperazinyl substituted with methyl which has a substituent selected from the group consisting of cyclopentyl and cyclohexyl, thiadiazolyl substituted with phenyl having piperidyl substituted with one or two substituent(s) selected from the group consisting of cyclohexyl, methoxy, cyclohexyloxy, methoxypentyloxy, methoxyhexyloxy, methoxybutoxymethyl and methoxypentyloxymethyl, thiadiazolyl substituted with pyridyl having piperazinyl substituted with cyclohexyl which has a substituent selected from the group consisting of methyl and ethyl, imidazothiadiazolyl substituted with phenyl having piperidyl substituted with cyclohexyl, imidazothiadiazolyl substituted with phenyl having piperazinyl substituted with cyclohexyl having methyl, phenyl substituted with piperazinyl having cyclohexyl substituted with one or two substituent(s) selected from the group consisting of ethyl, t-butyl, methoxy, cyclopentyl, cyclohexyl which may have methoxy or dimethyl, and phenyl which may have methoxy.

The more suitable example of "acyl group" may be benzoyl which has thiadiazolyl substituted with phenyl having phenyl substituted with morpholino having dimethyl, benzoyl which has thiadiazolyl substituted with phenyl having a substituent selected from the group consisting of methoxyhexyloxy and methoxyheptyloxy, benzoyl which has piperazinyl substituted with phenyl having piperidyl substituted with a substituent selected from the group consisting of phenyl having methoxybutoxy, cyclohexyloxy and methoxyhexylthio, benzoyl which has piperazinyl substituted with phenyl having phenyl substituted with morpholino having dimethyl, benzoyl which has imidazothiadiazolyl substituted with phenyl having piperidyl substituted with a substituent selected from the group consisting of methoxypropoxy, methoxybutoxy, methoxypentyloxy and methoxyhexylthio, benzoyl which has imidazothiadiazolyl substituted with phenyl having methoxybutoxy, benzoyl which has phenyl subsutituted with piperazinyl having phenyl substituted with morpholino having dimethyl, benzoyl which has isoxazolyl substituted with phenyl having methoxyhexyloxy, benzoyl which has isoxazolyl substituted with phenyl having heptyloxy substituted with morphlino having dimethyl, benzoyl which has thiadiazolyl substituted with phenyl having piperazinyl substituted with cyclohexyl which has one or two substituent(s) selected from the group consisting of methyl, methylene, methoxyheptyloxy, methoxyoctyloxy and phenyl, benzoyl which has thiadiazolyl substituted with phenyl having piperazinyl substituted with methyl which has a substituent selected from the group consisting of cyclopentyl and cyclohexyl, benzoyl which has thiadiazolyl substituted with phenyl having piperidyl substituted with one or two substituent(s) selected from the group consisting of cyclohexyl, methoxy, cyclohexyloxy, methoxypentyloxy, methoxyhexyloxy, methoxybutoxymethyl and methoxypentyloxymethyl, benzoyl which has thiadiazolyl substituted with pyridyl having piperazinyl substituted with cyclohexyl which has a substituent selected from the group consisting of methyl and ethyl, benzoyl which has imidazothiadiazolyl substituted with phenyl having piperidyl substituted with cyclohexyl, benzoyl which has imidazothiadiazolyl substituted with phenyl having piperazinyl substituted with cyclohexyl having methyl, benzoyl which has phenyl substituted with piperazinyl having cyclohexyl substituted with one or two substituent(s) selected from the group consisting of ethyl, t-butyl, methoxy, cyclopentyl, cyclohexyl which may have methoxy or dimethyl, and phenyl which may have methoxy.

Suitable example of "lower alkyl" in the term of "lower alkyl which has one or more hydroxy or protected hydroxy" can be referred to aforementioned "lower alkyl", in which the preferred one may be methyl, ethyl, propyl, isopropyl, butyl, pentyl and hexyl.

Suitable example of "hydroxy protective group" in the term of "protected hydroxy" may include acyl (e.g., lower alkanoyl, etc.) as mentioned above, phenyl(lower)alkyl which may have one or more suitable substituent(s) (e.g., benzyl, 4-methoxybenzyl, trityl, etc.), tri-substituted silyl [e.g., tri(lower)alkylsilyl(e.g., trimethylsilyl, t-butyldimethylsilyl, etc.), etc.], tetrahydropyranyl and the like.

Suitable example of "lower alkyl which has one or more hydroxy or protected hydroxy" may be dihydroxypropyl, dihydroxyisopropyl, trihydroxybutyl, tetrahydroxypentyl, pentahydroxyhexyl and diacetyloxyisopropyl.

Suitable example of "acyl group" of $R^2$ can be referred to aforementioned "acyl group", in which the preferred one may be "amino protective group" mentioned below, and the most preferred one may be acetyl, 2-acetyloxypropionyl, methylsulfonyl, 2,5-diaminopentanoyl, benzyloxycarbonyl, fluorenylmethoxycarbonyl, allyloxycarbonyl and tert-butoxycarbonyl.

Suitable example of "amino protective group" may be included
in aforementioned "acyl group", a conventional protective group such as ar(lower)alkoxycarbonyl and lower alkoxycarbonyl, in which the preferred one may be phenyl-$(C_1-C_4)$alkoxycarbonyl and fluorenyl$(C_1-C_4)$ alkoxycarbonyl and $(C_1-C_4)$alkoxycarbonyl, and the most preferred one may be benzyloxycarbonyl, fluorenyl-methoxycarbonyl and tert-butoxycarbonyl.

Suitable example of "acyl" moiety of "acyloxy" can be referred to aforementioned "acyl group", in which the preferred one may be lower alkenyloxycarbonyl, and the most preferred one may be allyloxycarbonyl.

Suitable example of "acyloxy" may be lower alkenyloxycarbonyloxy, and the more preferred one may be allyloxycarbonyloxy.

Particularly, the preferred examples of the cyclic polypeptide compound (I) of the present invention are as follows: the compound (I), wherein $R^1$ is hydrogen, lower alkoxycarbonyl, higher alkanoyl or benzoyl substituted with one or more suitable substituent(s), $R^2$ is hydrogen, $R^3$ is lower alkyl which has one or more hydroxy, $R^4$ is hydrogen or hydroxy;

$R^5$ is hydroxy or hydroxysulfonyloxy; and $R^6$ is hydroxy.

And, more preferred one may be the compound (I) wherein $R^1$ is hydrogen, lower alkoxycarbonyl, higher alkanoyl or benzoyl substituted with one or more suitable substituent(s), $R^2$ is hydrogen, $R^3$ is lower alkyl which has two hydroxy, $R^4$ is hydrogen or hydroxy;

$R^5$ is hydroxy or hydroxysulfonyloxy; and $R^6$ is hydroxy.

And, still more preferred one may be the compound (I) wherein $R^1$ is benzoyl substituted with a suitable substituent selected from the group consisting of thiadiazolyl substituted with phenyl having phenyl substituted with morphlino having lower alkyl, thiadiazolyl substituted with phenyl having a suitable substituent selected from the group consisting of lower alkoxy(lower)alkoxy and lower alkoxy(higher)alkoxy, piperazinyl substituted with phenyl having piperidyl substituted with a suitable substituent selected from the group consisting of phenyl having lower alkoxy(lower)alkoxy, cyclo(lower)alkyloxy and lower alkoxy(lower)alkylthio, piperazinyl substituted with phenyl having phenyl substituted with morpholino having lower alkyl, imidazothiadiazolyl substituted with phenyl having piperidyl substituted with a suitable substituent selected from the group consisting of lower alkoxy(lower)alkoxy and lower alkoxy(lower)alkylthio, imidazothiadiazolyl substituted with phenyl having lower alkoxy(lower)alkoxy, phenyl subsutituted with piperazinyl having phenyl substituted with morpholino having lower alkyl, isoxazolyl substituted with phenyl having lower alkoxy (lower)alkoxy, isoxazolyl substituted with phenyl having higher alkoxy substituted with morpholino having lower alkyl, thiadiazolyl substituted with phenyl having piperazinyl substituted with cyclo(lower)alkyl which has one or more suitable substituent(s) selected from the group consisting of lower alkyl, lower alkenyl, lower alkoxy(higher)alkoxy and phenyl, thiadiazolyl substituted with phenyl having piperazinyl substituted with lower alkyl having cyclo(lower)alkyl, thiadiazolyl substituted with phenyl having piperidyl substituted with one or more suitable substituent(s) selected from the group consisting of cyclo(lower)alkyloxy, lower alkoxy(lower)alkoxy and lower alkoxy(lower)alkoxy (lower)alkyl, thiadiazolyl substituted with phenyl having piperidyl substituted with cyclo(lower)alkyl and lower alkoxy, thiadiazolyl substituted with pyridyl having piperazinyl substituted with cyclo(lower)alkyl having lower alkyl, imidazothiadiazolyl substituted with phenyl having piperidyl substituted with cyclo(lower)alkyl, imidazothiadiazolyl substituted with phenyl having piperazinyl substituted with cyclo(lower)alkyl having lower alkyl, and phenyl substituted with piperazinyl having cyclo(lower) alkyl substituted with one or more suitable substituent(s) selected from the group consisting of cyclo(lower)alkyl which may have lower alkoxy, lower alkyl, lower alkoxy and phenyl which may have lower alkoxy, $R^2$ is hydrogen, $R^3$ is lower-alkyl which has two hydroxy, $R^4$ is hydrogen or hydroxy;

$R^5$ is hydroxy or hydroxysulfonyloxy; and $R^6$ is hydroxy.

And, the most preferred one may be the compound (I) wherein $R^1$ is benzoyl which has thiadiazolyl substituted with phenyl having piperazinyl substituted with cyclo(lower) alkyl which has lower alkyl, benzoyl which has thiadiazolyl substituted with phenyl having piperidyl substituted with cyclo(lower) alkyloxy, benzoyl which has phenyl substituted with piperazinyl having cyclo(lower)alkyl substituted with cyclo(lower)alkyl and lower alkoxy, benzoyl which has thiadiazolyl substituted with phenyl having piperidyl substituted with cyclo(lower)alkyl, $R^2$ is hydrogen, $R^3$ is lower alkyl which has two hydroxy, $R^4$ is hydrogen or hydroxy;

$R^5$ is hydroxy or hydroxysulfonyloxy; and $R^6$ is hydroxy.

The processes for preparing the polypeptide compound (I) of the present invention are explained in detail in the following.

Process 1

The object compound (Ia) or a salt thereof can be prepared by reacting the compound (II) or its reactive derivative at the amino group or a salt thereof with the compound (III) of the formula:

$$R^3=O \qquad\qquad\qquad (III)$$

or its reactive derivative, or a salt thereof.

Suitable reactive derivative of the compound (III) may include an acid halide, an acid anhydride, an activated ester, and the like. The suitable example may be an acid chloride; acid azide; a mixed acid anhydride with an acid such as substituted phosphoric acid (e.g., dialkylphosphoric acid, phenylphosphoric acid, diphenylphosphoric acid, dibenzylphosphoric acid, halogenated phosphoric acid, etc.), dialkylphosphorous acid, sulfurous acid, thiosulfuric acid, alkanesulfonic acid (e.g., methanesulfonic acid, ethanesulfonic acid, etc.), sulfuric acid, alkylcarbonic acid, aliphatic carboxylic acid (e.g., pivalic acid, pentanoic acid, isopentanoic acid, 2-ethylbutyric acid, trichloroacetic acid, etc.); aromatic carboxylic acid (e.g., benzoic acid, etc.); a symmetrical acid anydride; an activated amide with imidazole, 4-substitutd imidazole, dimethylpyrazole, triazole or tetrazole; an activated ester (e.g., cyanomethyl, ester methoxymethyl ester, dimethyliminomethyl

ester, vinyl ester, propargyl ester, p-nitrophenyl ester, 2,4-dinitrophenyl ester, trichlorophenyl ester, pentachlorophenyl ester, mesylphenyl ester, phenylazophenyl ester, phenylthioester, p-nitrophenyl thioester, p-cresyl thioester, carboxymethyl thioester, pyranyl ester, pyridyl ester, piperidyl ester, 8-quinolyl thioester, etc.); an ester with a N-hydroxy compound (e.g., N,N-dimethylhydroxylamine, 1-hydroxy-2-(1H)-pyridone, N-hydroxysuccinimide, N-hydroxybenzotriazole, N-hydroxyphthalimide, 1-hydroxy-6-chloro-1H-benzotriazole, etc.); and the like. These reactive derivatives can optionally be selected from them according to the kind of the compound (III) to be used.

The reaction is usually carried out in a conventional solvent such as water, acetone, dioxane, acetonitrile, chloroform, methylene chloride, ethylene chloride, tetrahydrofuran, ethyl acetate, N,N-dimethylformamide, pyridine or any other organic solvent which do not adversely affect the reaction, or the mixture thereof.

When the compound (III) is used in free acid form or its salt form in the reaction, the reaction is preferably carried out in the presence of a conventional condensing agent such as N,N'-dicyclohexylcarbodiimide; N-cyclohexyl-N'-morpholinoethylcarbodiimide); N-cyclohexyl-N'-(4-diethylaminocyclohexyl)carbodiimide; N,N'-diisopropylcarboxiimide; N-ethyl-N'-(3-dimethylaminopropyl)carbodiimide; N,N-carbonyl-bis(2-methylimidazole); pentamethyleneketene-N-cyclohexylimine; diphenylketene-N-cyclohexylimine, ethoxyacetylene; 1-alkoxy-1-chloroethylene; trialkyl phosphite; isopropyl polyphosphate; phosphorous oxychloride (phosphoryl chloride); phosphorous trichloride; thionyl chloride; oxalyl chloride; triphenylphosphite; 2-ethyl-7-hydroxybenzisoxazolium salt; 2-ethyl-5-(m-sulfophenyl) isoxazolium hydroxide intra-molecular salt; 1-(p-chlorobenzenesulfonyloxy)-6-chloro-1H-benzotriazole; so-called Vilsmeier reagent prepared by the reaction of N,N-dimethylformamide with thionyl chloride, phosgene, phosphorous oxychloride, etc.; or the like.

The reaction may also be carried out in the presence of an organic or inorganic base such as an alkali metal bicarbonate, tri(lower)alkylamine (e.g., triethylamine, diisopropylethylamine, etc.), pyridine, di(lower) alkylaminopyridine (e.g., 4-dimethylaminopyridine, etc.) N-(lower)alkylmorphorine, N,N-di(lower)alkylbenzylamine, or the like.

The reaction temperature is not critical, and the reaction is usually carried out under cooling to heating.

Process 2

The object compound (Ib) or a salt thereof can be prepared by reacting the compound (Ia) or its reactive derivative at the amino group or a salt thereof with the compound (IV) of the formula:

$$R_a^2-OH \qquad\qquad\qquad (IV)$$

(wherein $R_a^2$ is acyl group)

or its reactive derivative at the carboxy group or a salt thereof.

Suitable reactive derivative of the compound (IV) may include an acid halide, an acid anhydride, an activated ester, and the like. The suitable example may be an acid chloride; acid azide; a mixed acid anhydride with an acid such as substituted phosphoric acid (e.g., dialkylphosphoric acid, phenylphosphoric acid, diphenylphosphoric acid, dibenzylphosphoric acid, halogenated phosphoric acid, etc.), dialkylphosphorous acid, sulfurous acid, thiosulfuric acid, alkanesulfonic acid (e.g., methanesulfonic acid, ethanesulfonic acid, etc.), sulfuric acid, alkylcarbonic acid, aliphatic carboxylic acid (e.g., pivalic acid, pentanoic acid, isopentanoic acid, 2-ethylbutyric acid, trichloroacetic acid, etc.); aromatic carboxylic acid (e.g., benzoic acid, etc.); a symmetrical acid anydride; an activated amide with imidazole, 4-substitutd imidazole, dimethylpyrazole, triazole or tetrazole; an activated ester (e.g., cyanomethyl, ester methoxymethyl ester, dimethyliminomethyl

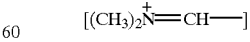

ester, vinyl ester, propargyl ester, p-nitrophenyl ester, 2,4-dinitrophenyl ester, trichlorophenyl ester, pentachlorophenyl ester, mesylphenyl ester, phenylazophenyl ester, phenylthioester, p-nitrophenyl thioester, p-cresyl thioester, carboxymethyl thioester, pyranyl ester, pyridyl ester, piperidyl ester, 8-quinolyl thioester, etc.); an ester with a N-hydroxy compound (e.g., N,N-dimethylhydroxylamine, 1-hydroxy-2-(1H)-pyridone, N-hydroxysuccinimide, N-hydroxybenzotriazole, N-hydroxyphthalimide, 1-hydroxy-6-chloro-1H-benzotriazole, etc.); and the like. These reactive derivatives can optionally be selected from them according to the kind of the compound (IV) to be used.

The reaction is usually carried out in a conventional solvent such as water, acetone, dioxane, acetonitrile, chloroform, methylene chloride, ethylene chloride, tetrahydrofuran, ethyl acetate, N,N-dimethylformamide, pyridine or any other organic solvent which do not adversely affect the reaction, or the mixture thereof.

When the compound (IV) is used in free acid form or its salt form in the reaction, the reaction is preferably carried out in the presence of a conventional condensing agent such as N,N'-dicyclohexylcarbodiimide; N-cyclohexyl-N'-morpholinoethylcarbodiimide); N-cyclohexyl-N'-(4-diethylaminocyclohexyl)carbodiimide; N,N'-diisopropylcarboxiimide; N-ethyl-N'-(3-dimethylaminopropyl)carbodiimide; N,N-carbonyl-bis(2-methylimidazole); pentamethyleneketene-N-cyclohexylimine; diphenylketene-N-cyclohexylimine, ethoxyacetylene; 1-alkoxy-1-chloroethylene; trialkyl phosphite; isopropyl polyphosphate; phosphorous oxychloride (phosphoryl chloride); phosphorous trichloride; thionyl chloride; oxalyl chloride; triphenylphosphite; 2-ethyl-7-hydroxybenzisoxazolium salt; 2-ethyl-5-(m-sulfophenyl) isoxazolium hydroxide intra-molecular salt; 1-(p-chlorobenzenesulfonyloxy)-6-chloro-1H-benzotriazole; so-called Vilsmeier reagent prepared by the reaction of N,N-dimethylformamide with thionyl chloride, phosgene, phosphorous oxychloride, etc.; or the like.

The reaction may also be carried out in the presence of an organic or inorganic base such as an alkali metal bicarbonate, tri(lower)alkylamine (e.g., triethylamine, diisopropylethylamine, etc.), pyridine, di(lower) alkylaminopyridine (e.g., 4-dimethylaminopyridine, etc.) N-(lower)alkylmorphorine, N,N-di(lower) alkylbenzylamine, or the like.

The reaction temperature is not critical, and the reaction is usually carried out under cooling to heating.

Process 3

The object compound (Ia) or a salt thereof can be prepared by subjecting a compound (Ib) or a salt thereof to elimination reaction of the acyl group.

This reaction is carried out in accordance with a conventional method such as hydrolysis, reduction or the like.

The hydrolysis is preferably carried out in the presence of a base or an acid including Lewis acid. Suitable base may include an inorganic base and an organic base such as an alkali metal [e.g. sodium, potassium, etc.], an alkaline earth metal [e.g. magnesium, calcium, etc.], the hydroxide or carbonate or bicarbonate thereof, trialkylamine [e.g. trimethylamine, triethylamine, etc.], picoline, 1,5-diazabicyclo[4.3.0]non-5-ene, 1,4-diazabicyclo[2.2.2] octane, 1,8-diazabicyclo[5.4.0]undec-7-ene, or the like.

Suitable acid may include an organic acid [e.g. formic acid, acetic acid, propionic acid, trichloroacetic acid, trifluoroacetic acid, etc.] and an inorganic acid [e.g. hydrochloric acid, hydrobromic acid, sulfuric acid, hydrogen chloride, hydrogen bromide, etc.]. The elimination using Lewis acid such as trihaloacetic acid [e.g. trichloroacetic acid, trifluoroacetic acid, etc.] or the like is preferably carried out in the presence of cation trapping agents [e.g. anisole, phenol, etc.].

The reaction is usually carried out in a solvent such as water, an alcohol [e.g. methanol, ethanol, etc.], methylene chloride, tetrahydrofuran, a mixture thereof or any other solvent which does not adversely influence the reaction. A liquid base or acid can be also used as the solvent. The reaction temperature is not critical and the reaction is usually carried out under cooling to warming.

The reduction method applicable for the elimination reaction may include chemical reduction and catalytic reduction.

Suitable reducing agents to be used in chemical reduction are a combination of metal [e.g. tin, zinc, iron, etc.] or metallic compound [e.g. chromium chloride, chromium acetate, etc.] and an organic or inorganic acid [e.g. formic acid, acetic acid, propionic acid, trifluoroacetic acid, p-toluenesulfonic acid, hydrochloric acid, hydrobromic acid, etc.].

Suitable catalysts to be used in catalytic reduction are conventional ones such as platinum catalysts [e.g. platinum plate, spongy platinum, platinum black, colloidal platinum, platinum oxide, platinum wire, etc.], palladium catalysts [e.g. spongy palladium, palladium black, palladium oxide, palladium on carbon, colloidal palladium, palladium on barium, sulfate, palladium on barium carbonate, etc.], nickel catalysts [e.g. reduced nickel, nickel oxide, Raney nickel, etc.], cobalt catalysts [e.g. reduced cobalt, Raney cobalt, etc], iron catalysts [e.g. reduced iron, Raney iron, etc], copper catalysts [e.g. reduced copper, Raney copper, Ullman copper, etc.] and the like.

The reduction is usually carried out in a conventional solvent which does not adversely influence the reaction such as water, methanol, ethanol, propanol, N,N-dimethylformamide, or a mixture thereof. Additionally, in case that the above-mentioned acids to be used in chemical reduction are in liquid, they can also be used as a solvent. Further, a suitable solvent to be used in catalytic reduction may be the above-mentioned solvent, and other conventional solvent such as diethyl ether, dioxane, tetrahydrofuran, etc., or a mixture thereof.

The reaction temperature of this reduction is not critical and the reaction is usually carried out under cooling to warming.

Process 4

The object compound (Id) or a salt thereof can be prepared by reacting the compound (Ic) or its reactive derivative at the amino group or a salt thereof with the compound (V) of the formula:

$$R_a^1 - OH \qquad (V)$$

(wherein

$R_a^1$ is acyl group)

or its reactive derivative at the carboxy group or a salt thereof.

Suitable reactive derivative at the carboxy group of the compound (V) may include an acid halide, an acid anhydride, an activated amide, an activated ester, and the like. Suitable examples of the reactive derivatives may be an acid chloride; an acid azide; a mixed acid anhydride with an acid such as substituted phosphoric acid [e.g., dialkylphosphoric acid, phenylphosphoric acid, diphenylphosphoric acid, dibenzylphosphoric acid, halogenated phosphoric acid, etc.], dialkylphosphorous acid, sulfurous acid, thiosulfuric acid, sulfuric acid, sulfonic acid [e.g., methanesulfonic acid, etc.], aliphatic carboxylic acid [e.g., acetic acid, propionic acid, butyric acid, isobutyric acid, pivaric acid, pentanoic acid, isopentanoic acid, 2-ethylbutyric acid trichloroacetic acid, etc.]; or aromatic carboxylic acid [e.g., benzoic acid, etc.]; a symmetrical acid, anhydride; an activated amide with imidazole, 4-substituted imidazole, dimethylpyrazole, triazole, tetrazole or 1-hydroxy-1H-benzotriazole; or an activated ester [e.g., cyanomethyl ester, methoxymethyl ester, dimethyliminomethyl

ester, vinyl ester, propargyl ester, p-nitrophenyl ester, 2,4-dinitrophenyl ester, trichlorophenyl ester, pentachloropentyl ester, mesylphenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, etc.], or an ester with a N-hydroxy compound [e.g. N,N-dimethylhydroxylamine, 1-hydroxy-2-(1H)-pyridone, N-hydroxysuccinimide, N-hydroxyphthalimide, 1-hydroxy-1H-benzotriazole, etc.], and the like. These reactive derivatives can optionally be selected from them according to the kind of the compound (V) to be used.

Suitable salts of the compound (V) and its reactive derivative can be referred to the ones as exemplified for the polypeptide compound (I).

The reaction is usually carried out in a conventional solvent such as water, alcohol [e.g., methanol, ethanol, etc.], acetone, dioxane, acetonitrile, chloroform, methylene chloride, ethylene chloride, tetrahydrofuran, ethyl acetate, N,N-dimethylformamide, pyridine or any other organic solvent which does not adversely influence the reaction. These conventional solvent may also be used in a mixture with water.

In this reaction, when the compound (V) is used in a free acid form or its salt form, the reaction is preferably carried out in the presence of a conventional condensing agent such as N,N'-dicyclohexylcarbodiimide; N-cyclohexyl-N'-morpholinoethylcarbodiimide; N-cyclohexyl-N'-(4-diethylaminocyclohexyl)carbodiimide; N,N'-diethylcarbodiimide; N,N'-diisopropylcarbodiimide; N-ethyl-N'-(3-dimethylaminopropyl)carbodiimide; N,N-carbonylbis-(2-methylimidazole); pentamethyleneketene-N-cyclohexylimine; diphenylketene-N-cyclohexylimine, ethoxyacetylene; 1-alkoxy-2-chloroethylene; trialkyl phosphite; ethyl polyphosphate; isopropyl polyphosphate; phosphorus oxychloride (phosphoryl chloride); phosphorus trichloride; thionyl chloride; oxalyl chloride; lower alkyl haloformate [e.g., ethyl chloroformate, isopropyl chloroformate, etc.]; triphenylphosphine; 2-ethyl-7-hydroxybenzisoxazolium salt; 2-ethyl-5-(m-sulfophenyl) isoxazolium hydroxide intramolecular salt; 1-(p-chlorobenzenesulfonyloxy)-6-chloro-1H-benzotriazole; so-called Vilsmeier reagent prepared by the reaction of N,N-dimethylformamide with thionyl chloride, phosgene, trichloromethyl chloroformate, phosphorous oxychloride, methanesulfonyl chloride, etc.; or the like.

The reaction may also be carried out in the presence of an inorganic or organic base such as an alkali metal carbonate, alkali metal bicarbonate, tri(lower)alkylamine (e.g., triethylamine, diisopropylethylamine, etc.), pyridine, di(lower)alkylaminopyridine (e.g., 4-dimethylaminopyridine, etc.), N-(lower)alkylmorpholine, N,N-di(lower)alkylbenzylamine, or the like.

The reaction temperature is not critical, and the reaction is usually carried out under cooling to warming.

The compounds obtained by the above Processes 1 to 4 can be isolated and purified by a conventional method such as pulverization, recrystallization, column-chromatography, high-performance liquid chromatography (HPLC), reprecipitation, desalting resin column chromatography, or the like.

The compounds obtained by the above Processes 1 to 4 may be obtained as its solvate (e.g., hydrate, ethanolate, etc.), and its solvate (e.g., hydrate, ethanolate, etc.) is included within the scope of the present invention.

It is to be noted that each of the polypeptide compound (I) may include one or more stereoisomer such as optical isomer(s) and geometrical isomer(s) due to asymmetric carbon atom(s) and double bond(s) and all such isomers and the mixture thereof are included within the scope of the present invention.

The polypeptide compound (I) or a salt thereof may include solvated compound [e.g., hydrate, ethanolate, etc.].

The polypeptide compound (I) or a salt thereof may include both its crystal form and non-crystal form.

It should be understood that the polypeptide compound (I) of the present invention may include the prodrug form.

The patent applications and publications cited herein are incorporated by reference.

In order to show the usefulness of the polypeptide compound (I) of the present invention, the biological data of the representative compound is explained in the following.

Biological Property of the Polypeptide Compound (I) of the Present Invention

Test (Antimicrobial Activity):

In vitro antimicrobial activity of the object compound of Examples 4, 9, 25 and 30 disclosed later was determined by $MIC_s$ in mouse serum as described below.

Test Method:

The $MIC_s$ in mouse serum were determined by the microdilution method using ICR mouse serum buffered with 20 mM HEPES buffer (pH 7.3) as a test medium. Inoculum suspension of $10^6$ cells/ml were prepared by a hemocytometric procedure and diluted to obtain an inoculum size of approximately $1.0 \times 10^3$ cells/ml. Microplates were incubated at 37° C. for 24 hours in 5% $CO_2$. The $MIC_s$ were defined as the lowest concentrations at which no visible growth was observed.

Test Result:

| | MIC (µg/ml) |
|---|---|
| Test organism | Candida albicans |
| Test compound | FP-633 |
| The object compound of Example 4 | <0.3 |
| The object compound of Example 9 | <0.3 |
| The object compound of Example 25 | <0.3 |
| The object compound of Example 30 | <0.3 |

From the test result, it is realized that the polypeptide compound (I) of the present invention has an antimicrobial activity (especially, antifungal activity).

In more details, the polypeptide compound (I) of the present invention have an antifungal activity, particularly against the following fungi.

*Acremonium;*

*Absidia* (e.g., *Absidia corymbifera*, etc);

*Aspergillus* (e.g., *Aspergillus clavatus, Aspergillus flavus, Aspergillus fumigatus, Aspergillus nidulans, Aspergillus*

*niger, Aspergillus terreus, Aspergillus versicolor*, etc);
*Blastomyces* (e.g., *Blastomyces dermatitidis*, etc);
*Candida* (e.g., *Candida albicans, Candida glabrata, Candida guilliermondii, Candida kefyr, Candida krusei, Candida parapsilosis, Candida stellatoidea, Candida tropicalis, candida utilis*, etc.);
*Cladosporium* (e.g., *Cladosporium trichloides*, etc);
*Coccidioides* (e.g., *Coccidioides immitis*, etc);
*Cryptococcus* (e.g., *Cryptococcus neoformans*, etc);
*Cunninghamella* (e.g., *Cunninghamella elegans*, etc);
*Dermatophyte;*
*Exophiala* (e.g., *Exophiala dermatitidis, Exophiala spinifera*, etc);
*Epidermophyton* (e.g., *Epidermophyton floccosum*, etc);
*Fonsecaea* (e.g., *Fonsecaea pedrosoi*, etc);
*Fusarium* (e.g., *Fusarium solani*, etc);
*Geotrichum* (e.g., *Geotrichum candiddum*, etc);
*Histoplasma* (e.g., *Histoplasma capsulatum* var. *capsulatum*, etc)
*Malassezia* (e.g., *Malassezia furfur*, etc);
*Microsporum* (e.g., *Microsporum canis, Microsporum gypseum*, etc);
*Mucor;*
*Paracoccidioides* (e.g., *Paracoccidioides brasiliensis*, etc);
*Penicillium* (e.g., *Penicillium marneffei*, etc);
*Phialophora;*
*Pneumocystis* (e.g., *Pneumocystis carinii*, etc);
*Pseudallescheria* (e.g., *Pseudallescheria boydii*, etc);
*Rhizopus* (e.g., *Rhizopus microsporus* var. *rhizopodiformis, Rhizopus oryzae*, etc);
*Saccharomyces* (e.g., *Saccharomyces cerevisiae*, etc);
*Scopulariopsis;*
*Sporothrix* (e.g., *Sporothrix schenckii*, etc);
*Trichophyton* (e.g., *Trichophyton mentagrophytes, Trichophyton rubrum*, etc);
*Trichosporon* (e.g., *Trichosporon asahii, Trichosporon cutaneum*, etc).

The above fungi are well-known to cause various infection diseases in skin, eye, hair, nail, oral mucosa, gastrointestinal tract, bronchus, lung, endocardium, brain, meninges, urinary organ, vaginal protion, oral cavity, ophthalmus, systemic, kidney, bronchus, heart, external auditory canal, bone, nasal cavity, paranasal cavity, spleen, liver, hypodermal tissue, lymph doct, gastrointestine, articulation, muscle, tendon, interstitial plasma cell in lung, blood, and so on.

Therefore, the polypeptide compound (I) of the present invention are useful for preventing and treating various infectious diseases, such as dermatophytosis (e.g., trichophytosis, etc), pityriasis versicolor, candidiasis, cryptococcosis, geotrichosis, trichosporosis, aspergillosis, penicilliosis, fusariosis, zygomycosis, sporotrichosis, chromomycosis, coccidioidomycosis, histoplasmosis, blastomycosis, paracoccidioidomycosis, pseudallescheriosis, mycetoma, mycotic keratitis, otomycosis, pneumocystosis, fungemia, and so on.

The combination use of azoles such as fluconazole, voriconazole, itraconazole, ketoconazole, miconazole, ER 30346 and SCH 56592; polyenes such as amphotericin B, nystatin, liposamal and lipid forms thereof such as Abelcet, AmBisome, and Amphocil; purine or pyrimidine nucleotide inhibitors such as flucytosine; or polyxins such as nikkomycines, in particular nikkomycine Z or nikkomycine X; other chitin inhibitors; elongation factor inhibitors such as sordarin and analogs thereof; mannan inhibitors such as predamycin, bactericidal/permeability-inducing (BPI) protein products such as XMP.97 or XMP.127; or complex carbohydrate antifungal agents such as CAN-296; or the combination use of immunosuppressant such as tacrolimus with the polypeptide compound (I) or a salt thereof is effective against above infectious diseases.

The pharmaceutical composition of the present invention can be used in the form of a pharmaceutical preparation, for example, in solid, semisolid or liquid form, which contains the polypeptide compound (I) or a pharmaceutically acceptable salt thereof, as an active ingredient in admixture with an organic or inorganic carrier or excipient which is suitable for rectal; pulmonary (nasal or buccal inhalation); ocular; external (topical); oral administration; parenteral (including subcutaneous, intravenous and intramuscular) administrations; insufflation (including aerosols from metered dose inhalator); nebulizer; or dry powder inhalator.

The active ingredient may be compounded, for example, with the usual non-toxic, pharmaceutically acceptable carriers in a solid form such as granules, tablets, dragees, pellets, troches, capsules, or suppositories; creams; ointments; aerosols; powders for insufflation; in a liquid form such as solutions, emulsions, or suspensions for injection; ingestion; eye drops; and any other form suitable for use. And, if necessary, there may be included in the above preparation auxiliary substance such as stabilizing, thickening, wetting, emulsifying and coloring agents; perfumes or buffer; or any other commonly may be used as additives.

The polypeptide compound (I) or a pharmaceutically acceptable salt thereof is/are included in the pharmaceutical composition in an amount sufficient to produce the desired antimicrobial effect upon the process or condition of diseases.

For applying the composition to humans, it is preferable to apply it by intravenous, intramuscular, pulmonary, oral administration, eye drop administration or insufflation. While the dosage of therapeutically effective amount of the polypeptide compound (I) varies from and also depends upon the age and condition of each individual patient to be treated, in the case of intravenous administration, a daily dose of 0.01–400 mg of the polypeptide compound (I) per kg weight of human being in the case of intramuscular administration, a daily dose of 0.1–20 mg of the polypeptide compound (I) per kg weight of human being, in case of oral administration, a daily dose of 0.5–50 mg of the polypeptide compound (I) per kg weight of human being is generally given for treating or preventing infectious diseases.

Especially in case of the treatment of prevention of *Pneumocystis carinii* infection, the followings are to be noted.

For administration by inhalation, the compounds of the present invention are conveniently delivered in the form of an aerosol spray presentation form pressurized as powders which may be formulated and the powder compositions may be inhaled with the aid of an insufflation powder inhaler device. The preferred delivery system for inhalation is a metered dose inhalation aerosol, which may be formulated as a suspension or solution of compound in suitable propellants such as fluorocarbons or hydrocarbons.

Because of desirability to directly treat lung and bronchi, aerosol administration is a preferred method of administration. Insufflation is also a desirable method, especially where infection may have spread to ears and other body cavities.

Alternatively, parenteral administration may be employed using drip intravenous administration.

For administration by intravenous administration, the preferred pharmaceutical composition is the lyophilized form containing the polypeptide compound (I) or its pharmaceutically acceptable salt.

The amount of the polypeptide compound (I) or its pharmaceutically acceptable salt contained in the composition for a single unit dosage of the present invention is 0.1 to 400 mg, more preferably 1 to 200 mg, still more preferably 5 to 100 mg, specifically 5, 10, 15, 20, 25, 30, 35, 40, 45, 50, 55, 60, 70, 75, 80, 85, 90, 95 and 100 mg.

The present invention further provides the following ones.

An article of manufacture, comprising packaging material and the compound (I) identified in the above contained within said packaging material, wherein said the compound (I) is therapeutically effective for preventing or treating infectious diseases caused by pathogenic microorganism, and wherein said packaging material comprises a label or a written material which indicates that said compound (I) can or should be used for preventing or treating infectious diseases caused by pathogenic microorganism.

A commercial package comprising the pharmaceutical composition containing the compound (I) identified in the above and a written matter associated therewith, wherein the written matter states that the compound (I) can or should be used for preventing or treating infectious diseases caused by pathogenic microorganism.

The following Preparations and Examples are given for the purpose of illustrating the present invention in more detail.

Preparation 1

To a solution of 1-N-t-butyloxycarbonyl-4-hydroxypiperidine (5.0 g) in dimethylformamide (DMF) (25 ml) was portionwise added sodium hydride (60% in oil) (1.29 g) with stirring under ice-cooling. The mixture was successively stirred at ambient temperature for 30 minutes, stirred at 60° C. for 1 hour and cooled with an ice bath. To the reaction mixture was added 1,5-dibromopentane (6.72 ml), and the mixture was stirred at ambient temperature for 3 hours. The reaction solution was poured into water (100 ml) and extracted twice with a mixture of ethyl acetate (80 ml) and n-hexane (30 ml). The extract was washed with saturated aqueous sodium chloride, dried over magnesium sulfate and evaporated in vacuo. The resulting residue was chromatographed on silica gel (200 ml) eluting with a mixture of n-hexane and ethyl acetate (5:1 v/v). The fractions containing the desired compound were collected and evaporated under reduced pressure to give 4-(5-bromopentyloxy)-1-N-t-butoxycarbonylpiperidine (2.44 g).

NMR (CDCl$_3$, δ): 1.46 (9H, s), 1.50–1.70 (6H, m), 1.70–1.96 (4H, m), 3.00–3.15 (2H, m), 3.35–3.50 (5H, m), 3.70–3.90 (2H, m)

APCI MASS (m/z): 250 (M$^+$–101)

Preparation 2

To a solution of 4-(5-bromopentyloxy)-1-N-t-butoxycarbonylpiperidine (2.44 g) in methanol (13 ml) was added 28% sodium methoxide methanol solution (14.2 ml), and the mixture was stirred under reflux for 4 hours. The reaction mixture was evaporated in vacuo. The resulting residue was chromatographed on silica gel (250 ml) eluting with a mixture of n-hexane and ethyl acetate (5:1 v/v). The fractions containing the object compound were collected and evaporated under reduced pressure to give 4-(5-methoxypentyloxy)-1-N-t-butoxycarbonylpiperidine (1.97 g).

NMR (CDCl$_3$, δ): 1.45 (9H, s), 1.45–1.95 (10H, m), 3.03 (1H, dd, J=3.47 and 9.20 Hz), 3.10 (1H, dd, J=3.47 and 9.20 Hz), 3.44 (3H, s), 3.34–3.50 (5H, m), 3.70–3.85 (2H, m)

APCI MASS (m/z): 202 (M$^+$–101)

Preparation 3

To a solution of 4-(5-methoxypentyloxy)-1-N-t-butoxycarbonylpiperidine (1.97 g) in ethyl acetate (20 ml) was added 4N-hydrogen chloride ethyl acetate solution (16.3 ml), and the mixture was stirred at ambient temperature for 2 hours. The reaction mixture was evaporated in vacuo. The resulting residue was dissolved in a mixture of dichloromethane and methanol (10:1; 50 ml: 5 ml). To this solution was added 1N-sodium hydroxide (5 ml) with stirring. The organic layer was separated and evaporated under reduced pressure to give 4-(5-methoxypentyloxy)-piperidine (0.62 g).

NMR (CDCl$_3$, δ): 1.25–1.50 (2H, s), 1.50–1.75 (6H, m), 1.9–2.10 (2H, m), 2.70–2.90 (2H, m), 2.95–3.20 (2H, m), 3.33 (3H, s), 3.35–3.50 (5H, m)

APCI MASS (m/z): 202 (M$^+$)

Preparation 4

A solution of 4-fluorobenzonitrile (0.38 g), 4-(5-methoxypentyloxy)piperidine (0.62 g) and potassium carbonate (0.87 g) in DMF (8 ml) was stirred at 90–95° C. for 6 hours. The reaction mixture was poured into water (50 ml) and extracted twice with a mixture of ethyl acetate and n-hexane (50 ml: 20 ml). The extracts were combined, washed with saturated aqueous sodium chloride, dried over magnesium sulfate and evaporated in vacuo. The resulting residue was chromatographed on silica gel (100 ml) eluting with a mixture of n-hexane and ethyl acetate (5:1 v/v–2:1 v/v). The fractions containing the desired compound were collected and evaporated under reduced pressure to give 4-(5-methoxypentyloxy)-N-(4-cyanophenyl)piperidine (294 mg).

NMR (CDCl$_3$, δ): 1.35–1.55 (2H, s), 1.55–1.75 (5H, m), 1.85–2.05 (2H, m), 3.13 (1H, dd, J=3.47 and 9.20 Hz), 3.17 (1H, dd, J=3.47 and 9.20 Hz), 3.33 (3H, s), 3.35–3.75 (8H, m), 6.85 (2H, d, J=9.01 Hz), 7.47 (2H, d, J=8.96 Hz)

APCI MASS (m/z): 303 (M$^+$)

Preparation 5

A solution of 4-(5-methoxypentyloxy)-N-(4-cyanophenyl)piperidine (294 mg) and thiosemicarbazide (0.68 g) in toluene (20 ml) and trifluoroacetic acid (10 ml) was stirred at 60–65° C. for 7 hours. After cooling, the reaction mixture was poured into a mixture of water (100 ml) and ethyl acetate (200 ml) and adjusted to pH 10 with 1N-sodium hydroxide. The mixture was dissolved in a mixture of THF (50 ml) and methanol (10 ml). The organic layer was separated, washed with saturated aqueous sodium chloride, dried over anhydrous magnesium sulfate and evaporated in vacuo. The resulting precipitate was washed with isopropyl ether and dried in vacuo to give 2-amino-5-[4-[4-(5-methoxypentyloxy)-piperidin-1-yl]phenyl]-1,3,4-thiadiazole (1.29 g).

NMR (CDCl$_3$+CD$_3$OD, δ): 1.30–1.50 (2H, m), 1.50–1.80 (6H, m), 1.90–2.10 (2H, m), 2.9–3.10 (2H, m), 3.34 (3H, s), 3.35–3.70 (7H, m), 6.93 (2H, d, J=8.91 Hz), 7.63 (2H, d, J=8.83 Hz)

APCI MASS (m/z): 377 (M$^+$)

Preparation 6

To a suspension of 2-amino-5-[4-[4-(5-methoxypentyloxy)piperidin-1-yl]phenyl]-1,3,4-thiadiazole (1.29 g) in ethanol (20 ml) was added ethyl 4-bromoacetylbenzoate (1.39 g) and stirred at reflux for 5 hours. The reaction mixture was cooled and poured into diisopropyl ether (IPE) (60 ml). The resulting precipitate was collected by filtration and dried. To a suspension of the precipitate in xylene (40 ml) was added trifluoroacetic acid (4 ml), and the mixture was stirred at reflux (130° C.) for 5 hours. The reaction mixture was cooled and poured into IPE (300 ml). The resulting precipitate was filtered and dried to give 4-[2-[4-[4-(5-methoxypentyloxy)piperidin-1-yl] phenyl]imidazo[2,1-b][1,3,4]thiadiazol-6-yl]benzoic acid ethyl ester trifluoroacetic acid salt (2.01 g).

NMR (CDCl$_3$, δ): 1.42 (3H, t, J=7.2 Hz), 1.45–1.75 (6H, m), 1.85–2.10 (2H, m), 2.30–2.50 (2H, m), 3.36 (3H, s), 3.35–3.55 (5H, m), 3.60–3.80 (2H, m), 4.40 (2H, q, J=7.14 Hz), 7.57 (2H, d, J=8.78 Hz), 7.84 (2H, d, J=8.40 Hz), 7.91 (2H, d, J=8.79 Hz), 8.13 (1H, s)

APCI MASS (m/z): 549 (M$^+$+1)

Preparation 7

To a solution of 4-[2-[4-[4-(5-methoxypentyloxy)-piperidin-1-yl]phenyl]imidazo[2,1-b][1,3,4]thiadiazol-6-yl] benzoic acid ethyl ester trifluoroacetic acid salt (2.01 g) in a mixture of methanol (40 ml) and tetrahydrofuran (20 ml) was added 4N-NaOH (20 ml), and the mixture was refluxed for 6 hours. The reaction mixture was cooled, poured into water (200 ml) and adjusted to pH 2 with conc. HCl. The resulting precipitate was collected by filtration, washed in turn with water, isopropyl alcohol (30 ml) and IPE (50 ml) to give 4-[2-[4-[4-(5-methoxypentyloxy)piperidin-1-yl] phenyl]-imidazo[2,1-b][1,3,4]thiadiazol-6-yl]benzoic acid (1.28 g).

ESI MASS (m/z)(Negative): 519.2 (M$^+$+1)

Preparation 8

To a solution of 4-[2-[4-[4-(5-methoxypentyloxy)-piperidin-1-yl]phenyl]imidazo[2,1-b][1,3,4]thiadiazol-6-yl] benzoic acid (1.28 g) and 1-hydroxybenzotriazole (465 mg) in dichloromethane (50 ml) was added 1-ethyl-3-(3'-dimethylaminopropyl)carbodiimide hydrochloride (WSCD.HCl) (943 mg), and the mixture was stirred overnight at ambient temperature. The reaction mixture was evaporated in vacuo. To the resulting precipitate was added water (50 ml) and filtered. The precipitate was washed with water and IPE (50 ml) and dried under reduced pressure for 3 hours to give 4-[2-[4-[4-(5-methoxypentyloxy)piperidin-1-yl]phenyl]imidazo-[2,1-b][1,3,4]thiadiazol-6-yl]benzoic acid benzotriazol-1-yl ester (1.26 g).

IR (KBr): 1774.2, 1708.6, 1604.5, 1471.4, 1365.4, 1230.4 cm$^{-1}$

NMR (CDCl$_3$, δ): 1.30–1.80 (8H, m), 1.85–2.10 (2H, m), 3.05–3.30 (2H, m), 3.33 (3H, s), 3.35–3.55 (4H, m), 3.55–3.75 (2H, m), 6.94 (2H, d, J=8.94 Hz), 7.30–7.60 (3H, m), 7.73 (2H, d, J=8.79 Hz), 8.00–8.20 (4H, m), 8.30 (2H, d, J=8.46 Hz)

ESI MASS (m/z)(Positive): 660.1 (M$^+$+Na)

The Starting Compounds used and the Object Compounds obtained in the following Preparation 9 is given in the table as below, in which the formula of the starting compound is in the upper column and the formula of the object compound are in the lower column, respectively.

| Preparation No. | Formula |
|---|---|
| 9 | 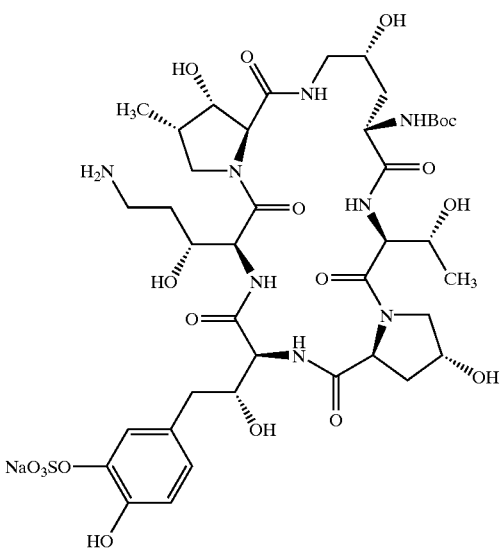 |

| Preparation No. | Formula |
|---|---|
| | 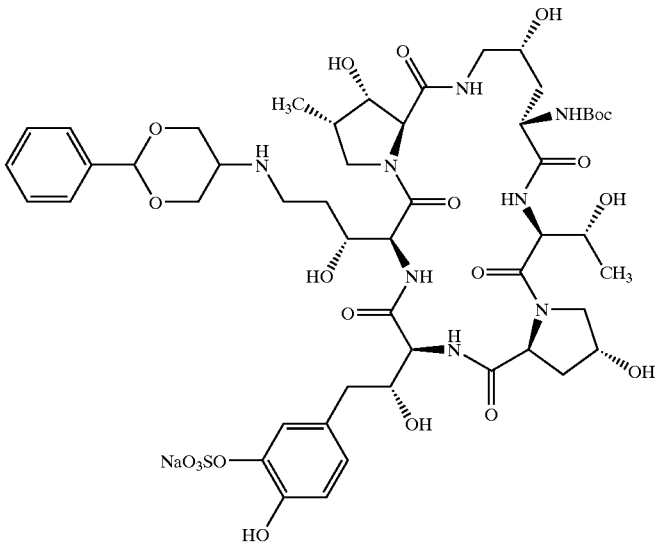 |

Preparation 9

To a solution of a mixture of the starting compound (9) (5.4 g), 2-oxo-1,3-diacetoxypropane (4.85 g) and acetic acid (0.78 ml) in a mixture of methanol (80 ml) and dimethylformamide (40 ml) was added sodium cyanoborohydride (1.71 g) with stirring at ambient temperature, and the mixture was stirred at the same temperature overnight. The reaction mixture was concentrated in vacuo. To the resulting residue was added pH 6.86 standard buffer solution (100 ml) and acetonitrile (20 ml), and the solution was adjusted to pH 8.5 with 1N sodium hydroxide. The solution was subjected to column chromatography on ODS (Daiso-gel, SP-120-40/60-ODS-B (Trademark: prepared by Daiso Co., Ltd.)) (400 ml) eluting in turn with water, 20% acetonitrile in water and 25% acetonitrile in water. The fractions containing the object compound were collected and evaporated under reduced pressure to remove acetonitrile. The residue was lyophilized to give the object compound (9) (4.44 g).

IR (KBr): 1632, 1516, 1452, 1273, 1248 $cm^{-1}$

NMR (DMSO-$d_6$, δ): 0.98 (3H, d, J=6.88 Hz), 1.11 (3H, d, J=5.64 Hz), 1.36 (9H, s), 1.40–2.00 (6H, m), 2.50–2.95 (4H, m), 3.30–3.55 (2H, m), 3.65–4.45 (16H, m), 4.70–4.85 (2H, m), 5.36 (1H, s), 6.71 (1H, d, J=8.05 Hz), 6.77 (1H, d, J=8.29 Hz), 6.99 (1H, s), 7.30–7.45 (5H, m)

APCI MASS (m/z)(Positive): 1175.4 ($M^+$+Na)

Elemental Analysis Calcd. for $C_{50}H_{72}N_8O_{21}S \cdot 5H_2O$: C, 46.80; H, 6.52; N, 8.73.

Found: C, 47.06; H, 6.44; N, 8.54.

Preparation 10

To a solution of trans-4-methylcyclohexanol (4.55 g) in ethyl acetate (50 ml) were added successively triethylamine (7.22 ml) and methanesulfonyl chloride (3.38 ml) with stirring under ice-water bath. The mixture was stirred at the same temperature for 1 hour. To the reaction mixture were added ethyl acetate (50 ml), water (50 ml) and 1N hydrochloric acid (20 ml) with stirring. The organic layer was separated, washed successively with water, saturated aqueous sodium hydrogen carbonate, water and saturated aqueous sodium chloride, dried over magnesium sulfate and evaporated in vacuo to give trans-4-methylcyclohexyl methanesulfonate (8.36 g).

NMR (CDCl$_3$, δ): 0.90 (3H, d, J=6.46 Hz), 0.95–1.70 (5H, m), 1.70–1.85 (2H, m), 2.00–2.20 (2H, m), 3.00 (3H, s), 4.50–4.70 (1H, m)

Preparation 11

Piperazine (54.9 g) and methanol (5 ml) was stirred at 120° C. to melt for 15 minutes. To the solution was dropwise added trans-4-methylcyclohexyl methanesulfonate (33.0 g) and the mixture was stirred at the same temperature for 2 hours. After cooling, to the reaction mixture was added water (150 ml) and extracted three times with a mixture of ethyl acetate (100 ml) and THF (100 ml). The extracts were collected, dried over magnesium sulfate and evaporated in vacuo. The resulting residue was chromatographed on silica gel (600 ml) eluting with a mixture of dichloromethane, methanol and conc. ammonium hydroxide (4:1:0.1 v/v). The fractions containing the desired compound were collected and evaporated under reduced pressure to give cis-1-(4-methylcyclohexyl)piperazine (17.76 g).

NMR (CDCl$_3$, δ): 0.92 (3H, d, J=6.96 Hz), 1.40–1.65 (8H, m), 1.65–1.85 (1H, m), 2.05–2.25 (1H, m), 2.45–2.60 (4H, m), 2.85–2.95 (4H, m)

APCI MASS (m/z) (Positive): 183.2 ($M^+$+1)

Preparation 12

A solution of ethyl 4-[4-(4-methylenecyclohexyl)-1-piperazinyl]benzoate (100 mg) and Iridium black (30 mg) in a mixture of t-butanol (1 ml) and methanol (2 ml) was stirred under atmospheric pressure of hydrogen for 4 hours. The catalyst was filtrated off and the filtrates were evaporated in vacuo. Ethyl 4-[cis-4-(4-methylcyclohexyl)-1-piperazinyl] benzoate and ethyl 4-[trans-4-(4-methylcyclohexyl)-1-piperazinyl]benzoate were obtained in the ratio 5:1–6:1 by thin-layer chromatography.

Preparation 13

To a suspension of 1-[4-[5-(4-iodophenyl)-1,3,4-thiadiazol-2-yl]phenyl]-4-(4-methylcyclohexyl)piperazine (2 g) in DMF (40 ml) was successively added ethyl formate (0.56 ml), dichlorobis(triphenylphosphine)palladium(II) (0.52 g) and 20% sodium ethoxide ethanol solution (4.43 ml) with stirring and the mixture was stirred at 40° C. for 2 hours. The reaction mixture was added diisopropyl ether (600 ml). The resulting precipitate was collected by filtration. The precipitate was dissolved THF (200 ml), insoluble materials were filtered off and solution was concentrated in vacuo. The resulting residue was washed with acetonitrile, and dried to give ethyl 4-[5-[4-[4-(4-methylcyclohexyl)-1-piperazinyl]phenyl]-1,3,4-thiadiazol-2-yl]benzoate (1.07 g).

NMR (CDCl$_3$, δ): 0.93–0.96 (3H, m), 1.39–3.37 (18H, m), 4.42 (2H, q, J=7.1 Hz), 6.96 (2H, d, J=8.9 Hz), 7.87–8.17 (6H, m)

MASS (m/z): 491.4 (M$^+$+1)

Preparation 14

To a solution of methyl triphenylphosphonium bromide (13.7 g) in DMSO (140 ml) was added potassium tert-butoxide (4.31 g) under ice-cooling and the mixture was stirred for 1.5 hours at ambient temperature. After cooling, 1,4-dioxaspiro[4,5]decan-8-one (5.0 g) was dropwise added to the solution under ice-cooling and then stirred for 1 hour at room temperature. The reaction mixture was poured into water (300 ml) and extracted twice with ethyl acetate (150 ml). The extracts were washed with saturated aqueous sodium chloride, dried over magnesium sulfate and evaporated in vacuo to give a residue. The residue was washed with a mixture of hexane and ethyl acetate (5:1 v/v) (300 ml). The resulting precipitates were collected and were chromatographed on silica gel (500 ml) eluting with a mixture of n-hexane and ethyl acetate (5:1 v/v). The fractions containing the desired compound were collected and evaporated under reduced pressure to give 8-methylene 1,4-dioxaspiro[4,5]decane (5.56 g).

NMR (CDCl$_3$, δ): 1.70 (4H, t, J=6.46 Hz), 2.29 (4H, t, J=6.84 Hz), 3.97 (4H, s), 4.67 (2H, s)

Preparation 15

A solution of 8-methylene 1,4-dioxaspiro[4,5]decane (5.55 g) in a mixture of acetone (60 ml) and water (4 ml) and p-toluenesulfonic acid monohydrate (1.37 g) was stirred at ambient temperature overnight. To a solution was added p-toluenesulfonic acid monohydrate (1.37 g) and the mixture was stirred at ambient temperature for 8 hours. Ethyl acetate (150 ml) was added to the reaction mixture and the solution was washed in turn with water, saturated aqueous sodium hydrogen carbonate and saturated aqueous sodium chloride, dried over magnesium sulfate and evaporated in vacuo. The resulting residue was chromatographed on silica gel (150 ml) eluting with a mixture of n-hexane and ethyl acetate (9:1 v/v). The fraction containing the desired compound were collected and evaporated under reduced pressure to give 4-methylenecyclohexan-1-one (0.98 g). This compound was immediately used as the starting compound for the next step.

Preparation 16

To a solution of 1,4-dioxaspiro[4,5]decan-8-one (96.9 g) in methanol (1 l) was added portionwise sodium borohydride (46.9 g) under ice-cooling. After stirring for 3.5 hours under ice cooling, the reaction mixture was successively stirred for 3 hours at room temperature. Then the solvent was evaporated in vacuo and the residue was purified by column chromatography on silica gel eluting with a mixture of hexane and ethyl acetate (1:1). The eluted fractions containing the desired product were collected and evaporated in vacuo to give 1,4-dioxaspiro-[4,5]decan-8-ol (97.9 g).

NMR (CDCl$_3$, δ): 1.4–2.0 (9H, m), 3.7–3.9 (1H, m), 3.95 (4H, s)

Preparation 17

To a solution of tert-butyl 4-(5-bromophenyloxy)-1-piperidinecarboxylate (12.98 g) in methanol (70 ml) was added 28% sodium methoxide methanol solution (37.8 ml) and the mixture was stirred under refluxing for 4 hours. After cooling, the reaction mixture was evaporated in vacuo. The resulting residue was chromatographed on silica gel (400 ml) eluting with a mixture of n-hexane and ethyl acetate (5:1 v/v). The fractions containing the object compound were collected and evaporated under reduced pressure to give tert-butyl 4-(5-methoxypentyloxy)-1-piperidinecarboxylate (16.31 g). This compound was immediately used as the starting compound for the next step.

Preparation 18

A solution of ethyl 4-fluorobenzoate (2.30 g), 4-4-(methoxybutyloxymethyl)piperidine trifluroacetate (3.6 g) and potassium carbonate (4.73 g) in DMSO (40 ml) was stirred at 140–150° C. for 4 hours. The reaction mixture was poured into water (150 ml) and extracted twice with ethyl acetate (80 ml). The extracts were collected, washed with saturated aqueous sodium chloride, dried over magnesium sulfate and evaporated in vacuo. The resulting residue was chromatographed on silica gel (200 ml) eluting with a mixture of n-hexane and ethyl acetate (2:1 v/v) The fractions containing the desired compound were collected and evaporated under reduced pressure to give ethyl 4-[4-(4-methoxybutyloxymethyl)-1-piperidyl]benzoate (2.76 g).

NMR (CDCl$_3$, δ): 1.20–1.45 (5H, m), 1.50–1.70 (3H, m), 1.70–1.90 (3H, m), 2.84 (2H, dt, J=2.49 and J=12.8 Hz), 3.28 (2H, d, J=6.01 Hz), 3.33 (3H, s), 3.35–3.50 (4H, m), 3.75–3.90 (2H, m), 4.32 (2H, q, J=7.11 Hz), 6.85 (2H, d, J=9.06 Hz), 7.92 (2H, d, J=9.01 Hz)

APCI MASS (m/z)(Positive): 350.4 (M$^+$+1)

Preparation 19

To a solution of tert-butyl 4-5-(methoxypentyloxymethyl)-1-piperidinecarboxylate (1.75 g) in dichloromethane (50 ml) and anisole (4.22 ml) was added trifluoroacetic acid (8.55 ml) under ice-cooling and the mixture was stirred at ambient temperature for 1 hour. The reaction mixture was evaporated in vacuo and azeotropically distilled three times with toluene (30 ml) and dried in vacuo to give 4-5-(methoxypentyloxymethyl)piperidine trifluoroacetate (7.30 g, crude oil). A solution of this compound (1.89 g), ethyl 4-fluorobenzoate (1.21 g), and potassium carbonate (2.30 g) in DMSO (20 ml) was stirred at 150° C. for 4 hours. The reaction mixture was poured into water (100 ml) and extracted twice with ethyl acetate (80 ml). The extracts were collected, washed with saturated aqueous sodium chloride, dried over magnesium sulfate and evaporated in vacuo. The resulting residue was chromatographed on silica gel (200 ml) eluting with a mixture of n-hexane and ethyl acetate (2:1 v/v). The fractions containing the desired compound were collected and evaporated under reduced pressure to give ethyl 4-[4-(5-methoxypentyloxymethyl)-1-piperidyl]benzoate (1.21 g).

NMR (CDCl$_3$, δ): 1.20–1.50 (6H, m), 1.50–1.70 (5H, m), 1.75–1.90 (3H, m), 2.84 (2H, dt, J=2.49 and 12.7 Hz), 3.28 (2H, d, J=6.02 Hz), 3.33 (3H, s), 3.39 (4H, q, J=6.57 Hz), 3.75–3.95 (2H, m), 4.32 (2H, q, J=7.10 Hz), 6.86 (2H, d, J=9.06 Hz), 7.90 (2H, d, J=9.00 Hz)

Preparation 20

A solution of methyl 6-chloronicotinate (25.4 g) and piperazine (38.3 g) in dimethylsulfoxide (125 ml) was heated at 100° C. for 2 hours then cooled and diluted with water, followed by extraction with ethyl acetate (4×). The combined organic layers were washed with water then dried over magnesium sulfate, filtered and evaporated to give a crude product that was triturated with isopropyl ether-hexane to yield methyl 6-(1-piperazinyl)nicotinate (25 g) as a light yellow powder.

NMR (CDCl$_3$, δ): 1.81 (1H, s), 2.94–3.01 (4H, m), 3.63–3.68 (4H, m), 3.87 (3H, s), 6.58 (1H, d, J=9 Hz), 8.01 (1H, dd, J=2.4 and 9 Hz), 8.79 (1H, d, J=2.4 Hz)

ESI MASS (m/z): 222 (M$^+$+1)

Preparation 21

A solution of tert-butyl-4-[4-(methoxycarbonyl)phenyl]-1-piperidinecarboxylate (3.95 g) in a mixture of methanol (80 ml), THF (40 ml) and 4N sodium hydroxide (30 ml) was stirred at 80° C. for 2 hours. The reaction mixture was concentrated in vacuo. To a residue was added water (100 ml) and adjusted to pH 3 with 1N hydrochloric acid. The solution was extracted twice with a mixture of ethyl acetate (100 ml) and THF (50 ml). The extracts was dried over magnesium sulfate and evaporated in vacuo to give 4-[1-(tert-butoxycarbonyl)-4-piperidyl]benzoic acid (3.64 g).

NMR (CDCl$_3$, δ): 1.49 (9H, s), 1.50–1.90 (4H, m), 2.60–2.95 (3H, m), 4.10–4.30 (2H, m), 7.30 (2H, d, J=8.33 Hz), 8.05 (2H, d, J=8.27 Hz)

ESI MASS (m/z)(Negative): 304.1 (M$^+$−1)

Preparation 22

To a solution of 4-[1-(tert-butoxycarbonyl)-4-piperidyl]benzoic acid (3.64 g) and 1-hydroxybenzotriazole (2.73 g) in dichloromethane (40 ml) was added 1-ethyl-3-(3'-dimethylaminopropyl)carbodiimide hydrochloride (WSCD-HCl) (4.56 g) and the mixture was stirred at ambient temperature for 3 hours. To the reaction mixture was added water (20 ml) and an organic layer was separated and washed with saturated aqueous sodium chloride, dried over magnesium sulfate and evaporated in vacuo. A solution of the resulting residue in THF (30 ml) was added to a solution of conc. ammonium hydroxide (10 ml) in THF (30 ml) at ambient temperature and the mixture was stirred at the same temperature for 1 hour. To a reaction mixture was added ethyl acetate (200 ml) and the organic layer was separated, washed with saturated aqueous sodium chloride, dried over magnesium sulfate and evaporated in vacuo. The precipitate was chromatographed on silica gel (200 ml) eluting with a mixture of dichloromethane and methanol (9:1 v/v). The fractions containing the desired compound were collected and evaporated under reduced pressure to give tert-butyl 4-[4-(aminocarbonyl)phenyl]-1-piperidinecarboxylate (3.34 g).

NMR (CDCl$_3$, δ): 1.48 (9H, s), 1.50–1.90 (4H, m), 2.60–2.95 (3H, m), 4.15–4.30 (2H, m), 5.75–6.25 (1H, broad m), 7.33 (2H, d, J=9.14 Hz), 7.76 (2H, d, J=8.28 Hz)

ESI MASS (m/z)(Positive): 327.3 (M$^+$+Na)

Preparation 23

To a solution of tert-butyl 4-[4-(aminocarbonyl)phenyl]-1-piperidinecarboxylate (3.34 g) in DMF (18 ml) was dropwise added phosphoryloxychloride (3.07 ml) keeping under 10° C. with stirring and the mixture was stirred at ambient temperature for 10 minutes. The reaction mixture was poured into a mixture of saturated aqueous sodium carbonate (60 ml) and ice-water (250 ml) with stirring and extracted twice with a mixture of ethyl acetate (200 ml) and hexane (80 ml). The extract was washed twice with saturated aqueous sodium chloride, dried over magnesium sulfate and evaporated in vacuo. The resulting residue was chromatographed on silica gel (300 ml) eluting with a mixture of n-hexane and ethyl acetate (4:1 v/v). The fractions containing the desired compound were collected and evaporated under reduced pressure to give tert-butyl 4-(4-cyanophenyl)-1-piperidine carboxylate (3.13 g).

IR (KBr): 2227.4, 1699.0, 1677.8, 1608.3, 1504.2, 1423.2, 1369.2 cm$^{-1}$

NMR (CDCl$_3$, δ): 1.48 (9H, s), 1.50–1.90 (4H, m), 2.60–2.95 (3H, m), 4.15–4.30 (2H, m), 7.30 (2H, d, J=8.26 Hz), 7.60 (2H, d, J=8.33 Hz)

APCI MASS (m/z)(Positive): 309.3 (M$^+$+Na)

Preparation 24

A mixture of cis-1-(4-methylcyclohexyl)piperazine (2.15 g), 4-fluorobenzonitrile (1.72 g) and potassium carbonate (4.89 g) in DMSO (25 ml) was stirred at 140° C. for 4 hours. The reaction mixture was poured into water (150 ml) and extracted twice with ethyl acetate (150 ml). The extracts were collected, washed with saturated aqueous sodium chloride, dried over magnesium sulfate and evaporated in vacuo. The resulting residue was chromatographed on silica gel (200 ml) eluting with a mixture of n-hexane and ethyl acetate (2:1 v/v). The fractions containing the desired compound were collected and evaporated under reduced pressure to give ethyl 4-[cis-4-(4-methylcyclohexyl)-1-piperazinyl]benzonitrile (2.81 g).

NMR (CDCl$_3$, δ): 0.93 (3H, d, J=6.87 Hz), 1.40–1.80 (9H, m), 2.15–2.30 (1H, m), 2.60–2.70 (4H, m), 3.25–3.35 (4H, m), 6.86 (2H, d, J=9.06 Hz), 7.48 (2H, d, J=9.04 Hz)

APCI MASS (m/z)(Positive): 284.3 (M$^+$+1)

Preparation 25

To a solution of 4-hydroxycyclohexylcyclohexane (25 g) in acetone (250 ml) was added dropwise with stirring 2.67N Jone's regend (77 ml) at 0° C. The mixture was then stirred for 1 hour at 0° C. The organic layer was collected and evaporated. The reaction mixture was added to a mixture of water and diethyl ether. The organic layer was washed with water, sodium hydrogen carbonate solution and brine. The organic layer was taken and dried over magnesium sulfate. The magnesium sulfate was filtered off, and the filtrate was concentrated under reduced pressure to give 4-cyclohexylcyclohexanone (19.57 g).

NMR (CDCl$_3$, δ): 0.8–1.4 (6H, m), 1.4–1.9 (8H, m), 1.9–2.15 (2H, m), 2.15–2.5 (4H, m)

MASS (m/z): 181 (M$^+$+1)

Preparation 26

A solution of oxalyl chloride (2.14 ml) in dichloromethane (80 ml) was cooled to −78° C. in nitrogen atmosphere, and a solution of dimethylsulfoxide (6 ml) in dichloromethane (6 ml) was added slowly and stirred for 10 minutes at −78° C. To the reaction mixture was added a solution of 4'-methoxy-1,1'-bi(cyclohexyl)-4-ol (2.6 g) in dichloromethane (26 ml) slowly to maintain the reaction temperature and stirred for 2.5 hours at −40° C. To the reaction mixture was added triethylamine (12.4 ml) slowly. Then the reaction mixture allowed to warm to room temperature. To the reaction mixture was added ammonium chloride solution and ethyl acetate. The organic layer was taken and dried over magnesium sulfate. The magnesium sulfate was filtered off, and the filtrate was concentrated under reduced pressure to give 4'-methoxy-1,1'-bi(cyclohexyl)-4-one (1.62 g).

NMR (CDCl$_3$, δ): 0.9–2.5 (18H, m), 3.0–3.2 (1H, m), 3.35 (3H, s)

MASS (m/z): 233 (M$^+$+1)

Preparation 27

A solution of 4-(4-hydroxyphenyl)cyclohexanone (5 g) and iodomethane (0.828 ml) in N,N-dimethylformamide (50 ml) was treated with potassium carbonate (4.36 g) at room temperature for 28 hours. Water was poured into the reaction mixture. And the resulting precipitate was collected by filtration and washed with isopropanol and diisopropyl ether to give 4-(4-methoxyphenyl)cyclohexanone (6.815 g).

NMR (CDCl$_3$, δ): 1.75–2.35 (4H, m), 2.4–2.6 (4H, m), 2.9–3.1 (1H, m), 3.80 (3H, s), 6.87 (2H, d, J=8.7 Hz), 7.17 (2H, d, J=8.7 Hz)

MASS (m/z): 227 (M$^+$+23)

Preparation 28

To a solution of 4,4-dimethyl-2-cyclohexen-1-one (10 g) in ethanol (100 ml) was added 10% palladium on carbon (1 g), and hydrogen gas at atmosphere pressure for 4 hours. To the reaction mixture was filtered. The filtrate was concentrated by evaporation under reduced pressure to give 4,4-dimethylcyclohexanone (10.03 g).

NMR (CDCl$_3$, δ): 0.92 (3H, s), 1.10 (3H, s), 1.25–1.4 (2H, m), 1.5–1.75 (4H, m), 2.3–2.45 (2H, m)

MASS (m/z): 149 (M$^+$+23)

Preparation 29

A mixture of cis-1-(4-methylcyclohexyl)piperazine (29.6 g), ethyl 4-fluorobenzoate (41.0 g) and potassium carbonate (67.3 g) in DMSO (300 ml) was stirred at 140° C. for 9 hours. The reaction mixture was poured into water (1.2 l) and extracted twice with ethyl acetate (400 ml). The extracts were collected, washed with saturated aqueous sodium chloride, dried over magnesium sulfate and evaporated in vacuo. The resulting residue was chromatographed on silica gel (1 l) eluting with a mixture of n-hexane and ethyl acetate (2:1 v/v). The fractions containing the desired compound were collected and evaporated under reduced pressure to give ethyl 4-[cis-4-(4-methylcyclohexyl)-1-piperazinyl] benzoate (37.64 g).

NMR (CDCl$_3$, δ): 0.93 (3H, d, J=6.87 Hz), 1.36 (3H, t, J=7.11 Hz), 1.40–1.80 (9H, m), 2.15–2.25 (1H, m), 2.60–2.70 (4H, m), 3.25–3.50 (4H, m), 4.32 (2H, q, J=7.11 Hz), 6.86 (2H, d, J=8.94 Hz), 7.92 (2H, d, J=8.87 Hz)

ESI MASS (m/z)(Positive): 683.4 (2M$^+$+Na), 331.3 (M$^+$+1)

The following compounds [Preparations 30 and 31] were obtained according to a similar manner to that of Preparation 29.

Preparation 30

Ethyl 4-[4-(5-methoxypentyloxy)-1-piperidyl]benzoate

NMR (CDCl$_3$, δ): 1.36 (3H, t, J=7.12 Hz), 1.37–1.75 (8H, m), 1.85–2.05 (2H, m), 3.00–3.18 (2H, m), 3.33 (3H, s), 3.34–3.60 (5H, m), 3.60–3.75 (2H, m), 4.32 (2H, q, J=7.11 Hz), 6.86 (2H, d, J=9.00 Hz), 7.90 (2H, d, J=8.93 Hz)

ESI MASS (m/z)(Positive): 372.3 (M$^+$+Na)

Preparation 31

Ethyl 4-[4-(6-methoxyhexyloxy)-1-piperidyl]benzoate

NMR (CDCl$_3$, δ): 1.3–1.8 (3H, m), 1.8–2.1 (12H, m), 3.0–3.2 (2H, m), 3.33 (3H, s), 3.3–3.5 (5H, m), 3.6–3.8 (2H, m), 4.32 (2H, q, J=7.1 Hz), 6.86 (2H, d, J=9.1 Hz), 7.8–8.0 (2H, m)

ESI MASS (m/z)(Positive): 364.33 (M$^+$+Na)

Preparation 32

To a suspension of 4-[4-(4-methylcyclohexyl)-1-piperazinyl]benzohydrazide (12.48 g) and pyridine (11.7 ml) in THF (374 ml) was added 4-iodobenzoyl chloride (11 g) under ice-cooling and the mixture was stirred at the same temperature for 1 hour. The reaction mixture was added water (3700 ml). The resulting precipitate was collected by filtration and dried to give N'-(4-iodobenzoyl)-4-[4-(4-methylcyclohexyl)-1-piperazinyl]benzohydrazide (22.45 g).

NMR (DMSO-d$_6$, δ): 0.88–0.92 (3H, m), 1.42–3.37 (18H, m), 6.99 (2H, d, J=8.9 Hz), 7.69 (2H, d, J=8.4 Hz), 7.80 (2H, d, J=8.80 Hz), 7.92 (2H, d, J=8.44 Hz), 10.21 (1H, s), 10.45 (1H, s)

MASS (m/z): 547 (M$^+$+1)

The following compounds [Preparations 33 to 46] were obtained according to a similar manner to that of Preparation 32.

Preparation 33

Methyl 4-[2-[4-(4-methylenecyclohexyl)-1-piperazinylbenzoyl]hydrazinocarbonyl]benzoate IR (KBr): 3458, 3253, 2943, 2837, 1722, 1678, 1645, 1608, 1510 cm$^{-1}$ NMR (DSMO-d$_6$, δ): 1.10–1.50 (2H, m), 1.60–2.10 (4H, m), 2.15–2.40 (2H, m), 2.50–2.70 (4H, m), 3.10–3.40 (4H, m), 3.80–4.00 (2H, m), 4.61 (1H, br s), 6.98 (2H, d, J=8.9 Hz), 7.81 (2H, d, J=8.8 Hz), 7.95 (4H, q, J=8.6 Hz), 10.26 (1H, s), 10.57 (1H, s)

MASS (m/z): 479 (M$^+$+1), 478 (M), 477 (M$^+$−1)

Preparation 34

Methyl 4-[2-[4-[4-(4-phenylcyclohexyl)-1-piperazinyl]benzoyl]hydrazinocarbonyl]benzoate APCI MASS (m/z): 541.4 (M$^+$+1)

Preparation 35

Methyl 4-[5-[4-(4-phenylcyclohexyl)-1-piperazinyl]phenyl]-1,3,4-thiadiazol-2-yl]benzoate APCI MASS (m/z): 539.4 (M$^+$+1)

Preparation 36

Methyl 4-[2-[4-[4-(cyclohexylmethyl)-1-piperazinyl]benzoyl]hydrazinocarbonyl]benzoate NMR (DMSO-d$_6$, δ): 0.7–1.0 (2H, m), 1.1–1.8 (9H, m), 2.12 (2H, d, J=7.1 Hz), 2.4–2.5 (4H, m), 3.2–3.4 (4H, m), 3.90 (3H, s), 6.98 (2H, d, J=9 Hz), 7.81 (2H, d, J=9 Hz), 8.02 (2H, d, J=8.7 Hz), 8.09 (2H, d, J=8.7 Hz), 10.26 (1H, s), 10.58 (1H, s)

APCI MASS (m/z)(Positive): 479.4 (M$^+$+1)

Preparation 37

4-[2-[4-[4-[4-(7-Methoxyheptyloxy) cyclohexyl]-1-piperazinyl]benzoyl]hydrazinocarbonyl]benzoate IR (Neat): 2933, 2858, 1724, 1682, 1645, 1608, 1279, 1242, 1113 cm$^{-1}$ NMR (DSMO-d$_6$, δ): 1.0–2.1 (18H, m), 2.2–2.4 (1H, m), 2.52 (4H, m), 3.0–3.5 (9H, m), 3.20 (3H, s), 3.90 (3H, s), 6.9–7.1 (2H, m), 7.7–7.9 (2H, m), 8.0–8.2 (4H, m), 10.26 (1H, s), 10.58 (1H, s)

ESI MASS (m/z)(Positive): 609.5 (M$^+$+1)

Preparation 38

4-[2-[4-[4-[4-(8-Methoxyoctyloxy) cyclohexyl]-1-piperazinyl]benzoyl]hydrazinocarbonyl]benzoate IR (Neat): 2931, 2856, 1724, 1680, 1647, 1608, 1520, 1281, 1240, 1113 cm$^{-1}$ NMR (DSMO-d$_6$, δ): 1.0–2.1 (20H, m), 2.2–2.4 (1H, m), 2.5–2.7 (4H, m), 3.0–3.6 (9H, m), 3.21 (3H, s), 3.90 (3H, s), 6.9–7.1 (2H, m), 7.7–7.9 (2H, m), 8.0–8.2 (4H, m), 10.26 (1H, s), 10.58 (1H, s)

ESI MASS (m/z)(Positive): 623.5 (M$^+$+1)

Preparation 39

Methyl 4-[2-[4-[4-(5-methoxypentyloxy)-1-piperidyl]benzoyl]hydrazinocarbonyl]benzoate NMR (DMSO-d$_6$, δ): 1.20–1.60 (8H, m), 1.80–1.95 (2H, m), 2.95–3.20 (2H, m), 3.21 (3H, s), 3.25–3.80 (7H, m), 3.90 (3H, s), 6.99 (2H, d, J=8.92 Hz), 7.80 (2H, d, J=8.76 Hz), 8.03 (2H, d, J=8.56 Hz), 8.09 (2H, d, J=8.54 Hz), 10.24 (1H, s), 10.57 (1H, s)

ESI MASS (m/z)(Positive): 520.3 (M$^+$+Na)

Preparation 40

Methyl 4-[2-[4-[4-(6-methoxyhexyloxy)-1-piperidyl]benzoyl]hydrazinocarbonyl]benzoate NMR (CDCl$_3$, δ): 1.3–2.1 (12H, m), 3.0–3.2 (2H, m), 3.33 (3H, s), 3.3–3.5 (5H, m), 3.5–3.7 (2H, m), 3.94 (3H, s), 6.83 (2H, d, J=9.0 Hz), 7.74 (2H, d, J=8.9 Hz), 7.90 (2H, d, J=8.5 Hz), 8.04 (2H, d, J=8.5 Hz), 9.52 (1H, d, J=5.0 Hz), 10.11 (1H, d, J=5.2 Hz)

(+) APCI MASS (m/z)(Positive): 512.40 (M$^+$+1)

Preparation 41

Methyl 4-[2-[4-[4-(4-methoxybutoxymethyl)-1-piperidyl]benzoyl]hydrazinocarbonyl]benzoate NMR (CDCl$_3$, δ): 1.2–1.9 (9H, m), 2.7–2.9 (2H, m), 3.2–3.5 (6H, m), 3.33 (3H, s), 3.8–4.0 (2H, m), 3.94 (3H, s), 6.84 (2H, d, J=9.0 Hz), 7.74 (2H, d, J=8.9 Hz), 7.91 (2H, d, J=8.4 Hz), 8.06 (2H, d, J=8.5 Hz), 9.40 (1H, d, J=5.0 Hz), 9.96 (1H, d, J=5.6 Hz)

(+) APCI MASS (m/z)(Positive): 497.93 (M$^+$+1)

Preparation 42

Methyl 4-[2-[4-[4-(5-methoxypentyloxymethyl)-1-piperidyl]benzoyl]hydrazinocarbonyl]benzoate NMR (CDCl$_3$, δ): 1.2–1.9 (11H, m), 2.7–2.9 (2H, m), 3.2–3.5 (6H, m), 3.33 (3H, s), 3.8–4.0 (2H, m), 3.94 (3H, s), 6.83 (2H, d, J=9.0 Hz), 7.74 (2H, d, J=8.8 Hz), 7.90 (2H, d, J=8.4 Hz), 8.05 (2H, d, J=8.4 Hz), 9.47 (1H, d, J=4.9 Hz), 10.06 (1H, d, J=5.3 Hz)

ESI MASS (m/z)(Positive): 534.4 (M$^+$+Na)

Preparation 43

Methyl 4-[2-[6-[4-(4-methylcyclohexyl)-1-piperazinyl-3-pyridyl]carbonyl]hydrazinocarbonyl]benzoate NMR (CDCl$_3$, δ): 0.94 (3H, d, J=6.9 Hz), 1.4–2.0 (9H, m), 2.1–2.3 (1H, m), 2.6–2.7 (4H, m), 3.6–3.8 (4H, m), 3.96 (3H, s), 6.62 (1H, d, J=9.1 Hz), 7.8–8.0 (3H, m), 8.13 (2H, d, J=8.4 Hz), 8.69 (1H, d, J=2.3 Hz)

(+) APCI MASS (m/z)(Positive): 480.27 (M$^+$+1)

Preparation 44

Methyl 4-[2-[6-[4-(4-methylcyclohexyl)-1-piperazinyl-3-pyridyl]carbonyl]hydrazinocarbonyl]benzoate NMR (CDCl$_3$, δ): 0.8–2.0 (12H, m), 2.2–2.4 (1H, m), 2.6–2.8 (4H, m), 3.6–3.8 (4H, m), 3.96 (3H, s), 6.62 (1H, d, J=9.2 Hz), 7.8–8.0 (3H, m), 8.14 (2H, d, J=8.5 Hz), 8.69 (1H, d, J=2.3 Hz)

(+) APCI MASS (m/z)(Positive): 480.20 (M$^+$+1)

Preparation 45

Methyl 4-[2-[6-[4-(4-ethylcyclohexyl)-1-piperazinyl-3-pyridyl]carbonyl]hydrazinocarbonyl]benzoate NMR (CDCl$_3$, δ): 0.8–1.0 (5H, m), 1.2–2.0 (9H, m), 2.1–2.3 (1H, m), 2.5–2.7 (4H, m), 3.6–3.8 (4H, m), 3.96 (3H, s), 6.62 (1H, d, J=9.1 Hz), 7.8–8.0 (3H, m), 8.13 (2H, d, J=8.3 Hz), 8.6–8.7 (1H, m)

(+) APCI MASS (m/z)(Positive): 494.20 (M$^+$+1)

Preparation 46

Methyl 4-[2-[6-[4-(4-ethylcyclohexyl)-1-piperazinyl-3-pyridyl]carbonyl]hydrazinocarbonyl]benzoate NMR (CDCl$_3$, δ): 0.8–2.0 (14H, m), 2.2–2.4 (1H, m), 2.6–2.8 (4H, m), 3.6–3.8 (4H, m), 3.96 (3H, s), 6.63 (1H, d, J=9.2 Hz), 7.8–8.0 (3H, m), 8.0–8.2 (2H, m), 8.6–8.7 (1H, m)

(+) APCI MASS (m/z)(Positive): 494.20 (M$^+$+1)

Preparation 47

A suspension of N'-(4-iodobenzoyl)-4-[4-(4-methylcyclohexyl)-1-piperazinyl]benzohydrazide (22.95 g) in pyridine (459 ml) was treated with phosphorus pentasulfide (11.2 g) and stirred at 120° C. for 2.5 hours. The reaction mixture was added a solution of sodium hydroxide (510 g) in water (9200 ml). The resulting precipitate was collected, washed with acetone. The powder was recrystallized from THF (800 ml) and dried to give 1-[4-[5-(4-iodophenyl)-1,3,4-thiadiazol-2-yl]phenyl]-4-(4-methylcyclohexyl)piperazine (16.42 g).

NMR (CDCl$_3$, δ): 0.93–0.96 (3H, m), 1.47–3.36 (18H, m), 6.95 (2H, d, J=9.0 Hz), 7.68–7.90 (6H, m)

MASS (m/z): 545 (M$^+$+1)

The following compounds [Preparations 48 to 55] were obtained according to a similar manner to that of Preparation 47.

Preparation 48

Methyl 4-[5-[4-[4-(cyclohexylmethyl)-1-piperazinyl]phenyl]-1,3,4-thiadiazol-2-yl]benzoate NMR (CDCl$_3$, δ): 0.8–1.05 (2H, m), 1.1–2.0 (9H, m), 2.22 (2H, d, J=7 Hz), 2.58 (4H, br s), 3.33–3.38 (4H, m), 3.96 (3H, s), 6.96 (2H, d, J=9 Hz), 7.89 (2H, d, J=9 Hz), 8.06 (2H, d, J=8.6 Hz), 8.15 (2H, d, J=8.6 Hz)

APCI MASS (m/z)(Positive): 477.47 (M$^+$+1)

Preparation 49

Methyl 4-[5-[4-[4-(6-methoxyhexyloxy)-1-piperidyl]phenyl]-1,3,4-thiadiazol-2-yl]benzoate NMR (CDCl$_3$, δ): 1.3–2.1 (12H, m), 3.0–3.2 (2H, m), 3.33 (3H, s), 3.3–3.6 (5H, m), 3.6–3.8 (2H, m), 3.96 (3H, s), 6.96 (2H, d, J=8.9 Hz), 7.88 (2H, d, J=8.6 Hz), 8.06 (2H, d, J=8.6 Hz), 8.15 (2H, d, J=8.6 Hz)

(+) APCI MASS (m/z)(Positive): 510.47 (M$^+$+1)

Preparation 50

Methyl 4-[5-[4-[4-(4-methoxybutoxymethyl)-1-piperidyl]phenyl]-1,3,4-thiadiazol-2-yl]benzoate NMR (CDCl$_3$, δ): 1.2–2.0 (9H, m), 2.8–3.0 (2H, m), 3.3–3.5 (6H, m), 3.34 (3H, s), 3.8–4.0 (2H, m), 3.96 (3H, s), 6.95 (2H, d, J=9.0 Hz), 7.88 (2H, d, J=8.9 Hz), 8.0–8.2 (4H, m)

(+) APCI MASS (m/z)(Positive): 496.27 (M$^+$+1)

Preparation 51

Methyl 4-[5-[4-[4-(5-methoxypentyloxymethyl)-1-piperidyl]phenyl]-1,3,4-thiadiazol-2-yl]benzoate NMR (CDCl$_3$, δ): 1.2–2.0 (11H, m), 2.7–2.9 (2H, m), 3.2–3.5 (6H, m), 3.34 (3H, s), 3.8–4.0 (2H, m), 3.96 (3H, s), 6.95 (2H, d, J=9.0 Hz), 7.88 (2H, d, J=8.9 Hz), 8.0–8.2 (4H, m)

(+) APCI MASS (m/z)(Positive): 510.40 (M$^+$+1)

Preparation 52

Methyl 4-[5-[6-[4-(4-methylcyclohexyl)-1-piperazinyl]-3-pyridyl]-1,3,4-thiadiazol-2-yl]benzoate NMR (CDCl$_3$, δ): 0.95 (3H, d, J=6.9 Hz), 1.4–1.8 (9H, m), 2.1–2.3 (1H, m), 2.6–2.8 (4H, m), 3.6–3.8 (4H, m), 3.96 (3H, s), 6.72 (1H, d, J=9.1 Hz), 8.0–8.2 (5H, m), 8.71 (1H, d, J=2.4 Hz)

(+) APCI MASS (m/z)(Positive): 478.13 (M$^+$+1)

Preparation 53

Methyl 4-[5-[6-[4-(4-methylcyclohexyl)-1-piperazinyl]-3-pyridyl]-1,3,4-thiadiazol-2-yl]benzoate NMR (CDCl$_3$, δ): 0.8–2.0 (12H, m), 2.2–2.4 (1H, m), 2.6–2.8 (4H, m), 3.6–3.8 (4H, m), 3.96 (3H, s), 6.72 (1H, d, J=9.0 Hz), 8.0–8.2 (5H, m), 8.71 (1H, d, J=2.3 Hz)

ESI MASS (m/z)(Positive): 478.3 (M$^+$+1)

Preparation 54

Methyl 4-[5-[6-[4-(4-ethylcyclohexyl)-1-piperazinyl]-3-pyridyl]-1,3,4-thiadiazol-2-yl]benzoate NMR (CDCl$_3$, δ): 0.8–1.0 (5H, m), 1.2–1.9 (9H, m), 2.2–2.4 (1H, m), 2.6–2.8 (4H, m), 3.6–3.8 (4H, m), 3.96 (3H, s), 6.72 (1H, d, J=9.1 Hz), 8.0–8.2 (5H, m), 8.71 (1H, d, J=2.3 Hz)

(+) APCI MASS (m/z)(Positive): 492.13 (M$^+$+1)

Preparation 55

Methyl 4-[5-[6-[4-(4-ethylcyclohexyl)-1-piperazinyl]-3-pyridyl]-1,3,4-thiadiazol-2-yl]benzoate NMR (CDCl$_3$, δ): 0.8–2.0 (14H, m), 2.2–2.4 (1H, m), 2.6–2.8 (4H, m), 3.6–3.8 (4H, m), 3.96 (3H, s), 6.72 (1H, d, J=8.9 Hz), 8.0–8.2 (5H, m), 8.71 (1H, d, J=2.4 Hz)

(+) APCI MASS (m/z)(Positive): 492.13 (M$^+$+1)

Preparation 56

To a mixture of ethyl 4-(piperazinyl)benzoate (2.00 g) and 4-methylenecyclohexan-1-one (0.98 g) in a mixture of methanol (40 ml) and acetic acid (1.47 ml) was portionwise added sodium cyanoborohydride (644 mg) with stirring under ice-cooling and the mixture was stirred at ambient temperature overnight. To the reaction mixture was added water (200 ml) and the mixture was adjusted to pH 8–9 with saturated aqueous sodium hydrogen carbonate. The resulting precipitates were collected and chromatographed on silica gel (200 ml) eluting with a mixture of n-hexane and ethyl acetate (2:1 v/v). The fractions containing the desired compound were collected and evaporated under reduced pressure to give ethyl 4-[4-(4-methylenecyclohexyl)-1-piperazinyl]benzoate (1.39 g).

NMR (CDCl$_3$, δ): 1.36 (3H, t, J=7.12 Hz), 1.39–1.50 (2H, m), 1.85–2.15 (4H, m), 2.30–2.60 (3H, m), 2.65–2.75 (4H, m), 3.25–3.35 (4H, m), 4.32 (2H, q, J=7.12 Hz), 4.63 (2H, s), 6.85 (2H, d, J=9.08 Hz), 7.92 (2H, d, J=9.04 Hz)

ESI MASS (m/z) (Positive): 329.4 (M$^+$+1)

The following compounds [Preparations 57 to 63] were obtained according to a similar manner to that of Preparation 56.

Preparation 57

Ethyl 4-[4-(4-phenylcyclohexyl)-1-piperazinyl]benzoate

NMR (CDCl$_3$, δ): 1.36 (3H, t, J=7.1 Hz), 1.40–2.12 (8H, m), 2.31 (1H, br), 2.62–2.67 (4H, m), 3.32–3.37 (4H, m), 3.6–3.8 (1H, m), 4.33 (2H, q, J=7.1 Hz), 6.87 (2H, d, J=9 Hz), 7.1–7.35 (5H, m), 7.92 (2H, d, J=9 Hz)

APCI MASS (m/z)(Positive): 393.33 (M$^+$+1)

Preparation 58

Ethyl 4-[4-(cyclohexylmethyl)-1-piperazinyl]benzoate

NMR (CDCl$_3$, δ): 0.75–1.00 (2H, m), 1.36 (3H, t, J=7.1 Hz), 1.10–1.82 (9H, m), 2.17 (2H, d, J=7.1 Hz), 2.50–2.55 (4H, m), 3.29–3.34 (4H, m), 4.32 (2H, q, J=7.1 Hz), 6.85 (2H, d, J=9 Hz), 7.92 (2H, d, J=9 Hz)

APCI MASS (m/z)(Positive): 331.4 (M$^+$+1)

Preparation 59

Ethyl 4-[4-[4-(7-methoxyheptyloxy)cyclohexyl]-1-piperazinyl]benzoate

IR (Neat): 1707, 1606, 1518, 1452, 1389, 1367, 1282, 1236, 1188, 1119, 1107 cm$^{-1}$ NMR (CDCl$_3$, δ): 1.2–2.2 (21H, m), 2.2–2.4 (1H, m), 2.7–2.8 (4H, m), 3.33 (3H, s), 3.1–3.8 (9H, m), 4.32 (2H, q, J=7.1 Hz), 6.86 (2H, d, J=9.0 Hz), 7.92 (2H, d, J=9.0 Hz)

(+) AOCU MASS (m/z)(Positive): 461.53 (M$^+$+1)

Preparation 60

Ethyl 4-[4-[4-(8-methoxyoctyloxy)cyclohexyl]-1-piperazinyl]benzoate

IR (Neat): 2933, 2856, 1705, 1608, 1516, 1454, 1282, 1238, 1111 cm$^{-1}$

NMR (CDCl$_3$, δ): 1.2–2.2 (23H, m), 2.2–2.4 (1H, m), 2.6–2.8 (4H, m), 3.1–3.5 (9H, m), 3.33 (3H, s), 4.32 (2H, q, J=7.1 Hz), 6.86 (2H, d, J=9.0 Hz), 7.92 (2H, d, J=9.0 Hz)

ESI MASS (m/z)(Positive): 475.5 (M$^+$+1)

Preparation 61

Methyl 6-[4-(cis-4-methylcyclohexyl)-1-piperazinyl]nicotinate

NMR (CDCl$_3$, δ): 0.94 (3H, d, J=6.9 Hz), 1.40–1.82 (9H, m), 2.16–2.26 (1H, m), 2.59–2.65 (4H, m), 3.65–3.71 (4H, m), 3.86 (3H, s), 6.58 (1H, d, J=9 Hz), 8.00 (1H, dd, J=2.4 and 9 Hz), 8.79 (1H, d, J=2.4 Hz)

API-ES MASS (m/z)(Positive): 318.3 (M$^+$+1)

Methyl 6-[4-(trans-4-methylcyclohexyl)-1-piperazinyl]nicotinate

NMR (CDCl$_3$, δ): 0.88 (3H, d, J=6.4 Hz), 0.90–1.40 (4H, m), 1.70–1.95 (5H, m), 2.20–2.35 (1H, m), 2.63–2.68 (4H, m), 3.65–3.70 (4H, m), 3.86 (3H, s), 6.57 (1H, d, J=9 Hz), 7.99 (1H, dd, J=2.4 and 9 Hz), 8.78 (1H, d, J=2.4 Hz)

API-ES MASS (m/z) (Positive): 318.3 (M$^+$+1)

Preparation 62

Methyl 6-[4-(cis-4-ethylcyclohexyl)-1-piperazinyl]nicotinate

NMR (CDCl$_3$, δ): 0.87 (3H, t, J=7.3 Hz), 1.25–1.67 (11H, m), 2.20–2.30 (1H, m), 2.59–2.64 (4H, m), 3.65–3.70 (4H, m), 3.86 (3H, s), 6.58 (1H, d, J=9.1 Hz), 8.00 (1H, dd, J=2.4 and 9.1 Hz), 8.79 (1H, d, J=2.4 Hz)

API-ES MASS (m/z)(Positive): 332.4 (M$^+$+1)

Methyl 6-[4-(trans-4-ethylcyclohexyl)-1-piperazinyl]nicotinate

NMR (CDCl$_3$, δ): 0.87 (3H, t, J=7.5 Hz), 0.91–1.40 (5H, m), 1.6–2.0 (6H, m), 2.64–2.69 (4H, m), 3.66–3.71 (4H, m), 3.86 (3H, s), 6.57 (1H, d, J=9 Hz), 8.00 (1H, dd, J=2.3 and 9 Hz), 8.79 (1H, d, J=23 Hz)

API-ES MASS (m/z)(Positive): 332.4

Preparation 63

4-(1-Cyclohexyl-4-piperidyl)benzonitrile

IR (KBr): 2927, 2852, 2222, 1605, 1504, 1450 cm$^{-1}$

NMR (DMSO-d$_6$, δ): 1.0–2.0 (14H, m), 2.2–2.7 (4H, m), 2.8–3.1 (2H, m), 7.45 (2H, d, J=8.3 Hz), 7.75 (2H, d, J=8.3 Hz)

(+) APCI MASS (m/z): 269.33 (M$^+$+1)

Preparation 64

A mixture of 7-bromo-1-heptanol (25 g) and sodiummethoxide, 28% solution in methanol (37 ml) in methanol (250 ml) was stirred for 7 hours at 90° C. After being cooled to room temperature, the solvent was evaporated in vacuo. The residue was purified by column chromatography on silica gel eluting with a mixture of dichloromethane and methanol (100:1→25:1). The eluted fractions containing the desired product were collected and evaporated in vacuo to give 7-methoxy-1-heptanol (18.2 g).

NMR (CDCl$_3$, δ): 1.2–1.7 (10H, m), 3.33 (3H, s), 3.3–3.4 (2H, m), 3.5–3.7 (2H, m)

The following compound was obtained according to a similar manner to that of Preparation 64.

Preparation 65

8-Methoxy-1-octanol

NMR (CDCl$_3$, δ): 1.2–1.7 (12H, m), 3.33 (3H, s), 3.3–3.4 (2H, m), 3.5–3.7 (2H, m)

Preparation 66

To a mixture of 7-methoxy-1-heptanol (18.1 g) and p-toluenesulfonyl chloride (28.4 g) in dichloromethane (180 ml) was added triethylamine. After stirring for 27.5 hours at room temperature, the solvent was evaporated in vacuo. Then the residue was poured into a mixture of ethyl acetate and water. The organic layer was successively washed with water and brine and dried over magnesium sulfate. The solvent was evaporated in vacuo and the residue was purified by column chromatography on silica gel eluting with a mixture of hexane and ethyl acetate (8:1→5:1). The eluted fractions containing the desired product were collected and evaporated in vacuo to give 7-methoxyheptyl 4-methylbenzenesulfonate (28.5 g).

NMR (CDCl$_3$, δ): 1.1–1.7 (10H, m), 2.45 (3H, s), 3.3–3.4 (5H, m), 4.02 (2H, t, J=6.5 Hz), 7.3–7.4 (2H, m), 7.7–7.8 (2H, m)

ESI MASS (m/z)(Positive): 323.3 (M$^+$+Na)

The following compound was obtained according to a similar manner to that of Preparation 66.

Preparation 67

8-Methoxyoctyl 4-methylbenzenesulfonate

NMR (CDCl$_3$, δ): 1.1–1.7 (12H, m), 2.45 (3H, s), 3.3–3.4 (5H, m), 4.01 (2H, d, J=6.5 Hz), 7.3–7.4.(2H, m), 7.7–7.9 (2H, m)

ESI MASS (m/z)(Positive): 337.2 (M$^+$+Na)

Preparation 68

A mixture of 8-(7-methoxyheptyloxy)-1,4-dioxaspiro[4.5]decane (9.8 g) and 3N aqueous hydrochloric acid (34 ml) in tetrahydrofuran (68 ml) was stirred for 25.5 hours at room temperature. The solvent was evaporated in vacuo and the residue was poured into a mixture of ethyl acetate and water. Then the solution was adjusted to pH 9 with potassium carbonate. The organic layer was successively washed with water and brine and dried over magnesium sulfate. The solvent was evaporated in vacuo to give 4-(7-methoxyheptyloxy)cyclohexanone (8.34 g).

NMR (CDCl₃, δ): 1.2–2.4 (16H, m), 2.5–2.7 (2H, m), 3.33 (3H, s), 3.3–3.5 (4H, m), 3.6–3.8 (1H, m)

ESI MASS (m/z)(Positive): 265.4 (M⁺+Na)

The following compound was obtained according to a similar manner to that of Preparation 68.

Preparation 69

4-(8-Methoxyoctyloxy)cyclohexanone

NMR (CDCl₃, δ): 1.2–2.4 (18H, m), 2.5–2.7 (2H, m), 3.33 (3H, s), 3.3–3.5 (4H, m), 3.6–3.8 (1H, m)

ESI MASS (m/z)(Positive): 279.3 (M⁺+Na)

Preparation 70

To a solution of tert-butyl 4-[4'-(methoxycarbonyl)-1,1'-biphenyl-4-yl]-1-piperazinecarboxylate (4.5 g) and anisole (6.17 ml) in dichloromethane (45 ml) was added dropwise with stirring trifluoroacetic acid (22.5 ml) at 0° C. The mixture was then stirred for 2 hours at room temperature. To the reaction mixture was added water. The resulting precipitate was collected by filtration and washed with isopropanol and diisopropyl ether to give methyl 4'-(1-piperazinyl)-1,1'-biphenyl-4-carboxylate trifluoroacetate (4.13 g).

NMR (CDCl₃, δ): 3.15–3.55 (8H, m), 3.87 (3H, s), 7.11 (2H, d, J=8.8 Hz), 7.69 (2H, d, J=8.7 Hz), 7.79 (2H, d, J=8.4 Hz), 8.00 (2H, d, J=8.4 Hz), 8.84 (2H, br s)

MASS (m/z)(Positive): 297 (M⁺+1)

The following compounds [Preparation 71 to 73] were obtained according to a similar manner to that of Preparation 70.

Preparation 71

4-(5-Methoxypentyloxy)-1-piperidine trifluoroacetate

This compound was immediately used as the starting compound for the next step.

Preparation 72

4-(6-Methoxyhexyloxy)piperidine

This compound was immediately used as the starting compound for the next step.

Preparation 73

4-(4-Piperidyl)benzonitrile

IR (KBr): 2937, 2227, 1684, 1608, 1541, 1504, 1450, 1419, 1201, 1134, 1014, 835 cm⁻¹

NMR (DMSO-d₆, δ): 1.4–1.8 (4H, m), 2.5–2.8 (3H, m), 3.0–3.1 (2H, m), 7.4–7.5 (2H, m), 7.7–7.8 (2H, m)

(+) APCI MASS (m/z): 187.27 (M⁺+1)

Preparation 74

To an ice cooled solution of 1-methoxy-bicyclohexyl-4-one (0.9 g) and methyl 4'-(1-piperazinyl)-1,1'-biphenyl-4-carboxylate trifluoroacetate (2.11 g) in a mixed solvent of methanol (18 ml), tetrahydrofuran (14 ml) and acetic acid (0.735 ml) was added sodium cyanoborohydride (296 mg) in a stream of nitrogen. The mixture was stirred at room temperature for 5 hours. The reaction mixture was quenched with saturated aqueous sodium hydrogen carbonate solution. The resulting precipitate collected by filtration, washed with water, isopropyl alcohol and diisopropyl ether, then dried to give methyl 4'-[4-[cis-1-methoxy-1,1'-bi (cyclohexyl)-4-yl]-1-piperazinyl]-1,1-biphenyl-4-carboxylate and 4'-[4-[trans-1-methoxy-1,1-bi(cyclohexyl)-4-yl]-1-piperazinyl]-1,1'-biphenyl-4-carboxylate (444 mg).

4'-[Cis-1-methoxy-1,1'-bi(cyclohexyl)-4-yl]-1-piperazinyl]-1,1'-biphenyl-4-carboxylate NMR (CDCl₃, δ): 0.8–1.9 (19H, m), 2.15–2.4 (1H, m), 2.7–2.9 (4H, m), 3.11 (3H, s), 3.2–3.4 (4H, m), 3.93 (3H, s), 6.99 (2H, d, J=8.8 Hz), 7.5–7.7 (4H, m), 8.06 (2H, d, J=8.5 Hz)

MASS (m/z): 491 (M⁺+1)

4'-[4-[Trans-1-methoxy-1,1'-bi(cyclohexyl)-4-yl]-1-piperazinyl]-1,1'-biphenyl-4-carboxylate NMR (CDCl₃, δ): 0.8–2.3 (20H, m), 2.6–2.75 (4H, m), 3.15 (3H, s), 3.2–3.4 (4H, m), 3.93 (3H, s), 7.00 (2H, d, J=8.8 Hz), 7.5–7.7 (4H, m), 8.06 (2H, d, J=8.4 Hz)

MASS (m/z): 491 (M⁺+1)

The following compounds [Preparation 75 to 81] were obtained according to a similar manner to that of Preparation 74.

Preparation 75

Benzyl 4-(trans-4-cyclohexylcyclohexyl)-1-piperazinecarboxylate

IR (KBr): 1682, 1466, 1429, 1240 cm⁻¹

NMR (CDCl₃, δ): 0.75–1.35 (12H, m), 1.5–1.95 (6H, m), 2.1–2.3 (1H, m), 2.4–2.6 (4H, m), 3.50 (4H, t, J=5.0 Hz), 5.13 (2H, s), 7.25–7.4 (5H, m)

ESI MASS (m/z) (Positive): 385 (M⁺+1)

Preparation 76

Benzyl 4-(trans-4-tert-butylcyclohexyl)-1-piperazinecarboxylate

IR (KBr): 1684, 1468, 1525, 1242 cm⁻¹

NMR (CDCl₃, δ): 0.83 (9H, s), 0.9–1.58 (5H, m), 1.7–2.35 (5H, m), 2.45–2.6 (4H, m), 3.51 (4H, t, J=5.1 Hz), 5.13 (2H, s), 7.35 (5H, s)

MASS (m/z): 359 (M⁺+1)

Preparation 77

Methyl 4'-[4-(trans-4-ethylcyclohexyl)-1-piperazinyl]-1,1'-biphenyl-4-carboxylate NMR (CDCl₃, δ): 0.8–2.05 (14H, m), 2.2–2.4 (1H, m), 2.65–2.8 (4H, m), 3.2–3.35 (4H, m), 3.92 (3H, s), 6.99 (2H, d, J=8.8 Hz), 7.55 (2H, d, J=8.8 Hz), 7.62 (2H, d, J=8.4 Hz), 8.06 (2H, d, J=8.4 Hz)

MASS (m/z): 407 (M⁺+1)

Methyl 4'-[4-(cis-4-ethylcyclohexyl)-1-piperazinyl]-1,1'-biphenyl-4-carboxylate

NMR (CDCl₃, δ): 0.88 (3H, t, J=7.2 Hz), 1.2–1.7 (11H, m), 2.2–2.4 (1H, m), 2.65–2.8 (4H, m), 3.2–3.35 (4H, m), 3.93 (3H, s), 7.00 (2H, d, J=8.8 Hz), 7.56 (2H, d, J=8.8 Hz), 7.62 (2H, d, J=8.4 Hz), 8.06 (2H, d, J=8.4 Hz)

MASS (m/z): 407 (M⁺+1)

Preparation 78

Methyl 4'-[4-[trans-4-(trans-4'-methoxycyclohexyl-1'-yl]cyclohexyl-1-yl]-1-piperazinyl]-1,1'-biphenyl-4-carboxylate NMR (CDCl₃, δ): 0.8–1.4 (10H, m), 1.65–2.4 (9H, m), 2.65–2.8 (4H, m), 2.95–3.15 (1H, m), 3.2–3.35 (4H, m), 3.35 (3H, s), 3.93 (3H, s), 6.99 (2H, d, J=-8.8 Hz), 7.55 (2H, d, J=8.8 Hz), 7.62 (2H, d, J=8.4 Hz), 8.06 (2H, d, J=8.44 Hz)

MASS (m/z): 491 (M⁺+1)

Methyl 4'-[4-[cis-4-(trans-4'-methoxycyclohexyl-1'-yl)cyclohexyl-1-yl]-1-piperazinyl]-1,1'-biphenyl-4-carboxylate NMR (CDCl₃, δ): 0.8–2.3 (19H, m), 2.6–2.75 (4H, m), 2.95–3.2 (1H, m), 3.2–3.35 (4H, m), 3.35 (3H, s), 3.93 (3H, s), 7.00 (2H, d, J=8.8 Hz), 7.56 (2H, d, J=8.8 Hz), 7.62 (2H, d, J=8.4 Hz), 8.06 (2H, d, J=8.4 Hz)

MASS (m/z): 491 (M⁺+1)

Preparation 79

Methyl 4'-[4-(trans-4-methoxyphenyl)cyclohexyl]-1-piperazinyl]-1,1'-biphenyl-4-carboxylate NMR (CDCl₃, δ): 1.4–1.7 (4H, m), 1.9–2.15 (4H, m), 2.3–2.6 (2H, m), 2.75–2.85 (4H, m), 3.2–3.4 (4H, m), 3.79 (3H, s), 3.93 (3H, s), 6.84 (2H, d, J=8.6 Hz), 7.01 (2H, d, J=8.8 Hz), 7.14 (2H, d, J=8.6 Hz), 7.56 (2H, d, J=8.8 Hz), 7.63 (2H, d, J=8.4 Hz), 7.06 (2H, d, J=8.4 Hz)

MASS (m/z): 485 (M⁺+1)

Methyl 4'-[4-[4-(cis-4-methoxyphenyl)cyclohexyl]-1-piperazinyl]-1,1'-biphenyl-4-carboxylate NMR (CDCl₃, δ): 1.5–2.6 (10H, m), 2.6–2.75 (4H, m), 3.2–3.4 (4H, m), 3.79 (3H, s), 3.93 (3H, s), 6.8–6.9 (2H, m), 7.01 (2H, d, J=8.8 Hz), 7.19 (2H, d, J=8.6 Hz), 7.5–7.65 (4H, m), 8.06 (2H, d, J=8.5 Hz)

MASS (m/z): 485 (M⁺+1)

Preparation 80

Methyl 4'-[4-[cis-4-methoxy-(4-cyclopentyl)cyclohexyl-1-yl]-1-piperazinyl]-1,1'-biphenyl-4-carboxylate NMR (CDCl₃, δ): 1.2–1.9 (16H, m), 2.05–2.4 (2H, m), 2.7–2.85 (4H, m), 3.16 (3H, s), 3.25–3.35 (4H, m), 3.93 (3H, s), 7.00 (2H, d, J=8.8 Hz), 7.5–7.7 (4H, m), 8.0–8.1 (2H, m)

MASS (m/z): 477 (M⁺+1)

Methyl 4'-[4-[trans-4-methoxy-(4-cyclopentyl)-cyclohexyl-1-yl]-1-piperazinyl]-1,1'-biphenyl-4-carboxylate NMR (CDCl₃, δ): 1.35–1.9 (16H, m), 2.2–2.35 (2H, m), 2.6–3.75 (4H, m), 3.19 (3H, s), 3.2–3.35 (4H, m), 3.93 (3H, s), 7.00 (2H, d, J=8.9 Hz), 7.56 (2H, d, J=8.9 Hz), 7.62 (2H, d, J=8.6 Hz), 8.06 (2H, d, J=8.6 Hz)

MASS (m/z): 477 (M⁺+1)

Preparation 81

Methyl 4'-[4-(cis-4-methoxy-4-phenylcyclohexyl)-1-piperazinyl]-1,1'-biphenyl-4-carboxylate NMR (CDCl₃, δ): 1.5–2.0 (6H, m), 2.1–2.6 (3H, m), 2.75–2.9 (4H, m), 2.99 (3H, s), 3.25–3.4 (4H, m), 3.93 (3H, s), 7.01 (2H, d, J=8.8 Hz), 7.2–7.5 (5H, m), 7.57 (2H, d, J=8.8 Hz), 7.63 (2H, d, J=8.5 Hz), 8.06 (2H, d, J=8.5 Hz)

MASS (m/z): 485 (M⁺+1)

Preparation 82

A mixture of methyl 4'-[4-[1-methoxy-1,1-bi(cyclohexyl)-4-yl]-1-piperazinyl]-1,1'-biphenyl-4-carboxylate (440 mg) and 10% sodium hydroxide solution (1.4 ml) in a mixed solvent of methanol (8 ml) and tetrahydrofuran (24 ml) was refluxed for 4 hours. After cooling to ambient temperature, the reaction mixture was poured into cold water and the mixture was adjusted to pH 7 with 1.0 mol/l hydrochloric acid. The resulting precipitates were filtered, washed with water, isopropyl alcohol land diisopropyl ether, then dried to give 4'-[4-[cis-1-methoxy-1,1'-bi(cyclohexyl)-4-yl]-1-piperazinyl]-1,1'-biphenyl-4-carboxylic acid (371 mg).

MASS (m/z): 477 (M⁺+1)

The following compounds [Preparations 83 to 111] were obtained according to a similar manner to that of Preparation 82.

Preparation 83

4-[5-[4-[4-(Cyclohexylmethyl)-1-piperazinyl]phenyl]-1,3,4-thiadiazol-2-yl]benzoic acid NMR (DMSO-d₆, δ): 0.8–1.8 (11H, m), 2.5–3.5 (10H, m), 7.1–7.2 (2H, m), 7.92 (2H, d, J=8.2 Hz), 8.12 (4H, s)

API-ES MASS (m/z): 463.4 (M⁺+1)

Preparation 84

4-[5-[4-[4-(7-Methoxyheptyloxy)cyclohexyl]-1-piperazinyl]phenyl]-1,3,4-thiadiazol-2-yl]benzoic acid NMR (DMSO-d₆, δ): 1.00–2.2 (19H, m), 2.8–3.6 (13H), 3.20 (3H, s), 7.14–7.18 (2H, m), 7.90–7.93 (2H, m), 8.03–8.22 (4H, m)

ESI MASS (m/z)(Positive): 593.4 (M⁺+1)

Preparation 85

4-[5-[4-[4-(8-Methoxyoctyl)cyclohexyl]-1-piperazinyl]phenyl]-1,3,4-thiadiazol-2-yl]benzoic acid NMR (DMSO-d₆, δ): 1.1–2.2 (21H, m), 3.0–3.6 (13H, m), 3.20 (3H, s), 7.14–7.18 (2H, m), 7.78–8.21 (6H, m)

ESI MASS (m/z)(Negative): 607 (M⁺+1)

Preparation 86

4-[5-[4-[4-(5-Methoxypentyloxy)-1-piperidyl]phenyl]-1,3,4-thiadiazol-2-yl]benzoic acid hydrochloride NMR (DMSO-d₆, δ): 1.25–1.60 (8H, m), 1.80–1.95 (2H, m), 3.00–3.20 (2H, m), 3.21 (3H, s), 3.25–3.55 (5H, m), 3.60–3.80 (2H, m), 7.08 (2H, d, J=8.96 Hz), 7.84 (2H, d, J=8.48 Hz), 8.10 (4H, s)

ESI MASS (m/z)(Negative): 480.2 (M⁺+1)

Preparation 87

4-[5-[4-[4-(6-Methoxyhexyloxy)-1-piperidyl]phenyl]-1,3,4-thiadiazol-2-yl]benzoic acid NMR (DMSO-d₆, δ): 1.2–1.6 (10H, m), 1.8–2.0 (2H, m), 3.0–3.8 (12H, m), 7.08 (2H, d, J=9.0 Hz), 7.84 (2H, d, J=8.8 Hz), 8.11 (4H, br s)

(+) APCI MASS (m/z)(Positive): 496.27 (M⁺+1)

Preparation 88

4-[5-[4-[4-(4-Methoxybutoxymethyl)-1-piperidyl]phenyl]-1,3,4-thiadiazol-2-yl]benzoic acid NMR (DMSO-d₆, δ): 1.2–1.9 (9H, m), 2.8–3.0 (2H, m), 3.2–3.5 (9H, m), 3.8–4.0 (2H, m), 7.07 (2H, d, J=8.9 Hz), 7.84 (2H, d, J=8.7 Hz), 8.10 (4H, br s)

(+) APCI MASS (m/z)(Positive): 482.20 (M⁺+1)

Preparation 89

4-[5-[4-[4-(5-Methoxypentyloxymethyl)-1-piperidyl]phenyl]-1,3,4-thiadiazol-2-yl]benzoic acid NMR (DMSO-d₆, δ): 1.1–1.8 (11H, m), 2.7–2.9 (2H, m), 3.2–3.5 (9H, m), 3.8–4.0 (2H, m), 7.07 (2H, d, J=9.0 Hz), 7.84 (2H, d, J=8.8 Hz), 8.0–8.2 (4H, m)

ESI MASS (m/z)(Negative): 494.3 (M⁺+1)

Preparation 90

4-[5-[6-[Cis-4-(4-methylcyclohexyl)-1-piperazinyl]-3-pyridyl]-1,3,4-thiadiazol-2-yl]benzoic acid (+) APCI MASS (m/z)(Positive): 464.13 (M⁺+1)

Preparation 91

4-[5-[6-[Trans-4-(4-methylcyclohexyl)-1-piperazinyl]-3-pyridyl]-1,3,4-thiadiazol-2-yl]benzoic acid (+) APCI MASS (m/z)(Positive): 464.20 (M⁺+1)

Preparation 92

4-[5-[6-[Cis-4-(4-ethylcyclohexyl)-1-piperazinyl]-3-pyridyl]-1,3,4-thiadiazol-2-yl]benzoic acid ESI MASS (m/z)(Positive): 478.3 (M⁺+1)

Preparation 93

4-[5-[6-[Trans-4-(4-ethylcyclohexyl)-1-piperazinyl]-3-pyridyl]-1,3,4-thiadiazol-2-yl]benzoic acid (+) APCI MASS (m/z)(Positive): 478.3 (M⁺+1)

Preparation 94

4-[2-[4-(1-Cyclohexyl-4-piperidyl)phenyl]imidazo[2,1-b]-[1,3,4]thiadiazol-6-yl]benzoic acid hydrochloride IR (KBr): 2937, 1699, 1608, 1471, 1414, 1373, 1255, 1174 cm⁻¹

NMR (DMSO-d₆, δ): 1.0–2.1 (14H, m), 2.8–4.0 (6H, m), 7.4–8.0 (8H, m), 8.86 (1H, s)

(+) APCI MASS (m/z): 487.33 (M⁺+1)

Preparation 95

4-[2-[4-[Cis-4-(4-methylcyclohexyl)-1-piperazinyl]phenyl]imidazo[2,1-b][1,3,4]thiadiazol-6-yl]benzoic acid hydrochloride ESI MASS (m/z)(Positive): 502.3 (M⁺+1)

Preparation 96

4'-[4-(Trans-4-cyclohexylcyclohexyl)-1-piperazinyl]-1,1'-biphenyl-4-carboxylic acid ESI MASS (m/z): 447 (M⁺+1)

Preparation 97

4'-[4-(Trans-4-tert-butylcyclohexyl)-1-piperazinyl]-1,1'-biphenyl-4-carboxylic acid ESI MASS (m/z): 421 (M⁺+1)

Preparation 98

4'-[4-(Trans-4-ethylcyclohexyl)-1-piperazinyl]-1,1'-biphenyl-4-carboxylic acid

IR (KBr): 1699, 1602, 1525, 1377 cm⁻¹

MASS (m/z): 393 (M⁺+1)

Preparation 99
4'-[4-(Cis-4-ethylcyclohexyl)-1-piperazinyl]-1,1'-biphenyl-4-carboxylic acid
IR (KBr): 1691, 1603, 1529, 1452, 1381 cm$^{-1}$
MASS (m/z): 393 (M$^+$+1)

Preparation 100
4'-[4-[Trans-1-methoxy-1,1'-bi(cyclohexyl)-4-yl]-1-piperazinyl]-1,1'-biphenyl-4-carboxylic acid
MASS (m/z): 477 (M$^+$+1)

Preparation 101
4'-[4-(Cis-4-(trans-4-methoxycyclohexyl-1-yl)-cyclohexyl-1-yl)-1-piperazinyl]-1,1'-biphenyl-4-carboxylic acid
MASS (m/z): 477 (M$^+$+1)

Preparation 102
4'-[4-[Trans-4-(cis-4-methoxycyclohexyl-1-yl)cyclohexyl-1-yl]-1-piperazinyl]-1,1'-biphenyl-4-carboxylic acid
MASS (m/z): 477 (M$^+$+1)

Preparation 103
4'-[4-[Cis-4-(4-methoxyphenyl)cyclohexyl]-1-piperazinyl]-1,1'-biphenyl-4-carboxylic acid
MASS (m/z): 471 (M$^+$+1)

Preparation 104
4'-[4-(4-Methoxyphenyl)-1-piperazinyl]-1,1'-biphenyl-4-carboxylic acid
MASS (m/z): 491 (M$^+$+1)

Preparation 105
4'-[4-[Trans-4-(4-methoxyphenyl)cyclohexyl]-1-piperazinyl]-1,1'-biphenyl-4-carboxylic acid
MASS (m/z): 471 (M$^+$+1)

Preparation 106
4'-[4-(4,4-Dimethylcyclohexyl)-1-piperazinyl]-1,1'-biphenyl-4-carboxylic acid
MASS (m/z): 393 (M$^+$+1)

Preparation 107
4'-[4-[Cis-4-methoxy-(4-cyclopentyl)cyclohexyl-1-yl]-1-piperazinyl]-1,1'-biphenyl-4-carboxylic acid
MASS (m/z): 463 (M$^+$+1)

Preparation 108
4'-[4-[Trans-4-methoxy-(4-cyclopentyl)cyclohexyl-1-yl]-1-piperazinyl]-1,1'-biphenyl-4-carboxylic acid
MASS (m/z): 461 (M$^+$+1)

Preparation 109
4'-[4-(Cis-4-methoxy-4-phenylcyclohexyl)-1-piperazinyl]-1,1'-biphenyl-4-carboxylic acid
MASS (m/z): 471 (M$^+$+1)

Preparation 110
4-[5-[4-[4-(4-Methylenecyclohexyl)-1-piperazinyl]phenyl]-1,3,4-thiadiazol-2-yl]benzoic acid dihydrochloride
IR (KBr): 3400, 2939, 2852, 2592, 2455, 1705, 1603, 1522 cm$^{-1}$
NMR (DMSO-d$_6$, δ): 1.20–1.80 (4H, m), 1.80–2.40 (4H, m), 2.50–2.60 (4H, m), 3.10–3.30 (4H, m), 4.70 (1H, br s), 7.16 (2H, d, J=8.6 hz), 7.92 (2H, d, J=9.2 Hz), 8.00–8.30 (4H, m)
API-ES MASS (m/z)(Positive): 463 (M$^+$−2HCl+1)

Preparation 111
4-[5-[4-[4-(4-Phenylcyclohexyl)-1-piperazinyl]-phenyl]-1,3,4-thiadiazol-2-yl]benzoic acid
API-ES MASS (m/z): 525.3 (M$^+$+1)

Preparation 112
A mixture of 4'-[cis-4-[1-methoxy-1,1'-bi(cyclohexyl)-4-yl]-1-piperazinyl]-1,1,1-biphenyl-4-carboxylic acid (367 mg), 1-hydroxybenzotriazole (208 mg), 1-ethyl-3-(3'-dimethylaminopropyl)carbodiimide hydrochloride (443 mg) and triethylamine (0.216 ml) in methylene chloride (37 ml) was stirred for 23.5 hours at room temperature then evaporated under reduced pressure. Water was added to the residue and the resulting precipitate collected by filtration, washed with water, isopropyl alchol and diisopropyl ether, then dried to give 1-[[4'-[cis-4-[1-methoxy-1,1'-bi(cyclohexyl)-4-yl]-1-piperazinyl]-1,1'-biphenyl-4-yl]carbonyloxy]-1H-1,2,3-benzotriazole (399 mg).
NMR (CDCl$_3$, δ): 0.8–2.2 (19H, m), 2.3–2.5 (1H, m), 2.75–2.95 (4H, m), 3.11 (3H, s), 3.25–3.5 (4H, m), 7.03 (2H, d, J=8.8 Hz), 7.4–7.7 (5H, m), 7.79 (2H, d, J=8.5 Hz), 8.12 (1H, d, J=8.1 Hz), 8.30 (2H, d, J=8.5 Hz)
MASS (m/z): 594 (M$^+$+1)

The following compounds [Preparations 113 to 138] were obtained according to a similar manner to that of Preparation 112.

Preparation 113
1-[4-[5-[4-[4-(Cyclohexylmethyl)-1-piperazinyl]phenyl]-1,3,4-thiadiazol-2-yl]benzoyloxy]-1H-1,2,3-benzotriazole
IR (KBr): 2922, 2845, 1780, 1603, 1441, 1416, 1232, 984, 822 cm$^{-1}$
NMR (CDCl$_3$, δ): 0.8–1.9 (11H, m), 2.22 (2H, d, J=7.1 Hz), 2.5–2.7 (4H, m), 3.3–3.5 (4H, m), 6.9–8.5 (12H, m)
(+) APCI MASS (m/z): 580.13 (M$^+$+1)

Preparation 114
1-[4-[5-[4-[4-(7-Methoxyheptyloxy)cyclohexyl]-1-piperazinyl]phenyl]-1,3,4-thiadiazol-2-yl]benzoyloxy]-1H-1,2,3-benzotriazole
IR (KBr): 2931, 2856, 1778, 1603, 1441, 1416, 1234, 1093, 984 cm$^{-1}$
NMR (CDCl$_3$, δ): 1.0–2.2 (19H, m), 2.4–3.7 (13H, m), 3.33 (3H, s), 6.8–8.5 (12H, m)

Preparation 115
1-[4-[5-[4-[4-(8-Methoxyoctyloxy)cyclohexyl]-1-piperazinyl]phenyl]-1,3,4-thiadiazol-2-yl]benzoyloxy]-1H-1,2,3-benzotriazole
IR (KBr): 2931, 2856, 1778, 1605, 1441, 1416, 1234, 1093, 984 cm$^{-1}$
NMR (CDCl$_3$, δ): 1.0–2.2 (21H, m), 2.7–3.7 (13H, m), 3.33 (3H, s), 6.9–8.5 (12H, m)

Preparation 116
1-[4-[5-[4-[4-(5-Methoxypentyloxy)-1-piperidyl]phenyl]-1,3,4-thiadiazol-2-yl]benzoyloxy]-1H-1,2,3-benzotriazole
NMR (DMSO-d$_6$, δ): 1.30–1.80 (8H, m), 1.85–2.10 (2H, m), 3.00–3.25 (2H, m), 3.34 (3H, s), 3.35–3.55 (5H, m), 3.60–3.80 (2H, m), 6.97 (2H, d, J=8.95 Hz), 7.35–7.65 (3H, m), 7.90 (2H, d, J=8.81 Hz), 8.13 (2H, d, J=8.19 Hz), 8.23 (2H, d, J=8.46 Hz), 8.39 (2H, d, J=8.41 Hz)

Preparation 117
1-[4-[5-[4-[4-(6-Methoxyhexyloxy)-1-piperidyl]phenyl]-1,3,4-thiadiazol-2-yl]benzoyloxy]-1H-1,2,3-benzotriazole
IR (KBr): 2931, 2856, 1778, 1603, 1439, 1416, 1230, 1109, 982 cm$^{-1}$
NMR (CDCl$_3$, δ): 1.3–2.1 (12H, m), 3.0–3.3 (2H, m), 3.33 (3H, s), 3.3–3.6 (5H, m), 3.6–3.8 (2H, m), 6.97 (2H, d, J=8.9 Hz), 7.4–7.7 (3H, m), 7.90 (2H, d, J=8.8 Hz), 8.1–8.3 (3H, m), 8.3–8.5 (2H, m)
(+) APCI MASS (m/z)(Positive): 612.93 (M$^+$+1)

Preparation 118
1-[4-[5-[4-[4-(4-Methoxybutoxymethyl)-1-piperidyl]phenyl]-1,3,4-thiadiazol-2-yl]benzoyloxy]-1H-1,2,3-benzotriazole
IR (KBr): 1778, 1603, 1439, 1412, 1248, 1230, 1115, 1090, 984 cm$^{-1}$
NMR (DMSO-d$_6$, δ): 1.0–2.1 (9H, m), 2.8–3.0 (2H, m), 3.1–3.5 (6H, m), 3.34 (3H, s), 3.8–4.0 (2H, m), 6.96 (2H, d, J=9.0 Hz), 7.3–7.6 (3H, m), 7.90 (2H, d, J=8.9 Hz), 8.12 (1H, d, J=7.2 Hz), 8.2–8.3 (2H, m), 8.3–8.5 (2H, m)

Preparation 119

1-[4-[5-[4-[4-(5-Methoxypentyloxymethyl)-1-piperidyl]phenyl]-1,3,4-thiadiazol-2-yl]benzoyloxy]-1H-1,2,3-benzotriazole NMR (CDCl$_3$, δ): 1.1–2.0 (11H, m), 2.7–2.9 (2H, m), 3.2–3.5 (6H, m), 3.33 (3H, s), 3.7–3.9 (2H, m), 6.90 (2H, m, J=9.0 Hz), 7.3–7.6 (3H, m), 7.83 (2H, d, J=8.8 Hz), 8.06 (1H, d, J=8.2 Hz), 8.16 (2H, d, J=8.5 Hz), 8.33 (2H, d, J=8.5 Hz)

(+) APCI MASS (m/z) (Positive): 613.13 (M$^+$+1)

Preparation 120

1-[4-[5-[6-[4-(4-Methylcyclohexyl)-1-piperazinyl]-3-pyridyl]-1,3,4-thiadiazol-2-yl]benzoyloxy]-1H-1,2,3-benzotriazole IR (KBr): 2947, 2922, 1778, 1601, 1429, 1400, 1236, 987 cm$^{-1}$ NMR (CDCl$_3$, δ): 0.8–1.5 (8H, m), 1.7–1.9 (2H, m), 1.9–2.1 (2H, m), 2.6–3.0 (1H, m), 3.0–3.2 (4H, br s), 3.5–4.2 (4H, br s), 6.6–6.8 (1H, m), 7.4–8.5 (9H, m), 8.75 (1H, d, J=2.3 Hz)

ESI MASS (m/z)(Positive): 581.3 (M$^+$+1)

Preparation 121

1-[4-[5-[6-[4-(4-Ethylcyclohexyl)-1-piperazinyl]-3-pyridyl]-1,3,4-thiadiazol-2-yl]benzoyloxy]-1H-1,2,3-benzotriazole IR (KBr): 2926, 1780, 1703, 1601, 1508, 1429, 1402, 1379, 1242, 984 cm$^{-1}$ NMR (CDCl$_3$, δ): 0.8–1.0 (5H, m), 1.2–1.9 (8H, m), 1.9–2.5 (2H, m), 2.6–2.8 (4H, m), 3.6–3.8 (4H, m), 6.73 (1H, d, J=9.1 Hz), 7.4–7.7 (3H, m), 8.0–8.5 (6H, m), 8.74 (1H, d, J=2.3 Hz)

ESI MASS (m/z)(Positive): 595.3 (M$^+$+1)

Preparation 122

1-[4-[5-[6-[Trans-4-(4-ethylcyclohexyl)-1-piperazinyl]-3-pyridyl]-1,3,4-thiadiazol-2-yl]benzoyloxy]-1H-1,2,3-benzotriazole IR (KBr): 2924, 2850, 1778, 1601, 1429, 1402, 1362, 1244, 984 cm$^{-1}$ NMR (CDCl$_3$, δ): 0.8–1.5 (10H, m), 1.7–2.1 (4H, m), 2.3–2.6 (1H, m), 2.7–2.9 (4H, br s), 3.6–3.9 (4H, br s), 6.6–6.8 (1H, m), 74–7.7 (3H, m), 7.9–8.5 (6H, m), 8.74 (1H, d, J=2.3 Hz)

ESI MASS (m/z)(Positive): 595.3 (M$^+$+1)

Preparation 123

1-[4-[2-[4-[Cis-4-(4-methylcyclohexyl)-1-piperazinyl]phenyl]imidazo[2,1-b][1,3,4]thiadiazol-6-yl]benzoyloxy]-1H-1,2,3-benzotriazole IR (KBr): 1795, 1697, 1649, 1605, 1539, 1473, 1383, 1234, 1095, 1018 cm$^{-1}$ Preparation 124

1-[4'-[4-(Trans-4-cyclohexylcyclohexyl)-1-piperazinyl]-1,1'-biphenyl-4-yl]carbonyloxy-1H-1,2,3-benzotriazole NMR (CDCl$_3$, δ): 0.8–2.5 (21H, m), 2.8–3.0 (4H, m), 3.3–3.45 (4H, m), 7.03 (2H, d, J=8.7 Hz), 7.4–7.7 (5H, m), 7.79 (2H, d, J=8.4 Hz), 8.12 (1H, d, J=8.4 Hz), 8.30 (2H, d, J=8.3 Hz)

MASS (m/z): 447 (M$^+$+1)

Preparation 125

1-[4-[5-[4-[4-(4-Methylenecyclohexyl)-1-piperazinyl]phenyl]-1,3,4-thiadiazol-2-yl]benzoyloxy]-1H-1,2,3-benzotriazole IR (KBr): 3425, 3404, 2929, 2831, 1780, 1600 cm$^{-1}$ NMR (DMSO-d$_6$, δ): 1.10–1.50 (4H, m), 1.60–2.20 (4H, m), 2.20–2.40 (2H, m), 2.50–2.80 (4H, m), 4.62 (1H, br s), 7.17 (2H, d, J=9.1 Hz), 7.70–7.60 (2H, m), 7.65 (1H, d, J=8.0 Hz), 7.75–8.00 (3H, m), 8.10–8.30 (4H, m)

API-ES MASS (m/z)(Positive): 584

Preparation 126

1-[4'-[4-(Trans-4-tert-butylcyclohexyl)-1-piperazinyl]-1,1'-biphenyl-4-yl]carbonyloxy-1H-1,2,3-benzotriazole IR (KBr): 1770, 1570, 1236 cm$^{-1}$ NMR (CDCl$_3$, δ): 0.86 (9H, s), 0.9–1.4 (5H, m), 1.7–2.5 (5H, m), 2.7–2.85 (4H, m), 3.2–3.4 (4H, m), 6.9–7.1 (2H, m), 7.3–7.7 (5H, m), 7.79 (2H, d, J=8.5 Hz), 8.11 (1H, d, J=8.4 Hz), 8.30 (2H, d, J=8.4 Hz)

MASS (m/z): 538 (M$^+$+1)

Preparation 127

1-[4'-[4-(Trans-4-ethylcyclohexyl)-1-piperazinyl]-1,1'-biphenyl-4-yl]carbonyloxy-1H-1,2,3-benzotriazole Preparation 128

1-[4'-[4-(Cis-4-ethylcyclohexyl)-1-piperazinyl]-1,1'-biphenyl-4-yl]carbonyloxy-1H-1,2,3-benzotriazole Preparation 129

1-[4'-[4-[Trans-1-methoxy-1,1'-bi(cyclohexyl)-4-yl]-1-piperazinyl]-1,1'-biphenyl-4-yl]carbonyloxy-1H-1,2,3-benzotriazole NMR (CDCl$_3$, δ): 0.8–2.6 (20H, m), 2.7–3.0 (4H, m), 3.15 (3H, s), 3.3–3.6 (4H, m), 7.03 (2H, d, J=8.7 Hz), 7.3–7.7 (5H, m), 7.79 (2H, d, J=8.4 Hz), 8.12 (1H, d, J=8.1 Hz), 8.31 (2H, d, J=8.4 Hz)

MASS (m/z): 594 (M$^+$+1)

Preparation 130

1-[4'-[4-[Cis-4-(cis-4'-methoxycyclohexyl-1'-yl)cyclohexyl-1-yl]-1-piperazinyl]-1,1'-biphenyl-4-yl]carbonyloxy-1H-1,2,3-benzotriazole NMR (CDCl$_3$, δ): 0.7–2.6 (19H, m), 2.7–3.2 (5H, m), 3.35 (3H, s), 3.3–3.5 (4H, m), 7.03 (2H, d, J=8.8 Hz), 7.35–7.7 (5H, m), 7.79 (2H, d, J=8.5 Hz), 8.12 (1H, d, J=8.2 Hz), 8.30 (2H, d, J=8.5 Hz)

MASS (m/z): 594 (M$^+$+1)

Preparation 131

1-[4'-[4-[Trans-4-(cis-4'-methoxycyclohexyl-1'-yl)cyclohexyl-1-yl]-1-piperazinyl]-1,1'-biphenyl-4-yl]carbonyloxy-1H-1,2,3-benzotriazole NMR (CDCl$_3$, δ): 0.8–1.5 (10H, m), 1.6–2.6 (9H, m), 2.8–3.2 (5H, m), 3.35 (3H, s), 3.3–3.5 (4H, m), 7.03 (2H, d, J=8.8 Hz), 7.4–7.7 (5H, m), 7.78 (2H, d, J=8.5 Hz), 8.12 (1H, d, J=8.2 Hz), 8.30 (2H, d, J=8.5 Hz)

MASS (m/z): 594 (M$^+$+1)

Preparation 132

1-[4'-[4-[Cis-4-(4-methoxyphenyl)cyclohexyl]-1-piperazinyl]-1,1'-biphenyl-4-yl]carbonyloxy-1H-1,2,3-benzotriazole NMR (CDCl$_3$, δ): 1.5–2.9 (14H, m), 3.3–3.5 (4H, m), 3.79 (3H, s), 6.85 (2H, d, J=8.7 Hz), 7.03 (2H, d, J=8.8 Hz), 7.21 (2H, d, J=8.7 Hz), 7.4–7.7 (5H, m), 7.79 (2H, d, J=8.5 Hz), 8.12 (1H, d, J=8.2 Hz), 8 30 (2H, d, J=8.5 Hz)

MASS (m/z): 588 (M$^+$+1)

Preparation 133

1-[4'-[4-(4-Methoxyphenyl)-1-piperazinyl]-1,1'-biphenyl-4-yl]carbonyloxy-1H-1,2,3-benzotriazole NMR (CDCl$_3$, δ): 3.2–3.55 (8H, m), 3.79 (3H, s), 6.8–7.2 (6H, m), 7.4–7.9 (7H, m), 8.0–8.15 (2H, m), 8.31 (1H, d, J=8.2 Hz)

MASS (m/z): 506 (M$^+$+1)

Preparation 134

1-[4'-[4-[4-(Trans-4-methoxyphenyl)cyclohexyl]-1-piperazinyl]-1,1'-biphenyl-4-yl]carbonyloxy-1H-1,2,3-benzotriazole NMR (CDCl$_3$, δ): 1.4–2.35 (8H, m), 2.3–2.5 (2H, m), 2.8–3.0 (4H, m), 3.3–3.5 (4H, m), 3.79 (3H, s), 6.85 (2H, d, J=8.7 Hz), 7.04 (2H, d, J=8.8 Hz), 7.13 (2H, d, J=8.7 Hz), 7.4–7.7 (5H, m), 7.79 (2H, d, J=8.5 Hz), 8.12 (1H, d, J=8.2 Hz), 8.30 (2H, d, J=8.5 Hz)

MASS (m/z): 588 (M$^+$+1)

Preparation 135

1-[4'-[4-(4,4-Dimethylcyclohexyl)-1-piperazinyl]-1,1'-biphenyl-4-yl]carbonyloxy-1H-1,2,3-benzotriazole NMR (CDCl$_3$, δ): 0.92 (6H, s), 1.1–1.9 (8H, m), 2.2–2.5 (1H, m), 2.75–2.95 (4H, m), 3.3–3.45 (4H, m), 7.03 (2H, d, J=8.8 Hz), 7.4–7.7 (5H, m), 7.79 (2H, d, J=8.5 Hz), 8.12 (1H, d, J=8.2 Hz), 8.30 (2H, d, J=8.5 Hz)

MASS (m/z): 510 (M$^+$+1)

Preparation 136

1-[4'-[4-[Cis-4-methoxy-(4-cyclopentyl)cyclohexyl-1-yl]-1-piperazinyl]-1,1'-biphenyl-4-yl]carbonyloxy-1H-1,2,3-benzotriazole IR (KBr): 1776, 1597 cm$^{-1}$ NMR (CDCl$_3$, δ): 1.2–2.0 (16H, m), 2.1–2.45 (2H, m), 2.75–2.9 (4H, m), 3.16 (3H, s), 3.25–3.4 (4H, m), 7.03 (2H, d, J=8.9 Hz), 7.4–7.7 (5H, m), 7.79 (2H, d, J=8.6 Hz), 8.11 (1H, d, J=8.2 Hz), 8.30 (2H, d, J=8.6 Hz)

MASS (m/z): 579 (M$^+$)

Preparation 137

1-[4'-4-[Trans-4-methoxy-(4-cyclopentyl)cyclohexyl-1-yl]-1-piperazinyl]carbonyloxy-1H-1,2,3-benzotriazole IR (KBr): 1772, 1597 cm$^{-1}$ NMR (CDCl$_3$, δ): 1.35–2.4 (18H, m), 2.65–2.8 (4H, m), 3.20 (3H, s), 3.25–3.4 (4H, m), 7.03 (2H, d, J=8.9 Hz), 7.4–7.7 (5H, m), 7.79 (2H, d, J=8.6 Hz), 8.05–8.15 (1H, m), 8.25–8.35 (2H, m)

MASS (m/z): 580 (M$^+$+1)

Preparation 138

1-[4'-[4-(Cis-4-methoxy-4-phenylcyclohexyl)-1-piperazinyl]-1,1'-biphenyl-4-yl]carbonyloxy-1H-1,2,3-benzotriazole NMR (CDCl$_3$, δ): 1.5–2.6 (9H, m), 2.8–2.95 (4H, m), 2.99 (3H, s), 3.3–3.45 (4H, m), 7.05 (2H, d, J=8.9 Hz), 7.2–7.7 (10H, m), 7.79 (2H, d, J=8.6 Hz), 8.11 (1H, d, J=8.1 Hz), 8.30 (2H, d, J=8.6 Hz)

MASS (m/z): 588 (M$^+$+1)

Preparation 139

A mixture of cesium trichloride (24.9 g) in tetrahydrofuran (45 ml) was stirred at room temperature for 5 hours. 1,4-Dioxa-spiro[4.5]decan-8-one (1.4 g) was added to the solution and stirred at room temperature for 1 hour. To the solution was added dropwise with stirring phenylmagnesium chloride (3.0M solution in dimethyl ether) (33.7 ml) at 0° C. The reaction mixture was quenched with 10% acetic acid aqueous solution. Dimethyl ether was added to the solution. The organic layer was washed with brine, sodium hydrogen carbonate solution and brine and dried over magnesium sulfate. The magnesium sulfate was filtered off, and the filtrate was concentrated under reduced pressure. The residue was purified by silica gel chromatography (3:1 hexane-ethyl acetate elution) to give 8-phenyl-1,4-dioxaspiro[4.5]decan-8-ol (5.94 g).

NMR (CDCl$_3$, δ): 1.65–2.3 (8H, m), 3.99 (4H, s), 4.03 (1H, s), 7.2–7.6 (5H, m)

MASS (m/z): 257 (M$^+$+23)

The following compound was obtained according to a similar manner to that of Preparation 139.

Preparation 140

8-Cyclopentyl-1,4-dioxaspiro[4.5]decan-8-ol

NMR (CDCl$_3$, δ): 1.2–2.1 (17H, m), 3.9–4.05 (4H, m), 4.03 (1H, s)

MASS (m/z): 249 (M$^+$+23)

Preparation 141

To a solution of 8-phenyl-1,4-dioxaspiro[4.5]decan-8-ol (5.76 g) and iodomethane (4.59 ml) in N,N-dimethylformamide (58 ml) was added sodium hydride (60% dispersion in mineral oil) (1.97 g) at 0° C. The solution was stirred for 2 hours at 0° C. and at room temperature for 7.5 hours. The reaction mixture was added to a mixture of water and ether. The organic layer was washed with brine and dried over magnesium sulfate. The magnesium sulfate was filtered off, and the filtrate was concentrated under reduced pressure. The residue was purified by silica gel chromatography (5:1 hexane-ethyl acetate elution) to give 8-methoxy-8-phenyl-1,4-dioxaspiro[4.5]decane (5.968 g).

NMR (CDCl$_3$, δ): 1.6–2.15 (8H, m), 3.00 (3H, s), 3.9–4.05 (4H, m), 7.2–7.5 (5H, m)

The following compounds [Preparations 142 and 143] were obtained according to a similar manner to that of Preparation 141.

Preparation 142

4'-Methoxy-1,1'-bi(cyclohexyl)-4-ol

NMR (CDCl$_3$, δ): 0.8–2.2 (18H, m), 2.9–3.6 (6H, m)

MASS (m/z): 235 (M$^+$+23)

Preparation 143

8-Cyclopentyl-8-methoxy-1,4-dioxaspiro[4.5]decane

NMR (CDCl$_3$, δ): 1.25–2.35 (17H, m), 3.16 (3H, s), 3.9–4.0 (4H, m)

Preparation 144

A solution of 8-methoxy-8-phenyl-1,4-dioxaspiro[4.5]decane (5.96 g) and 3N-hydrrochloric acid (24 ml) in tetrahydrofuran was stirred at room temperature for 24 hours. The reaction mixture was added to a mixture of sodium hydrogen carbonate solution and dimethyl ether. The organic layer was washed with sodium hydrogen carbonate solution and dried over magnesium sulfate. The magnesium sulfate was filtered off, and the filtrate was concentrated under reduced pressure. The residue was purified by silica gel chromatography (1:0–150:1 dichloromethane-methanol elution) to give 4-methoxy-4-phenylcyclohexanone (3.6 g).

NMR (CDCl$_3$, δ): 2.0–2.9 (8H, m), 3.09 (3H, s), 7.25–7.5 (5H, m)

MASS (m/z): 227 (M$^+$+23)

The following compound was obtained according to a similar manner to that of Preparation 144.

Preparation 145

4-Cyclopentyl-4-methoxycyclohexanone

NMR (CDCl$_3$, δ): 1.2–2.4 (15H, m), 2.45–2.7 (2H, m), 3.27 (3H, s)

MASS (m/z): 219 (M$^+$+23)

Preparation 146

A mixture of 4-[5-[4-[4-(4-phenylcyclohexyl)-1-piperazinyl]phenyl]-1,3,4-thiadiazol-2-yl]benzoic acid (0.81 g), 0-benzotriazol-1-yl-N,N,N',N'-tetramethyluronium hexafluorophosphate (0.66 g) and N,N-diisopropylethylamine (0.51 ml) in 1-methyl-2-pyrrolidinone (16 ml) was stirred for 2 hours at 50° C. The reaction mixture was poured into water. Then the resulting precipitate was collected by filtration and washed with water to give 1-4-[5-[4-[4-(4-phenylcyclohexyl)-1-piperazinyl]phenyl]-1,3,4-thiadiazol-2-yl]benzoyloxy-1H-1,2,3-benzotriazole (0.97 g).

IR (KBr): 1780, 1603, 1444, 1414, 1234; 1188, 980, 843 cm$^{-1}$

NMR (CDCl$_3$, δ): 1.6–2.2 (8H, m), 2.3–2.5 (1H, m), 2.7–2.9 (5H, m), 3.4–3.6 (4H, m), 6.9–8.5 (17H, m)

(+) APCI MASS (m/z): 642.07 (M$^+$+1)

The following compounds [Preparations 147 and 148] were obtained according to a similar manner to that of Preparation 146.

Preparation 147

1-[4-[5-[6-[4-(4-Methylcyclohexyl)-1-piperazinyl]-3-pyridyl]-1,3,4-thiadiazol-2-yl]benzoyloxy]-1H-1,2,3-benzotriazole IR (KBr): 2943, 2918, 1782, 1601, 1427, 1402, 987, 845 cm$^{-1}$ NMR (CDCl$_3$, δ): 0.94 (3H, d, J=6.9 Hz), 1.4–1.8 (9H, m), 2.3–2.5 (1H, m), 2.5–3.9 (4H, m), 3.7–3.9 (4H, m), 6.74 (1H, d, J=9.0 Hz), 7.4–7.7 (3H, m), 8.1–8.5 (6H, m), 8.74 (1H, d, J=2.3 Hz)

MASS (m/z)(Positive): 581.3 (M$^+$+1)

Preparation 148

1-4-[2-[4-(1-Cyclohexyl-1-piperidyl)phenyl]imidazo[2,1-b][1,3,4]thiadiazol-6-yl]benzoyloxy-1H-1,2,3-benzotriazole IR (KBr): 2926, 1776, 1608, 1471, 1230, 1176, 980, 845 cm$^{-1}$ NMR (CDCl$_3$, δ): 1.0–2.7 (18H, m), 3.1–3.3 (2H, m), 7.2–8.4 (13H, m)

(+) APCI MASS (m/z): 604.13 (M$^+$+1)

Preparation 149

To a solution of 1,4-dioxaspiro[4.5]decan-8-ol (9.5 g) in N,N-dimethylformamide (200 ml) was added portionwise sodium hydride (abt. 60% oil suspension) (2.6 g) under ice-cooling and nitrogen atmosphere. After stirring for 2 hours at room temperature, the reaction mixture was stirred for 1 hour at 60° C. To the reaction mixture was added a solution of 7-methoxyheptyl 4-methylbenzenesulfonate (15.0 g) in N,N-dimethylformamide (50 ml) at 60° C. and then the reaction mixture was stirred for 2 hours at 60° C. After being cooled to room temperature, the reaction mixture was poured into a mixture of ethyl acetate and water. The organic layer was successively washed with water and brine and dried over magnesium sulfate. The solvent was evaporated in vacuo and the residue was purified by column chromatography on silica gel eluting with a mixture of hexane and ethyl acetate (10:1→5:1). The eluted fractions containing the desired product were collected and evaporated in vacuo to give 8-(7-methoxyheptyloxy)-1,4-dioxaspiro[4.5]decane (9.77 g).

NMR (CDCl$_3$, δ): 1.3–1.9 (18H, m), 3.33 (3H, s), 3.3–3.5 (5H, m), 3.94 (4H, s)

ESI MASS (m/z)(Positive): 309.3 (M$^+$+Na)

The following compounds [Preparations 150 and 151] were obtained according to a similar manner to that of Preparation 149.

Preparation 150

8-(8-Methoxyoctyloxy)-1,4-dioxaspiro[4.5]decane

NMR (CDCl$_3$, δ): 1.2–1.9 (20H, m), 3.33 (3H, s), 3.3–3.5 (5H, m), 3.94 (4H, s)

ESI MASS (m/z)(Positive): 323.3 (M$^+$+Na)

Preparation 151 tert-Butyl 4-(6-methoxyhexyloxy)-1-piperidinecarboxylate

NMR (CDCl$_3$, δ): 1.3–1.7 (12H, m), 1.45 (9H, s), 1.7–1.9 (1H, m), 3.0–3.2 (2H, m), 3.33 (3H, s), 3.3–3.5 (4H, m), 3.7–3.9 (2H, m)

(+) APCI MASS (m/z)(Positive): 216.07 (M$^+$+1-Boc)

Preparation 152

A mixture of ethyl 4-[4-4-(7-methoxyheptyloxy)-cyclohexyl-1-piperazinyl]benzoate (2.8 g) and hydrazine monohydrate (26 ml) in ethanol (56 ml) and tetrahydrofuran (22 ml) was stirred for 15 hours at 100° C. After being cooled to room temperature, the reaction mixture was poured into water. The solvent was evaporated in vacuo and the residue was extracted with ethyl acetate. The extract was washed with water and dried over magnesium sulfate. The solvent was evaporated in vacuo to give 4-[4-4-(7-methoxyheptyloxy)cyclohexyl-1-piperazinyl]benzohydrazide (2.58 g).

IR (Neat): 2933, 2858, 1608, 1512, 1454, 1240, 1113 cm$^{-1}$

NMR (CDCl$_3$, δ): 1.2–2.2 (18H, m), 2.2–2.4 (1H, m), 2.62 (4H, m), 3.33 (3H, s), 3.2–3.5 (9H, m), 4.06 (2H, br s), 6.8–6.9 (2H, m), 7.30 (1H, s), 7.6–7.7 (2H, m)

(+) APCI MASS (m/z): 447.47 (M$^+$+1)

The following compounds [Preparations 153 to 164] were obtained according to a similar manner to that of Preparation 152.

Preparation 153

4-[4-(4-Phenylcyclohexyl)-1-piperazinyl]benzohydrazide

APCI MASS (m/z)(Positive): 379.4 (M$^+$+1)

Preparation 154

4-[4-(4-Methylenecyclohexyl)-1-piperazinyl]benzohydrazine

IR (KBr): 3429, 3402, 3307, 3280, 2933, 2837, 1608, 1504 cm$^{-1}$

NMR (DMSO-d$_6$, δ): 1.20–1.50 (2H, m), 1.60–2.20 (4H, m), 2.20–2.30 (2H, m), 2.50–2.70 (4H, m), 3.10–3.30 (4H, m), 4.36 (2H, br s), 4.61 (1H, s), 6.91 (2H, d, J=8.9 Hz), 7.69 (2H, d, J=8.8 Hz), 9.45 (1H, br s)

MASS (m/z): 317 (M$^+$+1)

Preparation 155

4-[4-(Cyclohexylmethyl)-1-piperazinyl]benzohydrazide

NMR (DMSO-d$_6$, δ): 0.70–1.00 (2H, m), 1.10–1.80 (9H, m), 2.11 (2H, d, J=7.2 Hz), 2.41–2.46 (4H, m), 3.19–3.24 (4H, m), 4.36 (2H, s), 6.92 (2H, d, J=8.9 Hz), 7.69 (2H, d, J=8.99 Hz), 9.46 (1H, s)

APCI MASS (m/z)(Positive): 317 (M$^+$+1)

Preparation 156

4-[4-[4-(8-Methoxyoctyloxy)cyclohexyl]-1-piperazinyl]benzohydrazide

IR (Neat): 2931, 2856, 1703, 1608, 1512, 1454, 1240, 1113 cm$^{-1}$

NMR (CDCl$_3$, δ): 1.2–2.2 (20H, m), 2.2–2.4 (1H, m), 2.6–2.8 (4H, m), 3.1–3.5 (9H, m), 3.33 (3H, s), 4.05 (2H, br s), 6.8–6.9 (2H, m), 7.27 (1H, s), 7.6–7.7 (2H, m)

MASS (m/z): 461.53 (M$^+$+1)

Preparation 157

4-[4-(5-Methoxypentyloxy)-1-piperidyl]benzohydrazide

NMR (CDCl$_3$, δ): 1.30–1.80 (8H, m), 1.85–2.05 (2H, m), 3.00–3.18 (2H, m), 3.33 (3H, s), 3.34–3.60 (5H, m), 3.60–3.70 (2H, m), 3.95–4.15 (2H, m), 6.88 (2H, d, J=8.95 Hz), 7.53 (1H, s), 7.65 (2H, d, J=8.91 Hz)

ESI MASS (m/z)(Positive): 358.4 (M$^+$+Na)

Preparation 158

4-[4-(6-Methoxyhexyloxy)-1-piperidyl]benzohydrazide

NMR (CDCl$_3$, δ): 1.3–2.1 (12H, m), 3.0–3.2 (2H, m), 3.33 (3H, s), 3.3–3.5 (5H, m), 3.5–3.8 (2H, m), 4.07 (2H, br s), 6.8–6.9 (2H, m), 7.36 (1H, br s), 7.6–7.7 (2H, m)

(+) APCI MASS (m/z)(Positive): 350.07 (M$^+$+1)

Preparation 159

4-[4-(4-Methoxybutoxymethyl)-1-piperidyl]benzohydrazide

NMR (CDCl$_3$, δ): 1.2–1.9 (9H, m), 2.7–2.9 (2H, m), 3.2–3.5 (6H, m), 3.33 (3H, s), 3.7–3.9 (2H, m), 4.06 (2H, br s), 6.8–7.0 (2H, m), 7.30 (1H, br s), 7.6–7.7 (2H, m)

(+) APCI MASS (m/z)(Positive): 335.93 (M$^+$+1)

Preparation 160

4-[4-(5-Methoxypentyloxymethyl)-1-piperidyl]-benzohydrazide

NMR (CDCl$_3$, δ): 1.2–2.0 (11H, m), 2.7–2.9 (2H, m), 3.2–3.5 (6H, m), 3.33 (3H, s), 3.8–4.2 (4H, m), 6.88 (2H, d, J=9.0 Hz), 7.34 (1H, br s), 7.6–7.7 (2H, m)

(+) APCI MASS (m/z)(Positive): 349.93 (M$^+$+1)

Preparation 161

6-[4-(4-Methylcyclohexyl)-1-piperazinyl]-nicotinohydrazide

NMR (CDCl$_3$, δ): 0.94 (3H, d, J=6.9 Hz), 1.4–2.0 (9H, m), 2.1–2.3 (1H, m), 2.5–2.7 (4H, m), 3.6–3.8 (4H, m), 3.9–4.3 (2H, m), 6.61 (1H, d, J=9.0 Hz), 7.43 (1H, br s), 7.86 (1H, dd, J=9.0 and 2.5 Hz), 8.54 (1H, d, J=2.3 Hz)

(+) APCI MASS (m/z)(Positive): 318.00 (M$^+$+1)

Preparation 162

6-[4-(Trans-4-methylcyclohexyl)-1-piperazinyl]-nicotinohydrazide

NMR (CDCl$_3$, δ): 0.88 (3H, d, J=6.4 Hz), 0.9–2.0 (9H, m), 2.2–2.4 (1H, m), 2.6–2.8 (4H, m), 3.5–3.7 (4H, m), 3.9–4.3 (2H, m), 6.61 (1H, d, J=9.1 Hz), 7.33 (1H, br s), 7.85 (1H, dd, J=9.0 and 2.5 Hz), 8.53 (1H, d, J=2.3 Hz)

(+) APCI MASS (m/z)(Positive): 318.00 (M$^+$+1)

Preparation 163

6-[4-(4-Ethylcyclohexyl)-1-piperazinyl]-nicotinohydrazide

NMR (CDCl$_3$, δ): 0.8–1.0 (5H, m), 1.2–2.0 (9H, m), 2.2–2.4 (1H, m), 2.5–2.7 (4H, m), 3.5–3.7 (4H, m), 3.8–4.2 (2H, m), 6.61 (1H, d, J=9.0 Hz), 7.38 (1H, br s), 7.86 (1H, dd, J=9.0 and 2.5 Hz), 8.54 (1H, d, J=2.4 Hz)

(+) APCI MASS (m/z)(Positive): 332.00 (M$^+$+1)

Preparation 164

6-[4-(Trans-4-ethylcyclohexyl)-1-piperazinyl]-nicotinohydrazide

NMR (CDCl$_3$, δ): 0.8–2.0 (14H, m), 2.2–2.4 (1H, m), 2.5–2.7 (4H, m), 3.5–3.7 (4H, m), 3.8–4.2 (2H, m), 6.61 (1H, d, J=9.0 Hz), 7.32 (1H, br s), 7.86 (1H, dd, J=9.0 and 2.5 Hz), 8.53 (1H, d, J=2.4 Hz)

(+) APCI MASS (m/z)(Positive): 331.93 (M$^+$+1)

Preparation 165

A mixture of methyl 4-[2-[4-[4-4-(7-methoxyheptyloxy)-cyclohexyl-1-piperazinyl]benzoyl]hydrazinocarbonyl] benzoate (1.9 g) and phosphorus pentasulfide (1.1 g) in ethylene glycol dimethyl ether (40 ml) was refluxed for 1.5 hours. After being added triethylamine, the reaction mixture was successively refluxed for 1.5 hours. After being cooled to room temperature, the reaction mixture was poured into ice-water. Then the solution was adjusted to pH 8 with 1N aqueous sodium hydroxide. The resulting precipitate was collected by filtration and washed with water to give methyl 4-[5-[4-[4-4-(7-methoxyheptyloxy)cyclohexyl-1-piperazinyl]phenyl]-1,3,4-thiadiazol-2-yl]benzoate (2.13 g).

IR (KBr): 2931, 2856, 1718, 1606, 1439, 1281, 1111, 953 cm$^{-1}$

NMR (DMSO-d$_6$, δ): 1.0–2.2 (19H, m), 2.8–3.6 (13H, m), 3.21 (3H, s), 3.90 (3H, s), 7.0–8.3 (8H, m)

ESI MASS (m/z)(Positive): 607.4 (M$^+$+1)

The following compounds [Preparations 166 to 168] were obtained according to a similar manner to that of Preparation 165.

Preparation 166

Methyl 4-[5-[4-[4-(4-methylenecyclohexyl)-1-piperazinyl]phenyl]-1,3,4-thiadiazol-2-yl]benzoate IR (KBr): 3423, 2939, 2829, 1719, 1603, 1439 cm$^{-1}$ NMR (DMSO-d$_6$, δ): 1.20–2.00 (6H, m), 2.10–2.40 (2H, m), 2.50–2.70 (4H, m), 3.15–3.30 (4H, m), 3.90 (7H, s), 4.62 (1H, br s), 7.08 (2H, d, J=8.4 Hz), 7.85 (2H, d, J=9.3 Hz), 7.80–8.30 (4H, m)

MASS (m/z): 477 (M$^+$+1), 476 (M), 475 (M$^+$)

Preparation 167

4-[5-[4-[4-4-(8-Methoxyoctyloxy)cyclohexyl-1-piperazinyl]phenyl]-1,3,4-thiadiazol-2-yl]benzoate IR (KBr): 2929, 2854, 1724, 1606, 1439, 1281, 1111, 955 cm$^{-1}$ NMR (DMSO-d$_6$, δ): 1.1–2.2 (21H, m), 2.8–3.6 (13H, m), 3.20 (3H, s), 3.8–3.9 (3H, m), 7.0–8.3 (8H, m)

ESI MASS (m/z)(Positive): 621.5 (M$^+$+1)

Preparation 168

Methyl 4-[5-[4-[4-(5-methoxypentyloxy)-1-piperidyl]phenyl]-1,3,4-thiadiazol-2-yl]benzoate NMR (DMSO-d$_6$, δ): 1.00–1.60 (8H, m), 1.80–1.95 (2H, m), 2.75–2.95 (2H, m), 3.21 (3H, s), 3.55–3.75 (7H, m), 3.90 (3H, s), 7.09 (2H, d, J=8.80 Hz), 7.84 (2H, d, J=8.78 Hz), 8.13 (4H, s)

ESI MASS (m/z)(Positive): 518.2 (M$^+$+Na)

Preparation 169

A mixture of 4-(1-cyclohexyl-4-piperidyl)benzonitrile (0.68 g), thiosemicarbazide (0.58 g) and trifluoroacetic acid (3.5 ml) in toluene (7 ml) was stirred for 7 hours at 70° C. After being cooled to room temperature, the solvent was evaporated in vacuo. Then the residue was dissolved in tetrahydrofuran and poured into water. The solution was adjusted to pH 8 with 1N aqueous sodium hydroxide. The resulting precipitate was collected by filtration and washed with water and isopropyl ether to give 5-[4-(1-cyclohexyl-4-piperidyl)phenyl]-1,3,4-thiadiazol-2-amine trifluroacetate (0.80 g).

IR (KBr): 3296, 2926, 1632, 1514, 1462 cm$^{-1}$

NMR (DMSO-d$_6$, δ): 1.0–1.9 (14H, m), 2.2–2.6 (4H, m), 2.8–3.0 (2H, m), 7.2–7.4 (4H, m), 7.66 (2H, d, J=8.2 Hz)

(+) APCI MASS (m/z): 343.20 (M$^+$+1)

The following compound was obtained according to a similar manner to that of Preparation 169.

Preparation 170

5-[4-[Cis-4-(4-methylcyclohexyl)piperazin-1-yl]phenyl]-1,3,4]thiadiazol-2-ylamine NMR (CDCl$_3$+CD$_3$OD δ): 0.95 (3H, d, J=7.01 Hz), 1.45–1.70 (8H, m), 1.70–1.85 (1H, m), 2.15–2.30 (1H, m), 2.65–2.80 (4H, m), 3.25–3.35 (4H, m), 6.92 (2H, d, J=8.94 Hz), 7.64 (2H, d, J=8.85 Hz)

ESI MASS (m/z)(Positive): 358.4 (M$^+$+1)

Preparation 171

A mixture of 5-[4-(1-cyclohexyl-4-piperidyl)phenyl]-1,3,4-thiadiazol-2-amine trifluoroacetate (0.78 g) and ethyl 4-(bromoacetyl)benzoate (0.6 g) in ethanol (15 ml) was stirred for 5 hours at 80° C. After being cooled to room temperature, the reaction mixture was poured into isopropyl ether. The resulting precipitate was collected by filtration, washed with isopropyl ether and added to a solution of trifluoroacetic acid (1.5 ml) in xylene (15 ml). Then a mixture was stirred for 3 hours at 130° C. After being cooled to room temperature, the reaction mixture was poured into isopropyl ether. The resulting precipitate was collected by filtration and washed with isopropyl ether to give ethyl 4-[2-[4-(1-cyclohexyl-4-piperidyl)phenyl]imidazo[2,1-b][1,3,4]thiadiazol-6-yl]benzoate trifluroacetate (0.45 g).

IR (KBr): 2941, 1701, 1676, 1610, 1471, 1279, 1200, 1180, 1132 cm$^{-1}$

NMR (DMSO-d$_6$, δ): 1.0–2.2 (17H, m), 2.8–3.4 (4H, m), 3.4–3.6 (2H, m), 3.8–4.5 (2H, m), 7.2–8.1 (8H, m), 8.94 (1H, s), 9.16 (1H, br s)

ESI MASS (m/z)(Positive): 515.3 (M$^+$+1)

The following compound was obtained according to a similar manner to that of Preparation 171.

Preparation 172

Ethyl 4-[2-[4-[cis-4-(4-methylcyclohexyl)-1-piperazinyl]phenyl]imidazo[2,1-b][1,3,4]thiadiazol-6-yl]benzoate bis (trifluoroacetate)

NMR (CDCl$_3$+CD$_3$OD, δ): 1.00 (3H, d, J=7.13 Hz), 1.42 (3H, t, J=7.11 Hz), 1.50–2.10 (10H, m), 2.90–3.20 (4H, m), 3.55–3.80 (4H, m), 4.39 (2H, q, J=7.12 Hz), 6.97 (2H, d, J=8.89 Hz), 7.78 (2H, d, J=8.78 Hz), 8.10 (2H, d, J=8.42 Hz), 8.11 (1H, s)

ESI MASS (m/z)(Positive): 529.7 (M$^+$+1)

Preparation 173

To a solution of benzyl 4-(trans-4-cyclohexylcyclohexyl)-1-piperazinecarboxylate (4 g) in ethanol (40 ml) and dioxane (40 ml) was added 10% palladium on carbon (0.8 g), and hydrogen gas at atmosphere pressure for 7 hours. To the reaction mixture was added dichloromethane (40 ml). The reaction mixture was filtered, and the filtrate was concentrated by evaporation under reduced pressure to give 1-(trans-4-cyclohexylcyclohexyl)piperazine (1.56 g).

IR (KBr): 1446, 1140, 835 cm$^{-1}$

NMR (CDCl$_3$, δ): 0.75–1.35 (12H, m), 1.5–2.25 (9H, m), 2.54 (4H, t, J=4.8 Hz), 2.89 (4H, t, J=4.8 Hz)

MASS (m/z): 251 (M$^+$+1)

The following compound was obtained according to a similar manner to that of Preparation 173.

Preparation 174

1-(Trans-4-tert-butylcyclohexyl)piperazine

IR (KBr): 1450, 1365, 1140 cm$^{-1}$

NMR (CDCl$_3$, δ): 0.84 (9H, s), 0.8–1.35 (5H, m), 1.7–2.25 (5H, m), 2.54 (4H, t, J=4.8 Hz), 2.89 (4H, t, J=4.9 Hz)

MASS (m/z): 225 (M$^+$+1)

Preparation 175

To a mixture of cesium carbonate (2.54 g), palladium(II) acetate (62 mg) and 2,2'-bis(diphenylphosphino)-1,1'-binaphthyl (260 mg) in toluene (6 ml) was successively added methyl 4'-trifluoromethylsulfonyloxy-1,1'-biphenyl-4-carboxylate (1 g) and 1-(trans-4-cyclohexylcyclohexyl)-piperazine (835 mg) in stream of nitrogen. The mixture was stirred at ambient temperature for 45 minutes and at 110° C. for further 23 hours. After cooling to room temperature, water and dichloromethane was added to the reaction mixture. The resulting precipitate was collected by filtration and washed with water and dried to give methyl 4'-[4-(trans-4-cyclohexylcyclohexyl)-1-piperazinyl]-1,1'-biphenyl-4-carboxylate (684.8 g).

NMR (CDCl$_3$, δ): 0.8–2.4 (21H, m), 2.65–2.8 (4H, m), 3.2–3.4 (4H, m), 3.93 (3H, s), 6.99 (2H, d, J=8.8 Hz), 7.55 (2H, d, J=8.9 Hz), 7.62 (2H, d, J=8.4 Hz), 8.06 (2H, d, J=8.3 Hz)

MASS (m/z): 461 (M$^+$+1)

The following compounds [Preparations 176 to 179] were obtained according to a similar manner to that of Preparation 175.

Preparation 176

Methyl 4'-[4-(Trans-4-tert-butylcyclohexyl)-1-piperazinyl]-1,1'-biphenyl-4-carboxylate NMR (CDCl$_3$, δ): 0.86 (9H, s), 0.9–1.4 (5H, m), 1.75–2.4 (5H, m), 2.75 (4H, t, J=4.9 Hz), 3.28 (4H, t, J=4.9 Hz), 3.93 (3H, s), 7.00 (2H, d, J=8.8 Hz), 7.56 (2H, d, J=8.7 Hz), 7.62 (2H, d, J=8.4 Hz), 8.06 (2H, d, J=8.3 Hz)

MASS (m/z): 435 (M$^+$+1)

Preparation 177 tert-Butyl 4-(4'-methoxycarbonyl-1,1'-biphenyl-4-yl)-1-piperazinecarboxylate

NMR (CDCl$_3$, δ): 1.49 (9H, s), 3.15–3.25 (4H, m), 3.55–3.65 (4H, m), 3.93 (3H, s), 6.99 (2H, d, J=6.8 Hz), 7.5–7.65 (4H, m), 8.06 (2H, d, J=6.8 Hz)

MASS (m/z): 396 (M$^+$+23)

Preparation 178

Methyl 4'-[4-(4-methoxyphenyl)-1-piperazinyl]-1,1'-biphenyl-4-carboxylate

NMR (CDCl$_3$, δ): 3.2–3.35 (4H, m), 3.4–3.5 (4H, m), 3.79 (3H, s), 3.93 (3H, s), 6.8–7.1 (6H, m), 7.5–7.7 (4H, m), 8.07 (2H, d, J=8.3 Hz)

MASS (m/z): 403 (M$^+$+1)

Preparation 179

Methyl 4'-[4-(4,4-dimethylcyclohexyl)-1-piperazinyl]-1,1'-biphenyl-4-carboxylate NMR (CDCl$_3$, δ): 0.92 (6H, s), 1.1–1.85 (8H, m), 2.1–2.3 (1H, m), 2.7–2.85 (4H, m), 3.2–3.4 (4H, m), 3.93 (3H, s), 7.00 (2H, d, J=8.8 Hz), 7.56 (2H, d, J=8.8 Hz), 7.62 (2H, d, J=8.4 Hz), 8.06 (2H, d, J=8.4 Hz)

MASS (m/z): 407 (M$^+$+1)

Preparation 180

To a solution of 2-(hydroxymethyl)-1,3-propanediol (3.0 g) and dimethoxymethyl)benzene (6.36 ml) in DMF (50 ml) was added D-10-camphorsulfonic acid (1.31 g), and the mixture was stirred at ambient temperature overnight. To a reaction mixture were added triethylamine (1.18 ml) and water (150 ml) and the solution was extracted twice with ethyl acetate (150 ml). The extracts were washed with saturated aqueous sodium chloride, dried over magnesium sulfate and evaporated in vacuo. The resulting residue was chromatographed on silica gel (200 ml) eluting with a mixture of hexane and ethyl acetate (1:1 v/v). The fractions containing the object compound were collected and evaporated under reduced pressure to give (2-phenyl-1,3-dioxan-5-yl)methanol (4.51 g).

NMR (CDCl$_3$, δ): 3.43, 3.46 (1H, each s), 3.68–3.79 (2H, m), 4.00, 4.04 (1H, each s), 4.10–4.27 (3H, m), 5.41, 5.51 (1H, each s), 7.30–7.50 (5H, m)

Preparation 181

To a solution of (2-phenyl-1,3-dioxan-5-yl)methanol (2.0 g) in dichloromethane (40 ml) were added pyridinium chlorochromate (11.6 g) and molecular seaves 4A powder (5.0 g) with stirring and the mixture was stirred at ambient temperature for 5 hours. To a reaction mixture was added dichloromethane (100 ml) and the insoluble material was filtered off with celite and the filtrates were washed in turn with water, saturated aqueous sodium hydrogen carbonate and saturated aqueous sodium chloride, dried over magnesium sulfate and evaporated in vacuo to give 2-phenyl-1,3-dioxane-5-carbaldehyde (0.52 g). This compound was immediately used as the starting compound for the next step.

Preparation 182

Anhydrous cerium(III) chloride (10.0 g) was added to THF (100 ml) with stirring under ice-cooling and a mixture was stirred at ambient temperature overnight and then cooled in an ice bath. A solution of cyclohexyl magnesium chloride (2M solution in diethyl ether) (20.3 ml) was dropwise added to the mixture with stirring on ice bath (keeping the temperature below 6° C.). To the mixture was added dropwise a solution of tert-butyl 4-oxo-1-piperidinecarboxylate (5.38 g) in THF (25 ml) and the mixture was stirred at 0–6° C. for 1 hour. 10% aqueous acetic acid (100 ml) was added to the reaction mixture and extracted twice with ethyl acetate (100 ml). The extracts were collected, washed with saturated aqueous sodium chloride, dried over magnesium sulfate and evaporated in vacuo. The resulting residue was chromatographed on silica gel (400 ml) eluting with a mixture of n-hexane and ethyl acetate (2:1 v/v). The fractions containing the desired compound were collected and evaporated under reduced pressure to give tert-butyl 4-cyclohexyl-4-hydroxy-1-piperidinecarboxylate (7.27 g).

NMR (CDCl$_3$, δ): 0.90–1.30 (5H, m), 1.46 (10H, s), 1.49–1.90 (9H, m), 2.90–3.15 (2H, m), 3.50–3.70 (1H, m), 3.80–4.00 (2H, m)

ESI MASS (m/z)(Positive): 306.3 (M$^+$+Na)

Preparation 183

To a solution of tert-butyl 4-cyclohexyl-4-hydroxy-1-piperidinecarboxylate (7.26 g) in DMF (70 ml) was added sodium hydride (60% in oil) (2.05 g) with stirring under ice-cooling. The mixture was stirred at ambient temperature for 1 hour. To the suspension was added methyl iodide (4.79 ml) and the mixture was stirred at ambient temperature overnight. The reaction mixture was poured into ice-water (300 ml) and extracted three times with ethyl acetate (200 ml). The extracts were collected, washed twice with saturated aqueous sodium chloride, dried over magnesium sulfate and evaporated in vacuo. The resulting residue was chromatographed on silica gel (400 ml) eluting with a mixture of n-hexane and ethyl acetate (4:1 v/v). The fractions containing the desired compound were collected and evaporated under reduced pressure to give tert-butyl 4-cyclohexyl-4-methoxy-1-piperidinecarboxylate (6.77 g).

NMR (CDCl$_3$, δ): 0.85–1.30 (5H, m), 1.45 (10H, s), 1.46–1.85 (9H, m), 2.85–3.10 (2H, m), 3.12 (3H, s), 3.80–3.95 (2H, m)

ESI MASS (m/z)(Positive): 320.3 (M$^-$+Na)

Preparation 184

To a solution of tert-butyl 4-cyclohexyl-4-methoxy-1-piperidinecarboxylate (2.04 g) in a mixture of dichloromethane (40 ml) and anisole (5.2 ml) was dropwise added trifluoroacetic acid (10.6 ml) with stirring under ice-cooling. The mixture was stirred at ambient temperature for 1 hour and then concentrated in vacuo. The resulting residue was azeotropically distilled three times with toluene (20 ml) and dried in vacuo. The obtained residue was dissolved in DMSO (20 ml). To the solution were added ethyl 4-fluorobenzoate (2.60 g) and potassium carbonate (2.84 g) and the mixture was stirred at 140° C. overnight. The reaction mixture was poured into water (100 ml) and extracted twice with ethyl acetate (80 ml). The extracts were collected, washed with saturated aqueous sodium chloride, dried over magnesium sulfate and evaporated in vacuo. The resulting residue was chromatographed on silica gel (200 ml) eluting with a mixture of n-hexane and ethyl acetate (9:1 v/v). The fractions containing the desired compound were collected and evaporated under reduced pressure to give ethyl 4-(4-cyclohexyl-4-methoxy-1-piperidyl)benzoate (1.81 g).

NMR (CDCl$_3$, δ): 0.85–1.32 (5H, m), 1.36 (3H, t, J=6.80 Hz), 1.50–1.90 (10H, m), 2.95–3.15 (2H, m), 3.16 (3H, s), 3.55–3.70 (2H, m), 4.32 (2H, q, J=7.12 Hz), 6.86 (2H, d, J=9.12 Hz), 7.90 (2H, d, J=9.08 Hz)

ESI MASS (m/z)(Positive): 368.3 (M$^+$+Na)

The following compound was obtained according to a similar manner to that of Preparation 152.

Preparation 185

4-(4-Cyclohexyl-4-methoxy-1-piperidyl)benzohydrazide

NMR (CDCl$_3$, δ): 0.9–1.9 (15H, m), 3.0–3.2 (2H, m), 3.16 (3H, s), 3.5–3.7 (2H, m), 4.06 (2H, br s), 6.8–7.0 (2H, m), 7.33 (1H, br s), 7.6–7.7 (2H, m)

(+) APCI MASS (m/z)(Positive): 332.40 (M$^+$+1)

The following compound was obtained according to a similar manner to that of Preparation 32.

Preparation 186

Methyl 4-[2-[4-(4-cyclohexyl-4-methoxy-1-piperidyl)benzoyl]hydrazinocarbonyl]benzoate NMR (CDCl$_3$, δ): 0.9–2.0 (15H, m), 3.0–3.2 (2H, m), 3.17 (3H, s), 3.5–3.8 (2H, m), 3.95 (3H, s), 6.8–7.0 (2H, m), 7.6–7.8 (2H, m), 7.8–8.0 (2H, m), 8.0–8.2 (2H, m), 9.1–9.2 (1H, m), 9.5–9.7 (1H, m)

(+) APCI MASS (m/z) (Positive): 494.47 (M$^+$+1)

The following compound was obtained according to a similar manner to that of Preparation 47.

Preparation 187

Methyl 4-[5-[4-(4-cyclohexyl-4-methoxy-1-piperidyl)phenyl]-1,3,4-thiadiazol-2-yl]benzoate ESI MASS (m/z) (Positive): 492.3 (M$^+$+1)

The following compound was obtained according to a similar manner to that of Preparation 82.

Preparation 188

4-[5-[4-(4-Cyclohexyl-4-methoxy-1-piperidyl)phenyl]-1,3,4-thiadiazol-2-yl]benzoic acid NMR (DMSO-d$_6$, δ): 0.8–1.8 (15H, m), 2.9–3.2 (5H, m), 3.6–3.8 (2H, m), 6.9–7.2 (2H, m), 7.7–8.3 (6H, m)

ESI MASS (m/z) (Negative): 476.1 (M$^-$1)

The following compound was obtained according to a similar manner to that of Preparation 112.

Preparation 189

1-4-[5-[4-(4-Cyclohexyl-4-methoxy-1-piperidyl)phenyl]-1,3,4-thiadiazol-2-yl]benzoyloxy-1H-1,2,3-benzotriazole IR (KBr): 2927, 1784, 1603, 1441, 1412, 1234, 1192, 1080, 987 cm$^{-1}$ NMR (CDCl$_3$, δ): 0.9–1.9 (15H, m), 3.0–3.3 (5H, m), 3.5–3.8 (2H, m), 6.9–7.1 (2H, m), 7.4–7.7 (3H, m), 7.90 (2H, d, J=8.9 Hz), 8.1–8.3 (3H, m), 8.3–8.5 (2H, m)

ESI MASS (m/z)(Negative): 476.1 (M$^-$HOBT-1)

The Starting Compounds used and the Object Compounds obtained in the following Examples 1 to 95 are given in the table as below, in which the formulas of the starting compounds are in the upper column, and the formulas of the object compounds are in the lower column, respectively.

| Example No. | Formula |
|---|---|
| 1 | |

| Example No. | Formula |
|---|---|
| | major / minor (chemical structures) |

-continued
| Example No. | Formula |
|---|---|
| 2 | 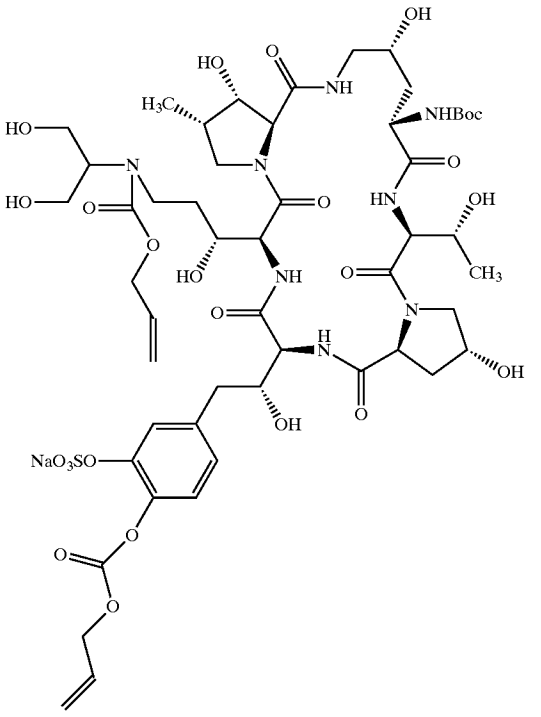 |

| Example No. | Formula |
|---|---|
| |  |

-continued
| Example No. | Formula |
|---|---|
| 3 | 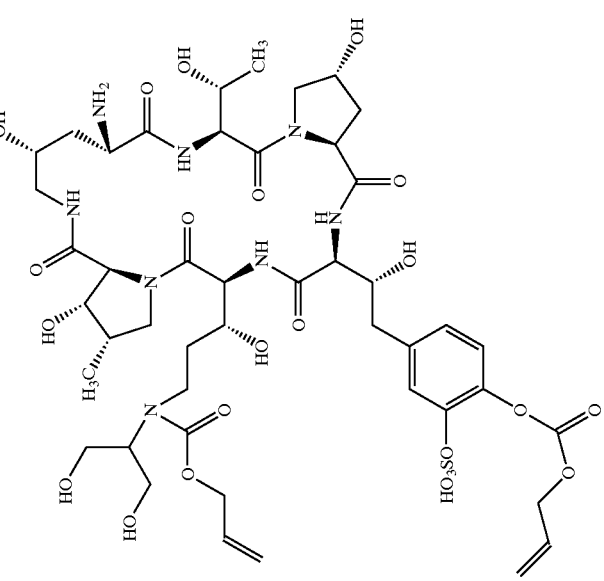 |

-continued
| Example No. | Formula |
|---|---|
| | 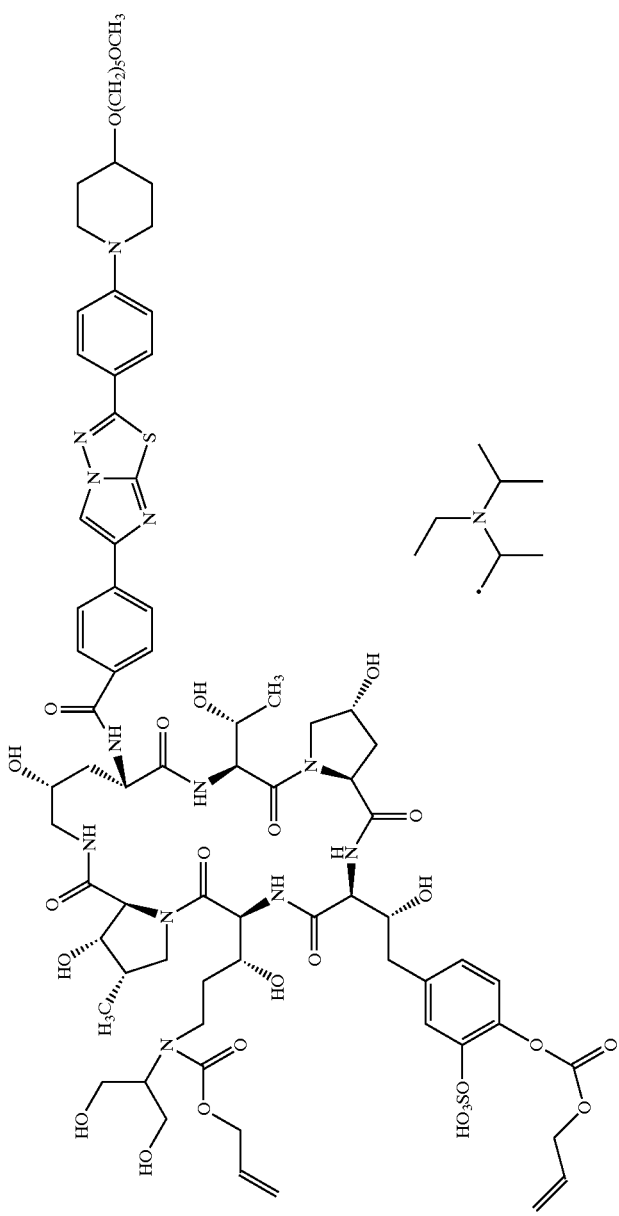 |

-continued
| Example No. | Formula |
|---|---|
| 4 | 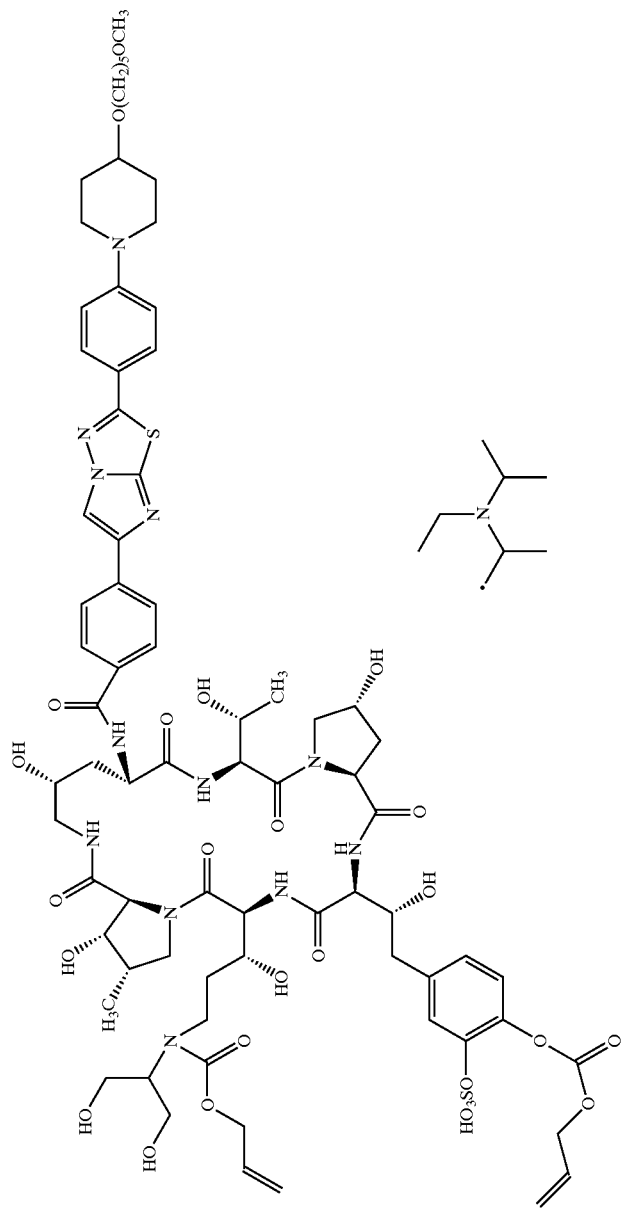 |

-continued
| Example No. | Formula |
|---|---|
| | 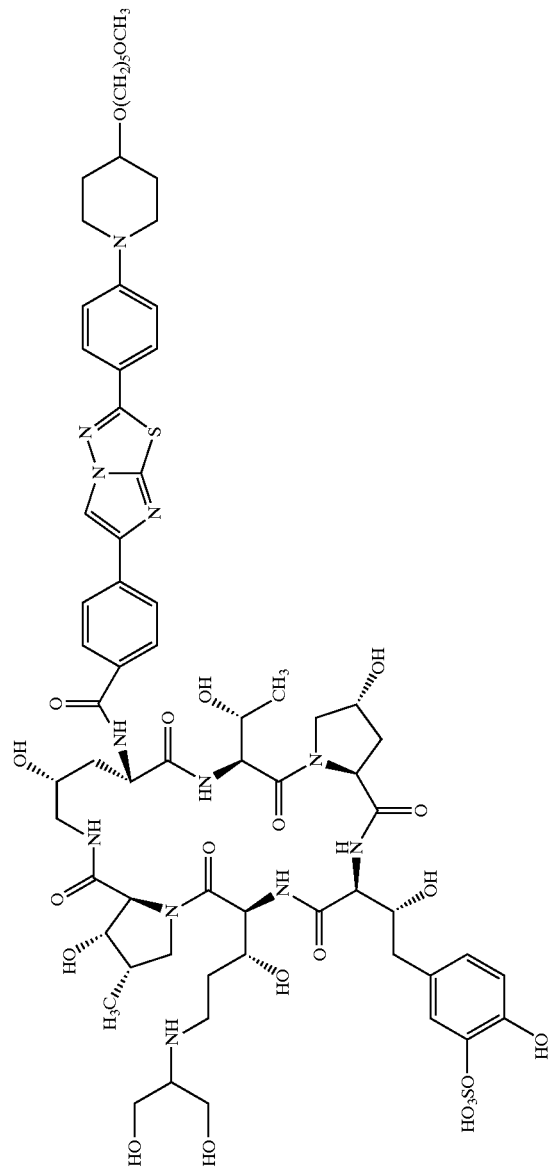 |

| Example No. | Formula |
|---|---|
| 5 | 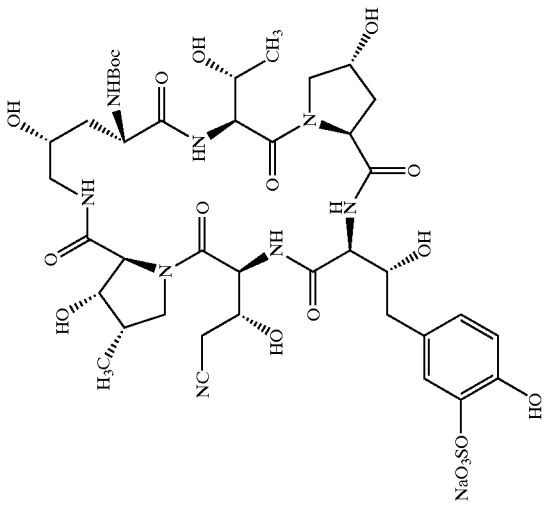 |

| Example No. | Formula |
|---|---|
| 6 | |

| Example No. | Formula |
|---|---|
| | (major and minor isomeric structures shown) |

| Example No. | Formula |
|---|---|
| 7 | -continued |

| Example No. | Formula |
|---|---|
| | -continued |

-continued
| Example No. | Formula |
|---|---|
| 8 | 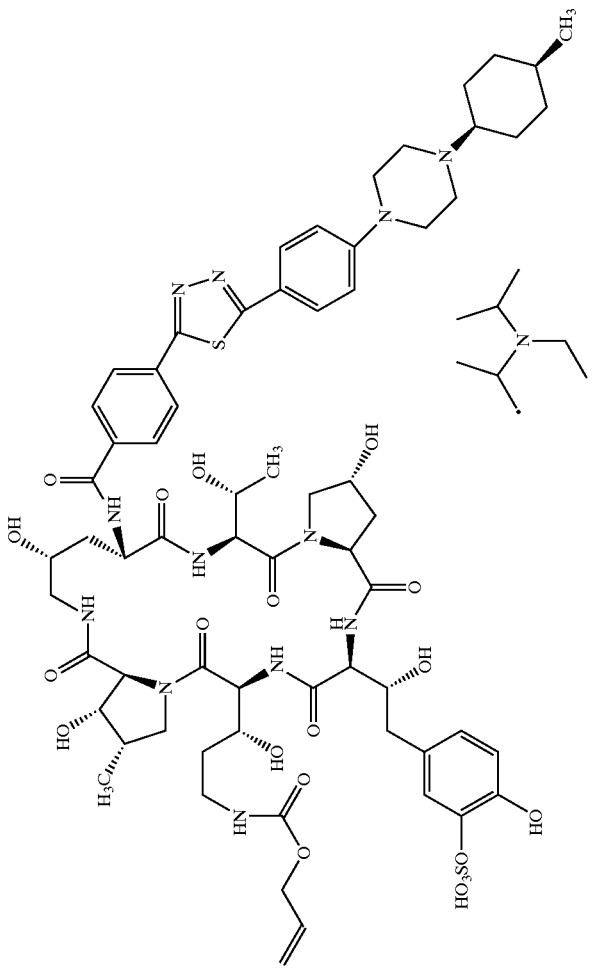 |

| Example No. | Formula |
|---|---|
| | 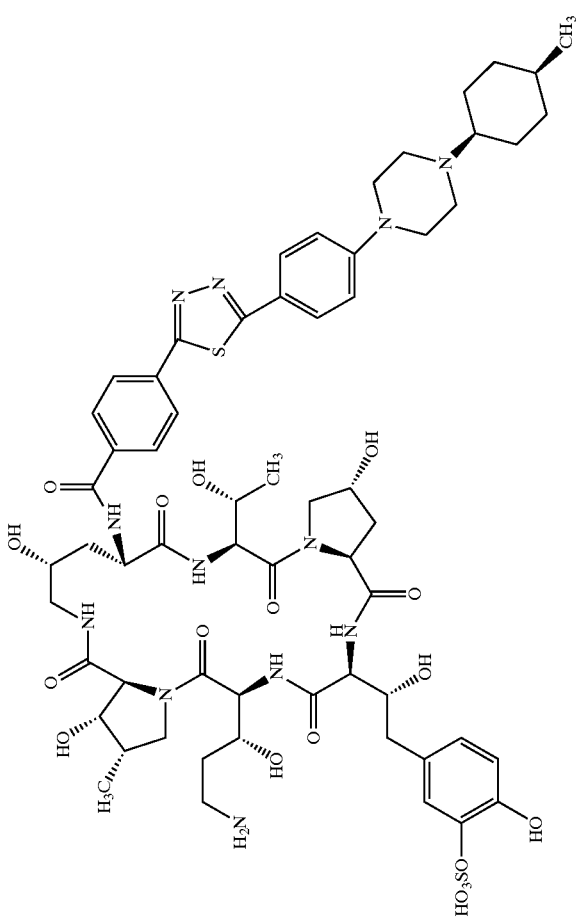 |

| Example No. | Formula |
|---|---|
| 9 | (structure) |

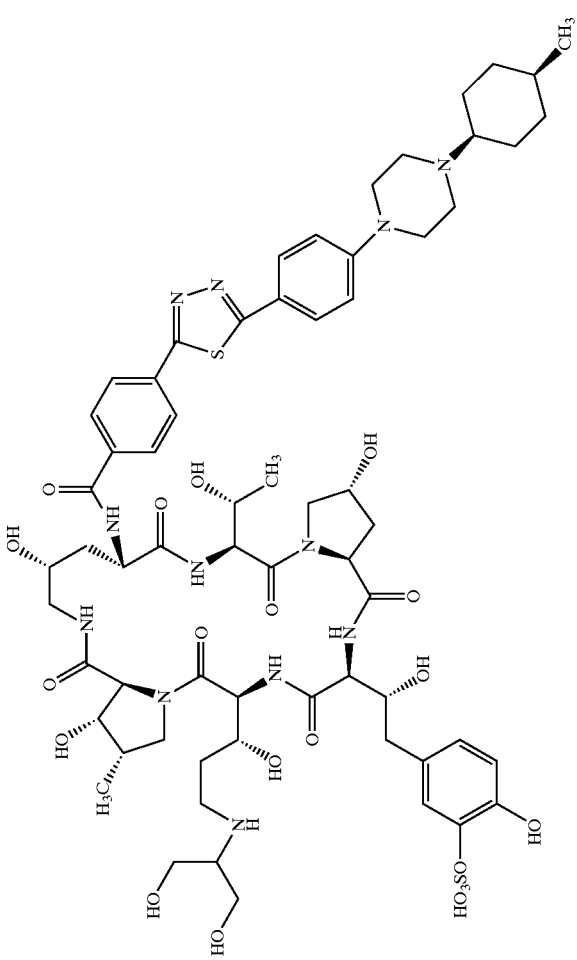

| Example No. | Formula |
|---|---|
| 10 | -continued (structure) |

| Example No. | Formula |
|---|---|
| | 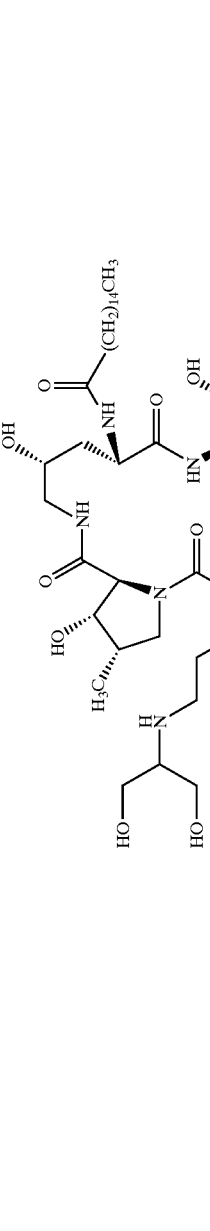 |

| Example No. | Formula |
|---|---|
| 11 | 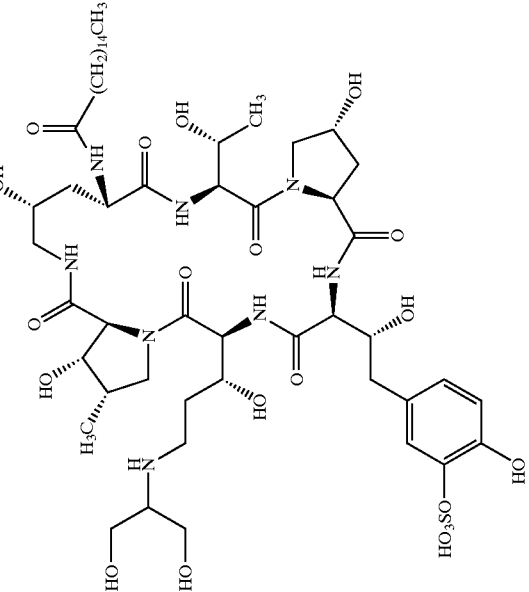 |

| Example No. | Formula |
|---|---|
| | -continued |

| Example No. | Formula |
|---|---|
| 12 | 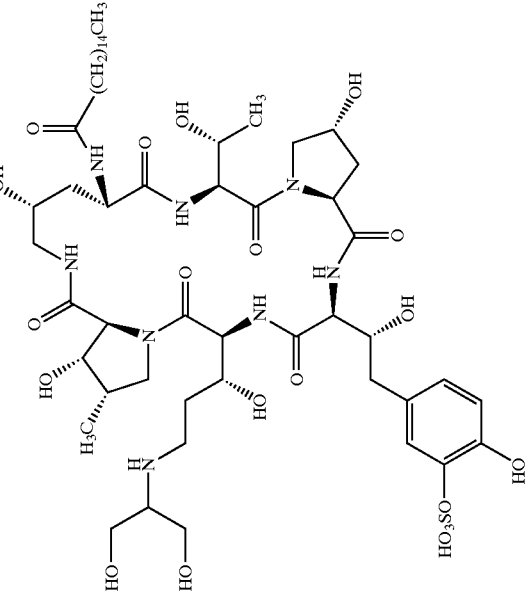 |

| Example No. | Formula |
|---|---|
| | 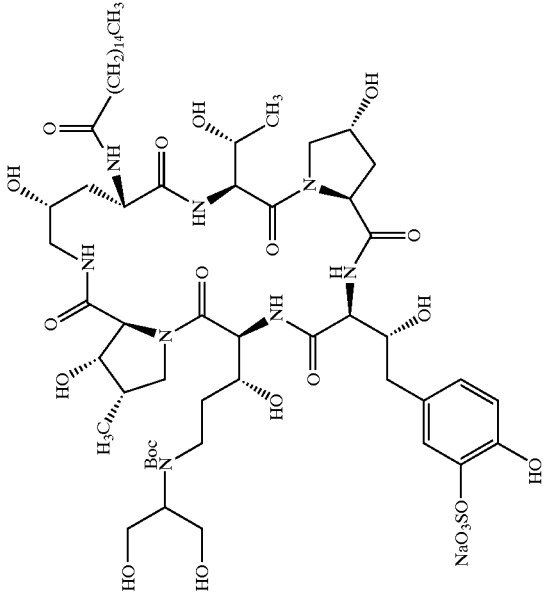 |

-continued
| Example No. | Formula |
|---|---|
| 13 | 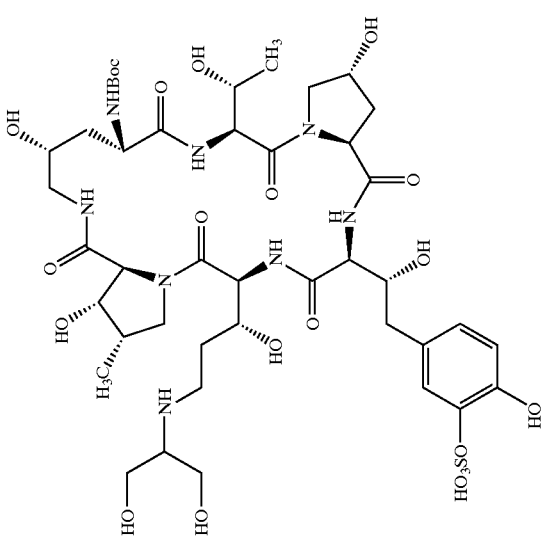 |

| Example No. | Formula |
|---|---|
| | -continued |

-continued
| Example No. | Formula |
|---|---|
| 14 | 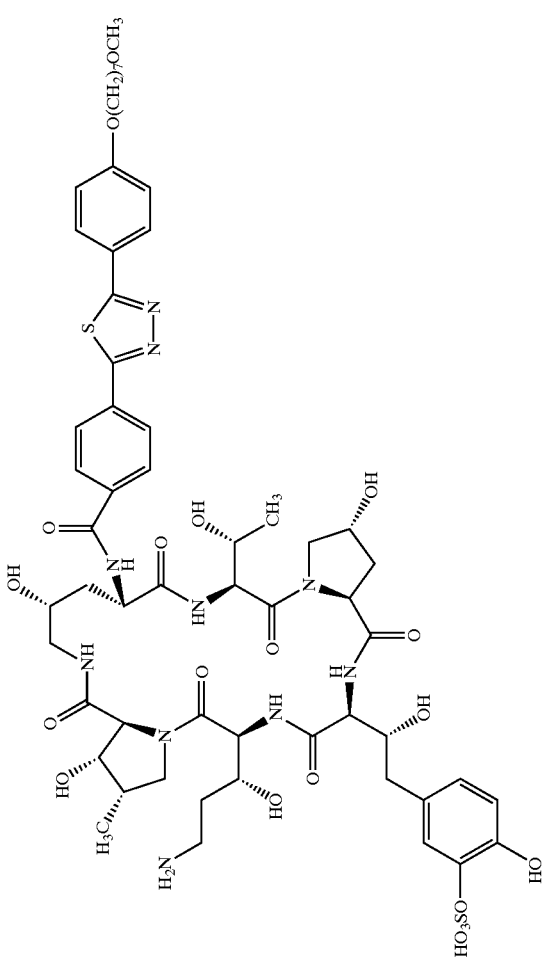 |

| Example No. | Formula |
|---|---|
| | |

| Example No. | Formula |
|---|---|
| 15 | (structure) |

-continued

| Example No. | Formula |
|---|---|
| | |

-continued
| Example No. | Formula |
|---|---|
| 16 | 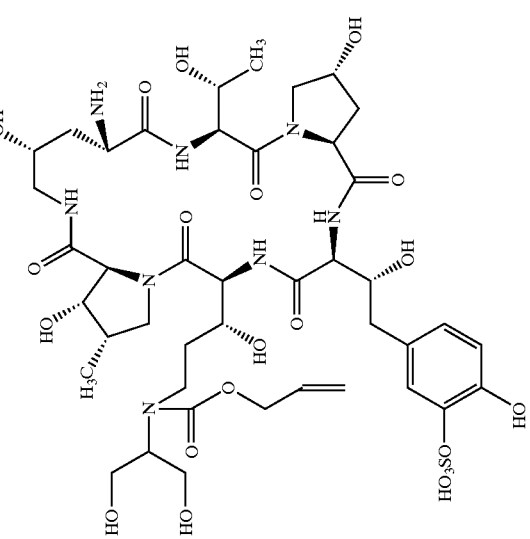 |

| Example No. | Formula |
|---|---|
| | -continued |

-continued
| Example No. | Formula |
|---|---|
| 17 | 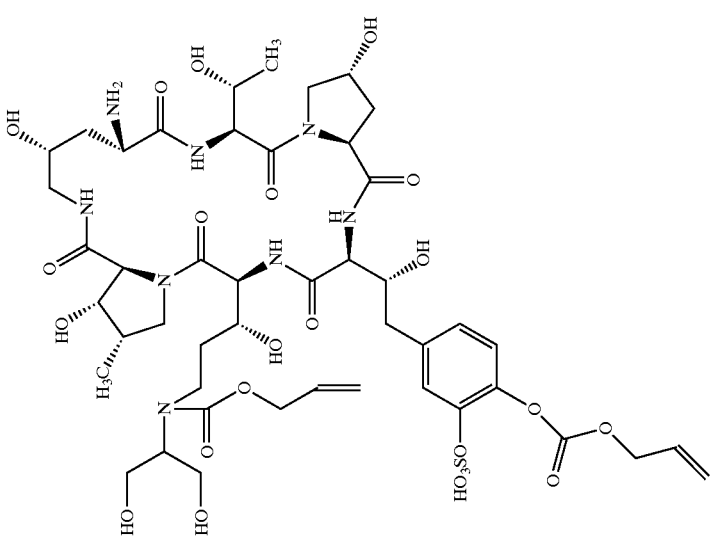 |

-continued
| Example No. | Formula |
|---|---|
| | 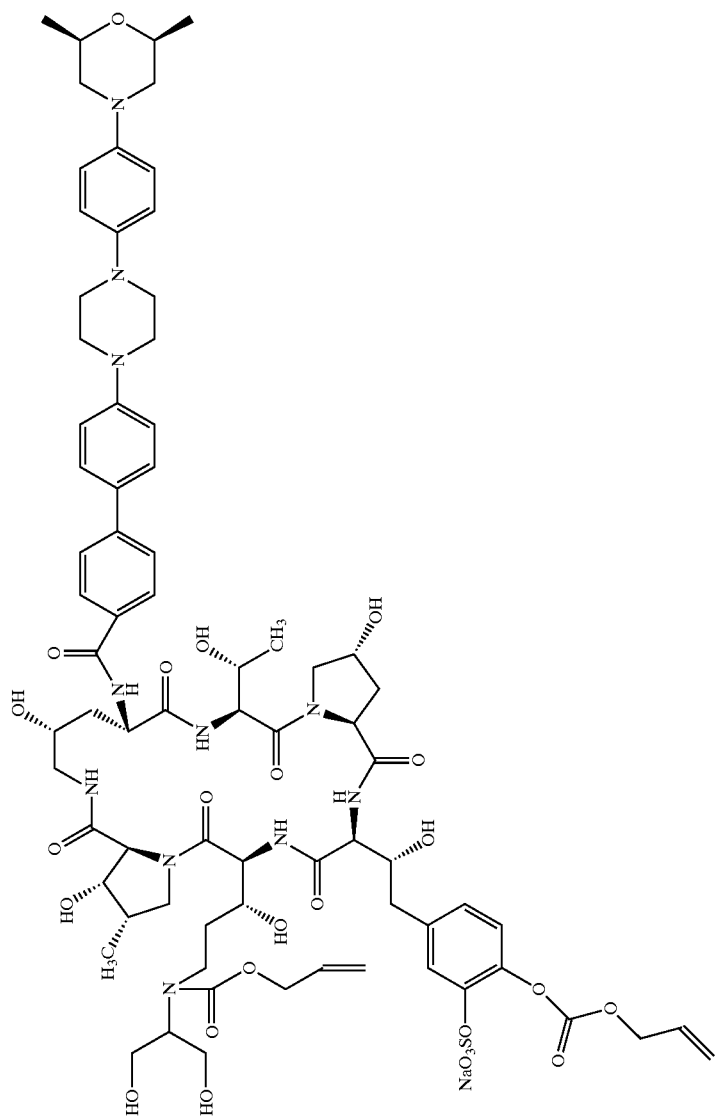 |

| Example No. | Formula |
|---|---|
| 18 | *-continued* chemical structure |

-continued
| Example No. | Formula |
|---|---|
| | 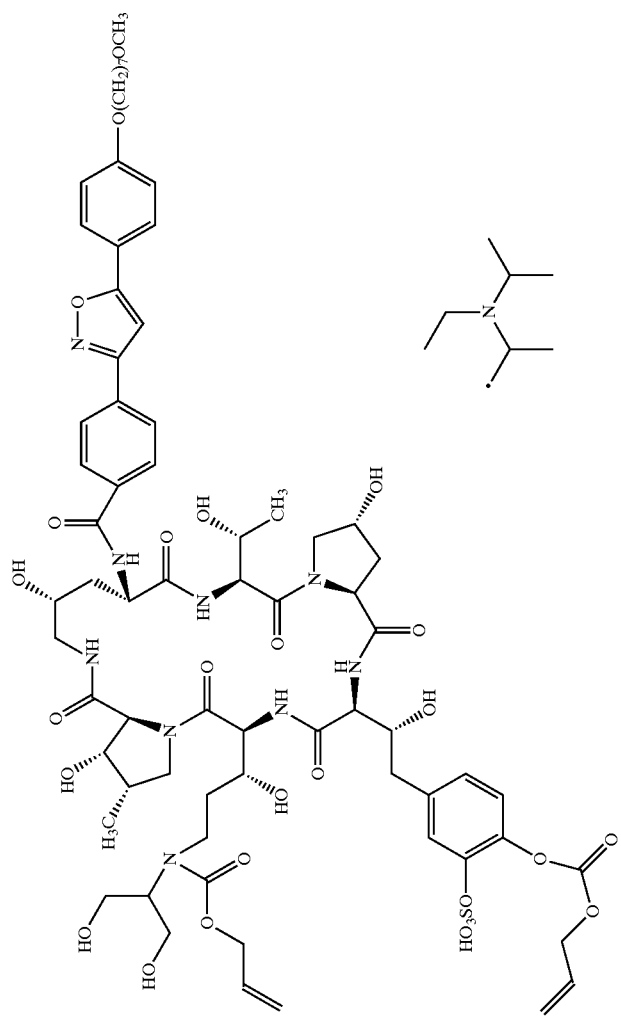 |

-continued
| Example No. | Formula |
|---|---|
| 19 | 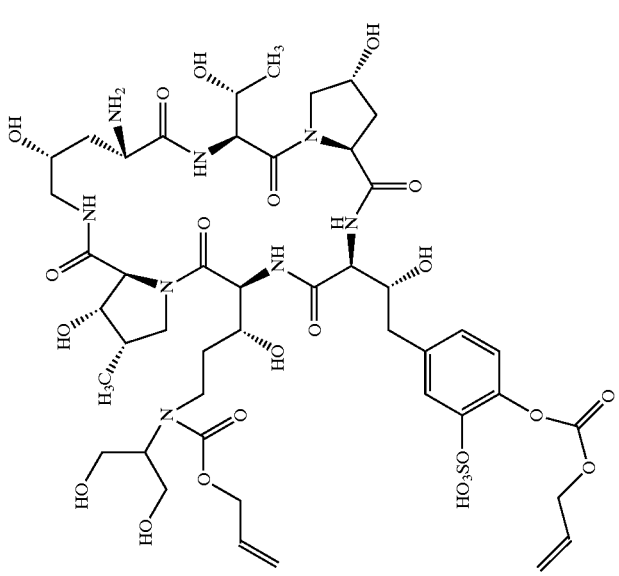 |

| Example No. | Formula |
|---|---|
| | *-continued* chemical structure |

-continued

| Example No. | Formula |
|---|---|
| 20 | |

| Example No. | Formula |
|---|---|
| | -continued |

| Example No. | Formula |
|---|---|
| 21 | 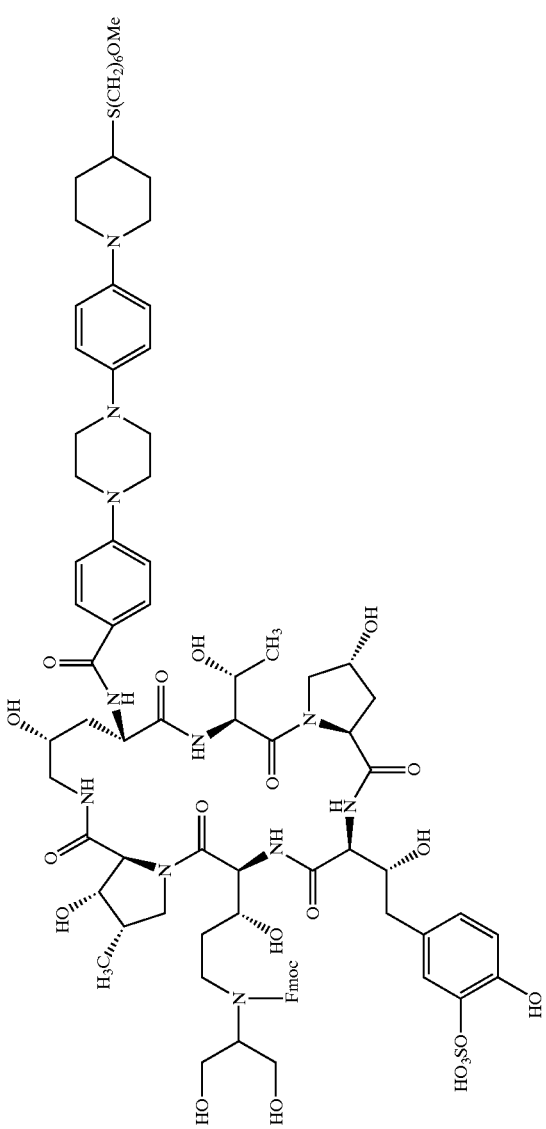 |

-continued
| Example No. | Formula |
|---|---|
| | 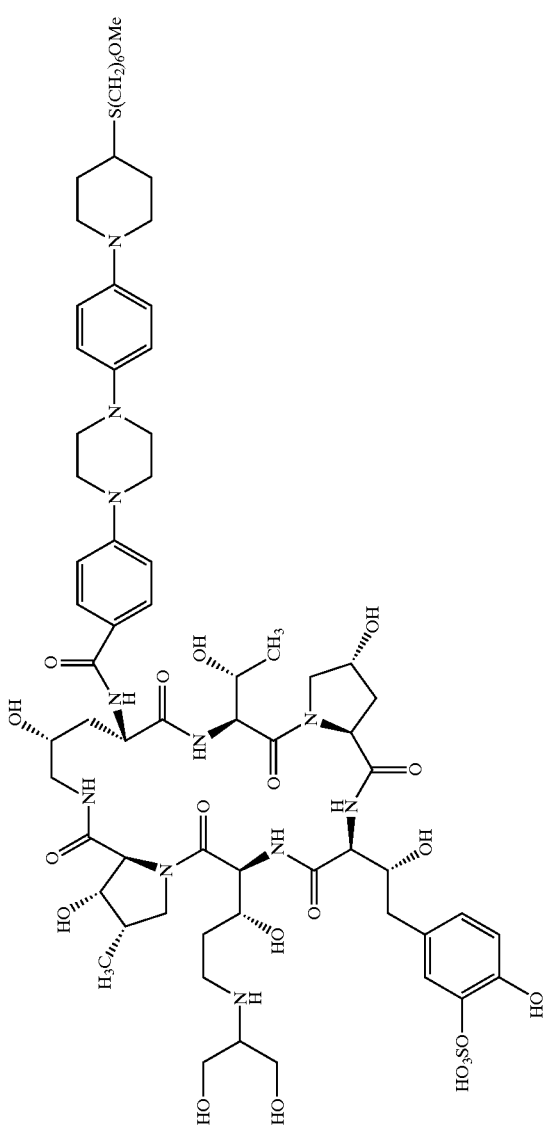 |

-continued
| Example No. | Formula |
|---|---|
| 22 | 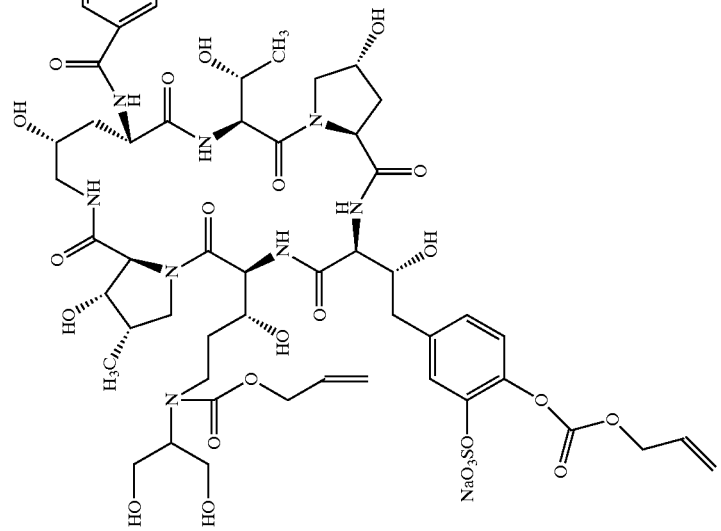 |

| Example No. | Formula |
|---|---|
| | 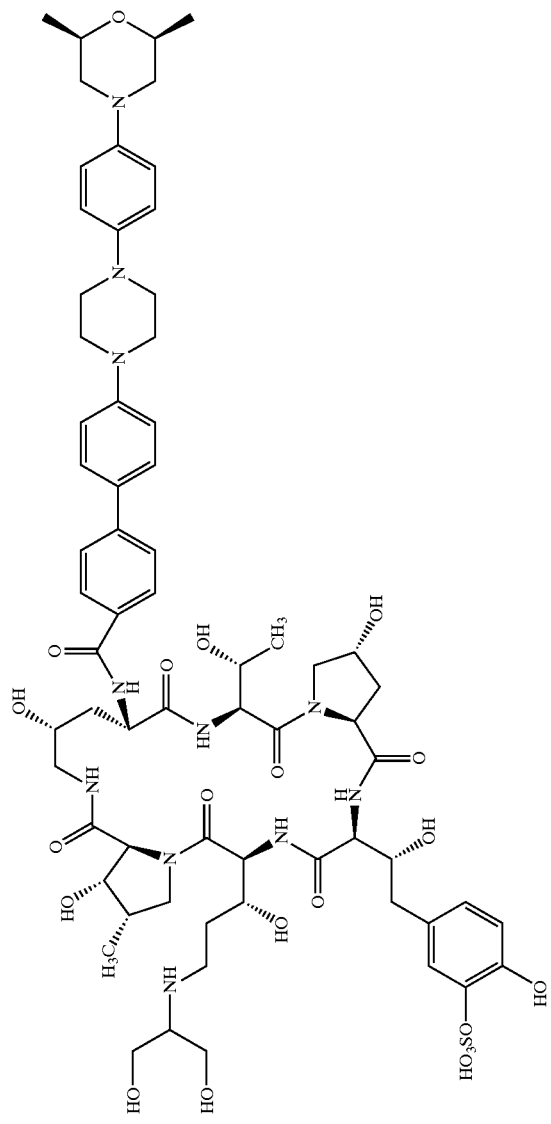 |

| Example No. | Formula |
|---|---|
| 23 | (structure) |

| Example No. | Formula |
|---|---|
| | -continued<br><br>(Chemical structure of a cyclic hexapeptide with the following substituents: an aromatic side chain consisting of a phenyl-thiadiazole-phenyl-O(CH$_2$)$_6$OCH$_3$ group attached via an amide linkage; hydroxyproline residues; a 3-hydroxy-4-hydroxyphenyl group with an HO$_3$SO substituent; and a CH(CH$_2$OH)$_2$ aminomethylene substituent.) |

-continued
| Example No. | Formula |
|---|---|
| 24 | 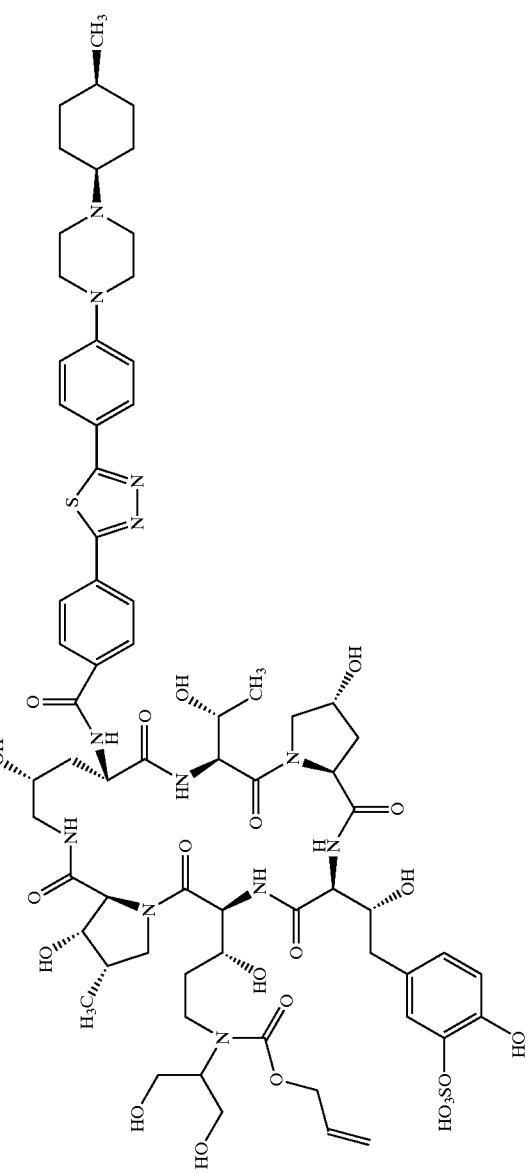 |

| Example No. | Formula |
|---|---|
| | (chemical structure) |

| Example No. | Formula |
|---|---|
| 25 | -continued |

| Example No. | Formula |
|---|---|
| | -continued |

-continued

| Example No. | Formula |
|---|---|
| 26 | (structure) |

-continued

| Example No. | Formula |
|---|---|

-continued
| Example No. | Formula |
|---|---|
| 27 | 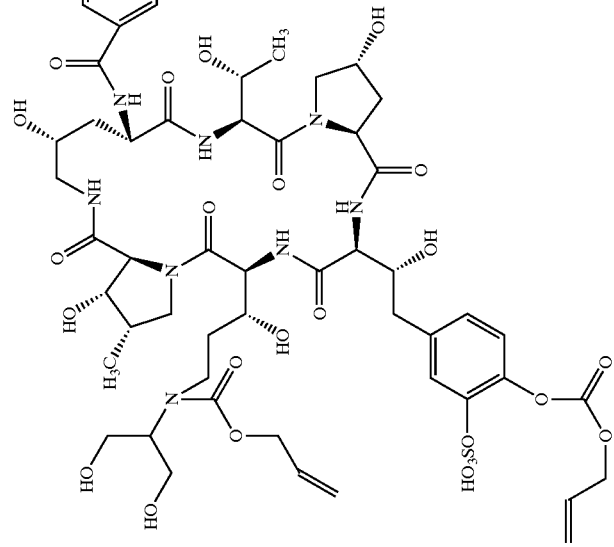 |

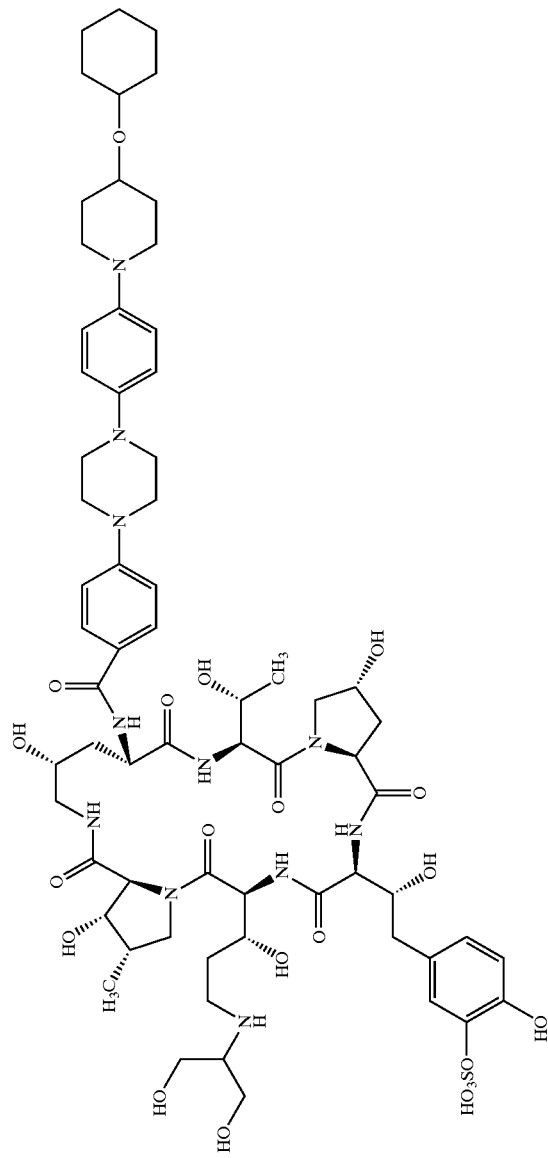

| Example No. | Formula |
|---|---|
| 28 | -continued |

| Example No. | Formula |
|---|---|
| | -continued |

-continued
| Example No. | Formula |
|---|---|
| 29 | 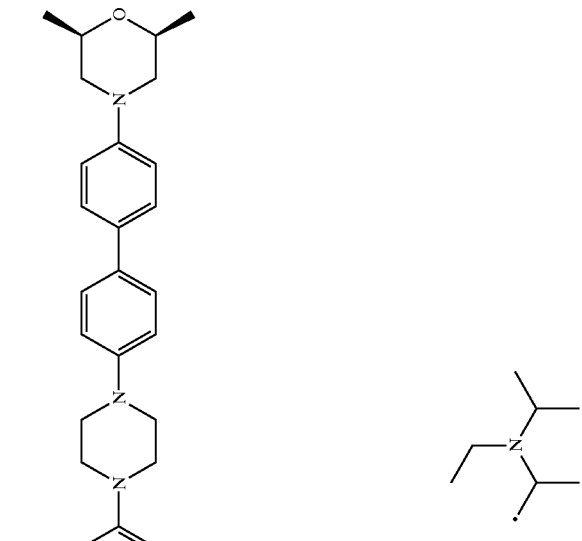 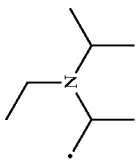 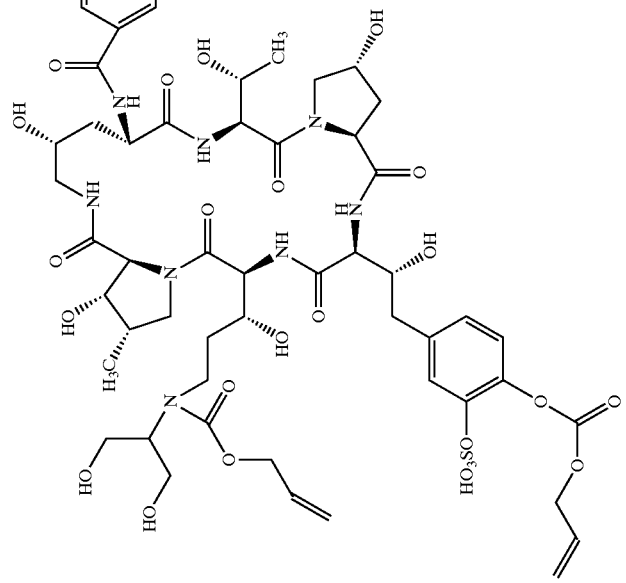 |

-continued
| Example No. | Formula |
|---|---|
| | 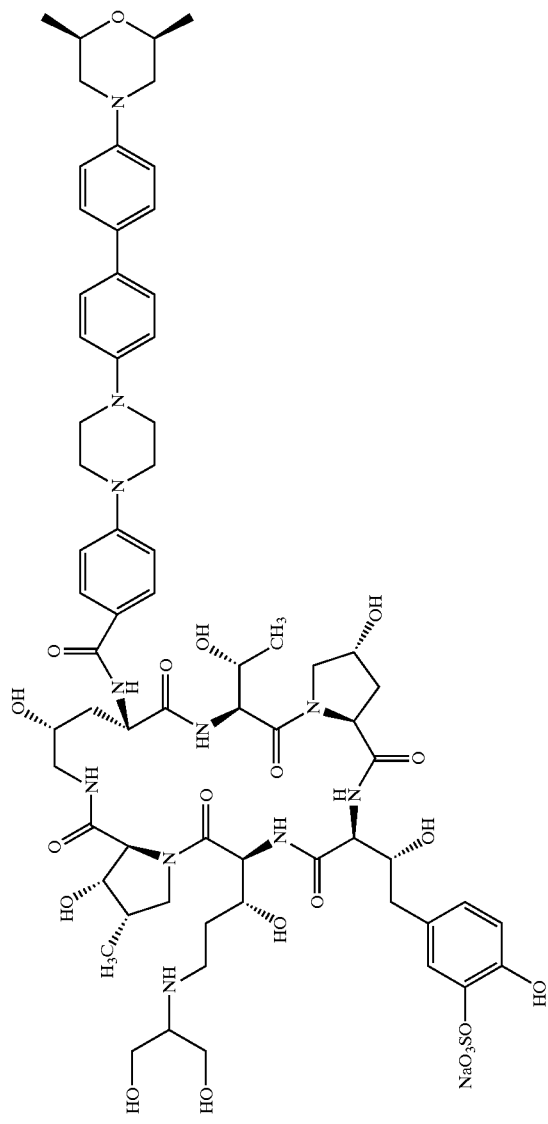 |

-continued
| Example No. | Formula |
|---|---|
| 30 | 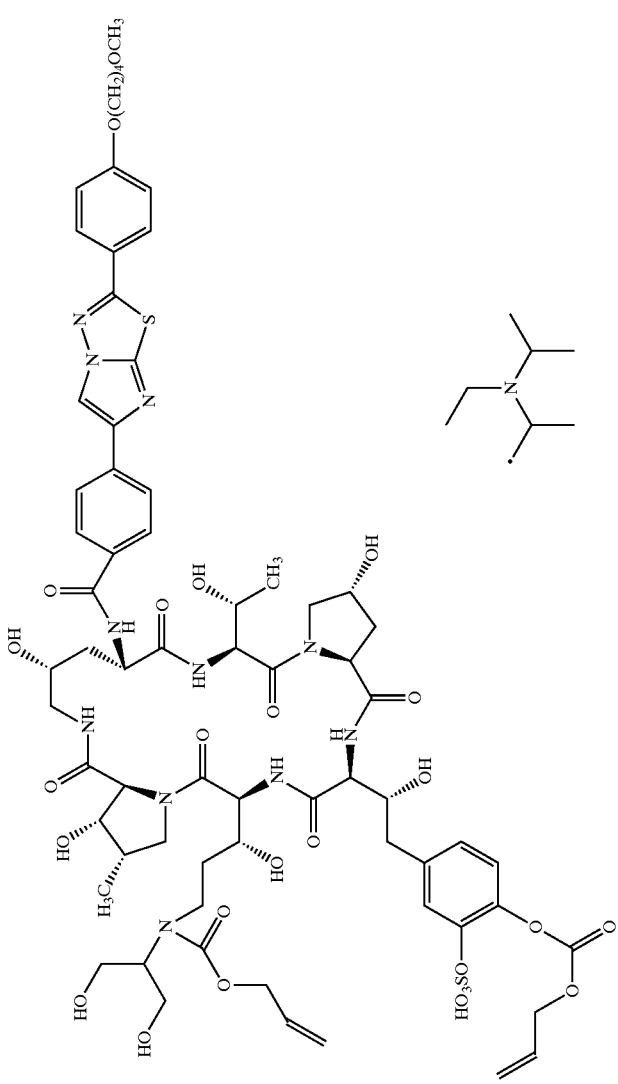 |

-continued
| Example No. | Formula |
|---|---|
| | 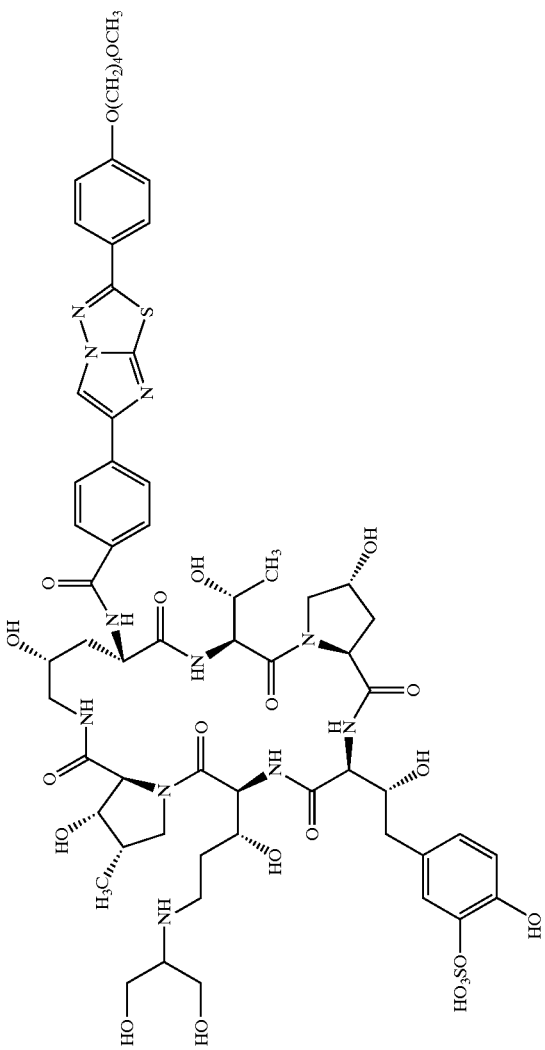 |

| Example No. | Formula |
|---|---|
| 31 | 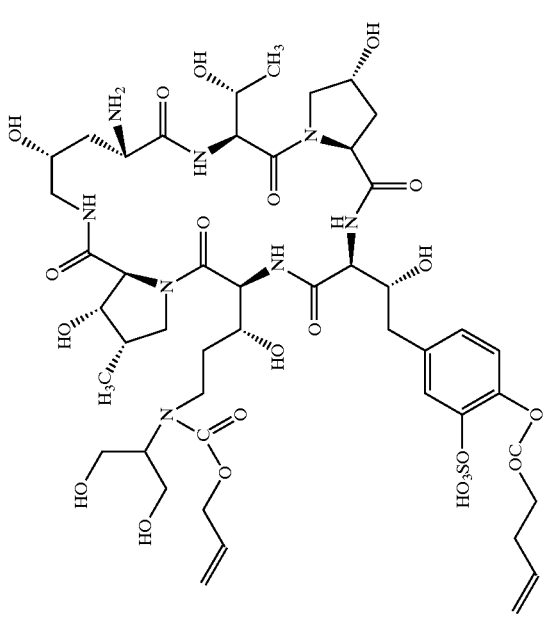 |

| Example No. | Formula |
|---|---|
| |  |

| Example No. | Formula |
|---|---|
| 32 | -continued |

-continued
| Example No. | Formula |
|---|---|
| | 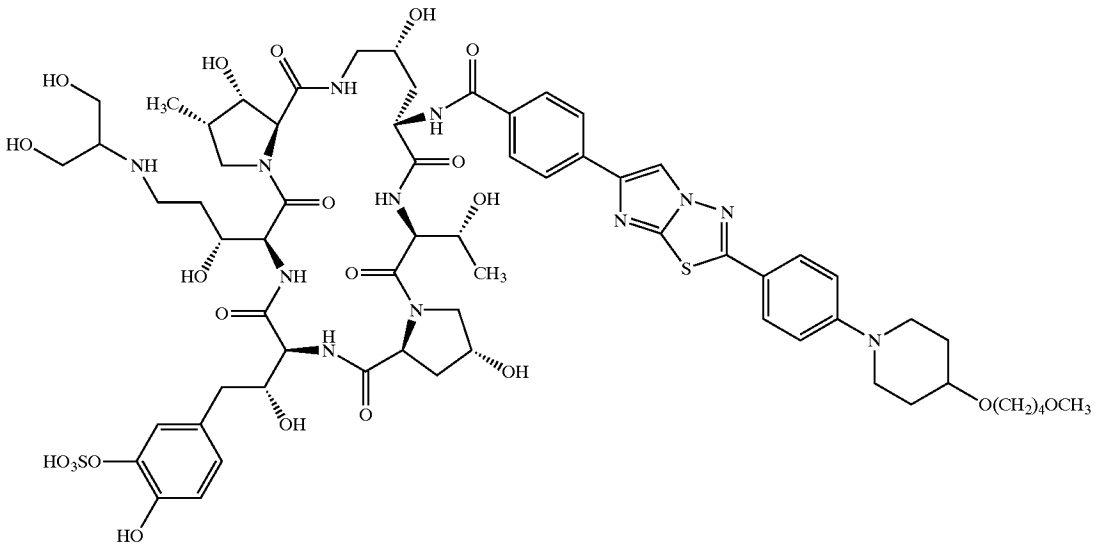 |

| Example No. | Formula |
|---|---|
| 33 | -continued (chemical structure) |

-continued
| Example No. | Formula |
|---|---|
| | 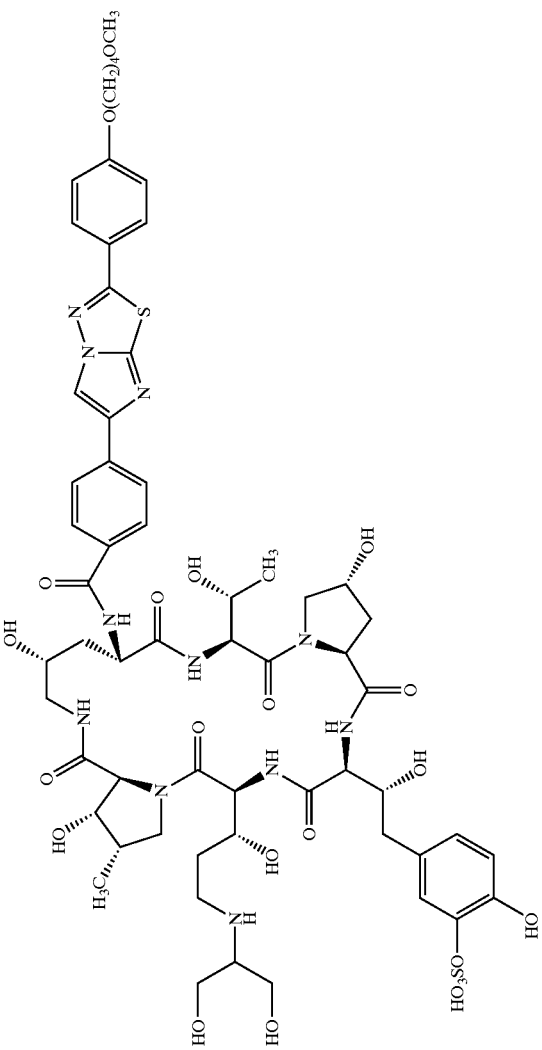 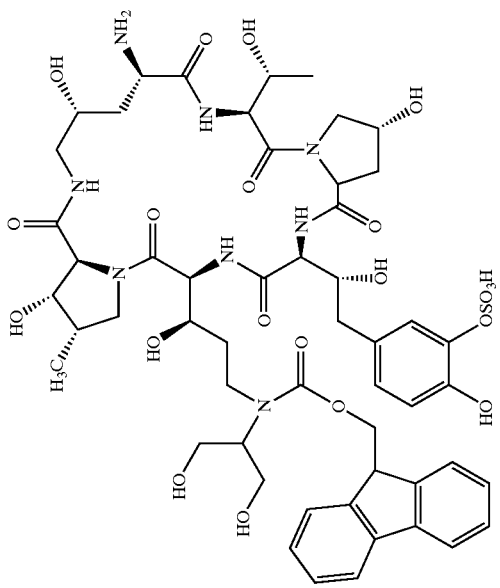 |

-continued
| Example No. | Formula |
|---|---|
| | 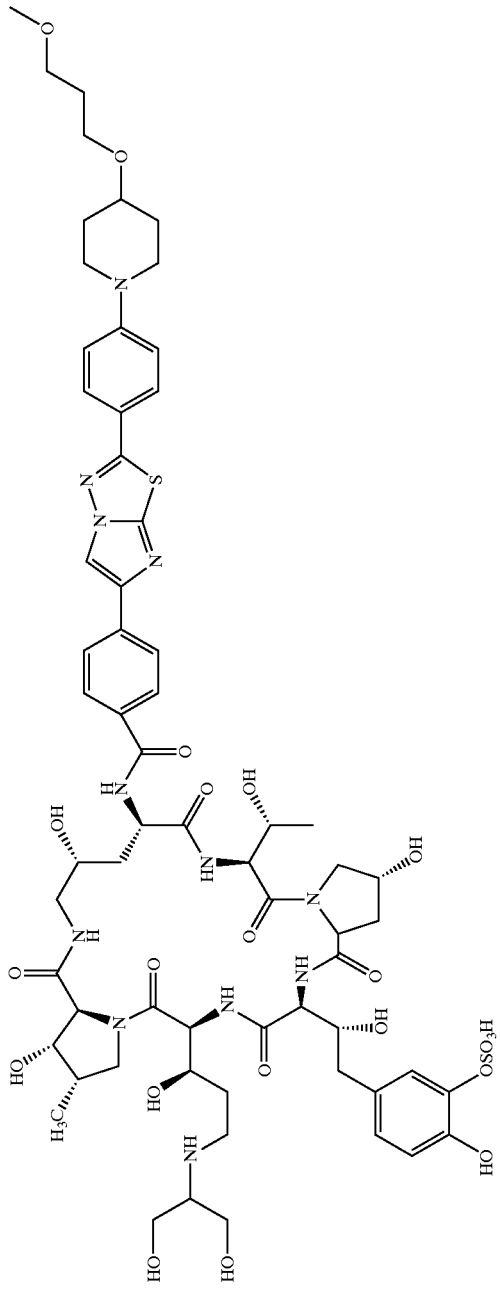 |

| Example No. | Formula |
|---|---|
| 35 | *(structure)* |

| Example No. | Formula |
|---|---|
| | (chemical structure) |

| Example No. | Formula |
|---|---|
| 36 | *(chemical structure)* |

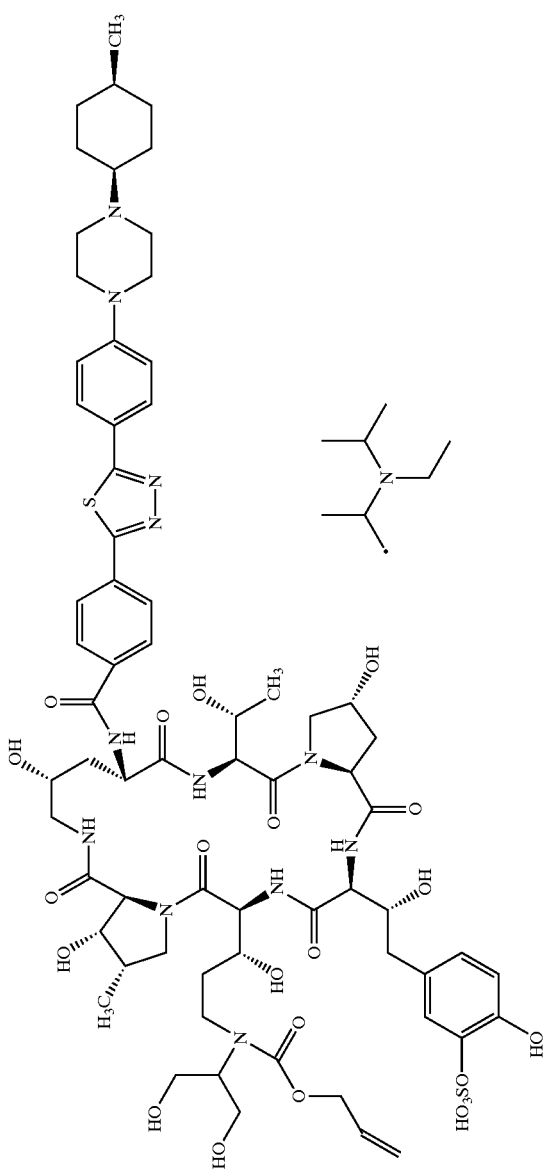

| Example No. | Formula |
|---|---|
| 37 | -continued |

| Example No. | Formula |
|---|---|

-continued
| Example No. | Formula |
|---|---|
| 38 | 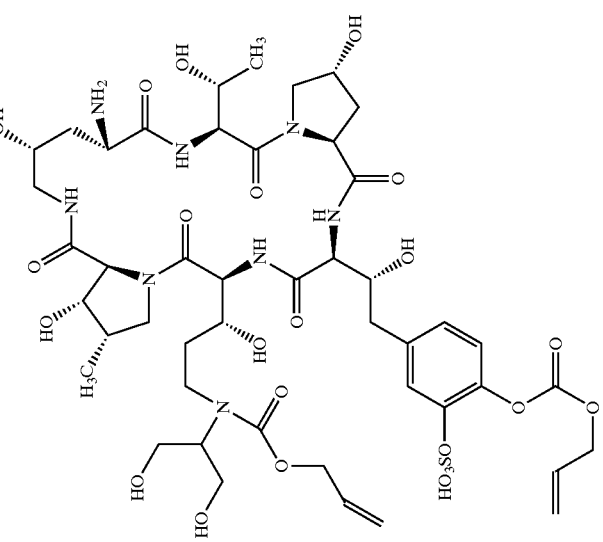 |

| Example No. | Formula |
|---|---|
| | 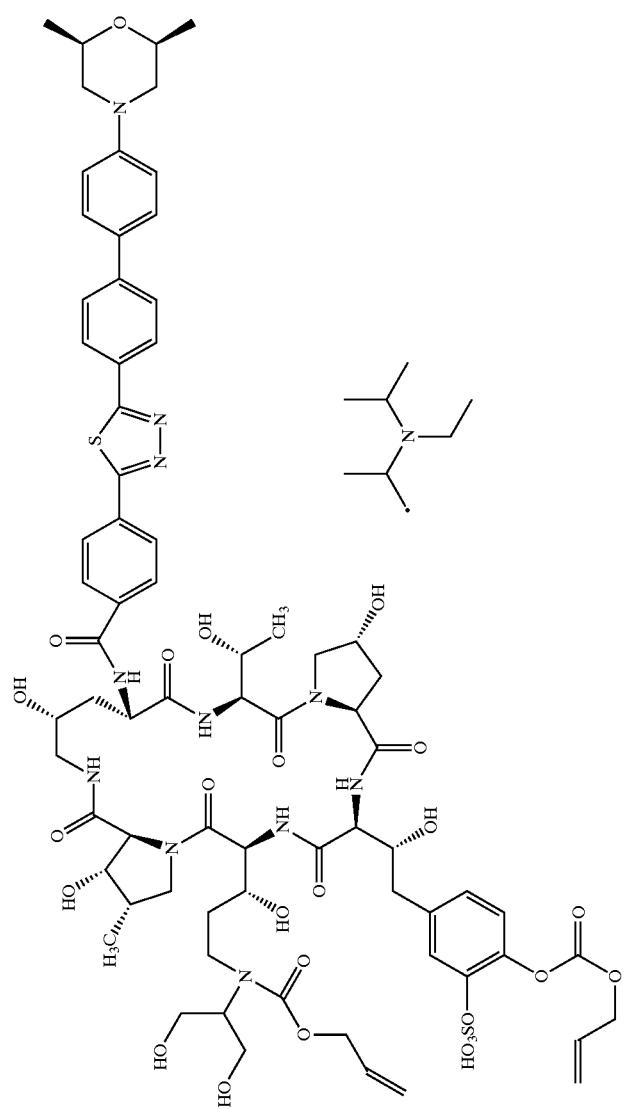 |

| Example No. | Formula |
|---|---|
| 39 | *(chemical structure)* |

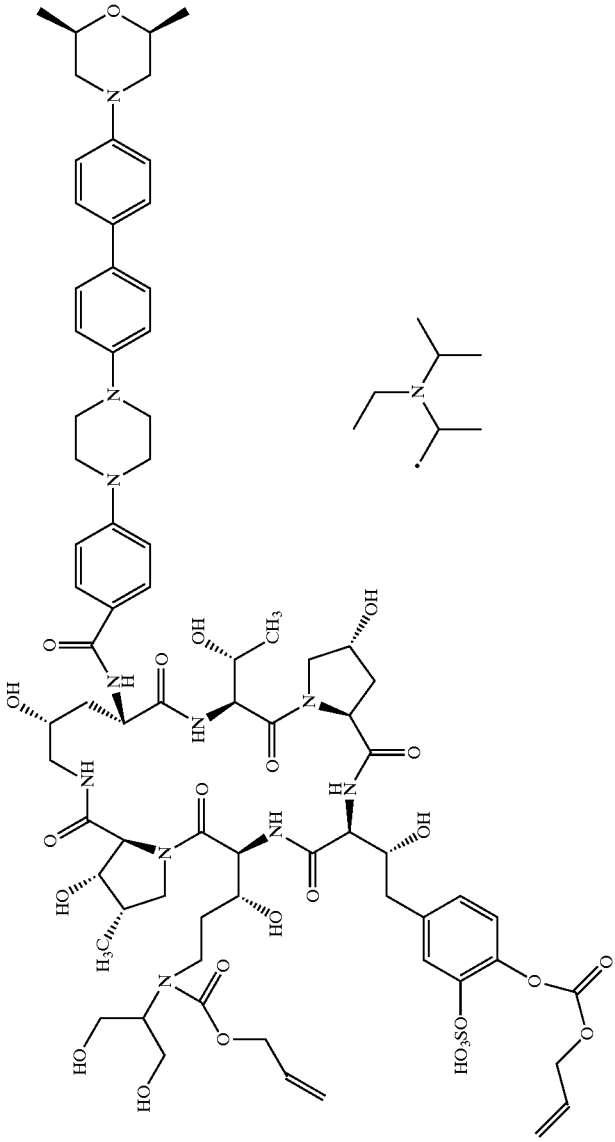

| Example No. | Formula |
|---|---|
| 40 | (structure) |

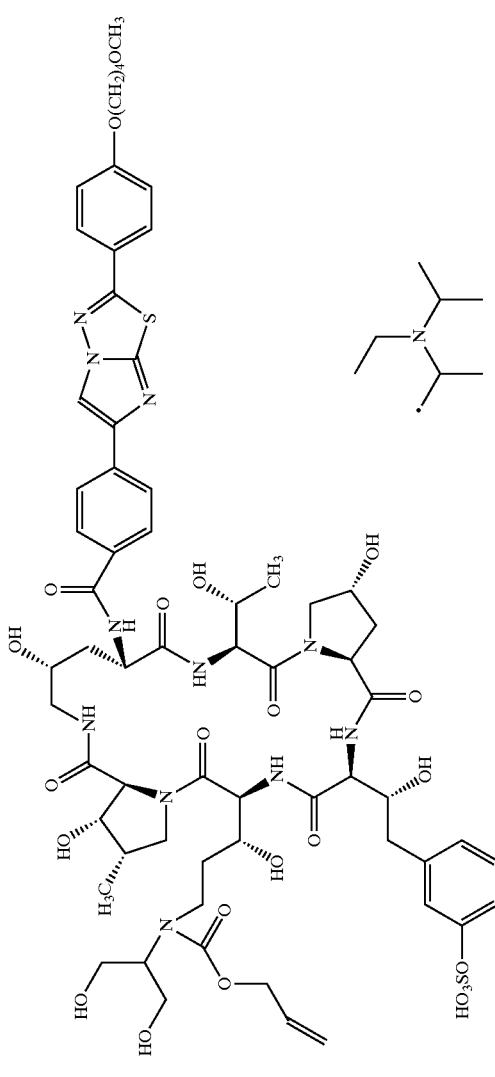

| Example No. | Formula |
|---|---|
| 41 | -continued (chemical structure) |

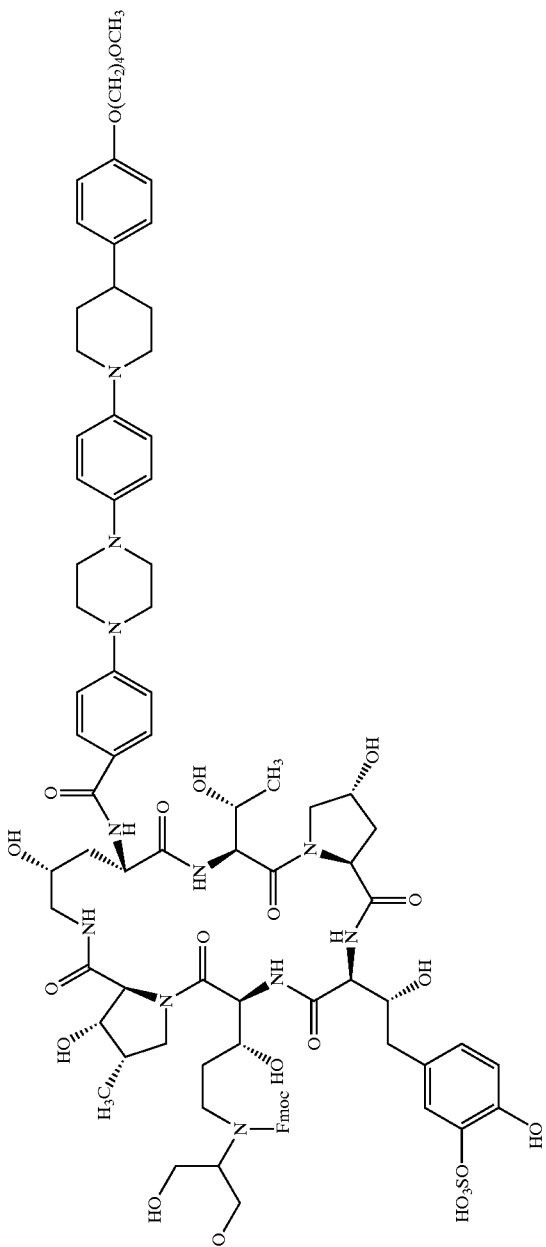

-continued
| Example No. | Formula |
|---|---|
| 42 | 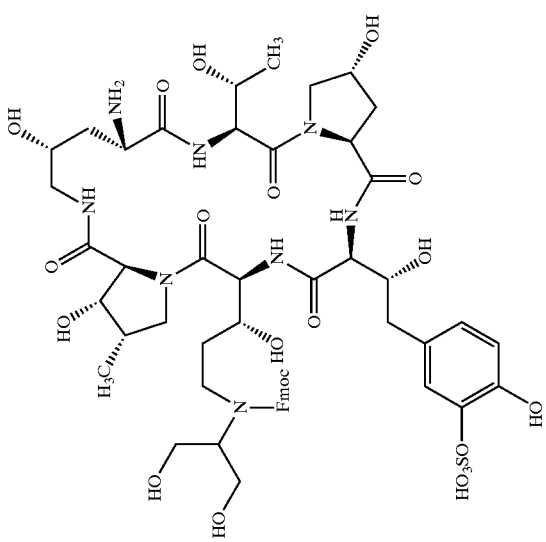 |

| Example No. | Formula |
|---|---|
| | 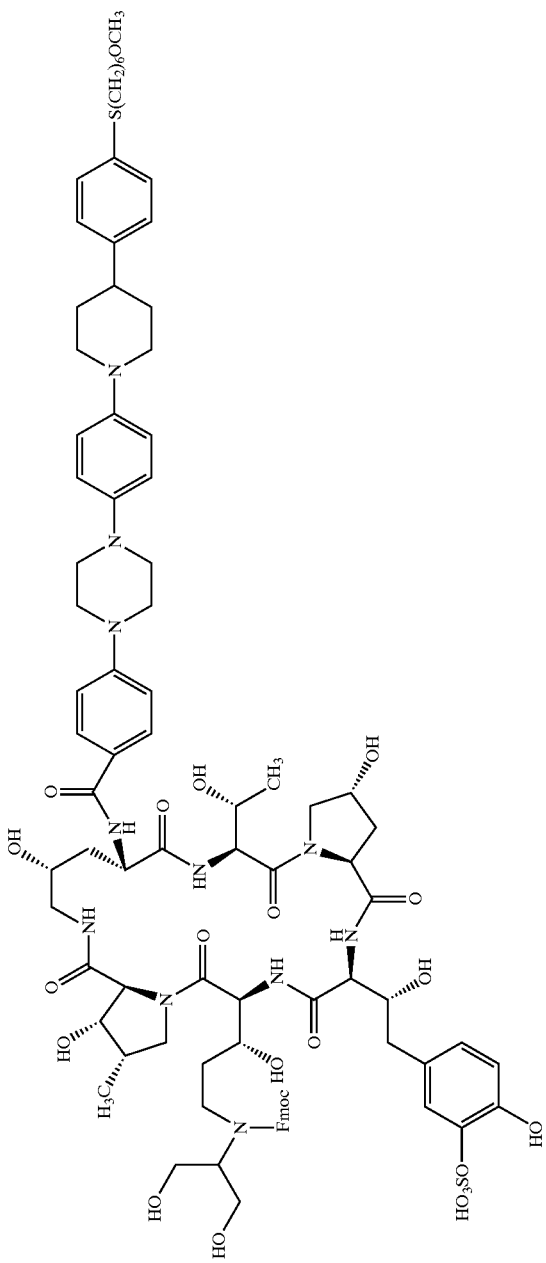 |

| Example No. | Formula |
|---|---|
| 43 | 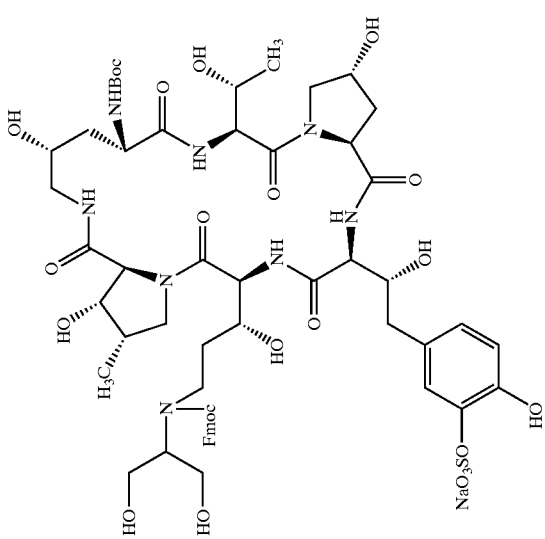 |

| Example No. | Formula |
|---|---|
| | 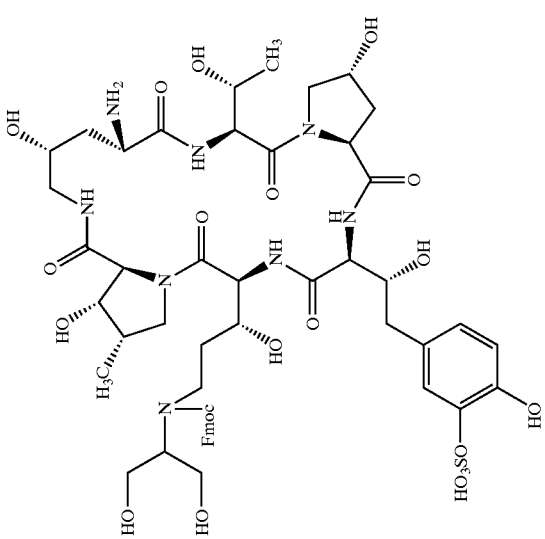 |

-continued
| Example No. | Formula |
|---|---|
| 44 | 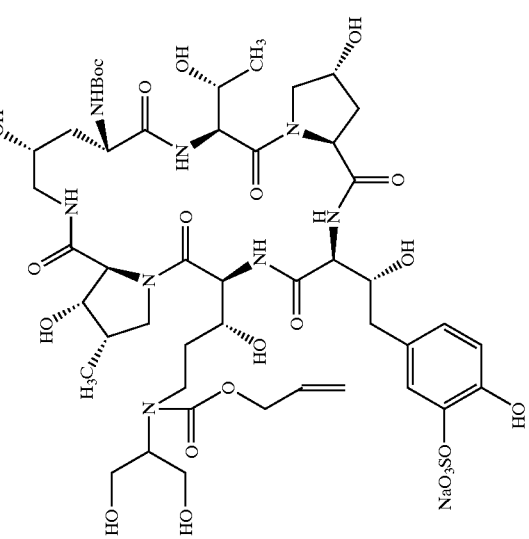 |

| Example No. | Formula |
|---|---|
| | -continued |

| Example No. | Formula |
|---|---|
| 45 | *(chemical structure)* |

| Example No. | Formula |
|---|---|
| | -continued |

-continued
| Example No. | Formula |
|---|---|
| 46 | 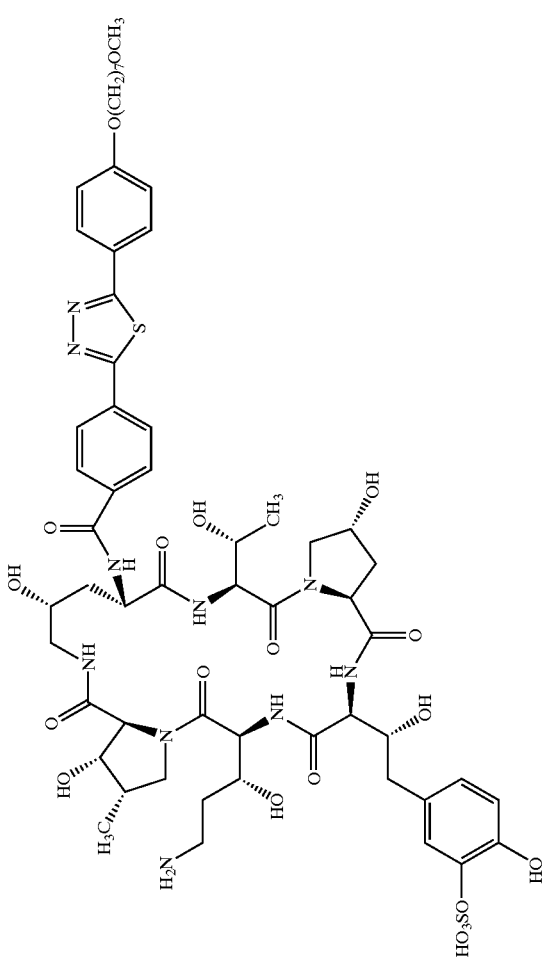 |

| Example No. | Formula |
|---|---|
| | 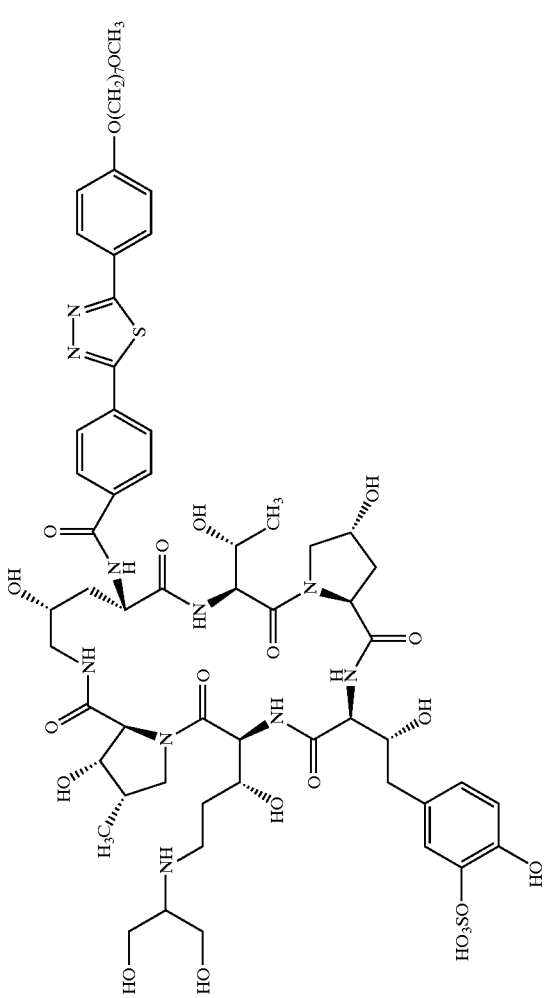 |

-continued
| Example No. | Formula |
|---|---|
| 47 | 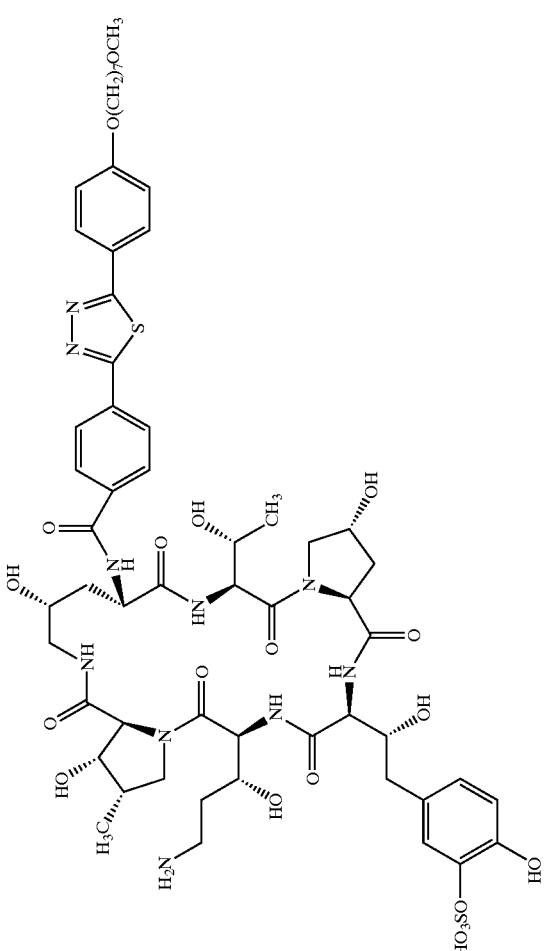 |

| Example No. | Formula |
|---|---|
| | -continued |

-continued
| Example No. | Formula |
|---|---|
| 48 | 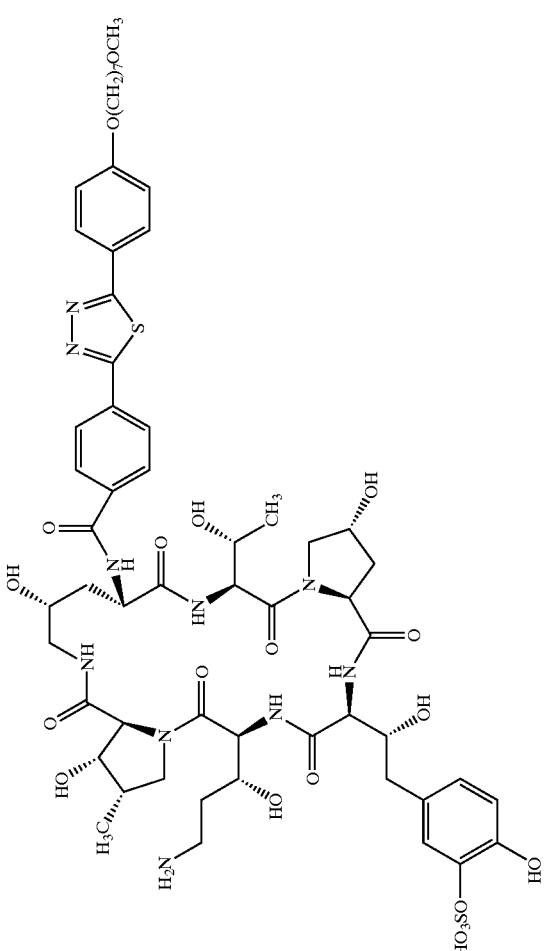 |

-continued

| Example No. | Formula |
|---|---|
| | (chemical structure) |

-continued
| Example No. | Formula |
|---|---|
| 49 | 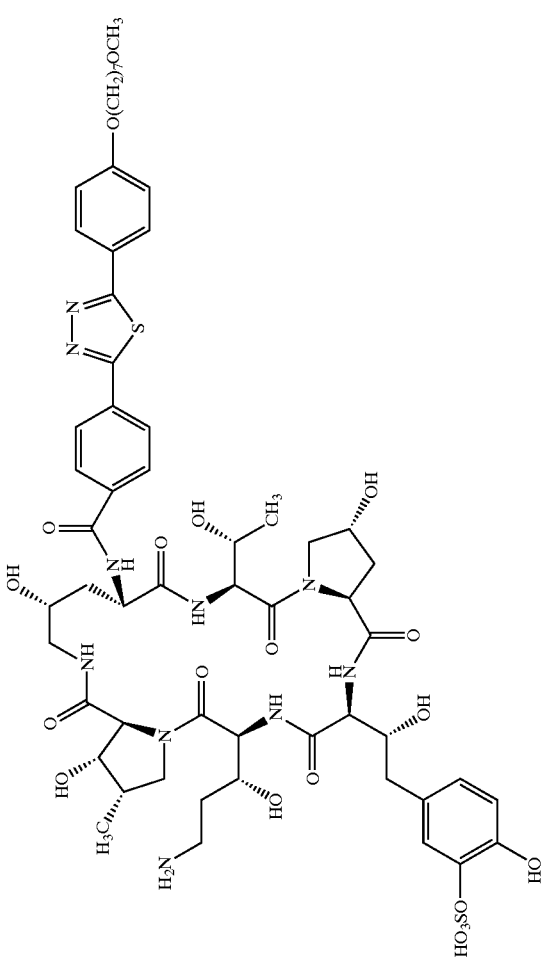 |

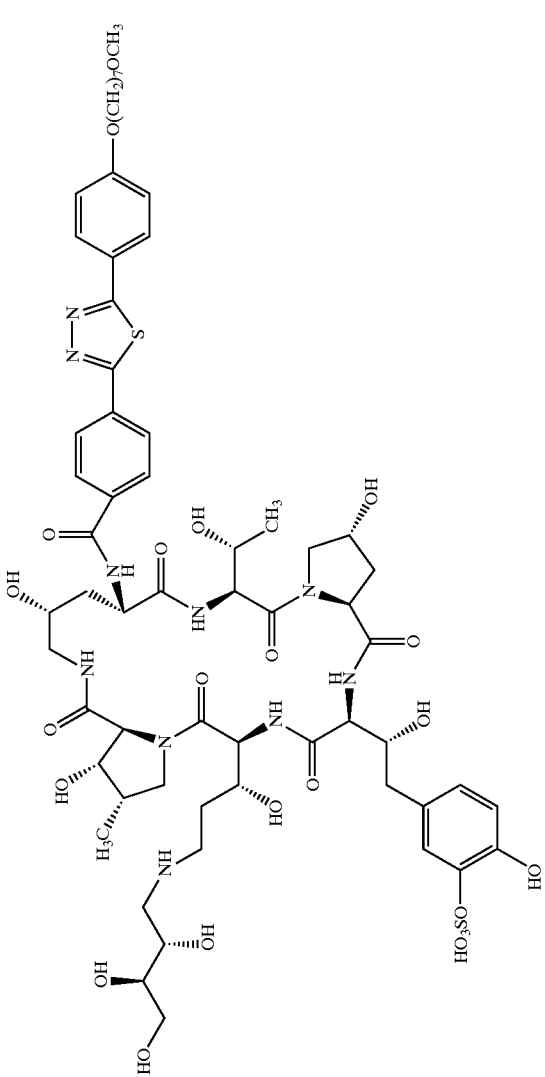

-continued
| Example No. | Formula |
|---|---|
| 50 | 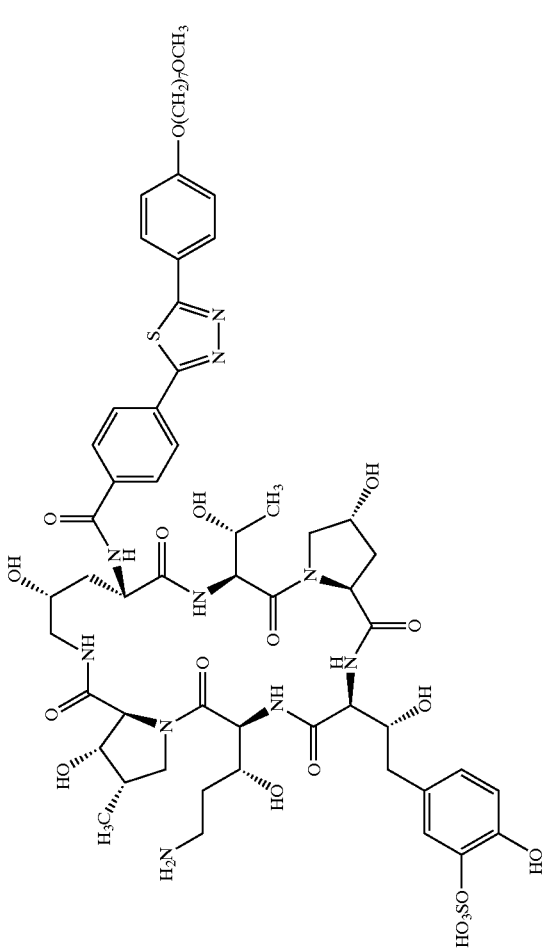 |

-continued
| Example No. | Formula |
|---|---|
| | 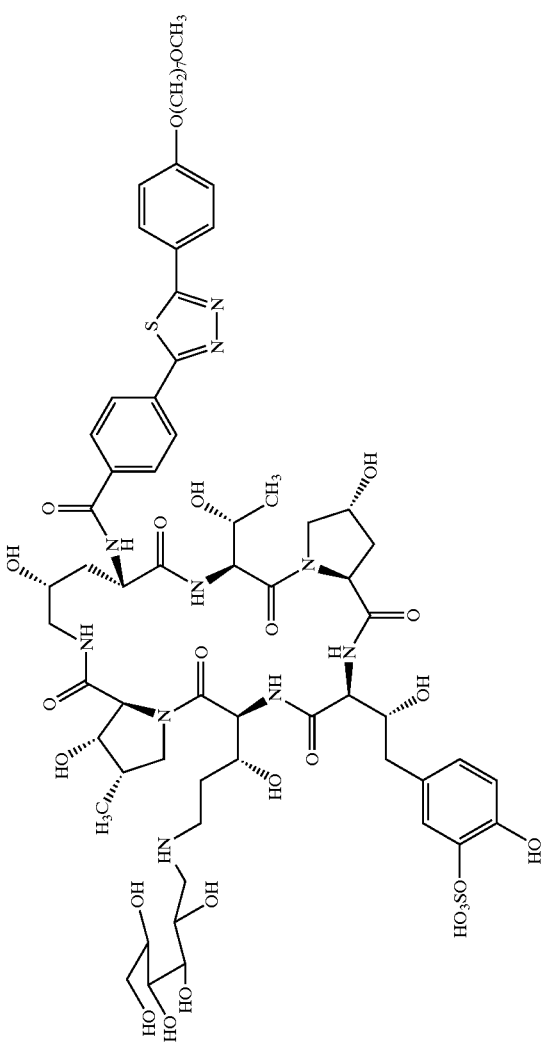 |

| Example No. | Formula |
|---|---|
| 51 | -continued |

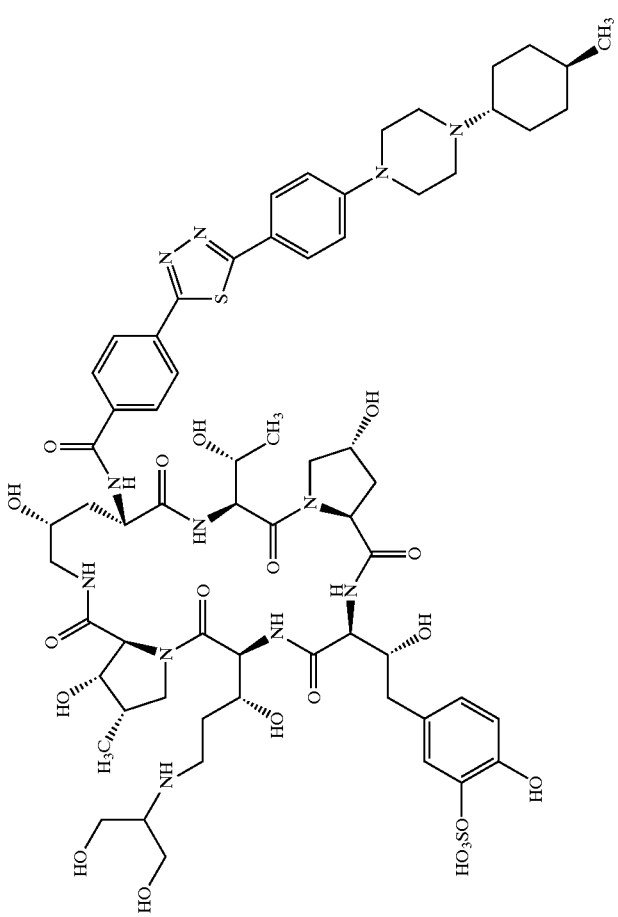

-continued
| Example No. | Formula |
|---|---|
| 52 | 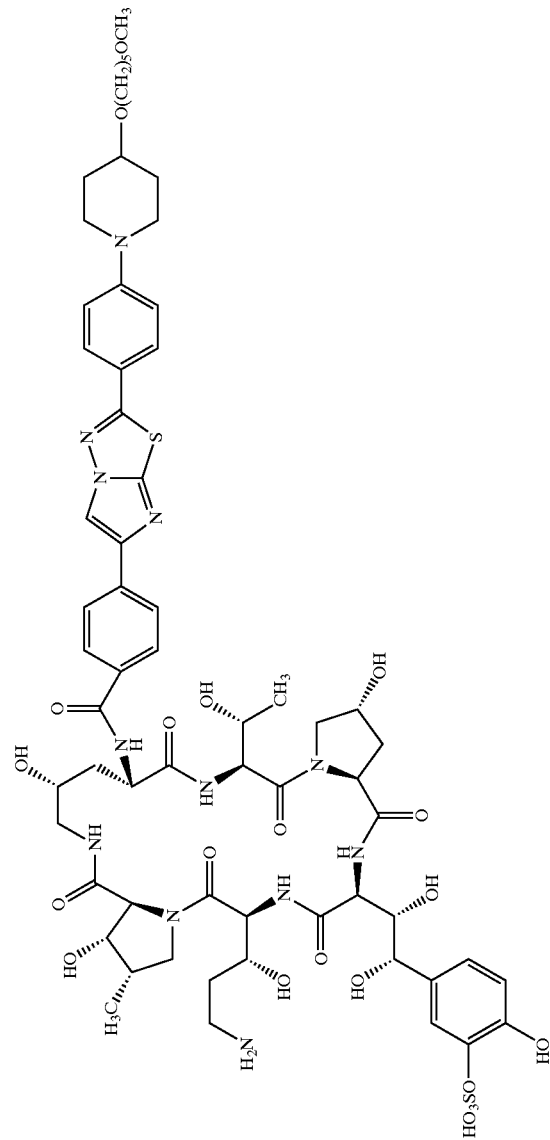 |

| Example No. | Formula |
|---|---|
| | -continued |

-continued
| Example No. | Formula |
|---|---|
| 53 | 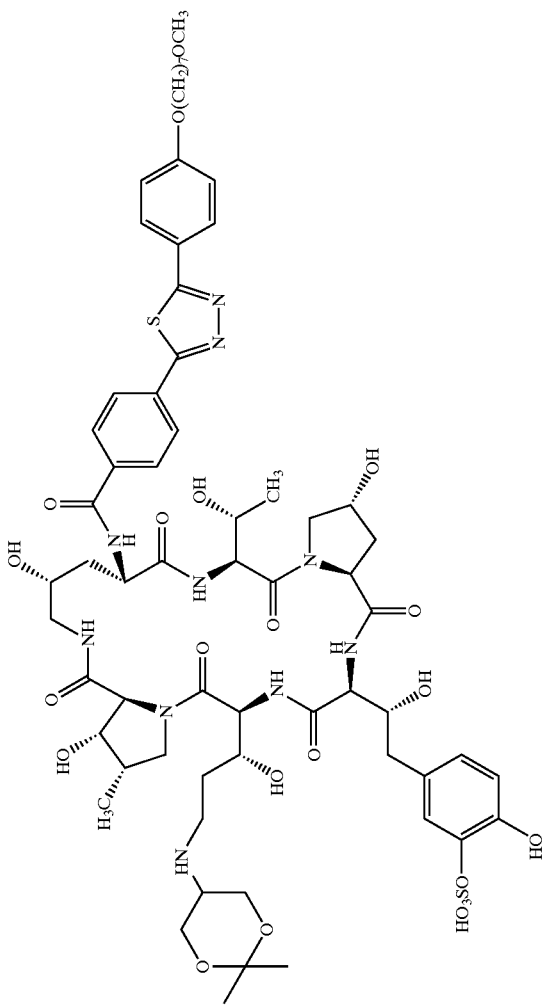 |

| Example No. | Formula |
|---|---|
| | 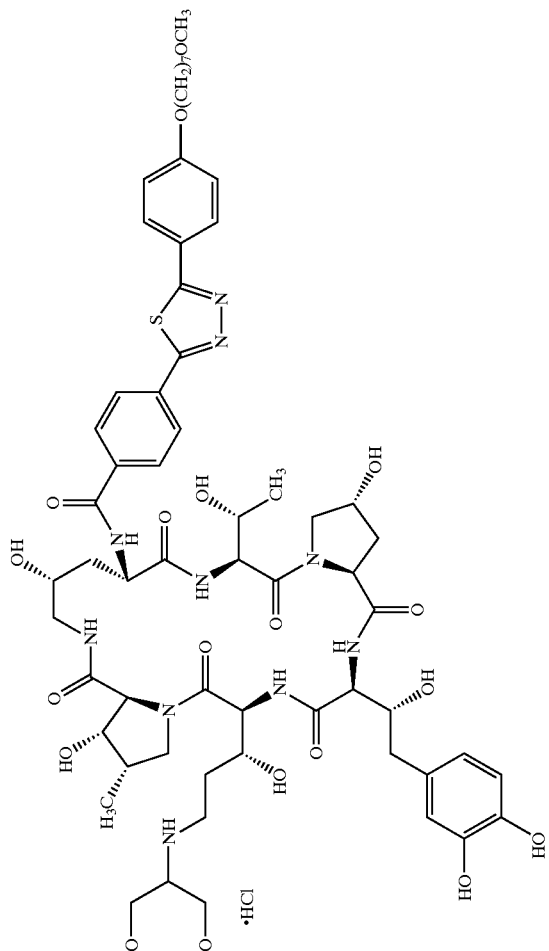 |

| Example No. | Formula |
|---|---|
| 54 | 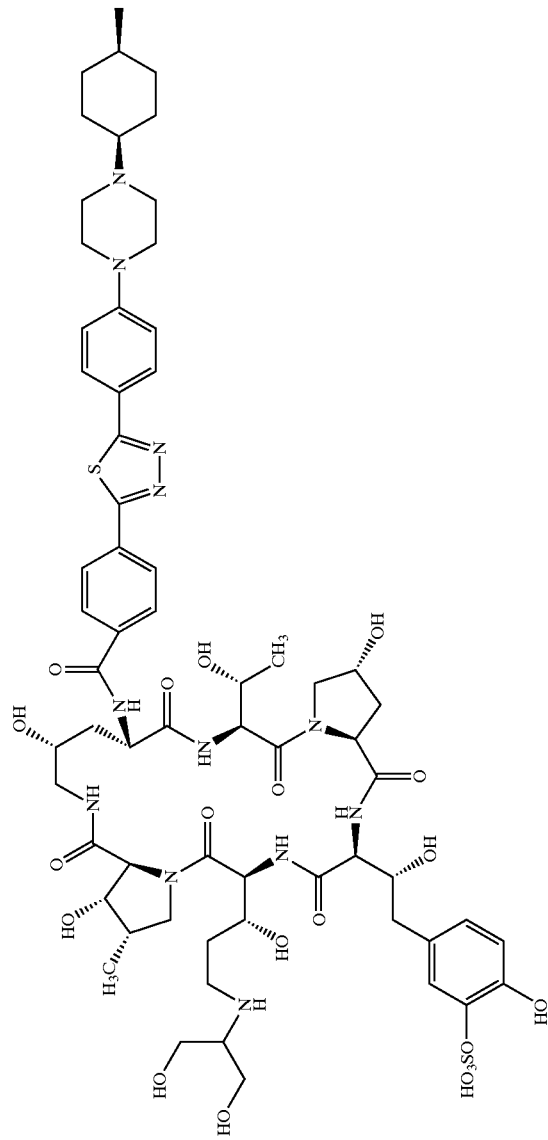 |

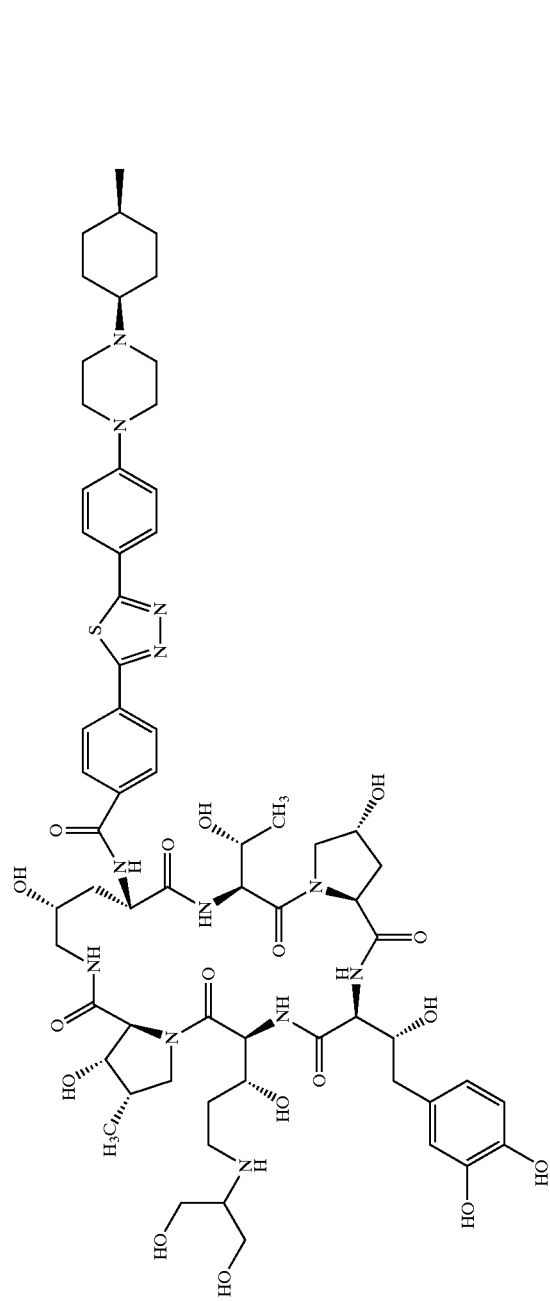

-continued

| Example No. | Formula |
|---|---|
| 55 | (chemical structure) |

-continued
| Example No. | Formula |
|---|---|
| | 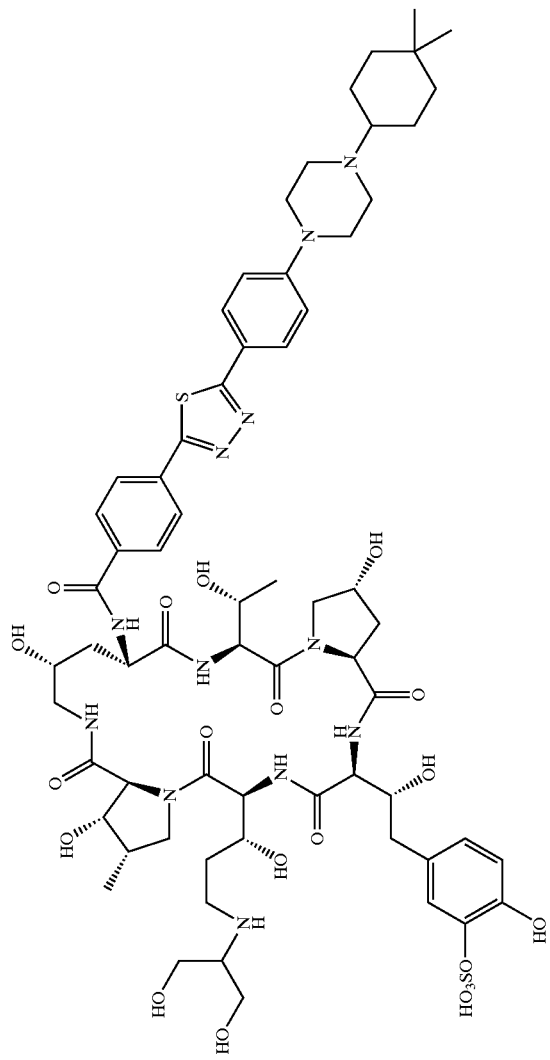 |

-continued
| Example No. | Formula |
|---|---|
| 56 | 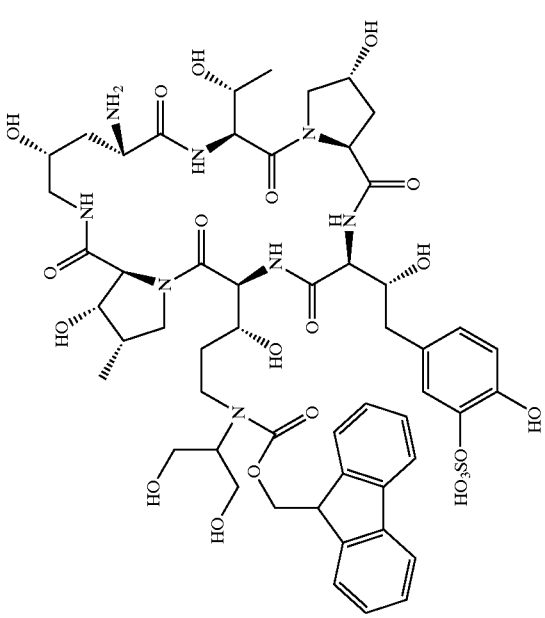 |

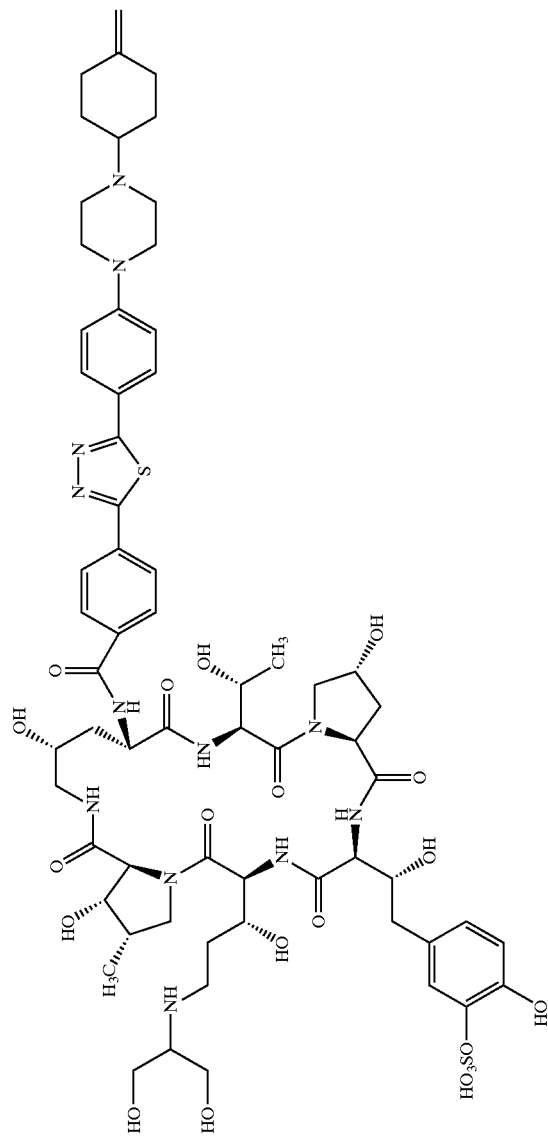

-continued
| Example No. | Formula |
|---|---|
| 57 | 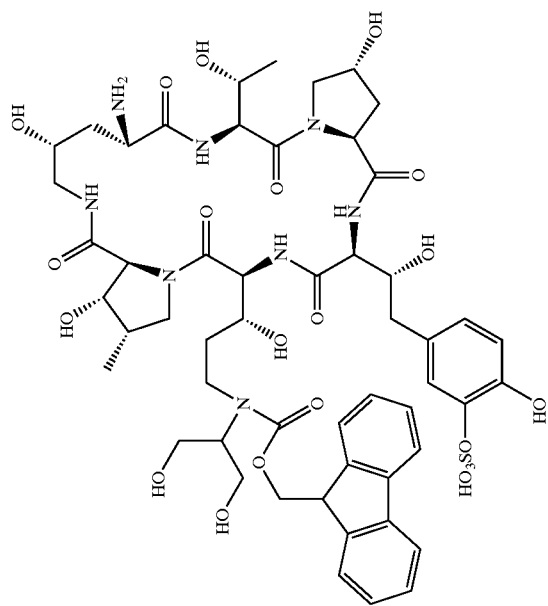 |

-continued
| Example No. | Formula |
|---|---|
| | 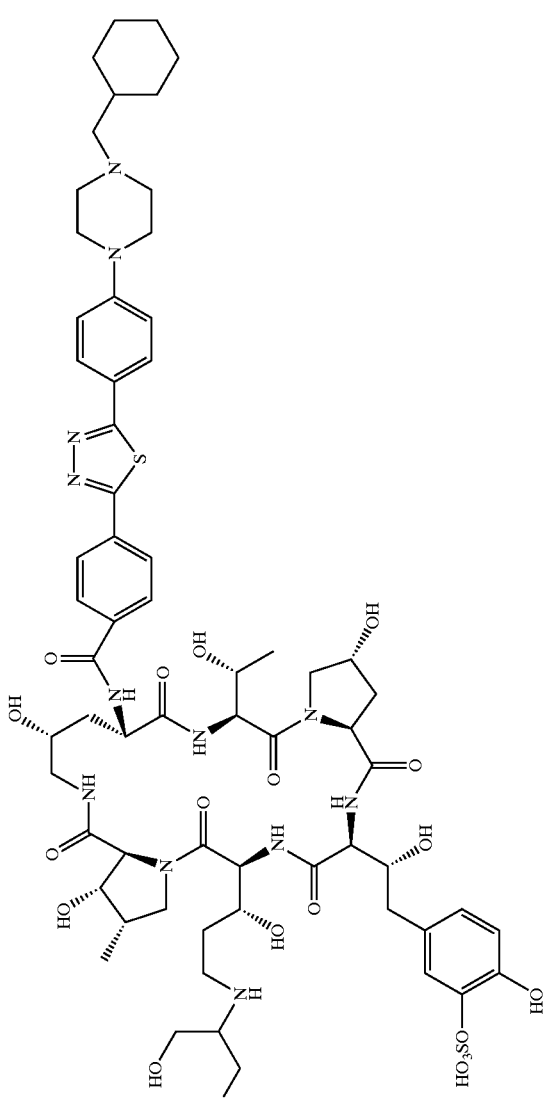 |

-continued
| Example No. | Formula |
|---|---|
| 58 | 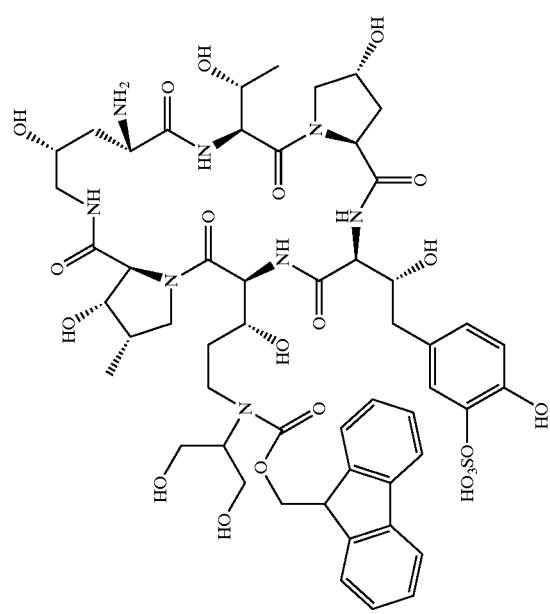 |

-continued
| Example No. | Formula |
|---|---|
| | 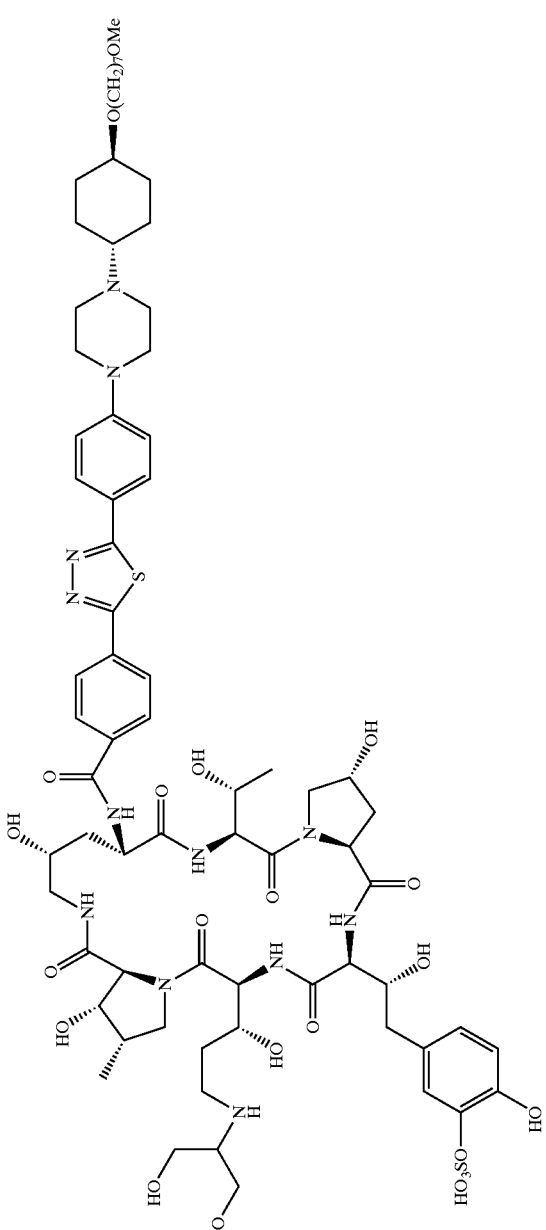<br>Major |

| Example No. | Formula |
|---|---|
| | (chemical structure) Minor |

-continued
| Example No. | Formula |
|---|---|
| 59 | 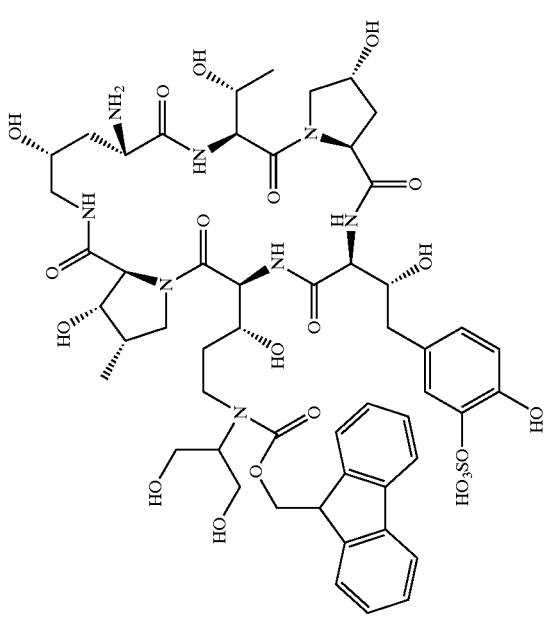 |

| Example No. | Formula |
|---|---|
| | 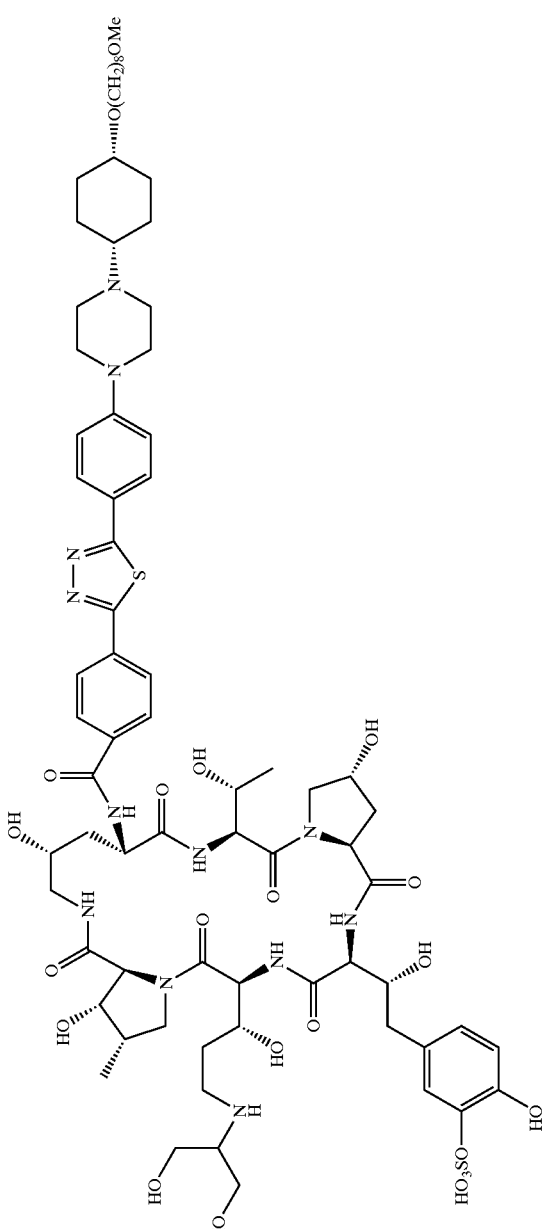<br>Major |

-continued
| Example No. | Formula |
|---|---|
| | 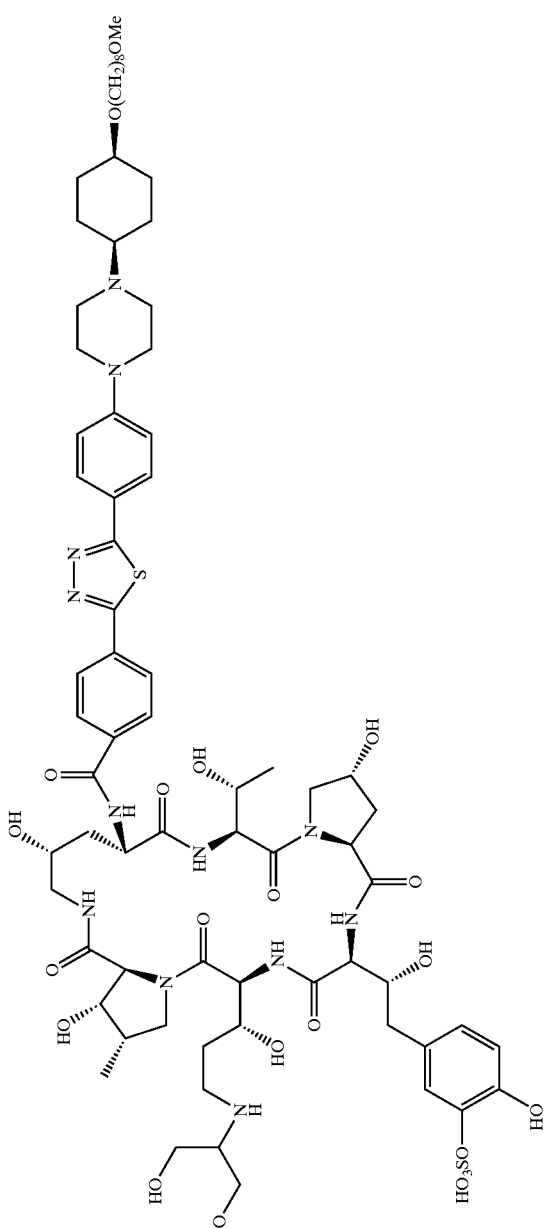
Minor |

-continued

| Example No. | Formula |
|---|---|
| 60 | (structure) |

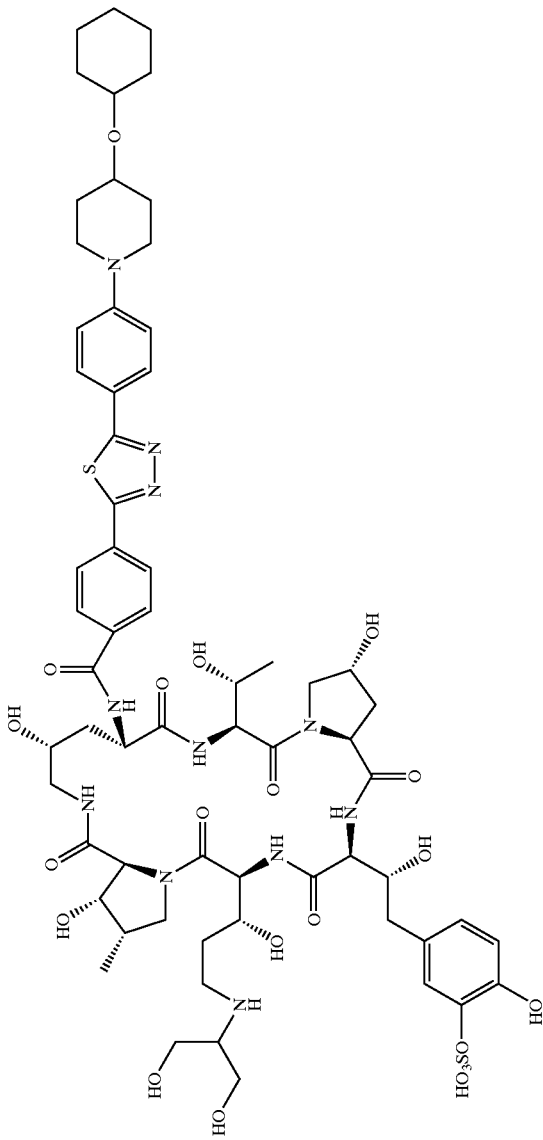

| Example No. | Formula |
|---|---|
| 61 | -continued |

| Example No. | Formula |
|---|---|
| | 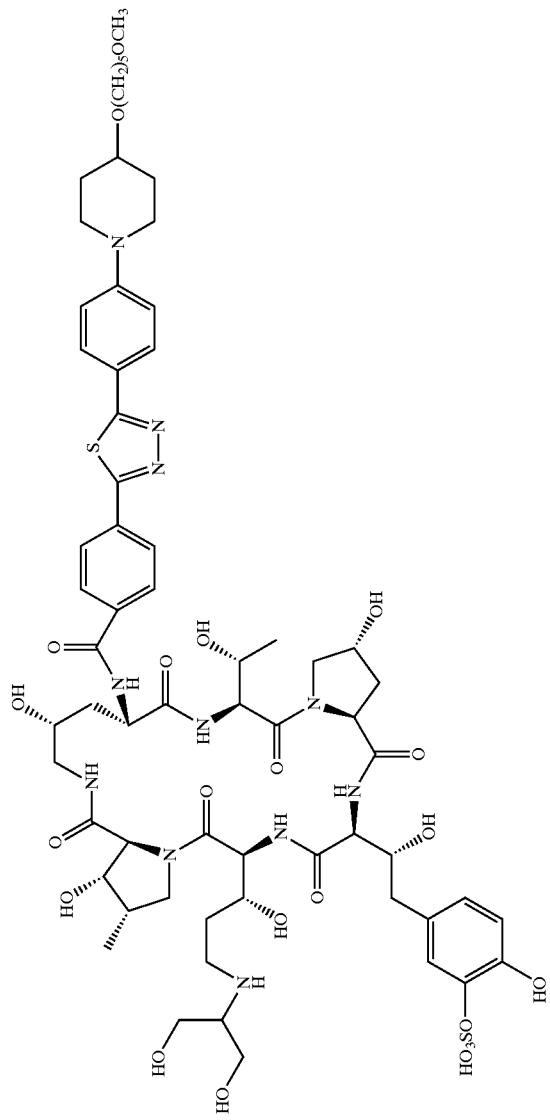 |

-continued
| Example No. | Formula |
|---|---|
| 62 | 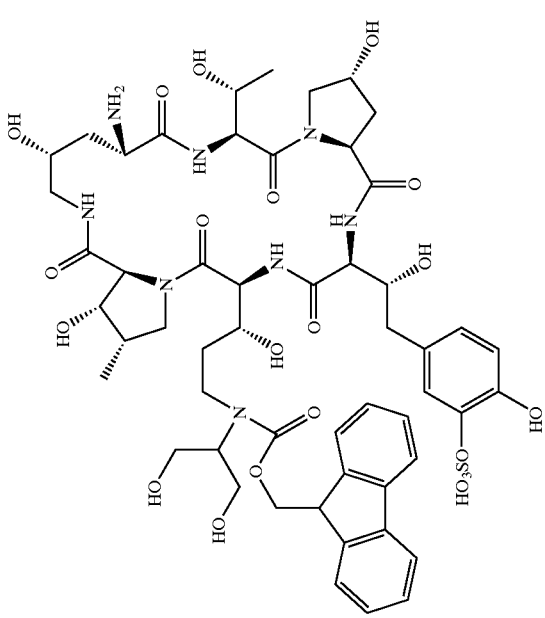 |

| Example No. | Formula |
|---|---|
| | 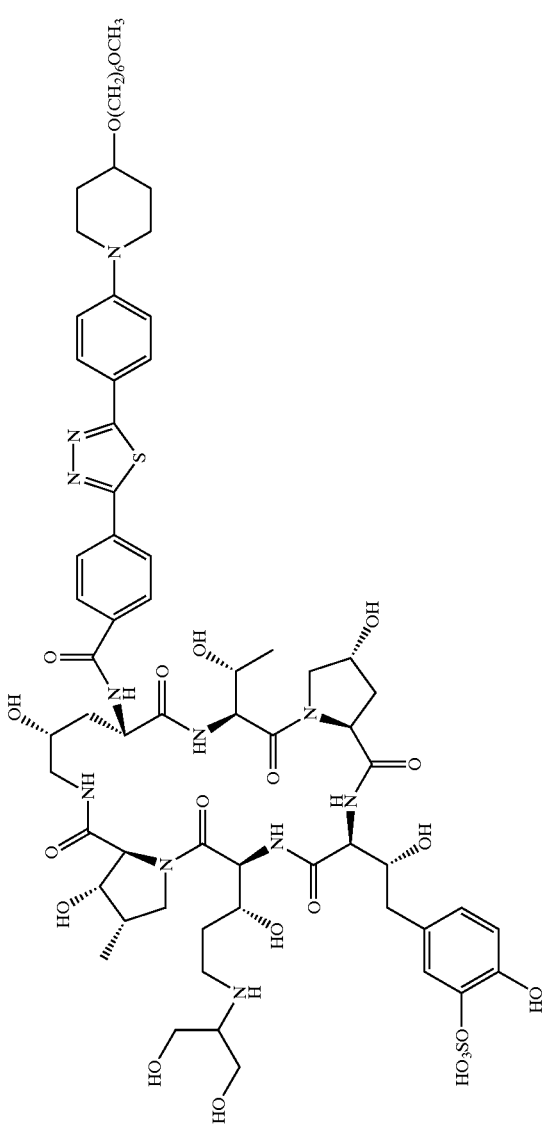 |

| Example No. | Formula |
|---|---|
| 63 | -continued (structure) |

-continued
| Example No. | Formula |
|---|---|
| | 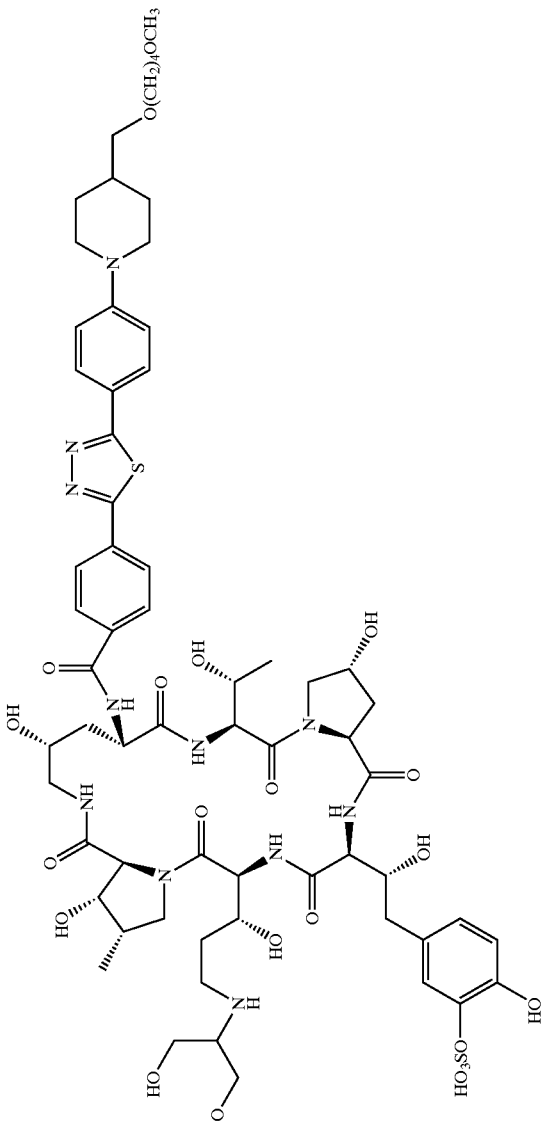 |

| Example No. | Formula |
|---|---|
| 64 | -continued (chemical structure) |

| Example No. | Formula |
|---|---|
| | 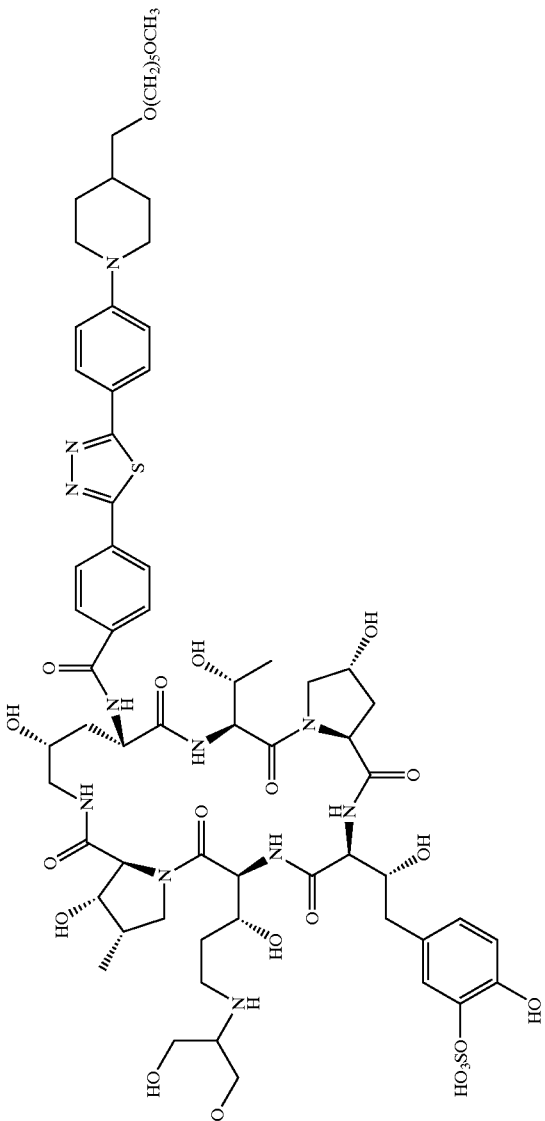 |

| Example No. | Formula |
|---|---|
| 65 | (structure) |

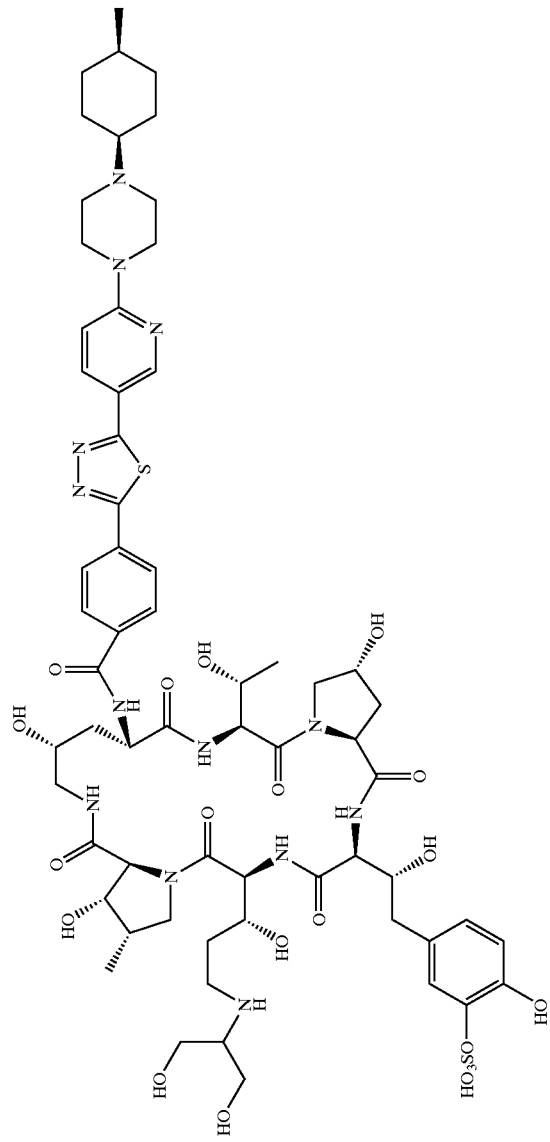

-continued
| Example No. | Formula |
|---|---|
| 66 | 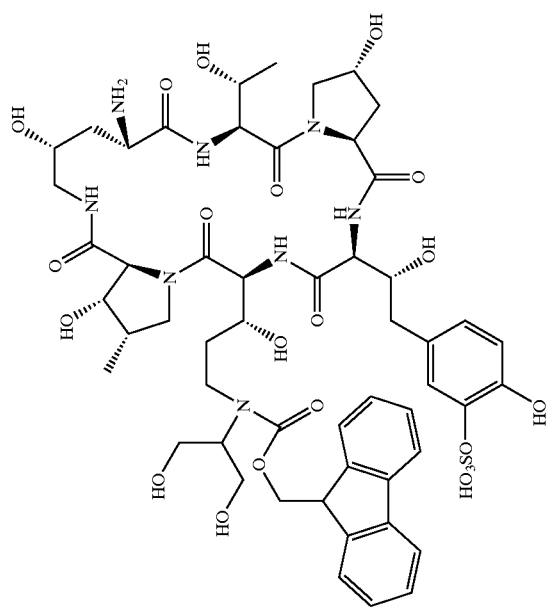 |

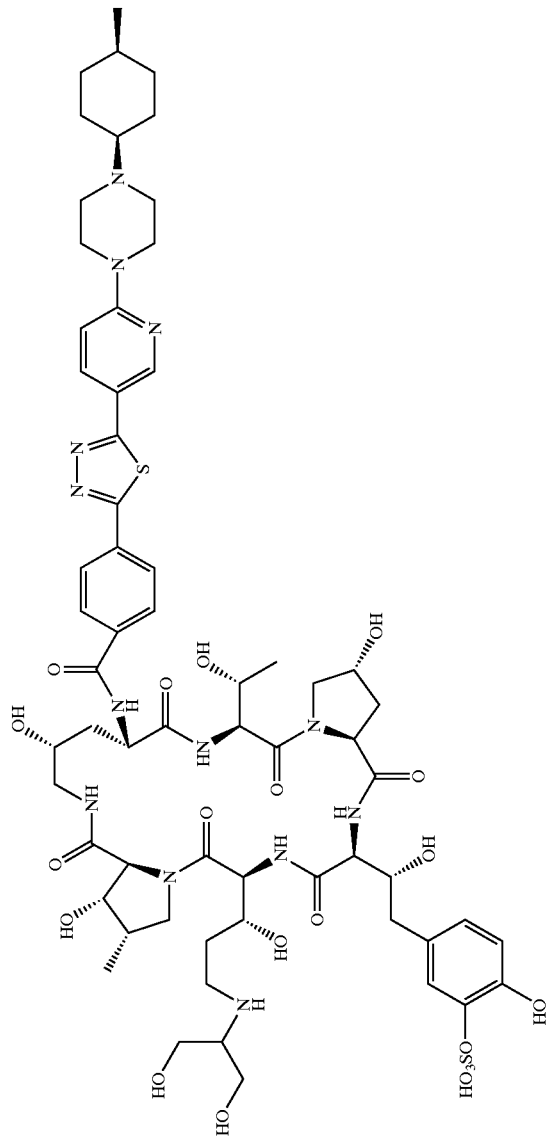

-continued
| Example No. | Formula |
|---|---|
| 67 | 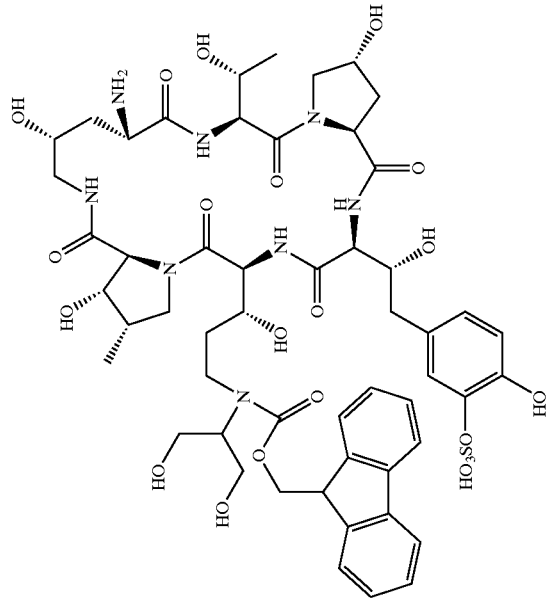 |

-continued
| Example No. | Formula |
|---|---|
| | 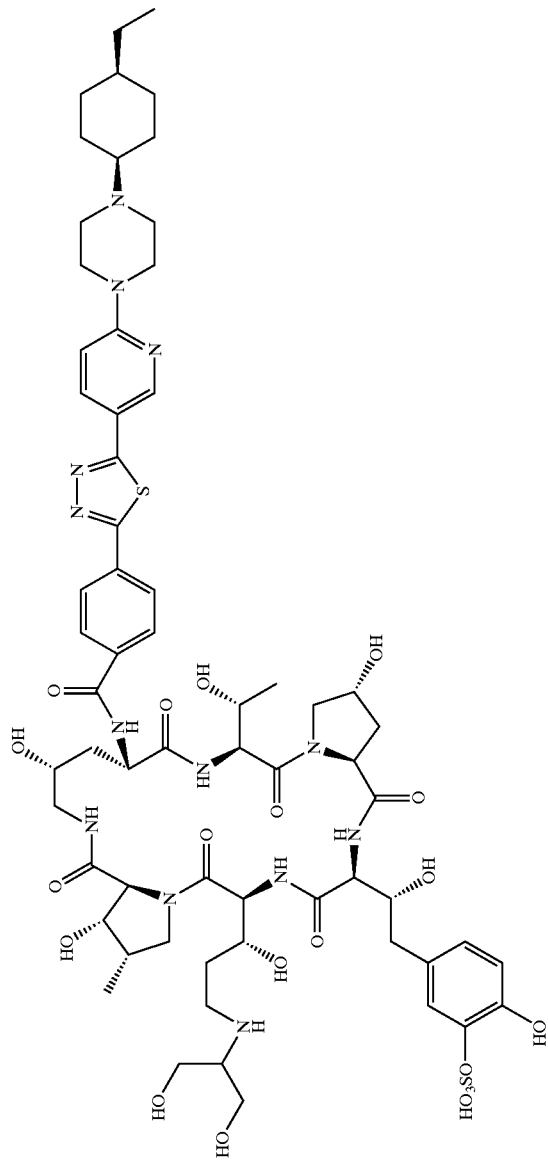 |

| Example No. | Formula |
|---|---|
| 68 | -continued (structure) |

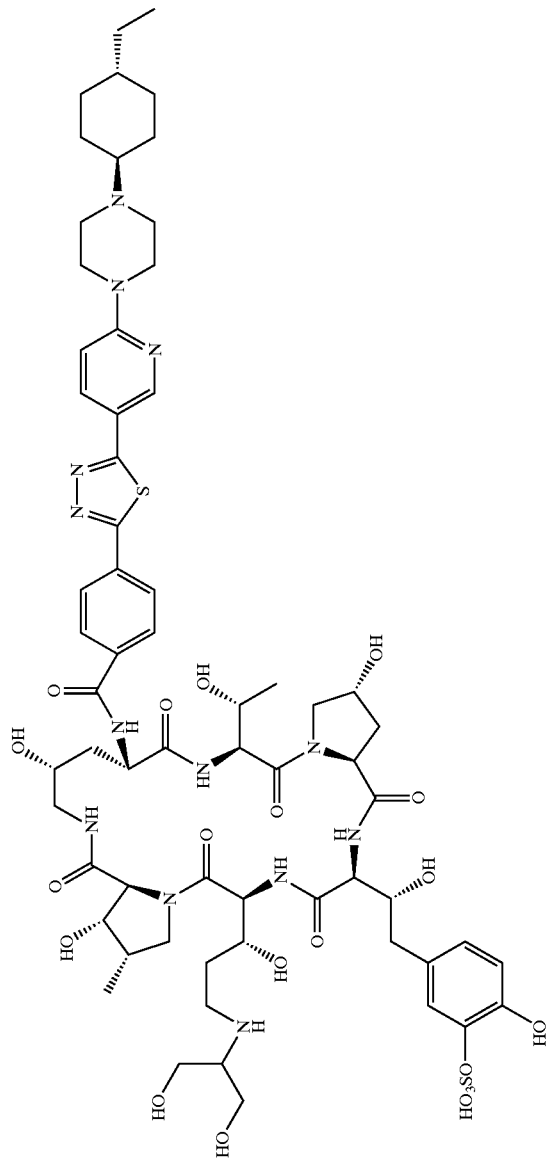

| Example No. | Formula |
|---|---|
| 69 | 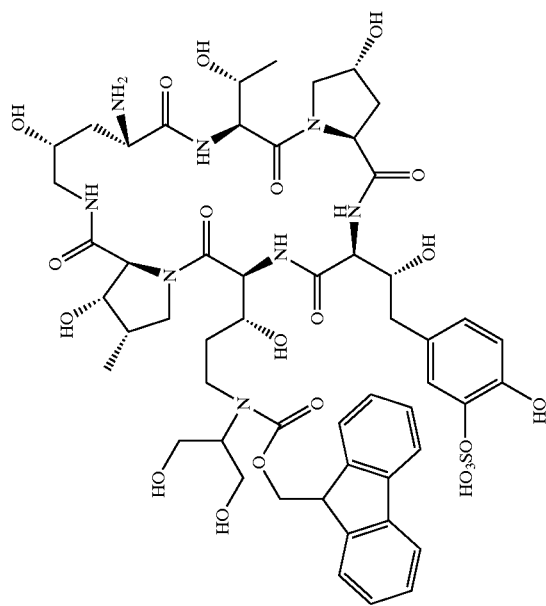 |

-continued
| Example No. | Formula |
|---|---|
| | 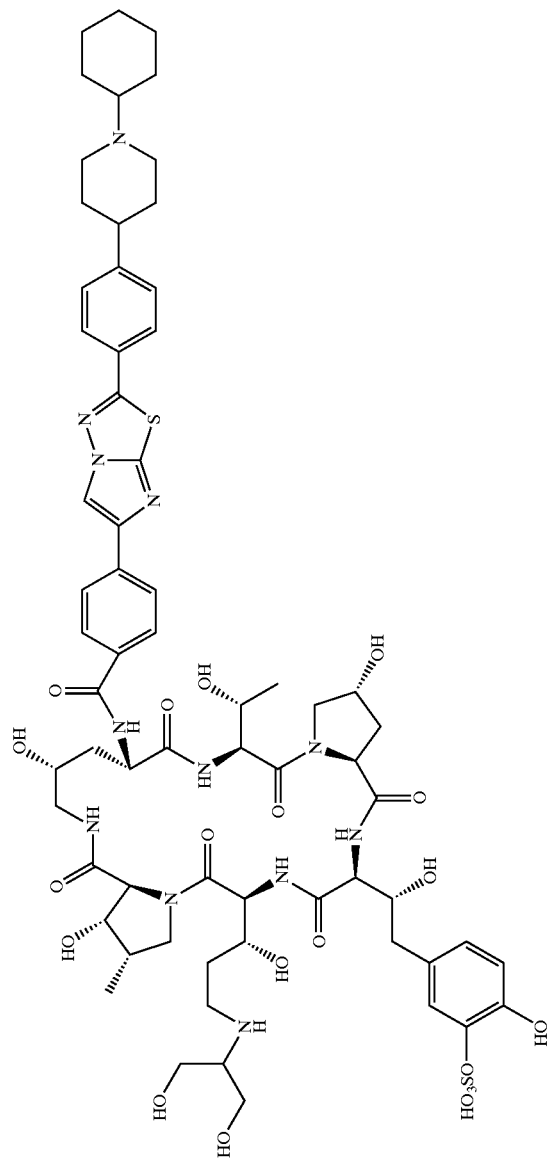 |

| Example No. | Formula |
|---|---|
| 70 | *-continued* chemical structure |

| Example No. | Formula |
|---|---|
| | 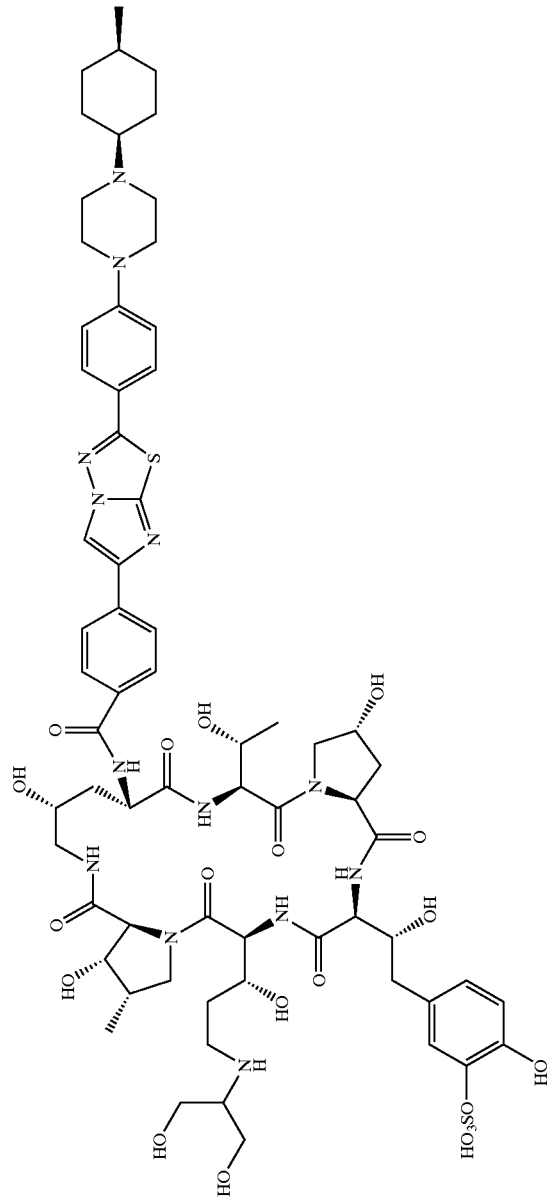 |

| Example No. | Formula |
|---|---|
| 71 | -continued (structure) |

-continued
| Example No. | Formula |
|---|---|
| | 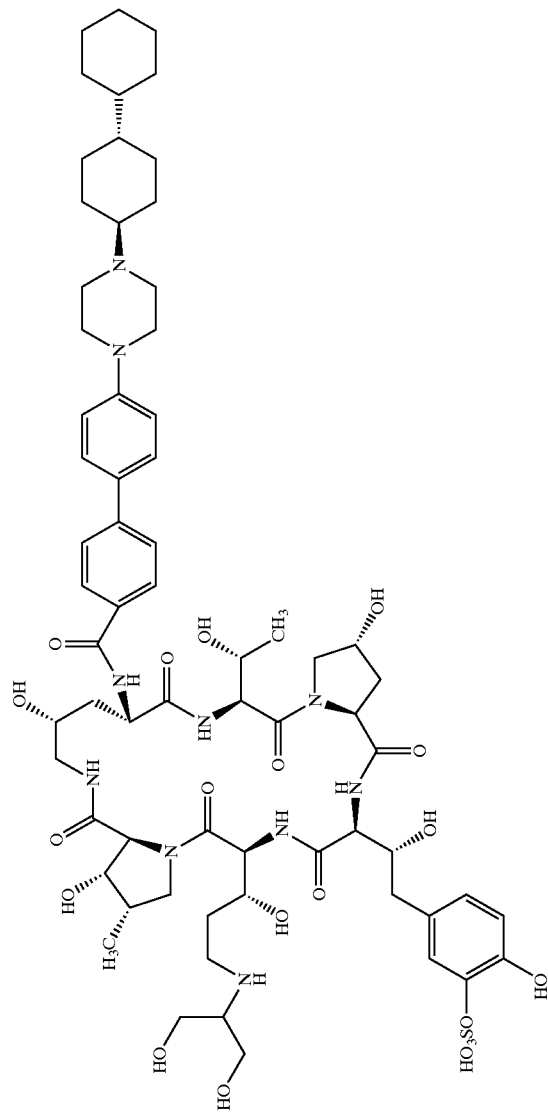 |

| Example No. | Formula |
|---|---|
| 72 | 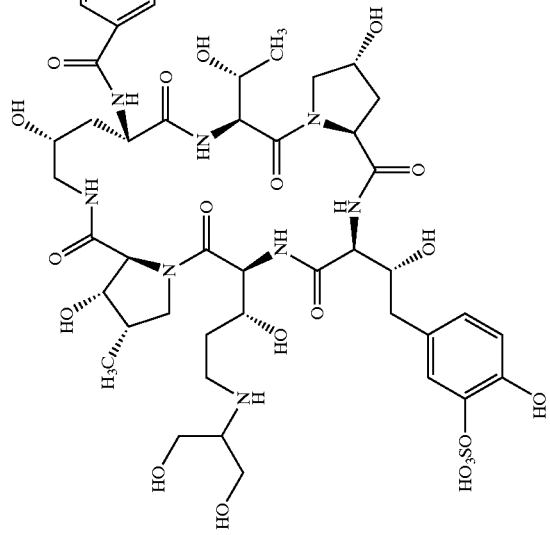 |

-continued
| Example No. | Formula |
|---|---|
| | 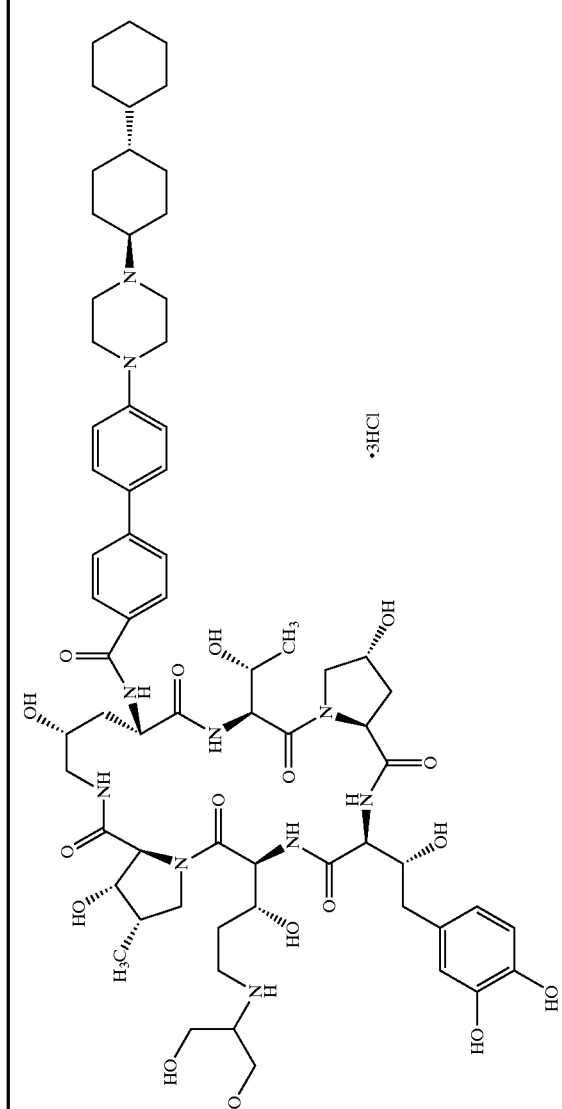 |

-continued
| Example No. | Formula |
|---|---|
| 73 | 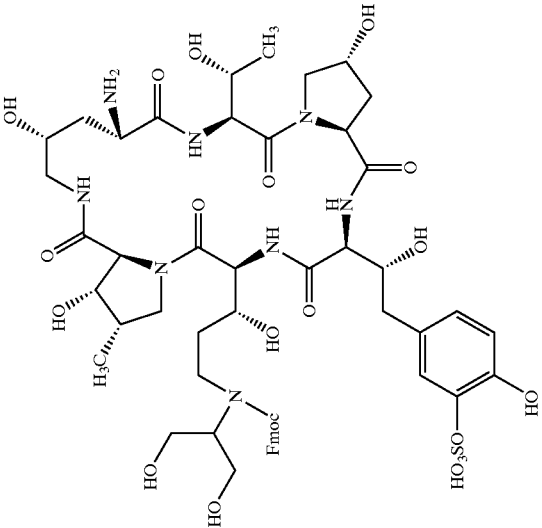 |

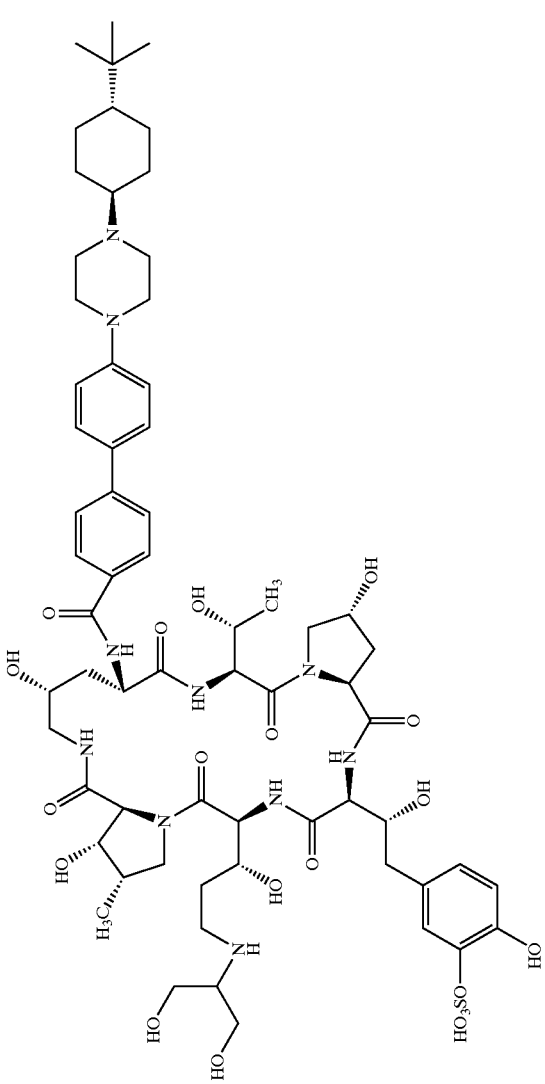

| Example No. | Formula |
|---|---|
| 74 | -continued |

-continued

| Example No. | Formula |
|---|---|
| | (chemical structure) |

| Example No. | Formula |
|---|---|
| 75 | (structure) |

| Example No. | Formula |
|---|---|
| | 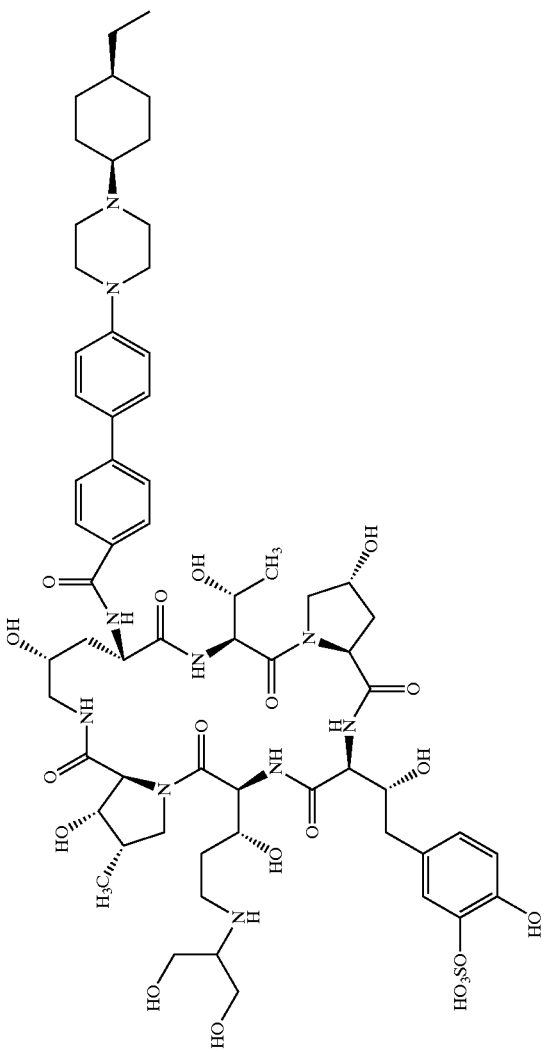 |

| Example No. | Formula |
|---|---|
| 76 | -continued |

-continued
| Example No. | Formula |
|---|---|
| | 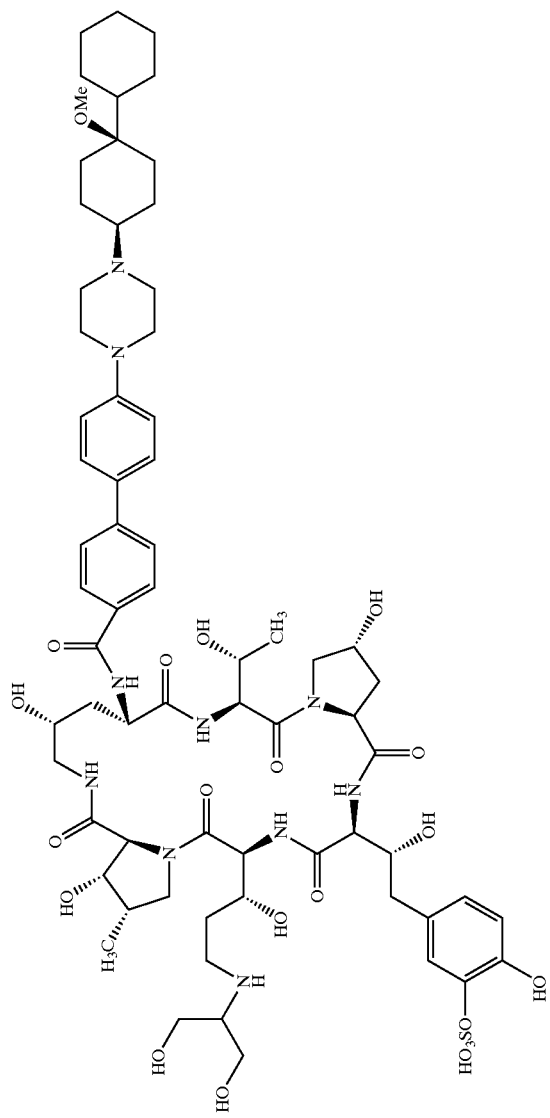 |

-continued
| Example No. | Formula |
|---|---|
| 77 | 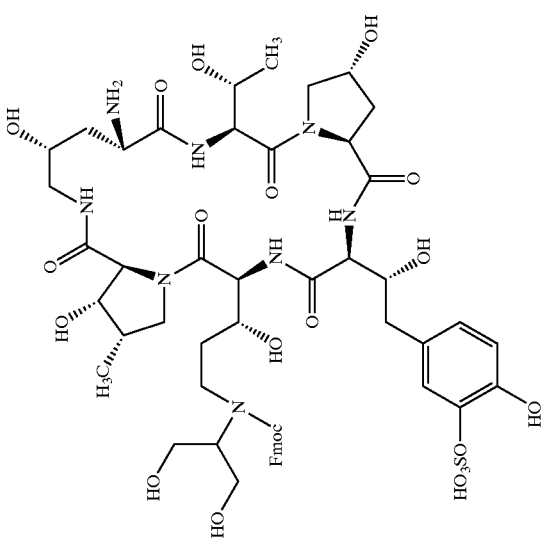 |

-continued
| Example No. | Formula |
|---|---|
| | 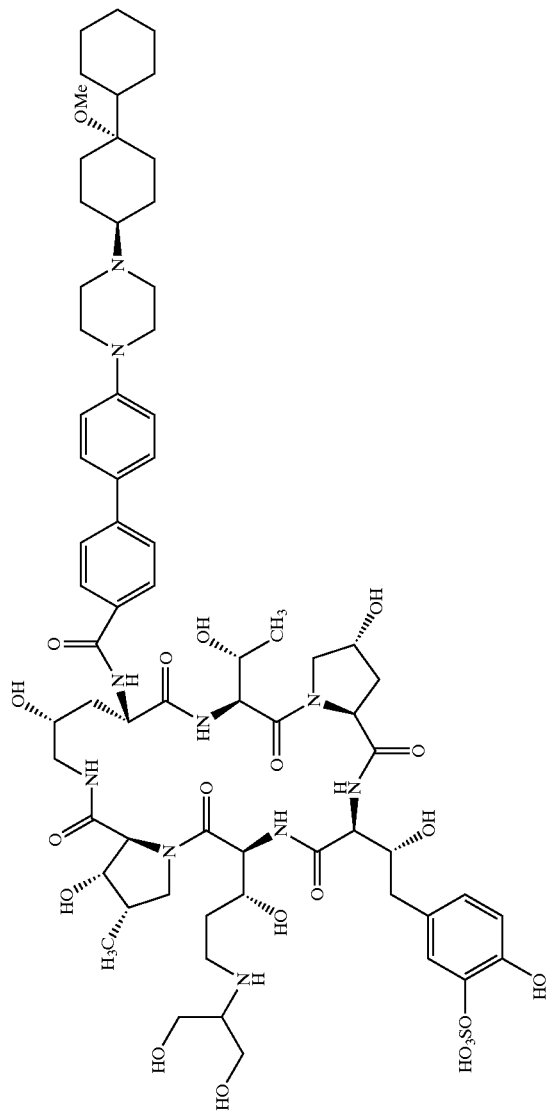 |

| Example No. | Formula |
|---|---|
| 78 | -continued |

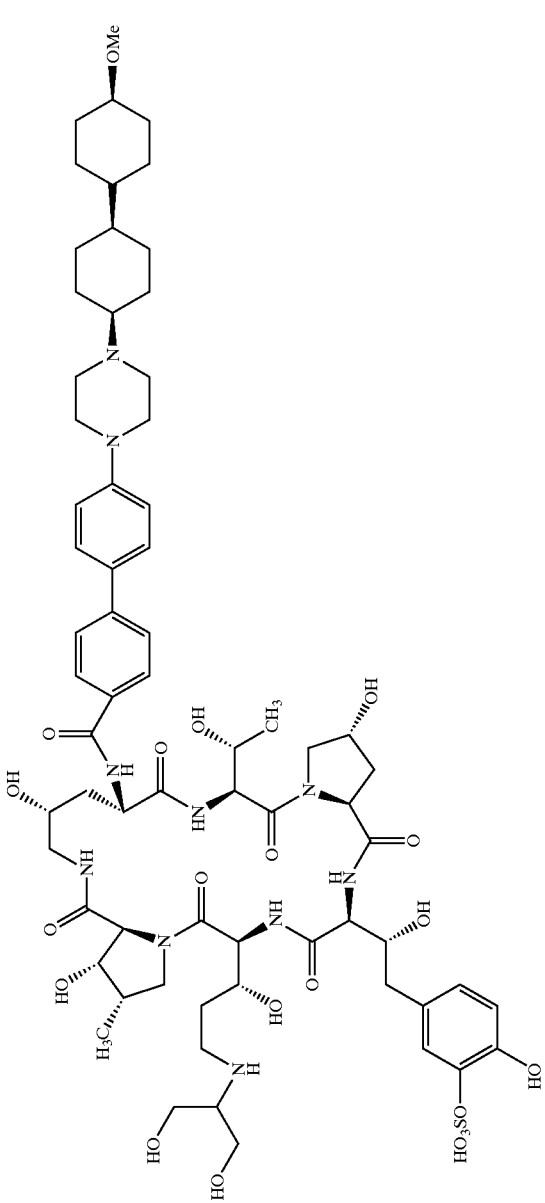

-continued

| Example No. | Formula |
|---|---|
| 79 | |

| Example No. | Formula |
|---|---|
| | 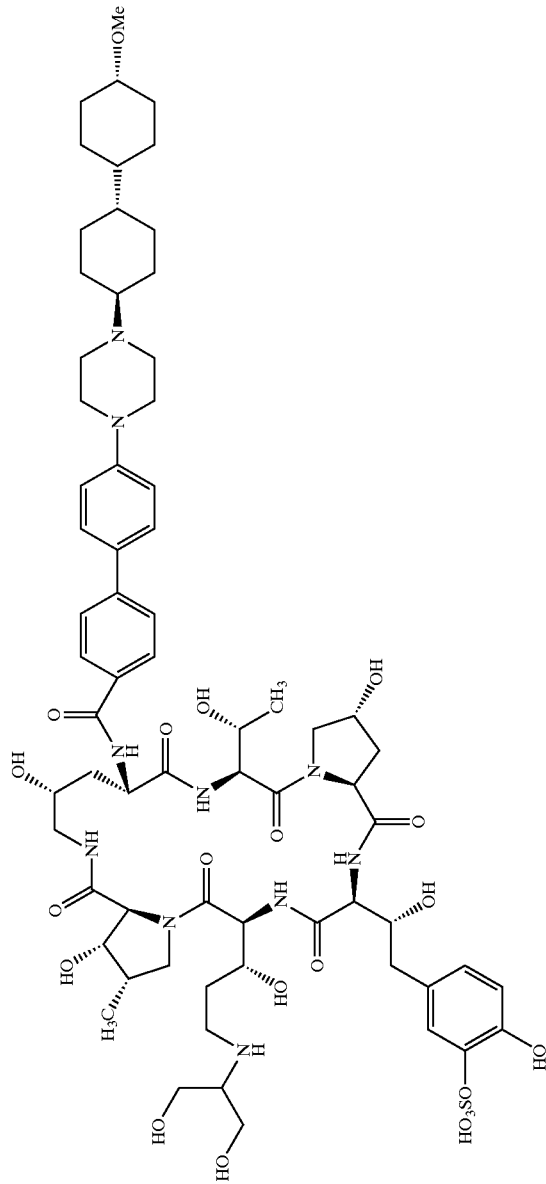 |

| Example No. | Formula |
|---|---|
| 80 | -continued (structure) |

| Example No. | Formula |
|---|---|
| | 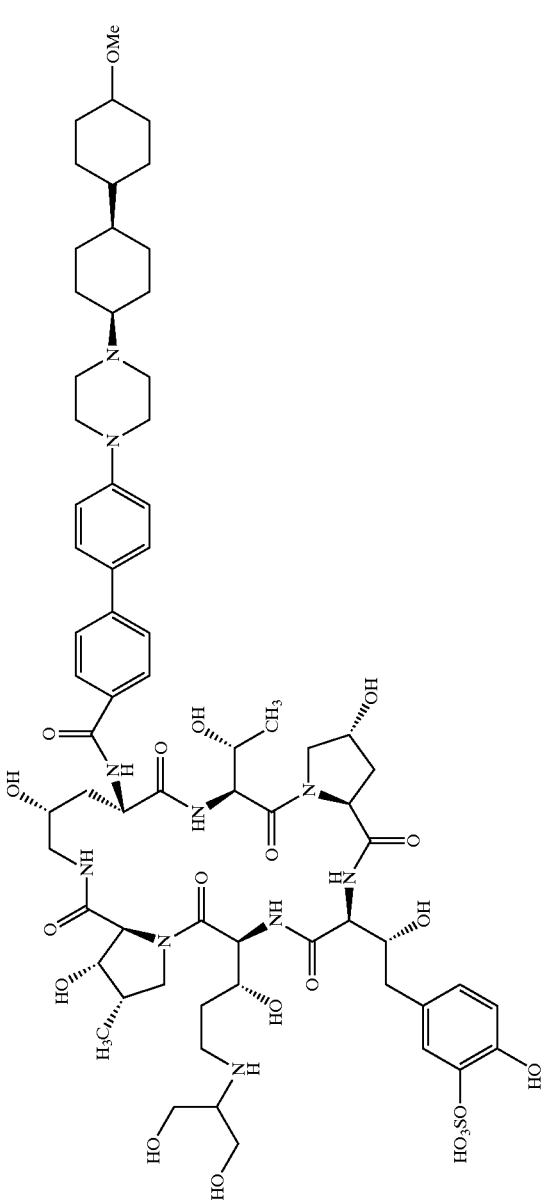 |

| Example No. | Formula |
|---|---|
| 81 | 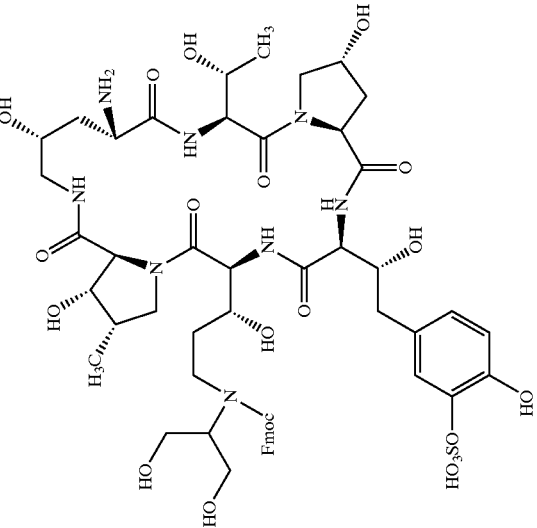 |

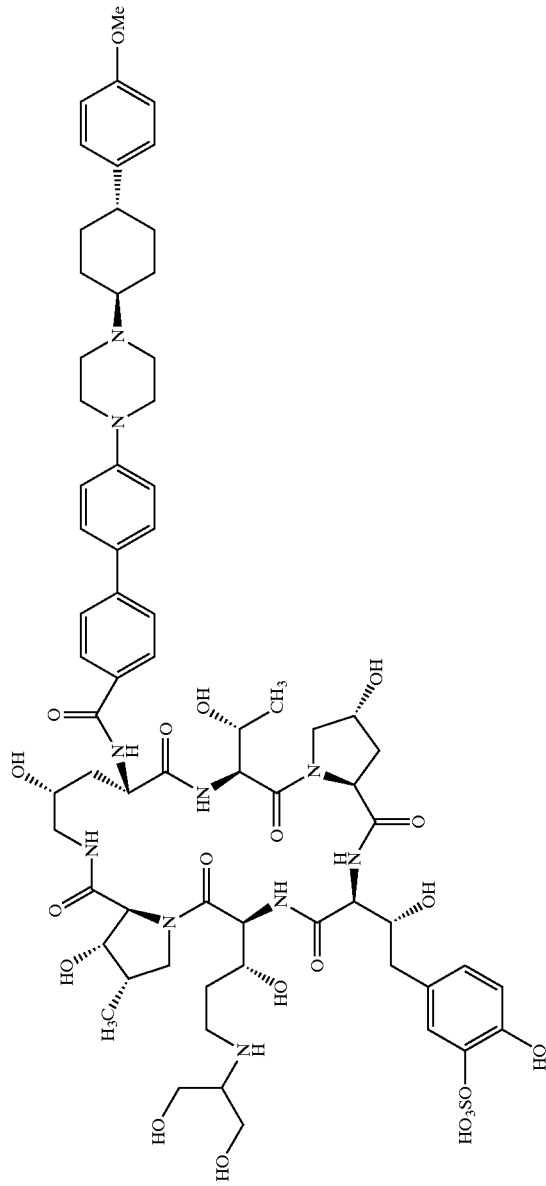

-continued
| Example No. | Formula |
|---|---|
| 82 | 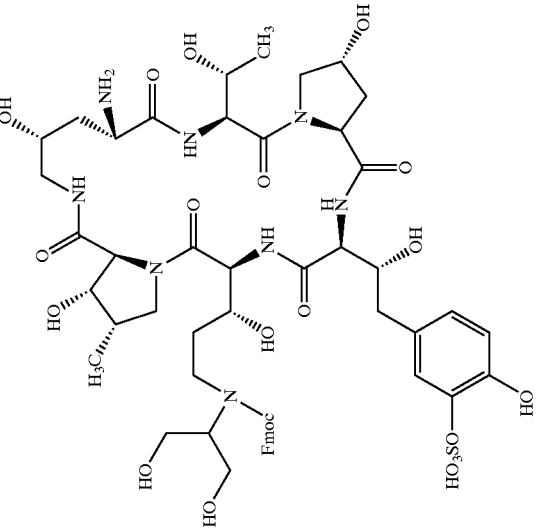 |

| Example No. | Formula |
|---|---|
| | *(chemical structure)* |

| Example No. | Formula |
|---|---|
| 83 | *(structure)* |

-continued
| Example No. | Formula |
|---|---|
| | 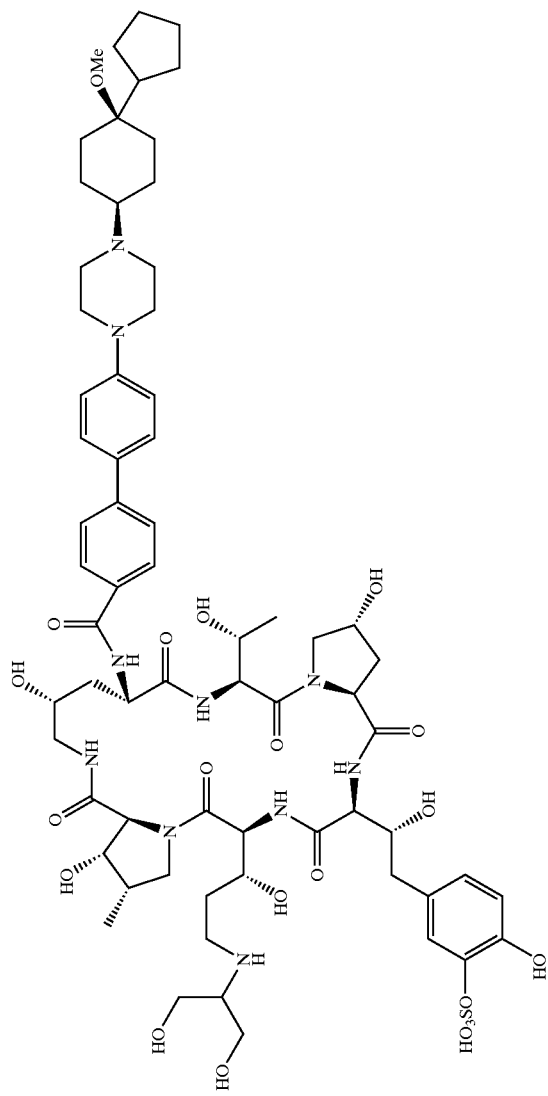 |

| Example No. | Formula |
|---|---|
| 84 | (structure) |

| Example No. | Formula |
|---|---|
| | 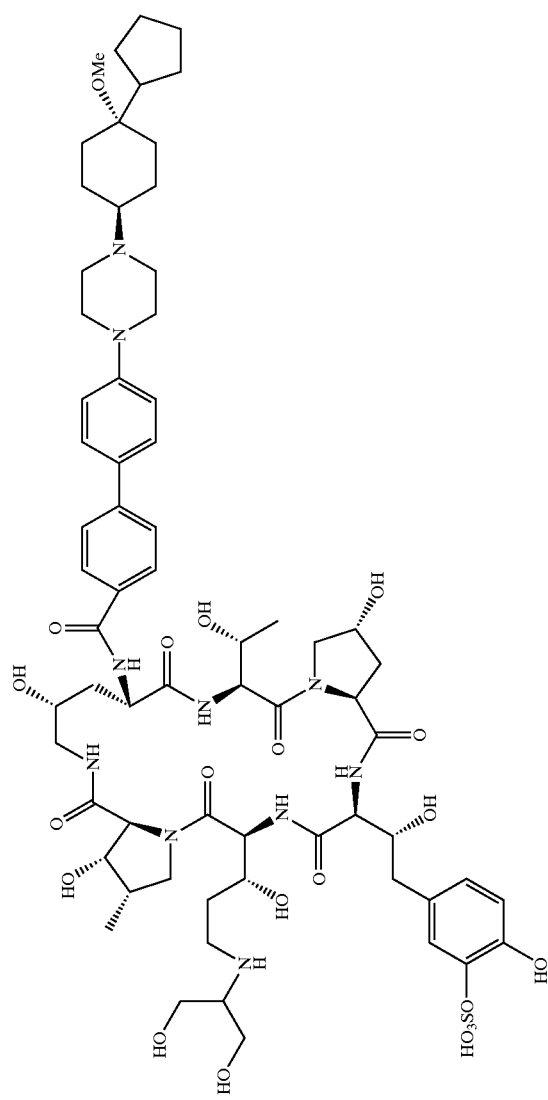 |

| Example No. | Formula |
|---|---|
| 85 | -continued (chemical structure) |

| Example No. | Formula |
|---|---|
| | 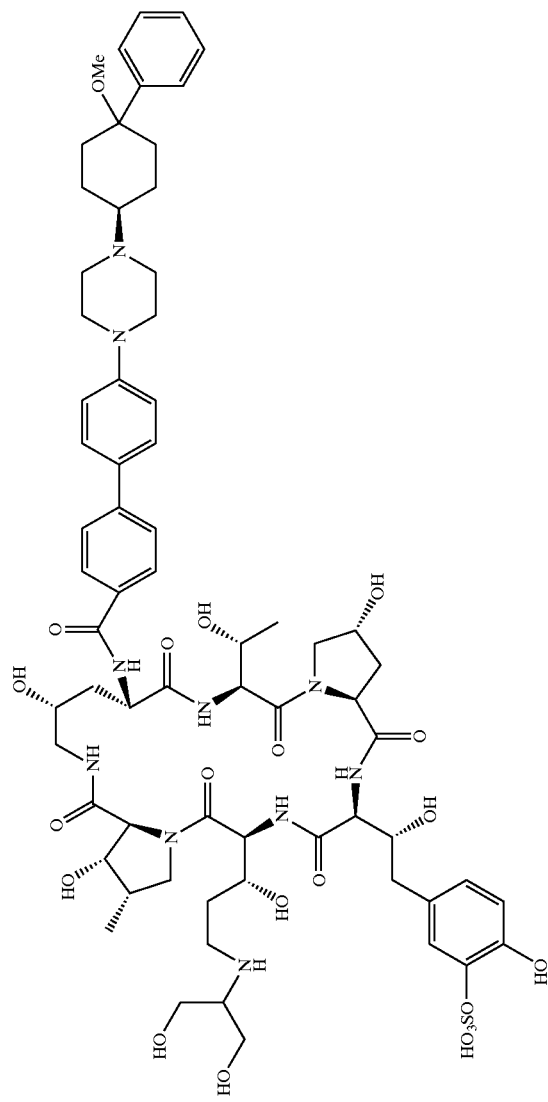 |

-continued
| Example No. | Formula |
|---|---|
| 86 | 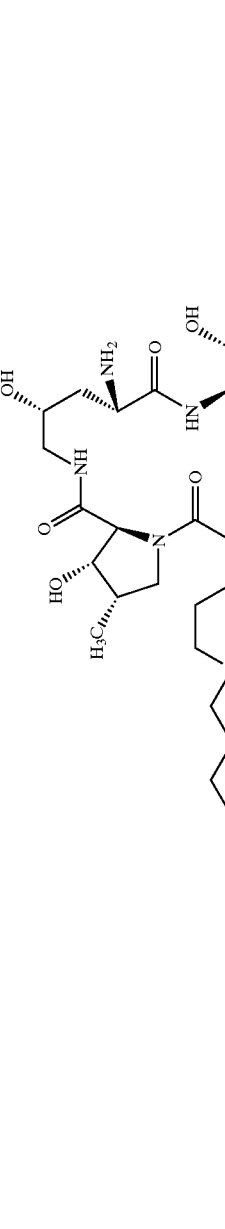 |

| Example No. | Formula |
|---|---|
| | -continued |

| Example No. | Formula |
|---|---|
| 87 | -continued |

-continued
| Example No. | Formula |
|---|---|
| | 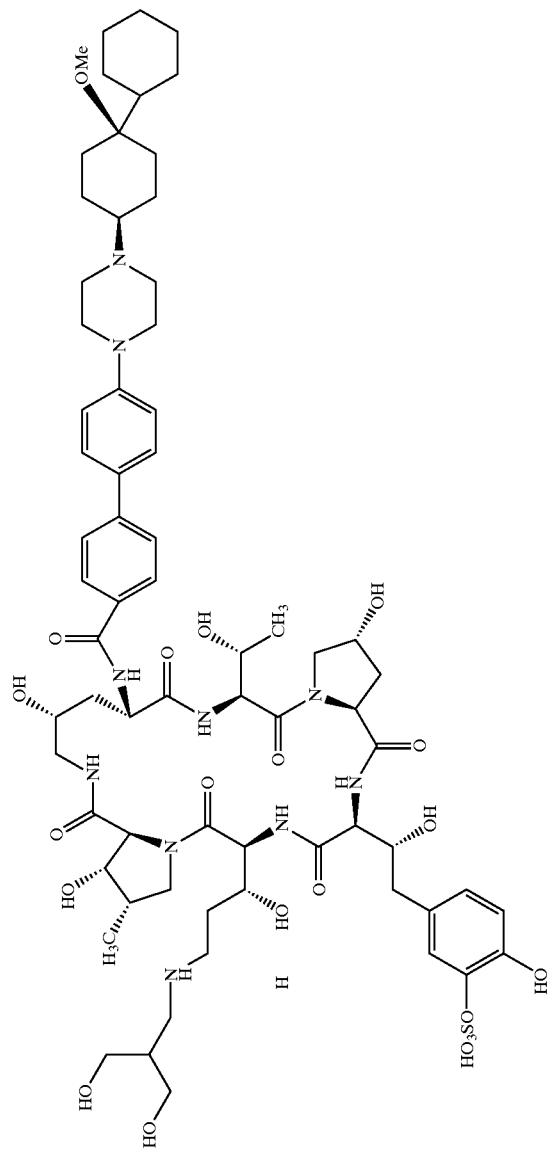 |

| Example No. | Formula |
|---|---|
| 88 | -continued (chemical structure) |

| Example No. | Formula |
|---|---|
| | *(chemical structure)* |

| Example No. | Formula |
|---|---|
| 89 | -continued (chemical structure) |

-continued
| Example No. | Formula |
|---|---|
| | 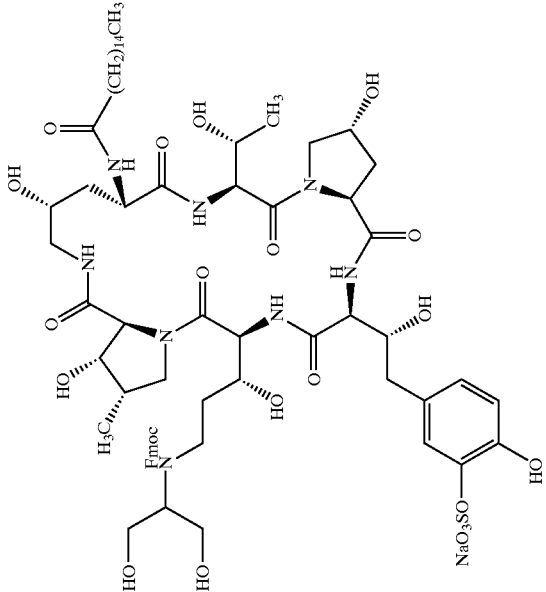 |

-continued

| Example No. | Formula |
|---|---|
| 90 | (chemical structure) |

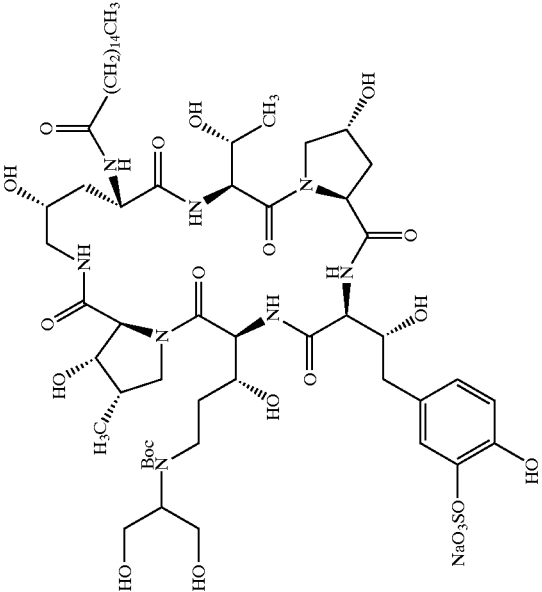

| Example No. | Formula |
|---|---|
| 91 | -continued (structure) |

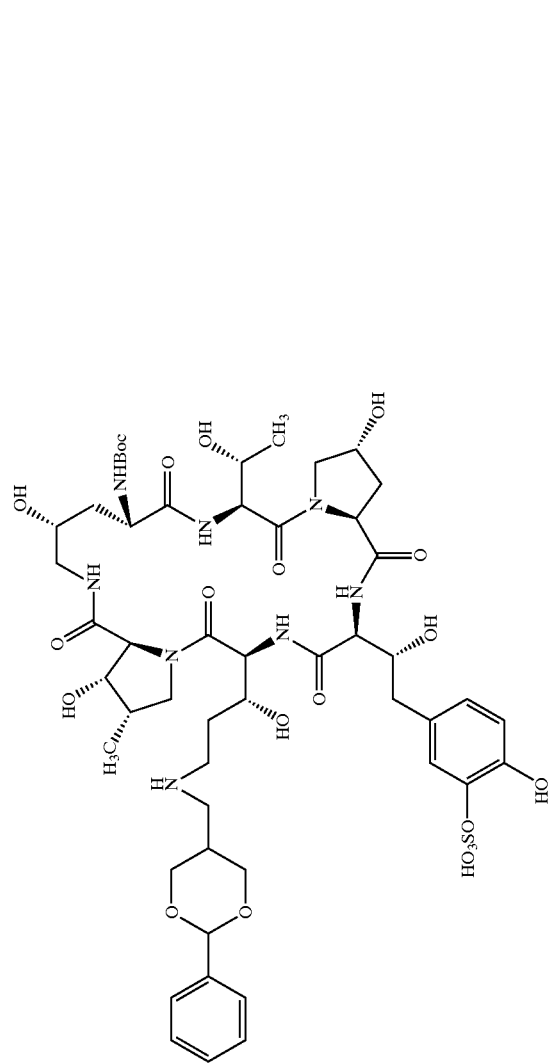

-continued
| Example No. | Formula |
|---|---|
| 92 | 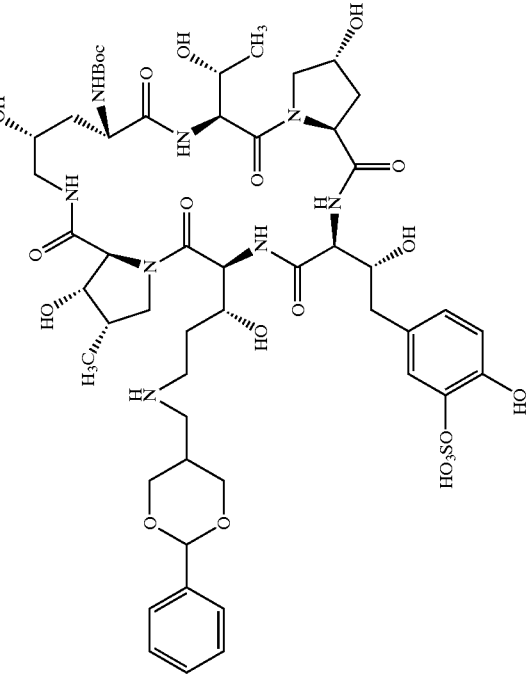 |

| Example No. | Formula |
|---|---|
| | -continued 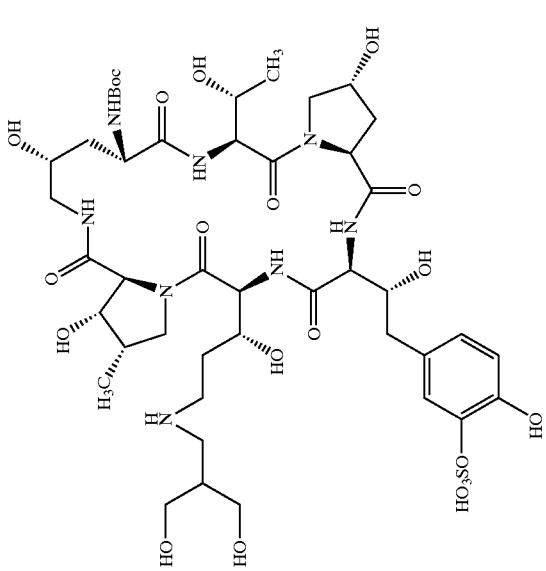 |

| Example No. | Formula |
|---|---|
| 93 | 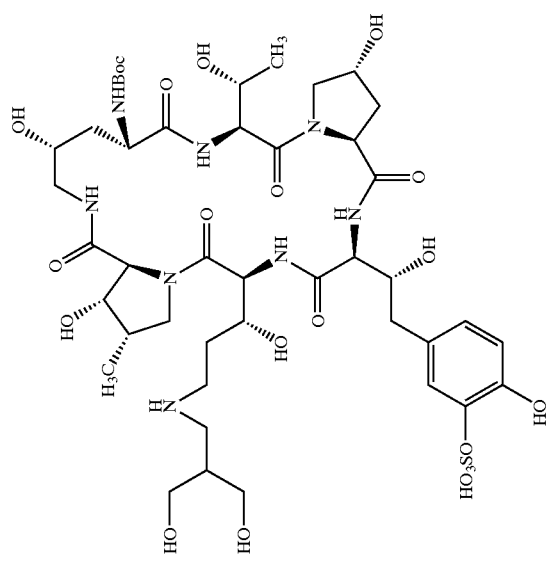 |

| Example No. | Formula |
|---|---|
| | 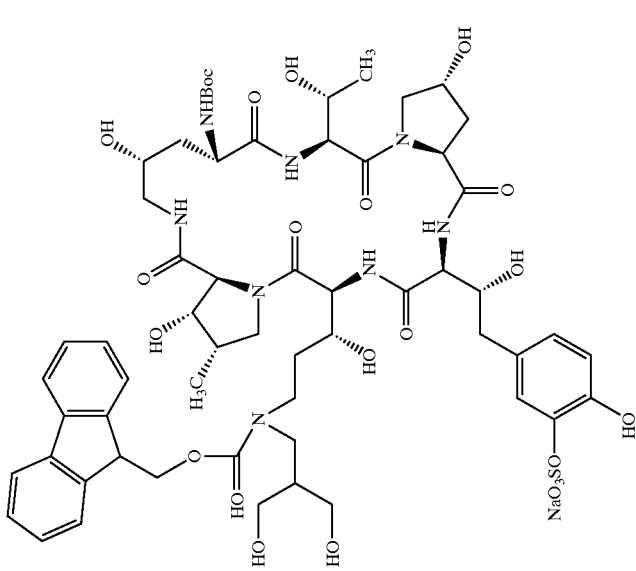 |

-continued
| Example No. | Formula |
|---|---|
| 94 | 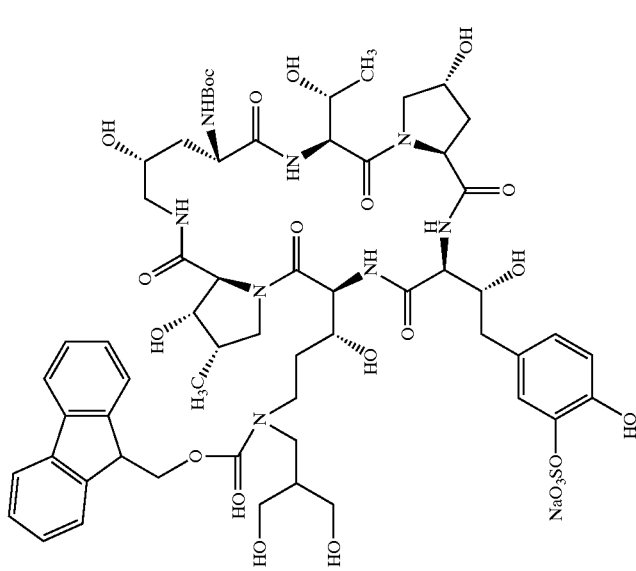 |

| Example No. | Formula |
|---|---|
| | 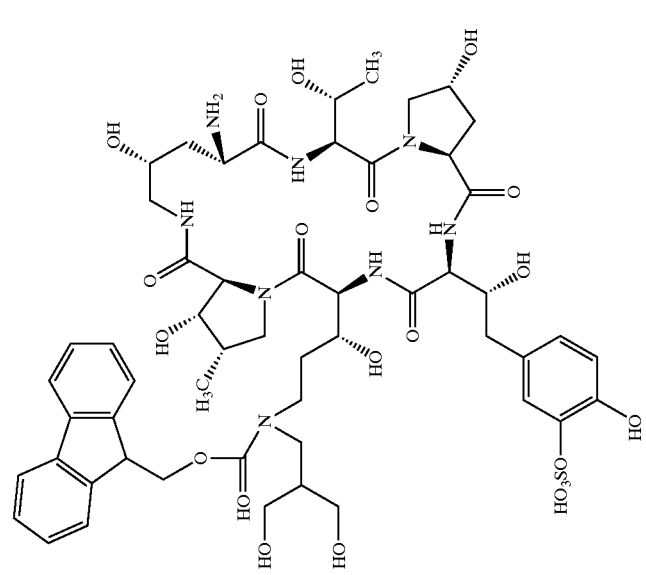 |

| Example No. | Formula |
|---|---|
| 95 | -continued (chemical structure) |

| Example No. | Formula |
|---|---|
| | |

EXAMPLE 1

A solution of the starting compound (1) (4.42 g) and 10% palladium on carbon (50% including water) (3.0 g) in a mixture of methanol (90 ml) and water (80 ml) was hydrogenated under an atmospheric pressure of hydrogen with stirring at ambient temperature for 8 hours. To the reaction mixture was added 10% palladium hydroxide on carbon (50% including water) (4.0 g), and the mixture was hydrogenated under an atmospheric pressure of hydrogen with stirring at ambient temperature for 16 hours. The catalyst was filtered off and washed with a mixture of methanol and water (1:1 v/v) (50 ml), and the filtrate and washes were combined. To the solution was dropwise added allyloxycarbonyl chloride (1.72 ml) in tetrahydrofuran (4 ml) adjusting to pH 8.5–10.0 with 1N sodium hydroxide with stirring on an ice-bath. The mixture was stirred at the same temperature for 2 hours and adjusted to pH 8.0 with 1N hydrochloric acid. The solution was subjected to column chromatography on ODS (Daiso-gel, SP-120-40/60-ODS-B (Trademark: prepared by Daiso Co., Ltd.)) (400 ml) eluting with 10% acetonitrile in water and then with 20% acetonitrile in water. The first fractions containing the object compound were collected and evaporated under reduced pressure to remove acetonitrile. The residue was lyophilized to give the major object compound (1) (0.47 g). The second fractions containing the object compound were collected and evaporated under reduced pressure to remove acetonitrile. The residue was lyophilized to give the minor object compound (1) (2.91 g).

Major Object Compound (1)

IR (KBr): 1761, 1672, 1635, 1512, 1450 cm$^{-1}$

NMR (DMSO-d$_6$+D$_2$O, δ): 0.96 (3H, d, J=6.79 Hz), 1.00–1.15 (3H, m), 1.35 (9H, s), 1.45–2.50 (9H, m), 2.80–3.40 (6H, m), 3.70–4.60 (16H, m), 4.65–4.90 (4H, m), 5.10–5.45 (4H, m), 5.80–6.10 (2H, m), 6.71 (1H, d, J=8.23 Hz), 6.77 (1H, d, J=9.01 Hz), 6.98 (1H, s)

ESI MASS (m/z)(Positive): 1277.2 (M$^+$+Na)

Minor Object Compound (1)

NMR (DMSO-d$_6$+D$_2$O, δ): 0.96 (3H, d, J=6.57 Hz), 1.06 (3H, d, J=4.94 Hz), 1.36 (9H, s), 1.45–2.45 (8H, m), 2.75–3.70 (9H, m), 3.75–4.60 (12H, m), 4.69 (2H, d, J=5.19 Hz), 4.70–4.90 (2H, m), 5.05–5.50 (3H, m), 5.80–6.10 (1H, m), 6.91 (1H, d, J=8.29 Hz), 7.10 (1H, d, J=8.31 Hz), 7.43 (1H, s)

ESI MASS (m/z)(Positive): 1193.3 (M$^+$+Na)

EXAMPLE 2

A suspension of the object compound (2) (1.73 g) in dichloromethane (40 ml) was stirred with cooling at 5° C. and treated with triethylsilane (1.1 ml), followed by trifluoroacetic acid (3.19 ml) dropwise over 30 minutes. After warming to room temperature, the clear solution was stirred for 2 hours, and then poured into a mixture of saturated aqueous sodium hydrogen carbonate (100 ml) and pH 6.86 standard buffer (100 ml). Organic solvent was removed by evaporation, and the remaining aqueous solution purified by ODS (Daiso-gel, SP-120-40/60-ODS-B (Trademark: prepared by Daiso Co., Ltd.)) (200 ml) column chromatography, eluting with aqueous acetonitrile (10–20%). The fractions containing the object compound were collected and evaporated under reduced pressure to remove acetonitrile. The residue was lyophilized to give the object compound (2) (1.10 g).

IR (KBr): 1761, 1668, 1647, 1539, 1512, 1437 cm$^{-1}$

NMR (DMSO-d$_6$+D$_2$O, δ): 0.95 (3H, d, J=6.77 Hz), 1.18 (3H, d, J=4.94 Hz), 1.40–2.40 (7H, m), 2.70–3.40 (4H, m), 3.60–4.60 (17H, m), 4.69 (2H, d, J=5.37 Hz), 4.70–4.90 (2H, m), 5.10–5.50 (4H, m), 5.80–6.20 (2H, m), 6.89 (1H, d), 7.08 (1H, d, J=8.21 Hz)

ESI MASS (m/z)(Positive): 1155.4 (M$^+$+Na)

Elemental Analysis Calcd. for C$_{46}$H$_{68}$N$_8$O$_{23}$S.4H$_2$O: C, 45.84; H, 6.36; N, 9.30.

Found: C, 45.85; H, 6.33; N, 9.16.

EXAMPLE 3

A solution of the starting compound (3) (0.43 g) in dimethylformamide (4 ml) was treated with 4-[2-[4-[4-(5-methoxypentyloxy)piperidin-1-yl]phenyl]imidazo[2,1-b][1,3,4]-thiadiazol-6-yl]benzoic acid benzotirazol-1-yl ester (194 mg) and diisopropylethylamine (78.4 μl) and stirred for 5 hours at room temperature. Ethyl acetate (50 ml) was added, and the resulting precipitate collected, washed with isopropyl ether, and dried to give the object compound (3) (610.6 mg) as a crude powder, that was used directly in the next reaction without purification.

EXAMPLE 4

To a solution of the starting compound (4) (610.6 mg) in a mixture of methanol (10 ml) and tetrahydrofuran (25 ml) were successively added triphenylphosphine (32 mg), tetrakis(triphenylphosphine)palladium(0) (35 mg) and morpholine (106 μl) with stirring, and the mixture was stirred at ambient temperature for 3.5 hours. Ethyl acetate (100 ml) was added, and the resulting precipitate collected, washed with isopropyl ether, and dried to give a crude pale yellow powder (535 mg). The crude powder was dissolved sodium hydroxide aqueous solution and subjected to column chromatography on ODS (YMC-gel ODS-AM-S-50 (Trademark: prepared by YMC Co., Ltd.)) (37% acetonitrile aqueous solution). The fractions containing the object compound were combined, and evaporated under reduced pressure to remove acetonitrile. The residue was lyophilized to give the object compound (4) (293.7 mg).

IR (KBr): 3355.5, 1633.4, 1608.3, 1529.3, 1517.7, 1463.7, 1444.4, 1267.0, 1230.4 cm$^{-1}$

NMR (DMSO-d$_6$, δ): 0.98 (3H, d, J=6.7 Hz), 1.10 (3H, d, J=5.6 Hz), 1.2–5.6 (65H, m), 6.71 (1H, d, J=8.1 Hz), 6.78 (1H, d, J=9.7 Hz), 7.00 (1H, s), 7.09 (2H, d, J=9.1 Hz), 7.75 (2H, d, J=8.7 Hz), 7.95 (4H, s), 7.3–8.7 (7H, m), 8.79 (1H, s)

MASS (m/z): 1465.5 (M–H)$^-$

Elemental Analysis Calcd. for C$_{66}$H$_{90}$N$_{12}$O$_{22}$S$_2$.7H$_2$O: C, 49.74; H, 6.58; N, 10.55.

Found: C, 49.72; H, 6.43; N, 10.40.

EXAMPLE 5

A solution of the starting compound (5) (10 g) in a mixture of methanol (500 ml) and water (100 ml) was treated with cobalt (II) chloride hexahydrate (9.43 g) and then stirred to give a pink solution. Sodium borohydride (7.5 g) was then added portionwise and stirred for 1 hour at ambient temperature. The reaction mixture was filtered through a bed of celite, washing with a mixture of methanol (100 ml) and water (20 ml). The ice-cooled filtrate was then treated dropwise with a solution of allyloxycarbonyl chloride (1.46 ml) in tetrahydrofuran (10 ml), keeping pH 8.0–9.5 with 1N sodium hydroxide and then stirred for 1 hour at the same temperature. The reaction mixture was evaporated in vacuo (about 200 ml) and added 1N sodium hydroxide (60 ml), and then the mixture was stayed in the refrigerator overnight. To the solution was added water (200 ml), and the mixture was purified by ODS (Daiso-gel, SP-120-40/60-ODS-B (Trademark: prepared by Daiso Co., Ltd.)) (200 ml) column chromatography, eluting with aqueous acetonitrile (5–20%). The fractions containing the object compound were collected and evaporated under reduced pressure to remove acetonitrile. The residue was lyophilized to give the object compound (5) (8.58 g)

IR (KBr): 1670, 1633, 1516, 1443, 1269 cm$^{-1}$

NMR (DMSO-d$_6$+D$_2$O, δ): 0.97 (3H, d, J=6.75 Hz), 1.08 (3H, d, J=5.52 Hz), 1.35 (9H, s), 1.40–2.00 (6H, m), 2.10–2.50 (3H, m), 2.80–3.40 (4H, m), 3.65–4.50 (14H, m), 4.65–4.85 (2H, m), 5.05–5.35 (2H, m), 5.70–6.00 (1H, m), 6.72 (1H, d, J=8.12 Hz), 6.78 (1H, d, J=10.1 Hz)

ESI MASS (m/z)(Positive): 1119.3 (M$^+$+Na)

Elemental Analysis Calcd. for C$_{45}$H$_{67}$N$_8$O$_{21}$SNa.5H$_2$O: C, 44.52; H, 6.37; N, 9.44.

Found: C, 44.59; H, 6.43; N, 9.47.

EXAMPLE 6

A suspension of the starting compound (6) (8.5 g) in dichloromethane (180 ml) was stirred with cooling at 5° C. and treated with triethylsilane (6.2 ml), followed by trifluoroacetic acid (17.9 ml) dropwise over 30 minutes. After warming to room temperature, the clear solution was stirred for 2 hours, then poured into a mixture of saturated aqueous sodium hydrogen carbonate (200 ml) and pH 6.86 standard buffer (200 ml). Organic solvent was removed by evaporation, and the remaining aqueous solution purified by ODS (Daiso-gel, SP-120-40/60-ODS-B (Trademark: prepared by Daiso Co., Ltd.)) (200 ml) column chromatography, eluting with aqueous acetonitrile (5–20%). The fractions containing the object compound were collected and evaporated under reduced pressure to remove acetonitrile. The residue was lyophilized to give the object compound (6) (5.53 g).

NMR (DMSO-d$_6$+D$_2$O, δ): 0.97 (3H, d, J=6.64 Hz), 1.15 (3H, d, J=5.52 Hz), 1.30–1.70 (3H, m), 1.80–2.50 (6H, m), 2.70–4.00 (14H, m), 4.20–4.60 (8H, m), 4.70–4.90 (2H, m), 5.10–5.40 (2H, m), 5.70–6.10 (1H, m), 6.70–6.90 (2H, m), 7.06 (1H, s)

ESI MASS (m/z)(Positive): 997.3 (M$^+$+Na)

EXAMPLE 7

A solution of the starting compound (7) (0.5 g) in dimethylformamide (10 ml) was treated with 4-[5-[4-[4-(cis-4-methylcyclohexyl) piperazinyl]phenyl]-1,3,4-thiadiazol-2-yl]benzoic acid benzotriazol-1-yl ester (0.3 g) and diisopropylethylamine (0.13 ml) and stirred for 20 hours at room temperature. Ethyl acetate (100 ml) was added and the resulting precipitate collected, washed with ethyl acetate, and dried to give the object compound (7) (0.5 g).

NMR (DMSO-d$_6$, δ): 0.90 (3H, d, J=6.8 Hz), 0.97 (3H, d, J=6.6 Hz), 1.13 (3H, d, J=5.0 Hz), 1.43–6.10 (78H, m), 6.69–8.72 (18H, m)

ESI MASS (m/z)(Negative): 1418.4 (M+)

EXAMPLE 8

To a suspension of the starting compound (8) (0.38 g) in a mixture of methanol (7.6 ml) and tetrahydrofuran (1.9 ml) were successively added triphenylphosphine (0.04 g), tetrakis(triphenylphosphine)palladium(0) (0.088 g) and morpholine (0.14 ml) with stirring and the mixture was stirred at ambient temperature for 15 hours. To the reaction mixture was added ethyl acetate (100 ml). The resulting precipitate was collected by filtration and dried in vacuo. The precipitate was dissolved in a mixture of water and 1N sodium hydroxide and the solution was subjected to column chromatography on ODS (Daiso-gel, SP-120-40/60-ODS-B (Trademark: prepared by Daiso Co., Ltd.)) (100 ml) eluting with 40% acetonitrile in water. The fractions containing the object compound were collected and evaporated under reduced pressure to remove acetonitrile. The residue was lyophilized to give the object compound (8) (0.25 g).

NMR (DMSO-d$_6$, δ): 0.90 (3H, d, J=6.7 Hz), 0.98 (3H, d, J=6.7 Hz), 1.11 (3H, d, J=5.7 Hz), 1.42–5.23 (56H, m), 6.69–8.92 (17H, m)

ESI MASS (m/z)(Negative): 1334.4 (M+)

Elemental Analysis Calcd. for C$_{61}$H$_{82}$N$_{12}$O$_{18}$S$_2$.8H$_2$O: C, 49.52; H, 6.68; N, 11.36.

Found: C, 49.25; H, 6.41; N, 11.20.

EXAMPLE 9

The suspension of a mixture of the starting compound (9) (100 mg), 1,3-dihydroxyacetate (13.5 mg) and acetic acid (0.13 ml) in a mixture of methanol (1.5 ml) and dimethylformamide (0.7 ml) was added sodium cyanoborohydride (9.4 mg) with stirring at ambient temperature, and the mixture was stirred at the same temperature overnight. To the reaction mixture was added ethyl acetate (20 ml). The resulting precipitate was collected by filtration and dried in vacuo. The precipitate was dissolved in a mixture of water and 1N sodium hydroxide and the solution was subjected to column chromatography on ODS (Daiso-gel, SP-120-40/60-ODS-B (Trademark: prepared by Daiso Co., Ltd.)) (50 ml) eluting with 40% acetonitrile in water. The fractions containing the object compound were collected and evaporated under reduced pressure to remove acetonitrile. The residue was lyophilized to give the object compound (9) (55 mg).

NMR (DMSO-d$_6$, δ): 0.90 (3H, d, J=6.8 Hz), 0.98 (3H, d, J=6.7 Hz), 1.11 (3H, d, J=5.5 Hz), 1.43–5.24 (62H, m), 6.69–8.85 (17H, m)

ESI MASS (m/z)(Negative): 1408.3(M$^+$)

EXAMPLE 10

To a solution of a mixture of the starting compound (10) (7.5 g), 1,3-dihydroxyacetone (1.19 g) and acetic acid (1.14 ml) in a mixture of methanol (120 ml) and dimethylformamide (55 ml) was added sodium cyanoborohydride (835 mg) with stirring at ambient temperature, and the mixture was stirred at the same temperature overnight. To a reaction mixture was poured into ethyl acetate (700 ml). The resulting precipitates were collected by filtration, washed with ethyl acetate (100 ml) and dried in vacuo. The precipitates were dissolved in a mixture of 30% aqueous acetonitrile (800 ml) and 1N sodium hydroxide (5 ml). The solution was subjected to column chromatography on ODS (Daiso-gel, SP-120-40/60-ODS-B (Trademark: prepared by Daiso Co., Ltd.)) (440 ml) eluting in turn with water and aqueous acetonitrile (30%–60%). The fractions containing the object compound were collected and evaporated under reduced pressure to remove acetonitrile. The residue was lyophilized to give the object compound (10) (5.22 g).

IR (KBr): 1632, 1535, 1518, 1443, 1269, 1082, 1047 cm$^{-1}$

NMR (DMSO-d$_6$+D$_2$O, δ): 0.82 (3H, d, J=6.83 Hz), 0.97 (3H, d, J=6.81 Hz), 1.02 (3H, d, J=6.18 Hz), 1.24 (26H, s), 1.35–2.45 (14H, m), 2.75–3.40 (5H, m), 3.60–4.50 (15H, m), 4.7–4.90 (2H, m), 6.65–6.80 (2H, m), 7.01 (1H, s)

ESI MASS (m/z)(Positive): 1088.4 (M$^+$+Na)

EXAMPLE 11

To a solution of the starting compound (11) (4.0 g) in dimethylformamide (40 ml) were successively added diisopropylethylamine (1.45 ml) and 9-fluorenylmethyl chloroformate (1.03 g), and the mixture was stirred at ambient temperature for 2 hours. The reaction mixture was poured into water (200 ml) The solution was purified by ODS (Daiso-gel, SP-120-40/60-ODS-B (Trademark: prepared by Daiso Co., Ltd.)) (200 ml) column chromatography, eluting in turn with a mixture of saturated aqueous sodium chloride (400 ml), saturated aqueous sodium hydrogen carbonate (50 ml) and water (400 ml), and aqueous acetonitrile (30–60%). The fractions containing the object compound were collected and evaporated under reduced pressure to remove acetonitrile. The residue was lyophilized to give the object compound (11) (2.82 g).

IR (KBr): 1666, 1632, 1518, 1446, 1273, 1246, 1082, 1047 cm$^{-1}$

NMR (DMSO-d$_6$+D$_2$O, δ): 0.80–1.10 (9H, m), 1.23 (26H, s), 1.35–2.45 (12H, m), 2.60–3.40 (6H, m), 3.60–4.55 (18H, m), 4.65–4.90 (2H, m), 6.65–6.85 (2H, m), 6.97 (1H, s), 7.30–7.50 (4H, m), 7.60–7.95 (4H, m)

ESI MASS (m/z)(Negative): 1423.7 (M$^+$−Na)

Elemental Analysis Calcd. for C$_{69}$H$_{99}$N$_8$O$_{22}$SNa.6H$_2$O: C, 53.27; H, 7.19; N, 7.20.

Found: C, 53.45; H, 7.21; N, 7.10.

EXAMPLE 12

To a solution of the object compound (12) (1.21 g) in dimethylformamide (15 ml) were successively added diisopropylethylamine (0.26 ml) and di-tert-butyl dicarbonate (285 mg), and the mixture was stirred at ambient temperature overnight. The reaction mixture was poured into a mixture of pH 6.86 standard buffer solution (150 ml), saturated aqueous sodium chloride (50 ml) and saturated aqueous sodium hydrogen carbonate (20 ml). The mixture was purified by ODS (Daiso-gel, SP-120-40/60-ODS-B (Trademark: prepared by Daiso Co., Ltd.)) (200 ml) column chromatography, eluting with aqueous acetonitrile (30–50%). The fractions containing the object compound were collected and evaporated under reduced pressure to remove acetonitrile. The residue was lyophilized to give the object compound (12) (1.19 g).

IR (KBr): 1662, 1632, 1535, 1518, 1444, 1367, 1272, 1250 cm$^{-1}$

NMR (DMSO-d$_6$+D$_2$O, δ): 0.85 (3H, d, J=6.76 Hz), 0.96 (3H, d, J=6.77 Hz), 1.04 (3H, d, J=5.50 Hz), 1.23 (26H, s), 1.37 (9H, s), 1.40–1.50 (2H, m), 1.55–2.50 (10H, m), 2.80–3.40 (6H, m), 3.50–4.45 (14H, m), 6.65–6.80 (2H, m), 6.96 (1H, s)

ESI MASS (m/z)(Negative): 1301.6 (M$^+$−Na)

EXAMPLE 13

To a solution of a mixture of starting compound (13) (1.62 g) and diisopropylethylamine (0.58 ml) in DMF (16 ml) was added 9-fluorenylmethyloxycarbonyl chloride (493 mg) with stirring at ambient temperature, and the mixture was stirred at the same temperature for 3 hours. The reaction mixture was poured into ethyl acetate (250 ml). To the mixtures was added pH 6.86 standard buffer solution (100 ml) and 5% aqueous sodium chloride (20 ml), and the aqueous layer was separated. The organic layer was extracted with 5% aqueous sodium chloride (100 ml), and these aqueous layers were collected and evaporated in vacuo to remove organic solvent. The solution was subjected to column chromatography on ODS (Daiso-gel, SP-120-40/60-ODS-B (Trademark: prepared by Daiso Co., Ltd.)) (200 ml) eluting with 40% acetonitrile in water. The fractions containing the object compound were collected and evaporated under reduced pressure to remove acetonitrile. The residue was lyophilized to give object compound (13) (1.38 g).

NMR (DMSO-d$_6$+D$_2$O, δ): 0.89 (3H, d, J=6.26 Hz), 1.09 (3H, broad s), 1.33 (9H, s), 1.40–2.10 (5H, m), 2.10–2.35 (2H, m), 2.75–3.40 (5H, m), 3.50–4.50 (16H, m), 4.60–4.90 (2H, m), 6.65–6.80 (2H, m), 6.97 (1H, s), 7.25–7.50 (4H, m), 7.70 (2H, d, J=6.82 Hz), 7.88 (2H, d, J=6.77 Hz)

ESI MASS (m/z)(Positive): 1331.3 (M$^+$+Na)

Elemental Analysis Calcd. for C$_{58}$H$_{77}$N$_8$O$_{23}$SNa.4H$_2$O: C, 50.43; H, 6.20; N, 8.11.

Found: C, 50.14; H, 6.28; N, 8.12.

EXAMPLE 14

To a solution of a mixture of starting compound (14) (300 mg), 2-oxo-1,3-diacetoxypropane (121 mg) and acetic acid (40 μl) in a mixture of methanol (4.0 ml) and DMF (4.0 ml) was added sodium cyanoborohydride (29 mg) with stirring at ambient temperature, and the mixture was stirred at the same temperature overnight. The reaction mixture was concentrated in vacuo. To the resulting residue was added pH 6.86 standard buffer solution (10 ml) and acetonitrile (2 ml), and the solution was subjected to column chromatography on ODS (Daiso-gel, SP-120-40/60-ODS-B (Trademark: prepared by Daiso Co., Ltd.)) (80 ml) eluting with 40% acetonitrile in water. The fractions containing the object compound were collected and evaporated under reduced pressure to remove acetonitrile. The residue was lyophilized to give object compound (14) (60 mg).

NMR (DMSO-d$_6$+D$_2$O, δ): 0.98 (3H, d, J=6.83 Hz), 1.07 (3H, d, J=5.34 Hz), 1.20–1.60 (10H, m), 1.60–1.90 (5H, m), 1.96 (3H, s), 2.01 (3H, s), 3.20 (3H, s), 3.31 (4H, t, J=6.33 Hz), 3.80–4.55 (16H, m), 4.75–4.90 (2H, m), 6.65–6.80 (2H, m), 7.03 (1H, s), 7.14 (2H, d, J=8.84 Hz), 7.90–8.15 (6H, m)

ESI MASS (m/z)(Negative): 1455.3 (M$^+$−1)

EXAMPLE 15

To a solution of starting compound (15) (58 mg) in a mixture of methanol (3 ml) and water (3 ml) were added morpholine (35 μl) and saturated aqueous sodium carbonate (1 ml), and the mixture was stirred at ambient temperature for 1 hour. The reaction mixture was poured into pH 6.86 standard buffer solution (60 ml), and the solution was subjected to column chromatography on ODS (Daiso-gel, SP-120-40/60-ODS-B (Trademark: prepared by Daiso Co., Ltd.)) (50 ml) eluting with 30% acetonitrile in water. The fractions containing the object compound were collected and evaporated under reduced pressure to remove acetonitrile. The residue was lyophilized to give object compound (15) (35 mg).

NMR (DMSO-d$_6$+D$_2$O, δ): 0.97 (3H, d, J=6.78 Hz), 1.12 (3H, broad s), 1.25–1.65 (8H, m), 1.65–2.00 (4H, m), 2.01 (3H, d, s), 3.21 (3H, s), 3.31 (4H, t, J=6.34 Hz), 3.70–4.50 (14H, m), 4.85–4.90 (2H, m), 6.60–6.95 (2H, m), 7.00 (1H, s), 7.14 (2H, d, J=8.74 Hz), 8.00 (2H, d, J=8.77 Hz), 8.03 (2H, d, J=7.63 Hz), 8.12 (2H, d, J=8.42 Hz)

ESI MASS (m/z) (Negative): 1413.4 (M$^+$−1−Na)

EXAMPLE 16

To a solution of starting compound (16) (100 mg) in DMF (3 ml) were added 4-[5-[4-(6-methoxyhexyl)phenyl][1,3,4]- thiadiazol-2-yl]benzoic acid benzotriazol-1-yl ester (71 mg) and diisopropylethylamine (23 µl) with stirring, and the mixture was stirred at ambient temperature overnight. To the reaction mixture was added ethyl acetate (30 ml). The resulting precipitates were collected by filtration, washed with ethyl acetate (10 ml) and dried in vacuo. The resulting residue was dissolved in a mixture of pH 6.86 standard buffer solution and 1N sodium hydroxide, and insoluble materials were filtered off and the solution was subjected to column chromatography on ODS (Daiso-gel, SP-120-40/60-ODS-B (Trademark: prepared by Daiso Co., Ltd.)) (50 ml) eluting with 30% acetonitrile in water. The fractions containing the object compound were collected and evaporated under reduced pressure to remove acetonitrile. The residue was lyophilized to give object compound (16) (86.5 mg).

NMR (DMSO-d$_6$+D$_2$O, δ): 0.97 (3H, d, J=6.53 Hz), 1.08 (3H, d, J=8.66 Hz), 1.30–2.00 (14H, m), 2.80–3.10 (4H, m), 3.22 (3H, s), 3.90–4.55 (16H, m), 4.65–4.90 (2H, m), 5.10–5.40 (2H, m), 6.82 (2H, br s), 7.00 (1H, s), 7.14 (2H, d, J=9.17 Hz), 7.90–8.20 (6H, m)

ESI MASS (m/z)(Negative): 1441.4 (M$^+$−1−Na)

EXAMPLE 17

To a solution of starting compound (17) (200 mg) in N,N-dimethylformamide (DMF) (3 ml) were added 4'-[4-4-(cis-2,6-dimethylmorpholin-4-yl)phenyl]piperazin-1-yl]-1,1'-biphenyl-4-carboxylic acid benzotriazol-1-yl ester (57 mg) and diisopropylethylamine (22 µl) with stirring, and the mixture was stirred at ambient temperature overnight. To the reaction mixture was added ethyl acetate (30 ml). The resulting precipitates were collected by filtration, washed with ethyl acetate (10 ml) and dried in vacuo. The resulting residue was dissolved in a mixture of pH 6.86 standard buffer solution and 1N sodium hydroxide, and insoluble material were filtered off and the solution was subjected to column chromatography on ODS (Daiso-gel, SP-120-40/60-ODS-B (Trademark: prepared by Daiso Co., Ltd.)) (100 ml) eluting with 40% acetonitrile in water. The fractions containing the object compound were collected and evaporated under reduced pressure to remove acetonitrile. The residue was lyophilized to give object compound (17) (230 mg).

NMR (DMSO-d$_6$+D$_2$O, δ): 0.97 (3H, d, J=6.82 Hz), 1.14 (6H, d, J=6.16 Hz), 1.25 (3H, d, J=6.34 Hz), 1.30–2.40 (6H, m), 3.00–3.40 (10H, m), 3.60–4.10 (10H, m), 4.10–4.55 (6H, m), 4.60–4.80 (4H, m), 5.05–5.50 (4H, m), 5.80–6.10 (2H, m), 6.80–7.00 (4H, m), 7.08 (2H, d, J=8.10 Hz), 7.11 (2H, d, J=8.88 Hz), 7.42 (1H, s), 7.66 (2H, d, J=8.64 Hz), 7.72 (2H, d, J=8.46 Hz), 7.93 (2H, d, J=8.38 Hz)

ESI MASS (m/z)(Negative): 1584.6 (M$^+$−Na)

EXAMPLE 18

A mixture of 4-[5-[4-(6-methoxyhexyloxy)phenyl]-isoxazol-3-yl]benzoic acid (70 mg), 1-hydroxybenzotriazole (35.8 mg), 1-ethyl-3-(3'-dimethylaminopropyl)carbodiimide hydrochloride (40.6 mg) and N,N-diisopropylethylamine (46.1 µl) in N,N-dimethylformamide (2 ml) was stirred for 3 hours. To the reaction mixture was added starting compound (18) (200 mg) and the resulting mixture was stirred for 19 hours. To the reaction mixture was added ethyl acetate (100 ml). The resulting precipitate was collected by filtration and washed with diisopropyl ether to give object compound (18) as a crude white powder (294.4 mg), that was used crude in the next reaction.

The following compound was obtained according to a similar manner to that of Example 18.

EXAMPLE 19

The object compound (19) was used directly in the next reaction without purification.

EXAMPLE 20

To a solution of starting compound (20) (287.9 mg) in N,N-dimethylformamide (3 ml) was added piperidine (0.17 ml) at room temperature. The solution was stirred for 1 hour at the same temperature. Ethyl acetate was added to the reaction mixture. The powder was collected by filtration to give crude material (203.8 mg). The crude material was purified by column chromatography on ODS to give object compound (20) (85.6 mg).

IR (KBr): 1632, 1512, 1446, 1230 cm$^{-1}$

NMR (DMSO-d$_6$, δ): 0.97 (3H, d, J=6.7 Hz), 1.08 (3H, d, J=5.2 Hz), 1.5–3.0 (23H, m), 3.0–4.5 (39H, m), 4.6–5.4 (10H, m), 6.6–7.1 (11H, m), 7.17 (2H, d, J=8.7 Hz), 7.3–7.6 (2H, m), 7.81 (2H, d, J=8.6 Hz), 8.0–8.5 (2H, m), 8.71 (1H, s)

MASS (m/z): 1488 (M$^+$+1)

The following compound was obtained according to a similar manner to that of Example 20.

EXAMPLE 21

IR (KBr): 1632, 1512, 1444, 1232 cm$^{-1}$

NMR (DMSO-d$_6$, δ): 0.97 (3H, d, J=6.8 Hz), 1.08 (3H, d, J=5.5 Hz), 1.2–3.0 (28H, m), 3.0–4.5 (38H, m), 4.6–5.4 (10H, m), 6.6–7.1 (9H, m), 7.3–7.7 (2H, m), 7.7–8.0 (3H, m), 8.0–8.5 (5H, m), 8.71 (1H, s)

MASS (m/z): 1456 (M$^+$−1)

EXAMPLE 22

To a solution of starting compound (22) (0.22 g) in a mixture of methanol (4 ml) and THF (1 ml) were successively added triphenylphosphine (14 mg), tetrakis(triphenylphosphine)palladium(0) (8 mg) and morpholine (40 µl) with stirring and the mixture was stirred at ambient temperature for 3 hours. The reaction mixture was concentrated in vacuo. The resulting residue was dissolved in a mixture of pH 6.86 standard buffer solution and 1N sodium hydroxide, insoluble materials were filtered off and the solution was subjected to column chromatography on ODS (Daiso-gel, SP-120-40/60-ODS-B (Trademark: prepared by Daiso Co., Ltd.)) (100 ml) eluting with 30% acetonitrile in water. The fractions containing the object compound were collected and evaporated under reduced pressure to remove acetonitrile. The residue was lyophilized to give object compound (22) (85 mg).

IR (KBr): 1633, 1537, 1516, 1450, 1234 cm$^{-1}$

NMR (DMSO-d$_6$+D$_2$O, δ): 0.98 (3H, d, J=7.09 Hz), 1.05 (3H, d, J=7.00 Hz), 1.15 (6H, d, J=6.21 Hz), 1.60–2.30 (8H, m), 2.75–3.45 (14H, m), 3.80–4.50 (10H, m), 4.81 (1H, br s), 6.65–7.20 (8H, m), 7.50–7.80 (5H, m), 7.94 (2H, d, J=8.49 Hz)

ESI MASS (m/z)(Negative): 1416.4 (M$^+$+1)

Elemental Analysis Calcd. for C$_{67}$H$_{91}$N$_{11}$O$_{21}$S.7H$_2$O: C, 52.10; H, 6.85; N, 9.97.

Found: C, 52.29; H, 6.60; N, 9.61.

The following compounds [Examples 23 to 32] were obtained according to a similar manner to that of Example 22.

EXAMPLE 23

NMR (DMSO-d$_6$+D$_2$O, δ): 0.97 (3H, d, J=6.84 Hz), 1.11 (3H, d, J=5.43 Hz), 1.30–1.90 (14H, m), 2.80–3.20 (5H, m), 3.22 (3H, s), 3.31 (2H, t, J=6.16 Hz), 3.80–4.20 (6H, m), 4.26 (2H, broad s), 4.30–4.50 (3H, m), 4.70–4.90 (1H, m), 6.72 (1H, d, J=8.14 Hz), 6.78 (1H, d, J=10.5 Hz), 7.01 (1H, s), 7.14 (2H, d, J=8.70 Hz), 7.98 (2H, d, J=8.90 Hz), 8.05 (2H, d, J=8.68 Hz), 8.12 (2H, d, J=8.68 Hz)

MASS (m/z)(Negative): 1357.5 ($M^+$−1)

EXAMPLE 24

IR (KBr): 2933, 1633, 1531, 1518, 1444, 1419, 1385, 1346 $cm^{-1}$

NMR (DMSO-$d_6$, δ): 0.90 (3H, d, J=6.7 Hz), 0.98 (3H, d, J=6.7 Hz), 1.12 (3H, d, J=5.5 Hz), 1.32–2.68 (23H, m), 2.82–2.98 (2H, m), 3.07–4.54 (25H, m), 4.74–5.50 (10H, m), 6.70 (1H, d, J=8.1 Hz), 6.78 (1H, d, J=8.1 Hz), 7.00 (1H, s), 7.09 (2H, d, J=9.0 Hz), 7.36–7.70 (2H, m), 7.86 (2H, d, J=8.8 Hz), 8.00–8.50 (6H, m), 8.71 (1H, s), 8.82–8.97 (1H, m)

ESI MASS (m/z): 1407.5 ($M^+$+1)

Elemental Analysis Calcd. for $C_{64}H_{88}N_{12}O_{20}S_2 \cdot 7H_2O$: C, 50.06; H, 6.69; N, 10.94.

Found: C, 49.99; H, 6.76; N, 10.73.

EXAMPLE 25

IR (KBr): 3353.6, 1666.2, 1648.8, 1631.5, 1540.8, 1508.1, 1452.1, 1436.7, 1257.4 $cm^{-1}$

NMR (DMSO-$d_6$, δ): 0.98 (3H, d, J=6.7 Hz), 1.11 (3H, d, J=5.5 Hz), 1.2–5.6 (59H, m), 6.71 (1H, d, J=8.2 Hz), 6.78 (1H, d, J=9.6 Hz), 7.00 (1H, s), 7.12 (2H, d, J=8.8 Hz), 7.44 (1H, d, J=8.5 Hz), 7.55 (1H, s), 7.85 (2H, d, J=8.6 Hz), 7.99 (2H, d, J=8.5 Hz), 8.05 (2H, d, J=8.6 Hz), 7.3–8.5 (3H, m), 8.71 (1H, s), 8.7–9.0 (1H, m)

MASS (m/z): 1340.4 ($M^-$−Na)

Elemental Analysis Calcd. for $C_{61}H_{83}N_9O_{23}S \cdot 6H_2O$: C, 50.51; H, 6.60; N, 8.69.

Found: C, 50.67; H, 6.60; N, 8.62.

EXAMPLE 26

IR (KBr): 3380.6, 1675.8, 1648.8, 1621.8, 1540.8, 1506.1, 1454.1, 1434.8, 1257.4 $cm^{-1}$

NMR (DMSO-$d_6$, δ): 0.98 (3H, d, J=6.8 Hz), 1.03 (6H, d, J=6.3 Hz), 1.12 (3H, d, J=5.5 Hz), 1.2–5.6 (64H, m), 6.71 (1H, d, J=8.1 Hz), 6.77 (1H, d, J=9.4 Hz), 7.00 (1H, s), 7.12 (2H, d, J=8.9 Hz), 7.43 (1H, d, J=7.7 Hz), 7.55 (1H, s), 7.85 (2H, d, J=8.6 Hz), 7.99 (2H, d, J=8.8 Hz), 8.05 (2H, d, J=8.8 Hz), 7.3–8.5 (3H, m), 8.71 (1H, s), 8.82 (1H, d, J=5.7 Hz)

MASS (m/z): 1437.4 ($M^-$−1)

Elemental Analysis Calcd. for $C_{67}H_{94}N_{10}O_{23}S \cdot 6H_2O$: C, 52.00; H, 6.90; N, 9.05.

Found: C, 51.91; H, 6.91; N, 8.77.

EXAMPLE 27

IR (KBr): 2931, 2854, 1632, 1510, 1446, 1385, 1325 $cm^{-1}$

NMR (DMSO-$d_6$, δ): 0.97 (3H, d, J=6.7 Hz), 1.12 (3H, d, J=5.5 Hz), 1.08–2.62 (23H, m), 2.62–4.50 (37H, m), 4.66–5.45 (10H, m), 6.70 (1H, d, J=8.1 Hz), 6.78 (1H, d, J=8.1 Hz), 6.83–7.09 (7H, m), 7.34–8.00 (3H, m), 7.80 (2H, d, J=8.7 Hz), 8.00–8.49 (2H, m), 8.71 (1H, s)

MASS (m/z): 1408.4 ($M^+$+1)

Elemental Analysis Calcd. for $C_{66}H_{95}N_{11}O_{21}S \cdot 7H_2O$: C, 51.59; H, 7.15; N, 10.03.

Found: C, 51.77; H, 7.05; N, 9.82.

EXAMPLE 28

IR (KBr): 2974, 2937, 1633, 1533, 1512, 1444, 1383, 1327 $cm^{-1}$

NMR (DMSO-$d_6$, δ): 0.98 (3H, d, J=6.7 Hz), 1.11 (3H, d, J=5.2 Hz), 1.18 (6H, d, J=6.1 Hz), 1.59–2.65 (11H, m), 2.65–4.56 (27H, m), 4.70–5.36 (10H, m), 6.71 (1H, d, J=8.1 Hz), 6.78 (1H, d, J=8.1 Hz), 7.00 (1H, s), 7.08 (2H, d, J=8.8 Hz), 7.38–7.99 (3H, m), 7.68 (2H, d, J=8.7 Hz), 7.86 (2H, d, J=8.5 Hz), 8.00–8.46 (7H, m), 8.71 (1H, s), 8.80–8.95 (1H, m)

MASS (m/z): 1440.3 ($M^+$+Na)

Elemental Analysis Calcd. for $C_{65}H_{85}N_{11}O_{21}S_2 \cdot 8H_2O$: C, 49.96; H, 6.39; N, 9.86.

Found: C, 50.03; H, 6.17; N, 9.47.

EXAMPLE 29

IR (KBr): 3386.4, 1633.4, 1502.3, 1446.4, 1232.3 $cm^{-1}$

NMR (DMSO-$d_6$, δ): 0.96 (3H, d, J=6.6 Hz), 1.0–1.3 (9H, m), 1.3–5.6 (57H, m), 6.70 (1H, d, J=8.1 Hz), 6.77 (1H, d, J=9.7 Hz), 6.9–7.2 (7H, m), 7.3–9.0 (13H, m)

MASS (m/z): 1416.4 ($M^-$−Na)

EXAMPLE 30

IR (KBr): 3365.2, 1631.5, 1517.7, 1465.6, 1444.4, 1257.4 $cm^{-1}$

MASS (m/z): 1368.3 ($M^-$1)

Elemental Analysis Calcd. for $C_{60}H_{79}N_{11}O_{22}S_2 \cdot 7H_2O$: C, 48.15; H, 6.26; N, 10.30.

Found: C, 48.26; H, 6.17; N, 10.35.

EXAMPLE 31

IR (KBr): 3458, 3425, 3398, 3386, 3363, 2935, 1635, 1523, 1462, 1244 $cm^{-1}$

NMR (DMSO-$d_6$, δ): 0.98 (3H, d, J=6.7 Hz), 1.12 (3H, d, J=5.6 Hz), 1.20–1.60 (12H, m), 1.70–2.45 (12H, m), 2.80–3.20 (9H, m), 3.21 (3H, s), 3.40–4.60 (24H, m), 4.70–5.40 (12H, m), 6.71 (1H, d, J=8.1 Hz), 6.60–6.80 (1H, m), 7.00 (1H, d, J=1.4 Hz), 7.08 (2H, d, J=9 Hz), 7.35–7.65 (2H, m), 7.75 (2H, d, J=8.8 Hz), 7.80–8.10 (5H, m), 8.20–8.40 (1H, m), 8.60–8.80 (2H, m), 8.80 (1H, s)

MASS (m/z) (API-ES-Negative): 1497 ($M^+$−1+Na)

Elemental Analysis Calcd. for $C_{67}H_{91}N_{12}O_{21}S_3 \cdot 8\text{-}1/2H_2O$: C, 48.75, M 6.55; N, 10.18.

Found: C, 48.52; H, 6.47; N, 9.74.

EXAMPLE 32

IR (KBr): 3464, 3425, 3398, 3386, 3363, 2940, 1635, 1523, 1461 $cm^{-1}$

NMR (DMSO-$d_6$, δ): 0.97 (3H, d, J=6.8 Hz), 1.12 (3H, d, J=5.6 Hz), 1.40–1.60 (6H, m), 1.65–2.45 (9H, m), 2.60–3.20 (6H, m), 3.21 (3H, s), 3.40–3.80 (15H, m), 3.80–4.60 (14H, m), 4.65–5.50 (9H, m), 6.71 (1H, d, J=8.1 Hz), 6.75 (1H, dd, J=1.6 and 8.3 Hz), 7.03 (1H, d, J=1.6 Hz), 7.09 (2H, d, J=9 Hz), 7.40–7.65 (2H, m), 7.75 (2H, d, J=8.8 Hz), 7.80–8.00 (4H, m), 8.18–8.30 (1H, m), 8.55–8.70 (1H, m), 8.75 (2H, d, J=8.7 Hz)

MASS (m/z)(API-ES-Negative): 1453 ($M^+$)

Elemental Analysis Calcd. for $C_{65}H_{88}N_{12}O_{22}S_2 \cdot 6H_2O$: C, 49.27; H, 6.25; N, 10.61.

Found: C, 49.03; H, 6.33; N, 10.30.

EXAMPLE 33

To a solution of starting compound (33) (12.50 g) and diisopropylethylamine (3.67 ml) in N,N-dimethylformamide (250 ml) was added 4-[2-[4-(4-methoxybutoxy)phenyl]imidazo-[2,1-b][1,3,4]thiadiazol-6-yl]benzoic acid benzotriazol-1-yl ester at room temperature. The solution was stirred for 4 hours at the same temperature, during which period additional 4-[2-[4-(4-methoxybutoxy) phenyl]imidazo[2,1-b][1,3,4]-thiadiazol-6-yl]benzoic acid benzotriazol-1-yl ester was added to the mixture. The reaction mixture was then filtered. To the filtrate was added piperidine (9.33 ml) at room temperature. The solution was stirred for 1 hour at the same temperature. Ethyl acetate was added to the reaction mixture. The powder was collected by filtration to give crude material (16.12 g). The crude material was purified by column chromatography on ODS to give object compound (33) (11.10 g).

IR (KBr): 1659, 1633, 1529, 1518, 1466, 1444, 1255 cm$^{-1}$

NMR (DMSO-d$_6$, δ): 0.98 (3H, d, J=6.7 Hz), 1.00 (3H, d, J=5.8 Hz), 1.5–2.6 (12H, m), 2.8–3.6 (33H, m), 4.7–5.4 (10H, m), 6.65–6.85 (2H, m), 7.00 (1H, s), 7.15 (2H, d, J=8.9 Hz), 7.3–7.7 (2H, m), 7.90 (2H, d, J=8.8 Hz), 7.96 (4H, s), 8.0–8.5 (2H, m), 8.71 (1H, s), 8.85 (1H, s)

MASS (m/z): 1392 (M$^+$+23)

Elemental Analysis Calcd. for C$_{60}$H$_{79}$N$_{11}$O$_{22}$S$_2$.5H$_2$O: C, 49.34; H, 6.14; N, 10.55.

Found: C, 49.30; H, 6.23; N, 10.53.

The following compounds [Examples 34 and 44] were obtained according to a similar manner to that of Example 33.

EXAMPLE 34

IR (KBr): 3463, 3423, 3359, 2941, 2883, 1633, 1614, 1523, 1462 cm$^{-1}$

NMR (DMSO-d$_6$, δ): 0.98 (3H, d, J=6.7 Hz), 1.10 (3H, d, J=5.6 Hz), 1.35–2.20 (10H, m), 2.80–3.20 (2H, m), 3.22 (3H, s), 3.30–3.80 (10H, m), 3.80–4.60 (10H, m), 4.70–5.35 (9H, m), 6.71 (1H, d, J=8.1 Hz), 6.65–6.90 (1H, m), 7.00 (1H, br s), 7.09 (2H, d, J=9 Hz), 7.40–7.70 (2H, m), 7.43 (2H, d, J=8.6 Hz), 7.80–8.00 (4H, m), 8.10–8.50 (2H, m), 8.60–8.80 (3H, m)

MASS (m/z)(API-ES-Negative): 1440 (M$^+$-1)

Elemental Analysis Calcd. for C$_{64}$H$_{86}$N$_{12}$O$_{22}$S$_2$.6-1/2H$_2$O: C, 49.36; H, 6.36; N, 10.80.

Found: C, 49.20; H, 6.50; N, 10.66.

EXAMPLE 35

NMR (DMSO-d$_6$, δ): 0.90 (3H, d, J=6.7 Hz), 0.98 (3H, d, J=6.8 Hz), 1.11 (3H, d, J=5.7 Hz), 1.43–5.24 (62H, m), 6.69–8.85 (17H, m)

MASS (m/z): 1408.5

EXAMPLE 36

MASS (m/z): 1491.4 (M$^+$-HN$^+$Et(iPr)$_2$)

EXAMPLE 37

MASS (m/z): 1576.5 (M$^+$-HN$^+$Et(iPr)$_2$)

EXAMPLE 38

MASS (m/z): 1584.4 (M$^+$-HN$^+$Et(iPr)$_2$)

EXAMPLE 39

The object compound (39) was used directly in the next reaction without purification.

EXAMPLE 40

The object compound (40) was used directly in the next reaction without purification.

EXAMPLE 41

The object compound (41) was used directly in the next reaction without purification.

EXAMPLE 42

The object compound (42) was used directly in the next reaction without purification.

The following compounds [Examples 43 and 44] were obtained according to a similar manner to that of Example 20.

EXAMPLE 43

NMR (DMSO-d$_6$+D$_2$O, δ): 0.89 (3H, d, J=6.22 Hz), 1.14 (3H, br s), 1.35–2.40 (6H, m), 2.65–3.00 (1H, m), 3.60–4.50 (14H, m), 4.55–4.80 (2H, m), 5.28 (1H, s), 6.65–6.80 (2H, m), 6.98 (1H, s), 7.20–7.50 (4H, m), 7.69 (2H, d, J=7.08 Hz), 7.84 (2H, d, J=7.27 Hz)

ESI MASS (m/z)(Negative): 1185.4 (M$^+$-1)

EXAMPLE 44

NMR (DMSO-d$_6$+D$_2$O, δ): 0.95 (3H, d, J=6.77 Hz), 1.12 (3H, d, J=4.94 Hz), 1.20–1.75 (4H, m), 1.80–2.50 (4H, m), 2.65–2.90 (1H, m), 3.00–3.40 (4H, m), 3.60–4.05 (6H, m), 4.17 (2H, J=7.17 Hz), 4.25–4.90 (7H, m), 5.05–5.35 (2H, m), 5.75–6.10 (1H, m), 6.65–6.85 (2H, m), 6.97 (1H, s)

ESI MASS (m/z)(Positive): 1048.3 (M$^+$)

EXAMPLE 45

To a solution of a mixture of starting compound (45) (2.0 g), 1,3-dihydroxyacetone (364 mg) and acetic acid (0.58 ml) in a mixture of methanol (30 ml) and DMF (14 ml) was added sodium cyanoborohydride (258 mg) with stirring at ambient temperature, and the mixture was stirred at the same temperature overnight. To the reaction mixture was added ethyl acetate (200 ml). The resulting precipitates were collected by filtration and dried in vacuo. The precipitates were dissolved in a mixture of pH 6.86 standard buffer solution (100 ml) and acetonitrile (20 ml), and the solution was subjected to column chromatography on ODS (Daiso-gel, SP-120-40/60-ODS-B (Trademark: prepared by Daiso Co., Ltd.)) (200 ml) eluting with 15% acetonitrile in water. The fractions containing the object compound were collected and evaporated under reduced pressure to remove acetonitrile. The residue was lyophilized to give object compound (45) (1.63 g).

NMR (DMSO-d$_6$+D$_2$O, δ): 0.98 (3H, d, J=6.75 Hz), 1.08 (3H, d, J=5.69 Hz), 1.35 (9H, s), 1.45–2.05 (5H, m), 2.15–2.50 (4H, m), 2.70–3.35 (7H, m), 3.50–4.50 (16H, m), 4.70–4.90 (2H, m), 6.71 (1H, d, J=8.13 Hz), 6.78 (1H, d, J=9.91 Hz), 7.01 (1H, s)

ESI MASS (m/z) (Positive): 1088.4(M$^+$+Na)

The following compounds [Examples 46 to 52] were obtained according to a similar manner to that of Example 45.

EXAMPLE 46

IR (KBr): 3353.6, 1635.3, 1444.4, 1257.4, 1085.7, 1047.2 cm$^{-1}$

NMR (DMSO-d$_6$, δ): 0.97 (3H, d, J=6.6 Hz), 1.14 (3H, d, J=5.4 Hz), 1.2–5.6 (61H, m), 6.71 (1H, d, J=8.0 Hz), 6.77

(1H, d, J=10.3 Hz), 6.96 (1H, s), 7.13 (2H, d, J=8.8 Hz), 7.97 (2H, d, J=8.7 Hz), 8.08 (4H, s), 7.4–8.9 (6H, m)

MASS (m/z): 1371.4 (M$^-$1)

EXAMPLE 47

IR (KBr): 3353.6, 1635.3, 1531.2, 1517.7, 1444.4, 1257.4, 1087.7, 1045.2 cm$^{-1}$

NMR (DMSO-d$_6$, δ): 0.97 (3H, d, J=6.7 Hz), 1.0–5.6 (64H, m), 6.6–6.8 (2H, m), 6.99 (1H, s), 7.14 (2H, d, J=8.9 Hz), 7.97 (2H, d, J=8.8 Hz), 8.08 (4H, s), 7.3–9.0 (6H, m)

MASS (m/z): 1371.3 (M$^-$–1)

Elemental Analysis Calcd. for C$_{61}$H$_{84}$N$_{10}$O$_{22}$S$_2$.7H$_2$O: C, 48.86; H, 6.59; N, 9.34.

Found: C, 49.00; H, 6.39; N, 9.24.

EXAMPLE 48

IR (KBr): 3384.5, 1658.5, 1635.3, 1529.3, 1517.7, 1446.4, 1257.4, 1085.7, 1045.2 cm$^{-1}$

NMR (DMSO-d$_6$, δ): 0.97 (3H, d, J=6.7 Hz), 1.13 (3H, d, J=5.5 Hz), 1.2–5.3 (65H, m), 6.91 (1H, d, J=8.1 Hz), 6.77 (1H, d, J=9.9 Hz), 6.97 (1H, s), 7.13 (2H, d, J=8.9 Hz), 7.97 (2H, d, J=8.8 Hz), 8.09 (4H, s), 7.4–8.9 (6H, m)

MASS (m/z): 1431.3 (M$^-$1)

Elemental Analysis Calcd. for C$_{63}$H$_{86}$N$_{10}$O$_{24}$S$_2$.8H$_2$O: C, 47.96; H, 6.64; N, 8.88.

Found: C, 48.21; H, 6.35; N, 8.87.

EXAMPLE 49

IR (KBr): 3371.0, 1648.8, 1631.5, 1538.9, 1513.8, 1442.5, 1257.4, 1083.8, 1045.2 cm$^{-1}$

NMR (DMSO-d$_6$, δ): 0.97 (3H, d, J=6.7 Hz), 1.10 (3H, d, J=5.5 Hz), 1.2–5.4 (65H, m), 6.71 (1H, d, J=8.2 Hz), 6.77 (1H, d, J=10.2 Hz), 6.99 (1H, s), 7.14 (2H, d, J=8.7 Hz), 7.97 (2H, d, J=8.7 Hz), 8.09 (4H, s), 7.3–9.0 (6H, m)

MASS (m/z): 1401.3 (M$^-$–1)

Elemental Analysis Calcd. for C$_{62}$H$_{86}$N$_{10}$O$_{23}$S$_2$.7H$_2$O: C, 48.68; H, 6.59; N, 9.16.

Found: C, 48.83; H, 6.39; N, 9.13.

EXAMPLE 50

IR (KBr): 3350, 2933, 2862, 1658.5, 1635, 1516, 1444, 1257, 1084, 1043 cm$^{-1}$

NMR (DMSO-d$_6$+D$_2$O, δ): 0.98 (3H, d, J=6.7 Hz), 1.09 (3H, d, J=5.8 Hz), 1.2–4.8 (49H, complex m), 3.21 (3H, s), 3.31 (2H, t, J=6.4 Hz), 6.8–6.9 (2H, m), 7.02 (1H, br s), 7.15 (2H, d, J=8.9 Hz), 7.98 (2H, d, J=8.9 Hz), 8.10 (4H, s)

MASS (m/z): 1485.4 (M$^+$+Na)

Elemental Analysis Calcd. for C$_{64}$H$_{90}$N$_{10}$O$_{25}$S$_2$.6H$_2$O: C, 48.91; H, 6.54; N, 8.91.

Found: C, 49.18; H, 6.55; N, 8.90.

EXAMPLE 51

NMR (DMSO-d$_6$, δ): 0.86 (3H, d, J=6.3 Hz), 0.98 (3H, d, J=6.8 Hz), 1.11 (3H, d, J=5.7 Hz), 1.21–5.24 (62H, m), 6.69–8.89 (17H, m)

MASS (m/z): 1408.5, 1407.4 (M$^+$–1)

Elemental Analysis Calcd. for C$_{64}$H$_{88}$N$_{12}$O$_{20}$S$_2$.7H$_2$O: C, 50.06; H, 6.69; N, 10.94.

Found: C, 49.96; H, 6.86; N, 10.82.

EXAMPLE 52

IR (KBr): 1633, 1606, 1529, 1518, 1466 cm$^{-1}$

NMR (DMSO-d$_6$, δ): 0.96 (3H, d, J=6.7 Hz), 1.11 (3H, d, J=5.7 Hz), 1.2–2.6 (18H, m), 2.8–4.6 (39H, m), 4.7–5.4 (9H, m), 6.7–6.9 (2H, m), 7.0–7.2 (3H, m), 7.3–7.6 (2H, m), 7.75 (2H, d, J=8.7 Hz), 7.7–8.0 (5H, m), 8.2–8.5 (1H, m), 8.6–8.75 (1H, m), 8.80 (1H, s), 8.85 (1H, s)

MASS (m/z): 1481 (M$^+$–1)

Elemental Analysis Calcd. for C$_{66}$H$_{90}$N$_{12}$O$_{23}$S$_2$.7H$_2$O: C, 49.25; H, 6.51; N, 10.44.

Found: C, 49.30; H, 6.34; N, 10.40.

The following compound was obtained according to a similar manner to that of Example 1.

EXAMPLE 53

IR (KBr): 2937.1, 1651, 1631.5, 1539, 1523.5 cm$^{-1}$

MASS (m/z): 1293.3 (M$^+$+1)

EXAMPLE 54

To a solution of starting compound (54) (300 mg) in methanol (12 ml) was added 10% hydrochlolic acid in methanol (6 ml) at room temperature. The solution was stirred for 3 hours at the same temperature. The solvent was evaporated under reduced pressure to remove hydrochloric acid and methanol. To the residue was added water and the mixture was lyophilized. The residue was purified by column chromatography on ODS to give object compound (54) (119 mg).

IR (KBr): 1649, 1633, 1608, 1539, 1525 cm$^{-1}$

MASS (m/z): 1351 (M$^+$+23)

Elemental Analysis Calcd. for C$_{64}$H$_{88}$N$_{12}$O$_{17}$S.8H$_2$O: C, 52.16; H, 7.11; N, 11.41.

Found: C, 52.13; H, 7.05; N, 11.36.

The following compounds [Example 55 to 71] were obtained according to a similar manner to that of Example 33.

EXAMPLE 55

IR (KBr): 3358, 1633, 1608, 1535, 1516, 1443, 1419, 1271, 1238 cm$^{-1}$

NMR (DMSO-d$_6$+D$_2$O, δ): 0.89 (6H, s), 0.98 (3H, d, J=6.7 Hz), 1.10 (3H, d, J=5.8 Hz), 1.1–2.6 (20H, m), 2.6–4.5 (29H, m), 4.7–4.9 (2H, m), 6.7–6.9 (2H, m), 7.0–7.1 (1H, m), 7.08 (2H, d, J=9.2 Hz), 7.86 (2H, d, J=8.5 Hz), 8.0–8.2 (4H, m)

ESI MASS (m/z)(Negative): 1422.3 (M$^-$–1)

Elemental Analysis Calcd. for C$_{65}$H$_{90}$N$_{12}$O$_{20}$S$_2$.7.5H$_2$O: C, 50.09; H, 6.79; N, 10.78.

Found: C, 49.94; H, 6.59; N, 10.52.

EXAMPLE 56

IR (KBr): 3462, 3458, 3425, 3399, 3367, 1633, 1578, 1440 cm$^{-1}$

NMR (DMSO-d$_6$, δ): 0.98 (3H, d, J=6.7 Hz), 1.11 (3H, d, J=5.6 Hz), 1.20–1.50 (3H, m), 1.60–2.40 (18H, m), 2.50–2.70 (4H, m), 2.75–3.20 (7H, m), 3.40–3.60 (6H, m), 3.70–4.50 (14H, m), 4.62 (2H, br s), 4.65–4.80 (3H, m), 4.80–5.40 (8H, m), 6.60–6.80 (2H, m), 7.00 (1H, br s), 7.07 (2H, d, J=8.9 Hz), 7.40–7.60 (2H, m), 7.85 (2H, d, J=8.7 Hz), 7.90–8.20 (4H, m), 8.20–8.40 (1H, m), 8.71 (1H, s), 8.85 (1H, d, J=6.9 Hz)

API-ES MASS (m/z)(Negative): 1408 (M$^+$+1)

Elemental Analysis Calcd. for $C_{64}H_{86}N_{12}O_{20}S_2 \cdot 7H_2O$: C, 50.10; H, 6.52; N, 10.96.

Found: C, 50.29, M 6.48; N, 10.77.

EXAMPLE 57

IR (KBr): 1666, 1649, 1632, 1554, 1541, 1514, 1450, 1443, 1419, 1240 cm$^{-1}$

NMR (DMSO-d$_6$+D$_2$O, δ): 0.7–1.3 (17H, m), 1.3–2.6 (7H, m), 2.7–4.5 (35H, m), 4.7–4.9 (2H, m), 6.7–6.9 (2H, m), 7.0–7.2 (3H, m), 7.87 (2H, d, J=8.6 Hz), 8.0–8.2 (4H, m)

ESI MASS (m/z)(Positive): 1453.4 (M+2Na)$^{2+}$

Elemental Analysis Calcd. for $C_{64}H_{88}N_{12}O_{20}S_2 \cdot 6H_2O$: C, 50.65; H, 6.64; N, 11.07.

Found: C, 50.28; H, 6.61; N, 10.80.

EXAMPLE 58

Major Compound:

ESI MASS (m/z)(Negative): 1538.6 (M$^-$–1)

Minor Compound:

IR (KBr): 3352, 1659, 1635, 1606, 1529, 1444, 1417, 1274, 1238 cm$^{-1}$

ESI MASS (m/z)(Negative): 1338.6 (M$^-$–1)

Elemental Analysis Calcd. for $C_{71}H_{102}N_{12}O_{22}S_2 \cdot 7H_2O$: C, 51.19; H, 7.02; N, 10.09.

Found: C, 51.19; H, 6.95; N, 9.73.

EXAMPLE 59

Major Compound:

ESI MASS (m/z)(Positive): 1598.3 (M+2Na)$^{2+}$

Minor Compound:

ESI MASS (m/z)(Negative): 1551.6 (M–2H)$^{2-}$

EXAMPLE 60

IR (KBr): 1664, 1635, 1605, 1446, 1410, 1350, 1329, 1281 cm$^{-1}$

NMR (DMSO-d$_6$, D$_2$O, δ): 0.98 (3H, d, J=6.7 Hz), 1.10 (3H, d, J=5.9 Hz), 1.1–2.6 (21H, m), 2.8–4.5 (31H, m), 4.7–4.9 (2H, m), 6.7–6.9 (2H, m), 7.0–7.2 (3H, m), 7.85 (2H, d, J=8.9 Hz), 8.0–8.2 (4H, m)

ESI MASS (m/z)(Negative): 1409.4 (M$^-$–1)

Elemental Analysis Calcd. for $C_{64}H_{87}N_{11}O_{21}S_2 \cdot 6H_2O$: C, 50.62; H, 6.57; N, 10.15.

Found: C, 50.40; H, 6.61; N, 9.92.

EXAMPLE 61

IR (KBr): 2937, 1676, 1651, 1556, 1541, 1514, 1452, 1441, 1419 cm$^{-1}$

NMR (DMSO-d$_6$+D$_2$O, δ): 0.98 (3H, d, J=6.8 Hz), 1.10 (3H, d, J=5.7 Hz), 1.2–2.6 (17H, m), 2.8–4.5 (37H, m), 4.7–4.9 (2H, m), 6.7–6.9 (2H, m), 7.0–7.2 (3H, m), 7.85 (2H, d, J=8.6 Hz), 8.0–8.2 (4H, m)

ESI MASS (m/z)(Negative): 1427.5 (M$^-$–1)

Elemental Analysis Calcd. for $C_{64}H_{89}N_{11}O_{22}S_2 \cdot 5.5H_2O$: C, 50.32; H, 6.60; N, 10.09.

Found: C, 50.31; H, 6.72; N, 10.04.

EXAMPLE 62

IR (KBr): 1633, 1606, 1529, 1518, 1444, 1419, 1279, 1252 cm$^{-1}$

NMR (DMSO-d$_6$+D$_2$O, δ): 0.98 (3H, d, J=6.7 Hz), 1.10 (3H, d, J=5.8 Hz), 1.2–2.6 (19H, m), 2.8–4.6 (37H, m), 4.7–4.9 (2H, m), 6.7–6.9 (2H, m), 7.0–7.2 (3H, m), 7.85 (2H, d, J=8.8 Hz), 8.0–8.2 (4H, m)

ESI MASS (m/z)(Negative): 1441.5 (M$^-$–1)

Elemental Analysis Calcd. for $C_{65}H_{91}N_{11}O_{22}S_2 \cdot 7H_2O$: C, 49.77; H, 6.75; N, 9.82.

Found: C, 49.80; H, 6.68; N, 9.80.

EXAMPLE 63

IR (KBr): 2935, 1633, 1606, 1529, 1518, 1444, 1419, 1273, 1232.cm$^{-1}$

NMR (DMSO-d$_6$+D$_2$O, δ): 0.98 (3H, d, J=6.8 Hz), 1.10 (3H, d, J=6.3 Hz), 1.2–2.6 (16H, m), 2.7–4.5 (38H, m), 4.7–4.9 (2H, m), 6.7–6.9 (2H, m), 7.0–7.2 (3H, m), 7.85 (2H, d, J=7.8 Hz), 8.0–8.2 (4H, m)

ESI MASS (m/z)(Negative): 1427.4 (M$^-$–1)

Elemental Analysis Calcd. for $C_{64}H_{89}N_{11}O_{22}S_2 \cdot 6H_2O$: C, 50.02; H, 6.62; N, 10.03.

Found: C, 49.99; H, 6.73; N, 9.67.

EXAMPLE 64

IR (KBr): 1659, 1633, 1605, 1547, 1529, 1518, 1444, 1419 cm$^{-1}$

NMR (DMSO-d$_6$+D$_2$O, δ): 0.98 (3H, d, J=6.8 Hz), 1.11 (3H, d, J=5.7 Hz), 1.2–2.6 (18H, m), 2.8–4.5 (38H, m), 4.7–4.9 (2H, m), 6.7–6.9 (2H, m), 7.0–7.2 (3H, m), 7.84 (2H, d, J=8.7 Hz), 8.0–8.2 (4H, m)

ESI MASS (m/z)(Negative): 1441.5 (M$^-$–1)

Elemental Analysis Calcd. for $C_{65}H_{91}N_{11}O_{22}S_2 \cdot 6H_2O$: C, 50.34; H, 6.69; N, 9.94.

Found: C, 50.12; H, 6.78; N, 9.87.

EXAMPLE 65

IR (KBr): 1664, 1628, 1605, 1529, 1444, 1408, 1281, 1252 cm$^{-1}$

NMR (DMSO-d$_6$+D$_2$O, δ): 0.91 (3H, d, J=6.8 Hz), 0.98 (3H, d, J=6.8 Hz), 1.10 (3H, d, J=5.9 Hz), 1.3–2.7 (16H, m), 2.8–4.5 (34H, m), 4.7–4.9 (2H, m), 6.7–6.9 (2H, m), 6.9–7.1 (3H, m), 8.0–8.2 (4H, m), 8.73 (1H, d, J=2.6 Hz)

ESI MASS (m/z)(Negative): 1408.5 (M–2H)$^{2-}$

Elemental Analysis Calcd. for $C_{63}H_{87}N_{13}O_{20}S_2 \cdot 8H_2O$: C, 48.67; H, 6.68; N, 11.71.

Found: C, 48.86; H, 6.64; N, 11.44.

EXAMPLE 66

IR (KBr): 1664, 1635, 1628, 1605, 1444, 1408, 1281, 1259 cm$^{-1}$

NMR (DMSO-d$_6$+D$_2$O, δ): 0.86 (3H, d, J=6.3 Hz), 0.98 (3H, d, J=6.9 Hz), 1.10 (3H, d, J=5.7 Hz), 1.1–1.4 (5H, m), 1.6–2.7 (11H, m), 2.8–4.5 (34H, m), 4.7–4.9 (2H, m), 6.7–6.9 (2H, m), 6.9–7.1 (3H, m), 8.0–8.2 (4H, m), 8.72 (1H, d, J=2.5 Hz)

ESI MASS (m/z)(Negative): 1408.6 (M–2H)$_{2-}$

Elemental Analysis Calcd. for $C_{63}H_{87}N_{13}O_{20}S_2 \cdot 7H_2O$: C, 49.24; H, 6.62; N, 11.85.

Found: C, 49.05; H, 6.73; N, 11.48.

EXAMPLE 67

IR (KBr): 3352, 1664, 1635, 1603, 1444, 1408, 1281, 1250 cm$^{-1}$

NMR (DMSO-d$_6$+D$_2$O, δ): 0.85 (3H, t, J=7.4 Hz), 0.98 (3H, d, J=6.8 Hz), 1.10 (3H, d, J=5.9 Hz), 1.3–2.6 (18H, m), 2.8–4.5 (34H, m), 4.7–4.9 (2H, m), 6.7–6.9 (2H, m), 6.9–7.1 (3H, m), 8.0–8.2 (4H, m), 8.73 (1H, d, J=2.6 Hz)

ESI MASS (m/z)(Negative): 1423.5 (M$^-$−1)

Elemental Analysis Calcd. for C$_{64}$H$_{89}$N$_{13}$O$_{20}$S$_2$.6H$_2$O: C, 50.15; H, 6.64; N, 11.88.

Found: C, 49.99; H, 6.74; N, 11.61.

EXAMPLE 68

IR (KBr): 1664, 1628, 1603, 1529, 1444, 1408, 1281, 1248 cm$^{-1}$

NMR (DMSO-d$_6$+D$_2$O, δ): 0.7–1.3 (12H, m), 1.6–2.6 (15H, m), 2.7–4.4 (34H, m), 4.7–4.9 (2H, m), 6.6–6.8 (2H, m), 6.8–7.0 (3H, m), 7.9–8.1 (4H, m), 8.66 (1H, d, J=2.5 Hz)

ESI MASS (m/z)(Negative): 1423.5 (M$^-$−1)

Elemental Analysis Calcd. for C$_{64}$H$_{89}$N$_{13}$O$_{20}$S$_2$.6H$_2$O: C, 50.15; H, 6.64; N, 11.88.

Found: C, 49.95; H, 6.74; N, 11.47.

EXAMPLE 69

IR (KBr): 1658, 1635, 1549, 1529, 1518, 1468, 1446, 1277, 1043 cm$^{-1}$

NMR (DMSO-d$_6$+D$_2$O, δ): 0.97 (3H, d, J=6.8 Hz), 1.0–1.4 (9H, m), 1.5–2.6 (15H, m), 2.7–4.5 (31H, m), 4.7–4.9 (2H, m), 6.7–6.9 (2H, m), 7.0–7.1 (1H, m), 7.49 (2H, d, J=8.6 Hz), 7.8–8.1 (6H, m), 8.86 (1H, s)

ESI MASS (m/z)(Negative): 1432.4 (M$^-$−1)

Elemental Analysis Calcd. for C$_{66}$H$_{88}$N$_{12}$O$_{20}$S$_2$.6H$_2$O: C, 51.42; H, 6.54; N, 10.90.

Found: C, 51.36; H, 6.65; N, 10.50.

EXAMPLE 70

IR (KBr): 3493, 3462, 3433, 3350, 1659, 1635, 1613, 1529, 1518, 1466, 1446 cm$^{-1}$

NMR (DMSO-d$_6$+D$_2$O, δ): 0.90 (3H, d, J=6.7 Hz), 0.98 (3H, d, J=6.6 Hz), 1.11 (3H, d, J=5.3 Hz), 1.3–2.7 (16H, m), 2.8–4.5 (34H, m), 4.7–4.9 (2H, m), 6.7–6.9 (2H, m), 7.0–7.2 (3H, m), 7.78 (2H, d, J=8.7 Hz), 7.9–8.1 (4H, m), 8.78 (1H, s)

ESI MASS (m/z)(Negative): 1447.5 (M$^-$−1)

Elemental Analysis Calcd. for C$_{66}$H$_{89}$N$_{13}$O$_{20}$S$_2$.8H$_2$O: C, 49.77; H, 6.64; N, 11.43.

Found: C, 50.09; H, 6.68; N, 11.14.

EXAMPLE 71

NMR (DMSO-d$_6$, δ): 0.8–2.8 (40H, m), 2.8–4.6 (28H, m), 4.7–5.4 (9H, m), 6.6–6.85 (2H, m), 6.9–7.1 (3H, m), 7.3–8.5 (12H, m), 8.6–8.8 (2H, m)

MASS (m/z): 1391 (M$^+$−1)

Elemental Analysis Calcd. for C$_{67}$H$_{96}$N$_{10}$O$_{20}$S.7H$_2$O: C, 52.95; H, 7.30; N, 9.22.

Found: C, 52.88; H, 7.33; N, 9.22.

The following compound was obtained according to a similar manner to that of Example 54.

EXAMPLE 72

NMR (DMSO-d$_6$+D$_2$O, δ): 0.7–4.5 (67H, m), 4.65–4.85 (2H, m), 6.3–6.45 (1H, m), 6.5–6.7 (2H, m), 7.12 (2H, d, J=8.8 Hz), 7.6–7.8 (4H, m), 7.95 (2H, d, J=8.4 Hz)

ESI MASS (m/z): 1311 (M$^+$−1)

Elemental Analysis Calcd. for C$_{67}$H$_{96}$N$_{10}$O$_{17}$-3HCl.10H$_2$O: C, 50.20; H, 7.48; N, 8.74.

Found: C, 50.28; H, 7.15; N, 8.67.

The following compounds [Examples 73 to 87] were obtained according to a similar manner to that of Example 33.

EXAMPLE 73

NMR (DMSO-d$_6$, δ): 0.84 (9H, s), 0.97 (3H, d, J=7.0 Hz), 1.0–1.4 (8H, m), 1.6–2.8 (18H, m), 2.8–4.6 (28H, m), 4.7–5.4 (9H, m), 6.6–6.8 (2H, m), 6.9–7.1 (3H, m), 7.3–8.5 (12H, m), 8.6–8.8 (2H, m)

MASS (m/z): 1365 (M$^+$−1)

Elemental Analysis Calcd. for C$_{65}$H$_{94}$N$_{10}$O$_{20}$S.7H$_2$O: C, 52.27; H, 7.29; N, 9.38.

Found: C, 52.15; H, 7.30; N, 9.30.

EXAMPLE 74

IR (KBr): 1649, 1539, 1514, 1454, 1439, 1045 cm$^{-1}$

NMR (DMSO-d$_6$, δ): 0.7–1.4 (16H, m), 1.6–2.8 (18H, m), 2.8–4.6 (28H, m), 4.7–5.5 (9H, m), 6.6–6.8 (2H, m), 6.9–7.1 (3H, m), 7.3–8.5 (12H, m), 8.5–8.8 (2H, m)

MASS (m/z): 1337 (M$^+$−1)

Elemental Analysis Calcd. for C$_{63}$H$_{90}$N$_{10}$O$_{20}$S.9H$_2$O: C, 50.39; H, 7.25; N, 9.33.

Found: C, 50.64; H, 6.96; N, 9.24.

EXAMPLE 75

IR (KBr): 1666, 1649, 1632, 1539, 1514, 1454, 1238 cm$^{-1}$

NMR (DMSO-d$_6$, δ): 0.85 (3H, t, J=7.0 Hz), 0.97 (3H, d, J=6.6 Hz), 1.09 (3H, d, J=5.5 Hz), 1.2–2.75 (25H, m), 2.8–4.6 (28H, m), 4.7–5.4 (9H, m), 6.6–6.8 (2H, m), 6.9–7.1 (3H, m), 7.3–8.5 (12H, m), 8.6–8.8 (2H, m)

MASS (m/z): 1337 (M$^+$−1)

Elemental Analysis Calcd. for C$_{63}$H$_{90}$N$_{10}$O$_{20}$S.7H$_2$O: C, 51.63; H, 7.15; N, 9.56.

Found: C, 51.74; H, 7.07; N, 9.52.

EXAMPLE 76

IR (KBr): 1666, 1649, 1632, 1539, 1514, 1236 cm$^{-1}$

NMR (DMSO-d$_6$, δ): 0.98 (3H, d, J=6.6 Hz), 1.10 (3H, d, J=5.7 Hz), 2.8–4.6 (64H, m), 4.7–5.4 (9H, m), 6.6–6.85 (2H, m), 6.9–7.15 (3H, m), 7.3–8.5 (12H, m), 8.6–8.8 (2H, m)

MASS (m/z): 1421 (M$^+$−1)

Elemental Analysis Calcd. for C$_{68}$H$_{98}$N$_{10}$O$_{21}$S.8H$_2$O: C, 52.10; H, 7.33; N, 8.93.

Found: C, 52.18; H, 7.22; N, 8.85.

EXAMPLE 77

EXAMPLE 78

IR (KBr): 1666, 1632, 1539, 1514, 1452, 1236 cm$^{-1}$

NMR (DMSO-d$_6$, δ): 0.7–2.7 (38H, m), 2.8–4.6 (32H, m), 4.7–5.4 (9H, m), 6.6–6.85 (3H, m), 6.9–7.1 (2H, m), 7.3–8.5 (12H, m), 8.6–8.8 (2H, m)

MASS (m/z): 1421 (M$^+$−1)

Elemental Analysis Calcd. for C$_{68}$H$_{98}$N$_{10}$O$_{21}$S.8H$_2$O: C, 52.10; H, 7.33; N, 8.94.

Found: C, 52.10; H, 7.17; N, 9.33.

EXAMPLE 79

IR (KBr): 1632, 1539, 1516, 1452, 1238 cm$^{-1}$

NMR (DMSO-d$_6$, δ): 0.8–1.4 (16H, m), 1.6–2.8 (22H, m), 2.8–5.55 (32H, m), 4.7–5.4 (9H, m), 6.65–6.85 (2H, m), 6.9–7.1 (3H, m), 7.3–8.5 (12H, m), 8.5–8.8 (2H, m)

MASS (m/z): 1421 (M$^+$–1)

Elemental Analysis Calcd. for C$_{68}$H$_{98}$N$_{10}$O$_{21}$S.8H$_2$O: C, 52.10; H, 7.33; N, 8.94.

Found: C, 51.82; H, 7.17; N, 9.23.

EXAMPLE 80

IR (KBr): 1666, 1645, 1632, 1539, 1514, 1452, 1240 cm$^{-1}$

NMR (DMSO-d$_6$, δ): 0.98 (3H, d, J=6.8 Hz), 1.10 (3H, d, J=5.5 Hz), 1.4–2.75 (23H, m), 2.8–4.5 (31H, m), 4.7–5.4 (9H, m), 6.65–6.9 (4H, m), 6.9–7.1 (3H, m), 7.15 (2H, d, J=8.7 Hz), 7.3–8.5 (12H, m), 8.6–8.8 (2H, m)

MASS (m/z): 1415 (M$^+$–1)

Elemental Analysis Calcd. for C$_{68}$H$_{92}$N$_{10}$O$_{21}$S.12H$_2$O: C, 49.99; H, 7.16; N, 8.57.

Found: C, 49.86; H, 6.81; N, 8.96.

EXAMPLE 81

IR (KBr): 1632, 1539, 1514, 1452, 1275 cm$^{-1}$

NMR (DMSO-d$_6$, δ): 0.97 (3H, d, J=6.7 Hz), 1.10 (3H, d, J=5.7 Hz), 1.2–2.8 (23H, m), 2.8–4.55 (31H, m), 4.7–5.4 (9H, m), 6.6–6.9 (4H, m), 6.9–7.1 (3H, m), 7.14 (2H, d, J=8.7 Hz), 7.3–8.5 (12H, m), 8.6–8.8 (2H, m)

MASS (m/z): 1415 (M$^+$–1)

Elemental Analysis Calcd. for C$_{68}$H$_{92}$N$_{10}$O$_{21}$S.8H$_2$O: C, 52.30; H, 6.97; N, 8.97.

Found: C, 52.48; H, 6.79; N, 9.44.

EXAMPLE 82

IR (KBr): 1676, 1649, 1632, 1539, 1514, 1456, 1236 cm$^{-1}$

NMR (DMSO-d$_6$, δ): 0.88 (6H, s), 0.97 (3H, d, J=6.6 Hz), 1.10 (3H, d, J=5.4 Hz), 1.1–2.8 (22H, m), 2.8–4.6 (28H, m), 4.7–5.5 (9H, m), 6.6–6.8 (2H, m), 6.9–7.1 (3H, m), 7.3–8.8 (14H, m)

MASS (m/z): 1339 (M$^+$+1)

Elemental Analysis Calcd. for C$_{63}$H$_{90}$N$_{10}$O$_{20}$S.8H$_2$O: C, 51.00; H, 7.20; N, 9.44.

Found: C, 51.31; H, 7.16; N, 9.44.

EXAMPLE 83

IR (KBr): 1664, 1635, 1626, 1605, 1446, 1408, 1350, 1329 cm$^{-1}$

NMR (DMSO-d$_6$+D$_2$O, δ): 0.98 (3H, d, J=6.8 Hz), 1.09 (3H, d, J=5.7 Hz), 1.2–2.8 (24H, m), 2.8–4.5 (37H, m), 4.7–4.9 (2H, m), 6.7–6.9 (2H, m), 7.0–7.1 (3H, m), 7.62 (2H, d, J=8.7 Hz), 7.70 (2H, d, J=8.4 Hz), 7.93 (2H, d, J=8.4 Hz)

ESI MASS (m/z)(Negative): 1407.6 (M–2H)$^{2-}$

Elemental Analysis Calcd. for C$_{67}$H$_{96}$N$_{10}$O$_{21}$S.6H$_2$O: C, 53.02; H, 7.17, N, 9.23.

Found: C, 52.98; H, 7.28; N, 9.13.

EXAMPLE 84

IR (KBr): 1664, 1628, 1606, 1531, 1497, 1446, 1281, 1238 cm$^{-1}$

NMR (DMSO-d$_6$+D$_2$O, δ): 0.97 (3H, d, J=6.7 Hz), 1.10 (3H, d, J=5.4 Hz), 1.3–2.7 (24H, m), 2.8–4.5 (37H, m), 4.7–4.9 (2H, m), 6.7–6.9 (2H, m), 7.0–7.2 (3H, m), 7.62 (2H, d, J=8.6 Hz), 7.70 (2H, d, J=8.5 Hz), 7.93 (2H, d, J=8.5 Hz)

ESI MASS (m/z)(Negative): 1408.4 (M$^-$–1)

Elemental Analysis Calcd. for C$_{67}$H$_{96}$N$_{10}$O$_{21}$S.5H$_2$O: C, 53.66; H, 7.12; N, 9.34.

Found: C, 53.58; H, 7.34; N, 9.15.

EXAMPLE 85

IR (KBr): 1664, 1628, 1606, 1529, 1497, 1446, 1408, 1281, 1238 cm$^{-1}$

NMR (DMSO-d$_6$+D$_2$O, δ): 0.97 (3H, d, J=6.9 Hz), 1.10 (3H, d, J=6.0 Hz), 1.5–4.5 (52H, m), 4.7–4.9 (2H, m), 6.7–6.9 (2H, m), 6.9–7.1 (3H, m), 7.2–7.5 (5H, m), 7.62 (2H, d, J=8.6 Hz), 7.71 (2H, d, J=8.6 Hz), 7.93 (2H, d, J=8.3 Hz)

ESI MASS (m/z)(Negative): 1415.4 (M–2H)$^{2-}$

Elemental Analysis Calcd. for C$_{68}$H$_{92}$N$_{10}$O$_{21}$S.6H$_2$O: C, 53.53; H, 6.87; N, 9.18.

Found: C, 53.55; H, 6.91; N, 9.00.

EXAMPLE 86

NMR (DMSO-d$_6$, δ): 0.9 (3H, d, J=6.8 Hz), 0.98 (3H, d, J=6.8 Hz), 1.10 (3H, d, J=6.1 Hz), 1.3–2.7 (24H, m), 2.8–4.6 (29H, m), 4.7–5.3 (9H, m), 6.6–6.8 (2H, m), 6.9–7.2 (3H, m), 7.3–8.2 (11H, m), 8.4–8.6 (1H, m), 8.7 (1H, s), 8.8–8.95 (1H, m)

MASS (m/z): 1421 (M$^+$–1)

Elemental Analysis Calcd. for C$_{65}$H$_{90}$N$_{12}$O$_{20}$S$_2$.8H$_2$O: C, 49.80; H, 6.81; N, 10.72.

Found: C, 50.07; H, 6.74; N, 10.73.

EXAMPLE 87

IR (KBr): 3351.7, 2931.3, 2854.1, 1658.5, 1635.3, 1546.6, 1531.2, 1496.5 cm$^{-1}$

NMR (DMSO-d$_6$+D$_2$O, δ): 0.97 (3H, d, J=7 Hz), 0.8–4.5 (65H, complex m), 3.01 (3H, s), 4.79–4.81 (2H, m), 6.72 (1H, d, J=8 Hz), 6.75–6.80 (1H, m), 7.01 (1H, s), 7.03 (2H, d, J=8 Hz), 7.61 (2H, d, J=8 Hz), 7.69 (2H, d, J=8.4 Hz), 7.94 (2H, d, J=8.4 Hz)

ESI MASS (m/z)(Negative): 1435.7 (M$^+$–1)

EXAMPLE 88

To a solution of a mixture of starting compound (88) (7.5 g), 1,3-dihydroxyacetone (1.19 g) and acetic acid (1.14 ml) in a mixture of methanol (120 ml) and DMF (55 ml) was added sodium cyanoborohydride (835 mg) with stirring at ambient temperature, and the mixture was stirred at the same temperature overnight. To a reaction mixture was poured into ethyl acetate (700 ml). The resulting precipitates were collected by filtration, washed with ethyl acetate (100 ml) and dried in vacuo. The precipitates were dissolved in a mixture of 30% aqueous acetonitrile (800 ml) and 1N sodium hydroxide (5 ml). The solution was subjected to column chromatography on ODS (Daiso-gel, SP-120-40/60-ODS-B (Trademark: prepared by Daiso Co., Ltd.)) (440 ml) eluting in turn with water and aqueous acetonitrile (30%–60%). The fractions containing the object compound were collected and evaporated under reduced pressure to remove acetonitrile. The residue was lyophilized to give object compound (88) (5.22 g).

IR (KBr): 1632, 1535, 1518, 1443, 1269, 1082, 1047 cm$^{-1}$

NMR (DMSO-d$_6$+D$_2$O, δ): 0.82 (3H, d, J=6.83 Hz), 0.97 (3H, d, J=6.81 Hz), 1.02 (3H, d, J=6.18 Hz), 1.24 (26H, s), 1.35–2.45 (14H, m), 2.75–3.40 (5H, m), 3.60–4.50 (15H, m), 4.70–4.90 (2H, m), 6.65–6.80 (2H, m), 7.01 (1H, s)

ESI MASS (m/z)(Positive): 1088.4 (M$^+$+Na)

EXAMPLE 89

To a solution of starting compound (89) (4.0 g) in DMF (40 ml) were successively added diisopropylethylamine (1.45 ml) and 9-fluorenylmethyl chloroformate (1.03 g), and the mixture was stirred at ambient temperature for 2 hours. The reaction mixture was poured into water (200 ml). The solution was purified by ODS (Daiso-gel, SP-120-40/60-ODS-B (Trademark: prepared by Daiso Co., Ltd.)) (200 ml) column chromatography, eluting in turn with a mixture of saturated aqueous sodium chloride (400 ml), saturated aqueous sodium hydrogen carbonate (50 ml) and water (400 ml), and aqueous acetonitrile (30–60%). The fractions containing the object compound were collected and evaporated under reduced pressure to remove acetonitrile. The residue was lyophilized to give object compound (89) (2.82 g).

IR (KBr): 1666, 1632, 1518, 1446, 1273, 1246, 1082, 1047 cm$^{-1}$

NMR (DMSO-d$_6$+D$_2$O, δ): 0.80–1.10 (9H, m), 1.23 (26H, s), 1.35–2.45 (12H, m), 2.60–3.40 (6H, m), 3.60–4.55 (18H, m), 4.65–4.90 (2H, m), 6.65–6.85 (2H, m), 6.97 (1H, s), 7.30–7.50 (4H, m), 7.60–7.95 (4H, m)

ESI MASS (m/z)(Negative): 1423.7 (M$^+$−Na)

Elemental Analysis Calcd. for C$_{69}$H$_{99}$N$_6$O$_{22}$SNa.6H$_2$O: C, 53.27; H, 7.19; N, 7.20.

Found: C, 53.45; H, 7.21; N, 7.10.

EXAMPLE 90

To a solution of starting compound (90) (1.21 g) in DMF (15 ml) were successively added diisopropylethylamine (0.26 ml) and di-tert-butyl dicarbonate (285 mg) and the mixture was stirred at ambient temperature overnight. The reaction mixture was poured into a mixture of pH 6.86 standard buffer solution (150 ml), saturated aqueous sodium chloride (50 ml) and saturated aqueous sodium hydrogen carbonate (20 ml). The mixture was purified by ODS (Daiso-gel, SP-120-40/60-ODS-B (Trademark: prepared by Daiso Co., Ltd.)) (200 ml) column chromatography, eluting with aqueous acetonitrile (30–50%). The fractions containing the object compound were collected and evaporated under reduced pressure to remove acetonitrile. The residue was lyophilized to give object compound (90) (1.19 g).

IR (KBr): 1662, 1632, 1535, 1518, 1444, 1367, 1272, 1250 cm$^{-1}$

NMR (DMSO-d$_6$+D$_2$O, δ): 0.85 (3H, d, J=6.76 Hz), 0.96 (3H, d, J=6.77 Hz), 1.04 (3H, d, J=5.50 Hz), 1.23 (26H, s), 1.37 (9H, s), 1.40–1.50 (2H, m), 1.55–2.50 (10H, m), 2.80–3.40 (6H, m), 3.50–4.45 (14H, m), 6.65–6.80 (2H, m), 6.96 (1H, s)

ESI MASS (m/z)(Negative): 1301.6 (M$^+$−Na)

EXAMPLE 91

To a solution of a mixture of starting compound (91) (2.0 g), 2-phenyl-1,3-dioxane-5-carbaldehyde (0.52 g) and acetic acid (0.35 ml) in a mixture of methanol (30 ml) and DMF (14 ml) was added sodium cyanoborohydride (254 mg) with stirring at ambient temperature and the mixture was stirred at the same temperature for 6 hours. The reaction mixture was poured into ethyl acetate (300 ml). The resulting precipitates were collected by filtration, washed with ethyl acetate (50 ml) and dried in vacuo. The precipitates were dissolved with pH 6.86 standard buffer solution (100 ml) and acetonitrile (200 ml) and the solution was subjected to column chromatography on ODS (Daiso-gel, SP-120-40/60-ODS-B (Trademark: prepared by Daiso Co., Ltd.)) (220 ml) eluting in turn with water (1 L), 20% acetonitrile in water and 30% acetonitrile in water. The fractions containing the object compound were collected and evaporated under reduced pressure to remove acetonitrile. The residue was lyophilized to give object compound (91) (2.27 g).

NMR (DMSO-d$_6$+D$_2$O, δ): 0.96 (3H, d, J=6.56 Hz), 1.07 (3H, d, J=5.42 Hz), 1.33, 1.37 (9H, broad s), 1.50–2.05 (6H, m), 2.10–2.45 (2H, m), 2.60–3.50 (6H, m), 3.75–4.50 (16H, m), 4.75–4.85 (2H, m), 5.44, 5.55 (1H, broad s), 6.75 (2H, m), 7.38 (5H, br s)

ESI MASS (m/z)(Negative): 1189.3 (M$^+$+Na)

EXAMPLE 92

A solution of starting compound (92) (2.26 g), 10% palladium on carbon (50% including water) (2.0 g) and 10% palladium hydroxide on carbon (2.0 g) in a mixture of methanol (45 ml) and water (23 ml) was hydrogenated under an atmospheric pressure of hydrogen with stirring at ambient temperature for 6 hours. The catalyst was filtered off and washed with a mixture of methanol and water (1:1 v/v) (50 ml), and the filtrates were combined. The mixture was evaporated in vacuo and dissolved in water (200 ml). The solution was subjected to column chromatography on ODS (Daiso-gel, SP-120-40/60-ODS-B (Trademark: prepared by Daiso Co., Ltd.)) (220 ml) eluting with water and 30% acetonitrile in water. The first fractions containing the object compound were collected and evaporated under reduced pressure to remove acetonitrile. The residue was lyophilized to give the object compound (92) (1.84 g).

NMR (DMSO-d$_6$+D$_2$O, δ): 0.97 (3H, d, J=6.75 Hz), 1.07 (3H, d, J=5.76 Hz), 1.35 (9H, s), 1.45–2.00 (6H, m), 2.10–2.45 (3H, m), 2.70–3.45 (9H, m), 3.55–4.55 (17H, m), 4.75–4.85 (2H, m), 6.65–6.80 (2H, m), 7.02 (1H, s)

ESI MASS (m/z)(Positive): 1123.3 (M$^+$+Na), 1101.3 (M$^+$+2Na),

EXAMPLE 93

To a solution of a mixture of starting compound (93) (1.83 g) and diisopropylethylamine (0.65 ml) in DMF (20 ml) was added 9-fluorenylmethyloxycarbonyl chloride (483 mg) with stirring at ambient temperature and the mixture was stirred at the same temperature for 2 hours. The reaction mixture was poured into water (300 ml). The mixture was adjusted to pH 7.5 with 1N HCl and washed with ethyl acetate (100 ml). The aqueous layer was evaporated to remove organic solvent. To a concentrated solution were added saturated aqueous sodium hydrogen carbonate (50 ml) and 5% aqueous sodium chloride (20 ml). The solution was subjected to column chromatography on ODS (Daiso-gel, SP-120-40/60-ODS-B (Trademark: prepared by Daiso Co., Ltd.)) (220 ml) eluting in turn with water (1 L), 20% acetonitrile in water (1 L) and 30% acetonitrile in water (1 L). The fractions containing the object compound were collected and evaporated under reduced pressure to remove acetonitrile. The residue was lyophilized to give object compound (93) (2.106 g)

NMR (DMSO-d$_6$+D$_2$O, δ): 0.89 (3H, br s), 1.07 (3%, br s), 1.34 (9H, s), 1.45–2.50 (10H, m), 2.60–3.40 (13H, m), 3.70–4.50 (14H, m), 4.65–4.90 (2H, m), 6.65–6.80 (2H, m), 6.99 (1H, s), 6.95–7.48 (4H, m), 7.60–7.70 (2H, m), 7.85–7.95 (2H, m)

ESI MASS (m/z)(Positive): 1345.3 (M$^+$+Na)

EXAMPLE 94

To a solution of a mixture of starting compound (94) (2.10 g) and triethylsilane (2.03 ml) in dichloromethane (35 ml) was dropwise added trifluoroacetic acid (3.70 ml) with stirring under ice-cooling and the mixture was stirred at ambient temperature for 1 hour. The reaction mixture was poured into a mixture of pH 6.86 standard buffer solution (150 ml) and saturated aqueous sodium hydrogen carbonate (20 ml). The mixture was adjusted to pH 8 with saturated aqueous sodium carbonate. The organic layer was separated and concentrated in vacuo to remove organic solvent. The solution was subjected to column chromatography on ODS (Daiso-gel, SP-120-40/60-ODS-B (Trademark: prepared by Daiso Co., Ltd.)) (220 ml) eluting in turn with water (1 L), 10% acetonitrile in water (800 ml), 20% acetonitrile in water (1 L) and then 30% acetonitrile in water (1 L). The fractions containing the object compound were collected and evaporated under reduced pressure to remove acetonitrile. The residue was lyophilized to give object compound (94) (1.704 g).

IR (KBr): 1668, 1633, 1539, 1516, 1440, 1273, 1082, 1045 cm$^{-1}$

NMR (DMSO-d$_6$+D$_2$O, δ): 0.89 (3H, br s), 1.05–1.20 (3H, m), 1.30–2.40 (8H, m), 2.60–3.40 (10H, m), 3.50–4.45 (16H, m), 4.60–4.85 (2H, m), 6.73 (2H, br s), 6.97 (1H, s), 7.25–7.48 (4H, m), 7.66 (2H, d, J=7.12 Hz), 7.88 (2H, d, J=7.24 Hz)

ESI MASS (m/z)(Positive): 1199.4 (M$^+$+1), 1200.4 (M$^+$)

Elemental Analysis Calcd. for C$_{54}$H$_{84}$N$_8$O$_{27}$S.6H$_2$O: C, 49.53; H, 6.47; N, 8.56.

Found: C, 49.30; H, 6.26; N, 8.49.

The following compound was obtained according to a similar manner to that of Example 33.

EXAMPLE 95

IR (KBr): 1664, 1628, 1605, 1446, 1417, 1279, 1084, 1047 cm$^{-1}$

NMR (DMSO-d$_6$+D$_2$O, δ): 0.8–1.3 (12H, m), 1.5–2.6 (16H, m), 2.8–4.5 (32H, m), 4.7–4.9 (2H, m), 6.7–6.9 (2H, m), 7.0–7.2 (3H, m), 7.85 (2H, d, J=8.6 Hz), 8.0–8.2 (4H, m)

ESI MASS (m/z)(Negative): 1423.5 (M$^-$–1)

What is claimed is:

1. A polypeptide compound of the following general formula (I):

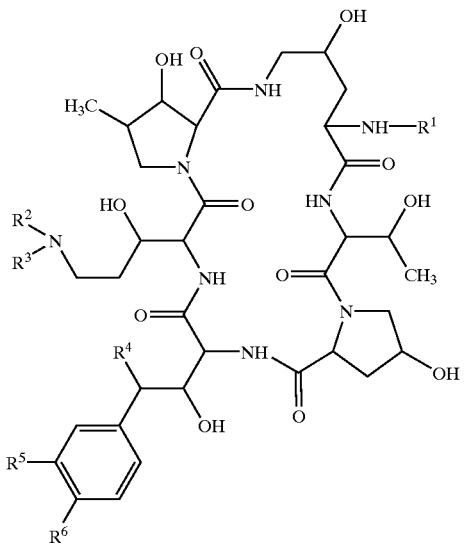

wherein
R$^1$ is hydrogen or acyl group,
R$^2$ is hydrogen or acyl group,
R$^3$ is lower alkyl which has one or more hydroxy or protected hydroxy,
R$^4$ is hydrogen or hydroxy,
R$^5$ is hydrogen, hydroxy, lower alkoxy or hydroxysulfonyloxy, and
R$^6$ is hydroxy or acyloxy,
or a salt thereof.

2. The compound of claim 1, wherein
R$^1$ is hydrogen, lower alkoxycarbonyl, higher alkanoyl or benzoyl substituted with one or more suitable substituent(s),
R$^2$ is hydrogen,
R$^3$ is lower alkyl which has one or more hydroxy,
R$^4$ is hydrogen or hydroxy,
R$^5$ is hydroxy or hydroxysulfonyloxy and
R$^6$ is hydroxy.

3. The compound of claim 2, wherein
R$^1$ is hydrogen, lower alkoxycarbonyl, higher alkanoyl or benzoyl substituted with one or more suitable substituent(s),
R$^2$ is hydrogen,
R$^3$ is lower alkyl which has two hydroxy,
R$^4$ is hydrogen or hydroxy;
R$^5$ is hydroxy or hydroxysulfonyloxy; and
R$^6$ is hydroxy.

4. The compound of claim 3, wherein
R$^1$ is benzoyl substituted with a suitable substituent selected from the group consisting of
thiadiazolyl substituted with phenyl having phenyl substituted with morphlino having lower alkyl,
thiadiazolyl substituted with phenyl having a suitable substituent selected from the group consisting of lower alkoxy(lower)alkoxy and lower alkoxy(higher)alkoxy,
piperazinyl substituted with phenyl having piperidyl substituted with a suitable substituent selected from the group consisting of phenyl having lower alkoxy(lower)alkoxy, cyclo(lower)alkyloxy and lower alkoxy(lower)alkylthio,
piperazinyl substituted with phenyl having phenyl substituted with morpholino having lower alkyl,
imidazothiadiazolyl substituted with phenyl having piperidyl substituted with a suitable substituent selected from the group consisting of lower alkoxy(lower)alkoxy and lower alkoxy(lower)alkylthio,
imidazothiadiazolyl substituted with phenyl having lower alkoxy(lower)alkoxy,
phenyl subsutituted with piperazinyl having phenyl substituted with morpholino having lower alkyl,
isoxazolyl substituted with phenyl having lower alkoxy (lower)alkoxy,
isoxazolyl substituted with phenyl having higher alkoxy substituted with morpholino having lower alkyl,
thiadiazolyl substituted with phenyl having piperazinyl substituted with cyclo(lower)alkyl which has one or more suitable substituent(s) selected from the group consisting of lower alkyl, lower alkenyl, lower alkoxy (higher)alkoxy and phenyl,
thiadiazolyl substituted with phenyl having piperazinyl substituted with lower alkyl having cyclo(lower)alkyl,
thiadiazolyl substituted with phenyl having piperidyl substituted with one or more suitable substituent(s) selected from the group consisting of cyclo(lower) alkyloxy, lower alkoxy(lower)alkoxy and lower alkoxy (lower)alkoxy(lower)alkyl,
thiadiazolyl substituted with phenyl having piperidyl substituted with cyclo(lower)alkyl and lower alkoxy,
thiadiazolyl substituted with pyridyl having piperazinyl substituted with cyclo(lower)alkyl having lower alkyl,
imidazothiadiazolyl substituted with phenyl having piperidyl substituted with cyclo(lower)alkyl,
imidazothiadiazolyl substituted with phenyl having piperazinyl substituted with cyclo(lower)alkyl having lower alkyl, and
phenyl substituted with piperazinyl having cyclo(lower) alkyl substituted with one or more suitable substituent (s) selected from the group consisting of cyclo(lower) alkyl which may have lower alkoxy, lower alkyl, lower alkoxy and phenyl which may have lower alkoxy,
$R^2$ is hydrogen,
$R^3$ is lower alkyl which has two hydroxy,
$R^4$ is hydrogen or hydroxy;
$R^5$ is hydroxy or hydroxysulfonyloxy; and
$R^6$ is hydroxy.
5. The compound of the claim 4, wherein
$R^1$ is benzoyl which has thiadiazolyl substituted with phenyl having piperazinyl substituted with cyclo (lower)alkyl which has lower alkyl,
benzoyl which has thiadiazolyl substituted with phenyl having piperidyl substituted with cyclo(lower) alkyloxy,
benzoyl which has phenyl substituted with piperazinyl having cyclo(lower)alkyl substituted with cyclo(lower) alkyl and lower alkoxy, or
benzoyl which has thiadiazolyl substituted with phenyl having piperidyl substituted with cyclo(lower)alkyl,
$R^2$ is hydrogen,
$R^3$ is lower alkyl which has two hydroxy,
$R^4$ is hydrogen or hydroxy;

$R^5$ is hydroxy or hydroxysulfonyloxy; and
$R^6$ is hydroxy.
6. The compound of claim 4, wherein
$R^1$ is benzoyl which has thiadiazolyl substituted with phenyl having a suitable substituent selected from the group consisting of
(1) piperazinyl substituted with cyclo(lower)alkyl which has lower alkyl, and
(2) piperidyl substituted with cyclo(lower)alkyl and (lower)alkoxy,
$R^2$ is hydrogen,
$R^3$ is lower alkyl which has two hydroxyl,
$R^4$ is hydrogen,
$R^5$ is hydroxysulfonyloxy, and
$R^6$ is hydroxyl.
7. The compound of claim 6, wherein
$R^1$ is 4-[5-[4-[cis-4-(4-methylcyclohexyl)-piperazin-1-yl] phenyl]-1,3,4-thiadiazol-2-yl]benzoyl,
$R^2$ is hydrogen,
$R^3$ is 2-hydroxy-1-(hydroxymethyl)ethyl,
$R^4$ is hydrogen,
$R^5$ is hydroxysulfonyloxy, and
$R^6$ hydroxyl.
8. The compound of claim 6, wherein
$R^1$ is 4-[5-[4-(4-methoxy-4-cyclohexyl-piperidin-1-yl)-phenyl]-1,3,4-thiadiazol-2-yl]benzoyl,
$R^2$ is hydrogen,
$R^3$ is 2-hydroxy-1-(hydroxymethyl)ethyl,
$R^4$ is hydrogen,
$R^5$ is hydroxysulfonyloxy, and
$R^6$ is hydroxyl.
9. A process for preparing a polypeptide compound (I) of claim 1, or a salt thereof,
which comprises,
i) reacting a compound (II) of the formula:

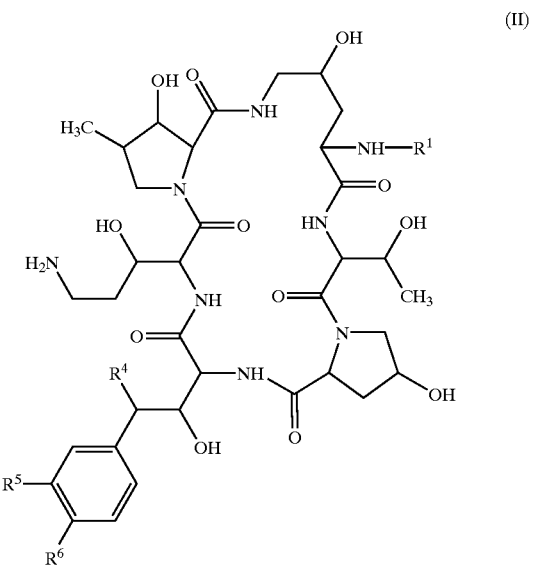

or a salt thereof, with a compound (III) of the formula:

or its reactive derivative or a salt thereof, to give a compound (Ia) of the formula:

or a salt thereof, or
iii) subjecting a compound (Ib) of the formula:

(Ia)

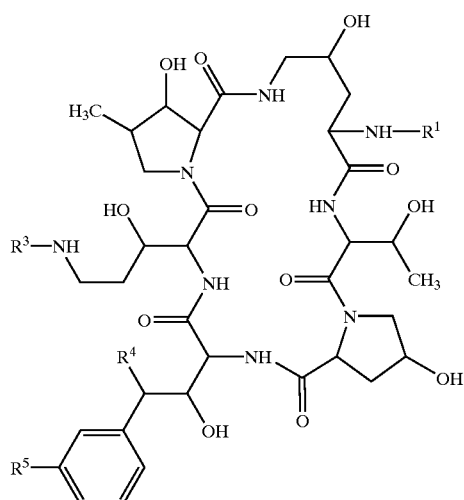

or a salt thereof, or
ii) reacting a compound (Ia) of the formula:

(Ia)

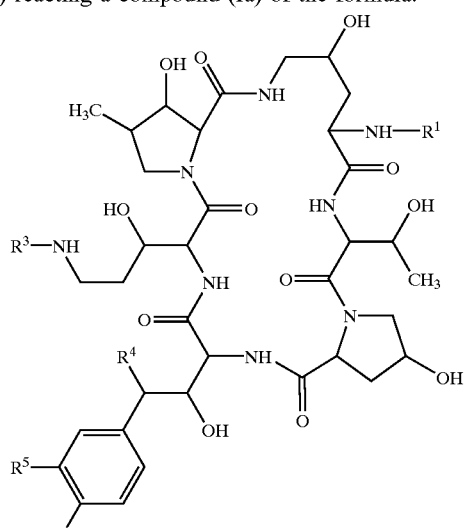

or a salt thereof, with a compound (IV) of the formula:
$R_a^2$—OH    (IV)
wherein $R_a^1$ is acyl group,
or its reactive derivative at the carboxy group or a salt thereof, to give a compound (Ib) of the formula:    (Ib)

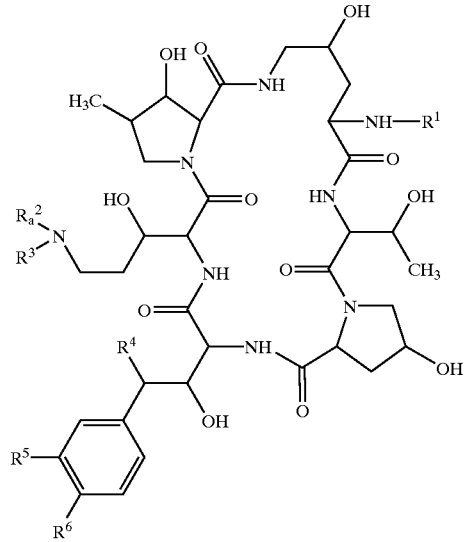

(Ib)

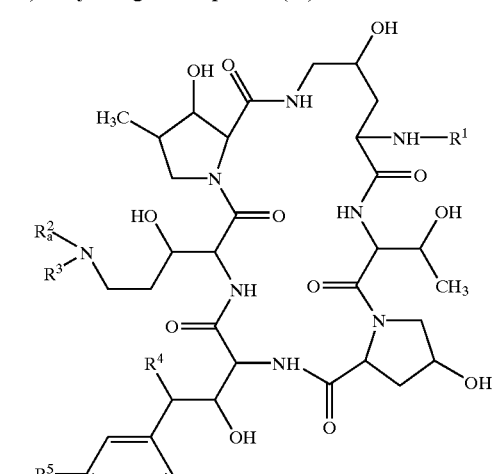

or a salt thereof, to elimination reaction of the acyl group, to give a (Ia) of the formula:    (Ia)

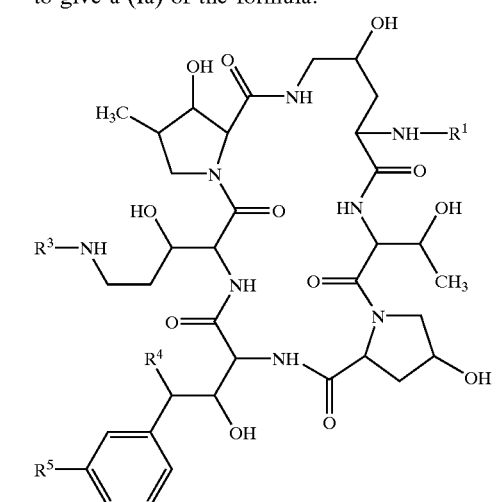

or a salt thereof, or
iv) reacting a compound (Ic) of the formula:    (Ic)

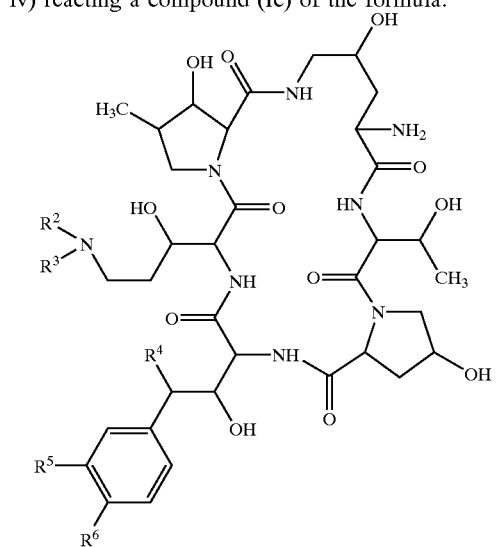

or a salt thereof, with a compound (V) of the formula:

(V)

wherein $R_a^1$ is acyl group,
or its reactive derivative at the carboxy group or a salt thereof, to give a compound (Id) of the formula:

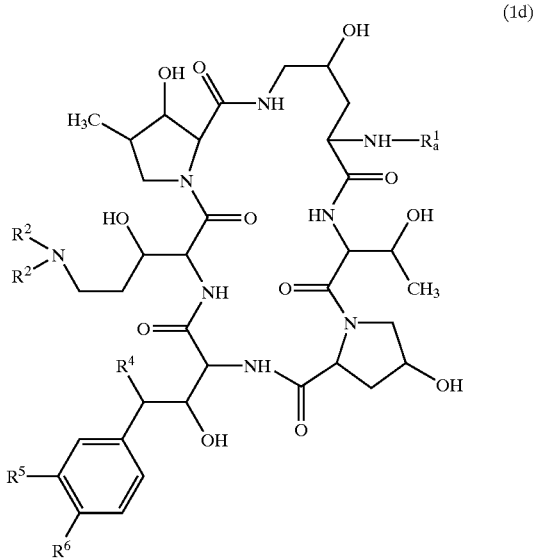

or a salt thereof.

10. A pharmaceutical composition which comprises, as an active ingredient, a compound of claim 1 or a pharmaceutically acceptable salt thereof in admixture with pharmaceutically acceptable carriers or excipients.

11. A method of treating an infectious disease caused by a fungus comprising administering to a human being or an animal subject in need thereof compound according to claim 1 for a time and under conditions to treat said disease.

12. The commercial package comprising the pharmaceutical composition of claim 10 and a written matter associated therewith, wherein the written matter states that the pharmaceutical composition can be used for treating an infectious disease caused by a fungus.

13. An article of manufacture, comprising packaging material and the compound (I) identified in claim 1 contained within said packaging material wherein said compound (I) is therapeutically effective for treating an infectious disease caused by a fungus, and wherein said packaging material comprises a label or a written material which indicates that said compound (I) can be used for treating an infectious disease caused by a fungus.

* * * * *

UNITED STATES PATENT AND TRADEMARK OFFICE
CERTIFICATE OF CORRECTION

PATENT NO. : 6,884,774 B2  
DATED : April 26, 2005  
INVENTOR(S) : Ayako Toda et al.

It is certified that error appears in the above-identified patent and that said Letters Patent is hereby corrected as shown below:

<u>Column 463,</u>

Line 2, "$R_a^2\text{-OH}$" should read --$R_a^1\text{-OH}$--.

Signed and Sealed this

Nineteenth Day of July, 2005

JON W. DUDAS  
*Director of the United States Patent and Trademark Office*